(12) United States Patent
Bermudes

(10) Patent No.: US 11,471,497 B1
(45) Date of Patent: Oct. 18, 2022

(54) COPPER CHELATION THERAPEUTICS

(71) Applicant: David Gordon Bermudes, Woodland Hills, CA (US)

(72) Inventor: David Gordon Bermudes, Woodland Hills, CA (US)

(*) Notice: Subject to any disclaimer, the term of this patent is extended or adjusted under 35 U.S.C. 154(b) by 165 days.

(21) Appl. No.: 16/812,237

(22) Filed: Mar. 6, 2020

Related U.S. Application Data

(60) Provisional application No. 62/895,961, filed on Sep. 4, 2019, provisional application No. 62/817,970, filed on Mar. 13, 2019.

(51) Int. Cl.
    *C12N 1/20* (2006.01)
    *A61K 35/74* (2015.01)
    *A61P 25/00* (2006.01)

(52) U.S. Cl.
    CPC .............. *A61K 35/74* (2013.01); *A61P 25/00* (2018.01); *C12N 1/20* (2013.01); *C12N 2510/00* (2013.01)

(58) Field of Classification Search
    CPC ....................................................... C12N 1/20
    See application file for complete search history.

(56) References Cited

U.S. PATENT DOCUMENTS

| | | |
|---|---|---|
| 4,678,667 A | 7/1987 | Meares et al. |
| 5,023,237 A | 6/1991 | Pickart |
| 5,039,529 A | 8/1991 | Bergendal et al. |
| 5,143,830 A | 9/1992 | Holland et al. |
| 5,145,838 A | 9/1992 | Pickart |
| 5,164,367 A | 11/1992 | Pickart |
| 5,470,719 A | 11/1995 | Meng et al. |
| 5,508,192 A | 4/1996 | Georgiou et al. |
| 5,523,215 A | 6/1996 | Cousens et al. |
| 5,681,746 A | 10/1997 | Bodner et al. |
| 5,736,119 A | 4/1998 | Goldenberg et al. |
| 5,824,502 A | 10/1998 | Honjo et al. |

(Continued)

FOREIGN PATENT DOCUMENTS

| | | |
|---|---|---|
| EP | 0973911 | 1/2000 |
| EP | 0973911 A1 | 1/2000 |

(Continued)

OTHER PUBLICATIONS

English machine translation of Yukio et al., JP 2004-313125 A, 2004.*

(Continued)

*Primary Examiner* — Rosanne Kosson
(74) *Attorney, Agent, or Firm* — Hoffberg & Associates; Steven M. Hoffberg

(57) ABSTRACT

Bacterial strains are provided having at least one enhanced mechanism to sequester, bind, precipitate, chemically oxidize or reduce copper ions or other toxic divalent transition metals. The bacteria may also have optional copper resistance mechanisms. The bacteria reduce the amount of available copper to tissues, which may be cancerous tissues, and reduce tumor growth, angiogenesis and/or metastasis, or tissues subject to excess copper due to host defects in copper metabolism. The bacteria are useful for treatment of neoplastic diseases including solid tumors and lymphomas, as well as Wilson's Disease, Menke's Disease, and possible Alzheimer's Disease, Parkinson's Disease, and Creutzfeldt-Jakob Disease.

20 Claims, 5 Drawing Sheets

Specification includes a Sequence Listing.

(56) References Cited

U.S. PATENT DOCUMENTS

| | | |
|---|---|---|
| 5,854,023 A | 12/1998 | Hillman et al. |
| 5,866,362 A | 2/1999 | Cousens et al. |
| 5,877,159 A | 3/1999 | Powell et al. |
| 5,922,302 A | 7/1999 | Goldenberg et al. |
| 5,989,868 A | 11/1999 | Harrison et al. |
| 6,030,624 A | 2/2000 | Russell et al. |
| 6,080,849 A | 6/2000 | Bermudes et al. |
| 6,083,715 A | 7/2000 | Georgiou et al. |
| 6,124,271 A | 9/2000 | Iversen et al. |
| 6,150,170 A | 11/2000 | Powell et al. |
| 6,190,657 B1 | 2/2001 | Pawelek et al. |
| 6,193,891 B1 | 2/2001 | Kent et al. |
| 6,207,648 B1 | 3/2001 | Waxman et al. |
| 6,306,387 B1 | 10/2001 | Galan |
| 6,372,262 B1 | 4/2002 | Peled et al. |
| 6,441,009 B1 | 8/2002 | Fernandez-Pol |
| 6,447,784 B1 | 9/2002 | Bermudes et al. |
| 6,475,482 B1 | 11/2002 | Bermudes et al. |
| 6,500,419 B1 | 12/2002 | Hone et al. |
| 6,506,550 B1 | 1/2003 | Fulton et al. |
| 6,548,287 B1 | 4/2003 | Powell et al. |
| 6,576,672 B1 | 6/2003 | Murphy |
| 6,596,510 B1 | 7/2003 | Lubitz et al. |
| 6,605,697 B1 | 8/2003 | Kwon et al. |
| 6,610,693 B2 | 8/2003 | Baker |
| 6,635,246 B1 | 10/2003 | Barrett et al. |
| 6,642,027 B2 | 11/2003 | Diaz-Torres |
| 6,673,569 B1 | 1/2004 | Kurokawa et al. |
| 6,682,729 B1 | 1/2004 | Powell et al. |
| 6,685,935 B1 | 2/2004 | Pawelek et al. |
| 6,703,050 B1 | 3/2004 | Brewer et al. |
| 6,770,632 B1 | 8/2004 | Aghi et al. |
| 6,783,775 B2 | 8/2004 | Peled et al. |
| 6,800,437 B1 | 10/2004 | Dierynck et al. |
| 6,828,121 B2 | 12/2004 | Chen |
| 6,838,437 B2 | 1/2005 | Kaufman et al. |
| 6,852,512 B2 | 2/2005 | Choi et al. |
| 6,855,340 B2 | 2/2005 | Brewer |
| 6,861,403 B2 | 3/2005 | Sanders |
| 6,863,894 B2 | 3/2005 | Bermudes et al. |
| 6,897,243 B2 | 5/2005 | Baker et al. |
| 6,916,918 B2 | 7/2005 | Yu et al. |
| 6,919,198 B1 | 7/2005 | Korpela et al. |
| 6,921,659 B2 | 7/2005 | Joly |
| 6,923,972 B2 | 8/2005 | Bermudes et al. |
| 6,951,890 B2 | 10/2005 | Cooper et al. |
| 6,962,696 B1 | 11/2005 | Bermudes et al. |
| 6,962,698 B1 | 11/2005 | Peled et al. |
| 7,015,027 B1 | 3/2006 | Redshaw |
| 7,041,449 B2 | 5/2006 | Prolla et al. |
| 7,045,312 B2 | 5/2006 | Dierynck et al. |
| 7,052,867 B2 | 5/2006 | Kwon et al. |
| 7,056,732 B2 | 6/2006 | Hua et al. |
| 7,060,458 B1 | 6/2006 | Doucette-Stamm et al. |
| 7,070,989 B2 | 7/2006 | Lee et al. |
| 7,083,791 B2 | 8/2006 | Sleeman et al. |
| 7,084,105 B2 | 8/2006 | Chakrabarty et al. |
| 7,094,579 B2 | 8/2006 | Gray et al. |
| 7,105,327 B1 | 9/2006 | Kuppusamy et al. |
| 7,109,033 B2 | 9/2006 | Harper et al. |
| 7,112,434 B2 | 9/2006 | Cannon et al. |
| 7,125,718 B2 | 10/2006 | Powell et al. |
| 7,169,605 B2 | 1/2007 | Peled et al. |
| 7,189,865 B2 | 3/2007 | Ternansky et al. |
| 7,195,757 B2 | 3/2007 | Curtiss, III et al. |
| 7,199,099 B2 | 4/2007 | DiSpirito et al. |
| 7,202,059 B2 | 4/2007 | Habermann et al. |
| 7,247,296 B2 | 7/2007 | Redshaw |
| 7,291,325 B2 | 11/2007 | Lee et al. |
| 7,312,078 B2 | 12/2007 | Peled et al. |
| 7,320,988 B2 | 1/2008 | Rahbar et al. |
| 7,344,710 B2 | 3/2008 | Dang et al. |
| 7,344,881 B2 | 3/2008 | Peled et al. |
| 7,354,592 B2 | 4/2008 | Bermudes et al. |
| 7,393,525 B2 | 7/2008 | Powell et al. |
| 7,404,963 B2 | 7/2008 | Sotomayor et al. |
| 7,410,788 B2 | 8/2008 | Beckwith et al. |
| 7,416,741 B2 | 8/2008 | Brewer |
| 7,429,489 B2 | 9/2008 | Peled et al. |
| 7,438,931 B2 | 10/2008 | Brewer et al. |
| 7,452,531 B2 | 11/2008 | Bermudes et al. |
| 7,459,446 B2 | 12/2008 | Baker et al. |
| 7,459,534 B2 | 12/2008 | Kaufman et al. |
| 7,470,667 B2 | 12/2008 | Luo et al. |
| 7,491,528 B2 | 2/2009 | Lee et al. |
| 7,514,089 B2 | 4/2009 | Bermudes et al. |
| 7,557,081 B2 | 7/2009 | Kiss |
| 7,588,767 B2 | 9/2009 | Szalay et al. |
| 7,588,771 B2 | 9/2009 | Szalay et al. |
| 7,601,525 B2 | 10/2009 | Batich et al. |
| 7,611,712 B2 | 11/2009 | Karp |
| 7,611,883 B2 | 11/2009 | Cranenburgh |
| 7,615,624 B2 | 11/2009 | Budworth et al. |
| 7,618,634 B2 | 11/2009 | Bush et al. |
| 7,652,037 B2 | 1/2010 | Rahbar et al. |
| 7,655,225 B2 | 2/2010 | Peled et al. |
| 7,662,398 B2 | 2/2010 | Szalay et al. |
| 7,687,474 B2 | 3/2010 | Matin et al. |
| 7,691,383 B2 | 4/2010 | Chakrabarty et al. |
| 7,692,065 B2 | 4/2010 | Harper et al. |
| 7,700,104 B2 | 4/2010 | Hensel et al. |
| 7,713,533 B2 | 5/2010 | Svanborg |
| 7,718,180 B2 | 5/2010 | Karp |
| 7,736,898 B1 | 6/2010 | Fulton et al. |
| 7,740,835 B2 | 6/2010 | Fujimori et al. |
| 7,754,221 B2 | 7/2010 | Szalay et al. |
| 7,754,765 B2 | 7/2010 | Wang et al. |
| 7,758,898 B2 | 7/2010 | Brewer |
| 7,763,420 B2 | 7/2010 | Stritzker et al. |
| 7,786,288 B2 | 8/2010 | Karp |
| 7,790,177 B2 | 9/2010 | Karp |
| 7,803,531 B2 | 9/2010 | Fulton et al. |
| 7,816,403 B2 | 10/2010 | Kennedy |
| 7,820,184 B2 | 10/2010 | Stritzker et al. |
| 7,842,290 B2 | 11/2010 | Holden |
| 7,847,156 B2 | 12/2010 | Inze et al. |
| 7,851,505 B2 | 12/2010 | Ternansky et al. |
| 7,855,075 B2 | 12/2010 | Peled et al. |
| 7,855,274 B2 | 12/2010 | Fay et al. |
| 7,887,816 B2 | 2/2011 | Feldman et al. |
| 7,888,389 B2 | 2/2011 | Brewer et al. |
| 7,893,289 B2 | 2/2011 | Goel |
| 7,897,836 B2 | 3/2011 | Lee et al. |
| 7,915,218 B2 | 3/2011 | Capecchi et al. |
| 7,928,094 B2 | 4/2011 | Baker et al. |
| 7,932,052 B1 | 4/2011 | DiSpirito et al. |
| 7,939,319 B2 | 5/2011 | Polack et al. |
| 7,955,600 B2 | 6/2011 | Hensel et al. |
| 7,998,461 B2 | 8/2011 | Forbes et al. |
| 8,008,283 B2 | 8/2011 | Hochman et al. |
| 8,021,662 B2 | 9/2011 | Szalay et al. |
| 8,034,799 B2 | 10/2011 | Cooper et al. |
| 8,039,690 B2 | 10/2011 | Harper et al. |
| 8,066,987 B2 | 11/2011 | Moore et al. |
| 8,080,417 B2 | 12/2011 | Peled et al. |
| 8,097,771 B2 | 1/2012 | Wan et al. |
| 8,137,904 B2 | 3/2012 | Szalay et al. |
| 8,163,494 B2 | 4/2012 | Neufeld et al. |
| 8,168,180 B2 | 5/2012 | Neufeld et al. |
| 8,173,369 B2 | 5/2012 | Geschwind et al. |
| 8,183,344 B2 | 5/2012 | Kaufman et al. |
| 8,198,430 B2 | 6/2012 | Prior et al. |
| 8,202,724 B2 | 6/2012 | Peled et al. |
| 8,221,769 B2 | 7/2012 | Szalay et al. |
| 8,241,623 B1 | 8/2012 | Bermudes |
| 8,282,919 B2 | 10/2012 | Eisenstark et al. |
| 8,314,153 B2 | 11/2012 | Miller et al. |
| 8,318,171 B2 | 11/2012 | Bush et al. |
| 8,323,959 B2 | 12/2012 | Szalay et al. |
| 8,343,509 B2 | 1/2013 | Stritzker et al. |
| 8,357,486 B2 | 1/2013 | Stritzker et al. |
| 8,367,621 B2 | 2/2013 | Ruoslahti et al. |
| 8,426,576 B2 | 4/2013 | Budworth et al. |
| 8,436,162 B2 | 5/2013 | Brown |

(56) References Cited

U.S. PATENT DOCUMENTS

| | | |
|---|---|---|
| 8,440,207 B2 | 5/2013 | Bermudes |
| 8,440,827 B2 | 5/2013 | Franz et al. |
| 8,524,220 B1 | 9/2013 | Bermudes |
| 8,551,471 B2 | 10/2013 | Filutowicz et al. |
| 8,558,056 B2 | 10/2013 | Wan et al. |
| 8,568,707 B2 | 10/2013 | Szalay et al. |
| 8,586,022 B2 | 11/2013 | Szalay et al. |
| 8,591,862 B2 | 11/2013 | Brahmbhatt et al. |
| 8,604,178 B2 | 12/2013 | Bottje et al. |
| 8,623,350 B1 | 1/2014 | Bermudes |
| 8,629,239 B2 | 1/2014 | Semrau et al. |
| 8,642,257 B2 | 2/2014 | Szalay et al. |
| 8,647,642 B2 | 2/2014 | Bermudes |
| 8,653,144 B2 | 2/2014 | Miller et al. |
| 8,663,634 B2 | 3/2014 | Koenig et al. |
| 8,673,980 B2 | 3/2014 | Behnken et al. |
| 8,685,939 B2 | 4/2014 | Wei et al. |
| 8,703,153 B2 | 4/2014 | Telfer et al. |
| 8,715,641 B2 | 5/2014 | Filutowicz et al. |
| 8,722,668 B2 | 5/2014 | Hochman |
| 8,734,779 B2 | 5/2014 | Hamaji et al. |
| 8,735,538 B1 | 5/2014 | DiSpirito et al. |
| 8,753,604 B2 | 6/2014 | Ruoslahti et al. |
| 8,771,669 B1 | 7/2014 | Bermudes |
| 8,772,461 B2 | 7/2014 | Gonzalez et al. |
| 8,784,836 B2 | 7/2014 | Szalay et al. |
| 8,815,533 B2 | 8/2014 | Bren et al. |
| 8,815,823 B2 | 8/2014 | Neufeld et al. |
| 8,815,945 B2 | 8/2014 | Nagai et al. |
| 8,822,194 B2 | 9/2014 | Zhao et al. |
| 8,828,681 B2 | 9/2014 | Bell, III et al. |
| 8,846,393 B2 | 9/2014 | Peled |
| 8,852,888 B2 | 10/2014 | Grillberger et al. |
| 8,859,256 B2 | 10/2014 | Szalay et al. |
| 8,895,610 B1 | 11/2014 | Kay |
| 8,969,420 B2 | 3/2015 | Miller et al. |
| 8,987,244 B2 | 3/2015 | Cooper et al. |
| 9,012,180 B2 | 4/2015 | Drapeau et al. |
| 9,017,953 B2 | 4/2015 | Henderson et al. |
| 9,040,267 B2 | 5/2015 | Herrema |
| 9,040,774 B2 | 5/2015 | Ivashuta et al. |
| 9,062,094 B2 | 6/2015 | Rau et al. |
| 9,085,643 B2 | 7/2015 | Svanborg et al. |
| 9,085,784 B1 | 7/2015 | Herrema |
| 9,175,266 B2 | 11/2015 | Peled et al. |
| 9,226,984 B2 | 1/2016 | Petersen et al. |
| 9,255,271 B2 | 2/2016 | Neufeld |
| 9,284,535 B2 | 3/2016 | Yao et al. |
| 9,339,479 B2 | 5/2016 | Cooper |
| 9,365,593 B2 | 6/2016 | Franz et al. |
| 9,399,612 B2 | 7/2016 | Miller |
| 9,402,911 B2 | 8/2016 | Baker, Jr. et al. |
| 9,409,971 B2 | 8/2016 | Grillberger et al. |
| 9,458,222 B2 | 10/2016 | Grillberger et al. |
| 9,487,561 B2 | 11/2016 | Svanborg et al. |
| 9,951,340 B2 | 4/2018 | Lesser et al. |
| 2002/0023281 A1 | 2/2002 | Gorlach et al. |
| 2002/0026655 A1 | 2/2002 | Bermudes |
| 2002/0040489 A1 | 4/2002 | Gorlach et al. |
| 2002/0054916 A1 | 5/2002 | Peled et al. |
| 2002/0098519 A1 | 7/2002 | Numao |
| 2002/0102242 A1 | 8/2002 | Briles et al. |
| 2002/0114789 A1 | 8/2002 | Peled et al. |
| 2002/0132306 A1 | 9/2002 | Kaufman et al. |
| 2002/0151063 A1 | 10/2002 | Lasham et al. |
| 2002/0160378 A1 | 10/2002 | Harper et al. |
| 2002/0176848 A1 | 11/2002 | Sizemore et al. |
| 2003/0008839 A1 | 1/2003 | van Rooij et al. |
| 2003/0009015 A1 | 1/2003 | Ulrich et al. |
| 2003/0022835 A1 | 1/2003 | Watson et al. |
| 2003/0031628 A1 | 2/2003 | Zhao et al. |
| 2003/0032030 A1 | 2/2003 | Prolla et al. |
| 2003/0036644 A1 | 2/2003 | Ulrich |
| 2003/0045492 A1 | 3/2003 | Tang et al. |
| 2003/0055113 A1 | 3/2003 | Wang et al. |
| 2003/0059400 A1 | 3/2003 | Szalay |
| 2003/0087830 A1 | 5/2003 | Dupont et al. |
| 2003/0109026 A1 | 6/2003 | Bermudes et al. |
| 2003/0113293 A1 | 6/2003 | Bermudes et al. |
| 2003/0115639 A1 | 6/2003 | Gorlach et al. |
| 2003/0125278 A1 | 7/2003 | Tang et al. |
| 2003/0130797 A1 | 7/2003 | Skolnick et al. |
| 2003/0135888 A1 | 7/2003 | Zhu et al. |
| 2003/0143676 A1 | 7/2003 | Strachan et al. |
| 2003/0148953 A1 | 8/2003 | Kaufman et al. |
| 2003/0153527 A1 | 8/2003 | Powell et al. |
| 2003/0170211 A1 | 9/2003 | Goudsmit et al. |
| 2003/0170276 A1 | 9/2003 | Bermudes et al. |
| 2003/0232799 A1 | 12/2003 | Wang et al. |
| 2003/0233670 A1 | 12/2003 | Edgerton et al. |
| 2003/0233681 A1 | 12/2003 | Zhu et al. |
| 2004/0005695 A1 | 1/2004 | Miksch et al. |
| 2004/0009237 A1 | 1/2004 | Brewer |
| 2004/0009476 A9 | 1/2004 | Harper et al. |
| 2004/0009936 A1 | 1/2004 | Tang et al. |
| 2004/0013680 A1 | 1/2004 | Bush et al. |
| 2004/0019087 A1 | 1/2004 | Ternansky et al. |
| 2004/0019102 A1 | 1/2004 | Kennedy |
| 2004/0049350 A1 | 3/2004 | Numao |
| 2004/0054142 A1 | 3/2004 | Cassart et al. |
| 2004/0058849 A1 | 3/2004 | Sleeman et al. |
| 2004/0078852 A1 | 4/2004 | Thomashow et al. |
| 2004/0092442 A1 | 5/2004 | Kaufman et al. |
| 2004/0115174 A1 | 6/2004 | Gilboa et al. |
| 2004/0138103 A1 | 7/2004 | Patt |
| 2004/0171519 A1 | 9/2004 | DiSpirito et al. |
| 2004/0202648 A1 | 10/2004 | Cabezon et al. |
| 2004/0202663 A1 | 10/2004 | Hu et al. |
| 2004/0219169 A1 | 11/2004 | Bermudes et al. |
| 2004/0229338 A1 | 11/2004 | King |
| 2004/0229796 A1 | 11/2004 | Maciag et al. |
| 2004/0234455 A1 | 11/2004 | Szalay |
| 2004/0259945 A1 | 12/2004 | Brewer et al. |
| 2004/0266003 A1 | 12/2004 | Powell et al. |
| 2005/0008618 A1 | 1/2005 | Kaufman et al. |
| 2005/0009750 A1 | 1/2005 | Sleeman et al. |
| 2005/0026866 A1 | 2/2005 | Pawelek |
| 2005/0031595 A1 | 2/2005 | Peled et al. |
| 2005/0036987 A1 | 2/2005 | Pawelek et al. |
| 2005/0037341 A1 | 2/2005 | Dierynck et al. |
| 2005/0058720 A1 | 3/2005 | Brewer et al. |
| 2005/0064526 A1 | 3/2005 | Ulrich et al. |
| 2005/0069491 A1 | 3/2005 | Szalay et al. |
| 2005/0112139 A1 | 5/2005 | Karp |
| 2005/0112140 A1 | 5/2005 | Karp |
| 2005/0112642 A1 | 5/2005 | Sleeman et al. |
| 2005/0118150 A1 | 6/2005 | Peled et al. |
| 2005/0118193 A1 | 6/2005 | Andino-Pavlovsky et al. |
| 2005/0147694 A1 | 7/2005 | Brewer |
| 2005/0159364 A1 | 7/2005 | Cooper |
| 2005/0171150 A1 | 8/2005 | Rahbar et al. |
| 2005/0196423 A1 | 9/2005 | Batich et al. |
| 2005/0214262 A1 | 9/2005 | Peled et al. |
| 2005/0214317 A1 | 9/2005 | Karp |
| 2005/0214318 A1 | 9/2005 | Karp |
| 2005/0249706 A1 | 11/2005 | Bermudes et al. |
| 2005/0255088 A1 | 11/2005 | Bermudes et al. |
| 2005/0267103 A1 | 12/2005 | Hochman |
| 2006/0014683 A1 | 1/2006 | Kaufman et al. |
| 2006/0021088 A1 | 1/2006 | Inze et al. |
| 2006/0025387 A1 | 2/2006 | Hochman |
| 2006/0040980 A1 | 2/2006 | Lind et al. |
| 2006/0057152 A1 | 3/2006 | Marshall |
| 2006/0068438 A1 | 3/2006 | Prolla et al. |
| 2006/0083716 A1 | 4/2006 | Kaufman et al. |
| 2006/0089350 A1 | 4/2006 | Hochman et al. |
| 2006/0104955 A1 | 5/2006 | Redshaw |
| 2006/0115483 A1 | 6/2006 | Sleeman et al. |
| 2006/0127408 A1 | 6/2006 | Young et al. |
| 2006/0134708 A1 | 6/2006 | Yang |
| 2006/0140975 A1 | 6/2006 | Curtiss et al. |
| 2006/0147512 A1 | 7/2006 | Sabin |
| 2006/0148891 A1 | 7/2006 | Ternansky et al. |
| 2006/0160805 A1 | 7/2006 | Ternansky et al. |

(56) References Cited

U.S. PATENT DOCUMENTS

| | | |
|---|---|---|
| 2006/0183137 A1 | 8/2006 | Harper et al. |
| 2006/0210647 A1 | 9/2006 | Maciag et al. |
| 2006/0270043 A1 | 11/2006 | Blattner et al. |
| 2006/0293238 A1 | 12/2006 | Kaufman et al. |
| 2006/0293505 A1 | 12/2006 | Stoddard et al. |
| 2007/0004666 A1 | 1/2007 | Lasham et al. |
| 2007/0009489 A1 | 1/2007 | Bermudes et al. |
| 2007/0031382 A1 | 2/2007 | Powell et al. |
| 2007/0104689 A1 | 5/2007 | Gillies et al. |
| 2007/0110721 A1 | 5/2007 | Cranenburgh |
| 2007/0110752 A1 | 5/2007 | Murison et al. |
| 2007/0134264 A1 | 6/2007 | Marshall |
| 2007/0191262 A1 | 8/2007 | Racila et al. |
| 2007/0202591 A1 | 8/2007 | Ulrich |
| 2007/0207191 A1 | 9/2007 | Kanzer et al. |
| 2007/0248689 A1 | 10/2007 | Brewer |
| 2007/0265199 A1 | 11/2007 | Fay et al. |
| 2007/0280927 A1 | 12/2007 | Hopf et al. |
| 2007/0287171 A1 | 12/2007 | Inouye |
| 2007/0292533 A1 | 12/2007 | Brewer |
| 2007/0298012 A1 | 12/2007 | King et al. |
| 2007/0298030 A1 | 12/2007 | Brewer |
| 2007/0298122 A1 | 12/2007 | Brewer |
| 2007/0299002 A1 | 12/2007 | Kiss |
| 2008/0003301 A1 | 1/2008 | Brewer |
| 2008/0031817 A1 | 2/2008 | Mazar et al. |
| 2008/0031975 A1 | 2/2008 | Brewer |
| 2008/0038296 A1 | 2/2008 | Brahmbhatt et al. |
| 2008/0057093 A1 | 3/2008 | Wan et al. |
| 2008/0064062 A1 | 3/2008 | Leonhartsberger et al. |
| 2008/0069874 A1 | 3/2008 | Hall et al. |
| 2008/0076157 A1 | 3/2008 | Leonhartsberger et al. |
| 2008/0118519 A1 | 5/2008 | Brewer |
| 2008/0120750 A1 | 5/2008 | Budworth et al. |
| 2008/0124355 A1 | 5/2008 | Bermudes |
| 2008/0166757 A1 | 7/2008 | Bron et al. |
| 2008/0166764 A1 | 7/2008 | Schloesser et al. |
| 2008/0182295 A1 | 7/2008 | Patkar et al. |
| 2008/0187520 A1 | 8/2008 | Polack et al. |
| 2008/0193974 A1 | 8/2008 | Coleman et al. |
| 2008/0200502 A1 | 8/2008 | Rahbar et al. |
| 2008/0206284 A1 | 8/2008 | Williams et al. |
| 2008/0206814 A1 | 8/2008 | Lee et al. |
| 2008/0206818 A1 | 8/2008 | Wich et al. |
| 2008/0249013 A1 | 10/2008 | Cabezon et al. |
| 2008/0254511 A1 | 10/2008 | Dassler et al. |
| 2008/0256665 A1 | 10/2008 | Lee et al. |
| 2008/0260769 A1 | 10/2008 | Capecchi et al. |
| 2008/0280346 A1 | 11/2008 | de Lorenzo Prieto et al. |
| 2008/0311081 A1 | 12/2008 | Fruehauf et al. |
| 2009/0004158 A1 | 1/2009 | Peled et al. |
| 2009/0011995 A1 | 1/2009 | Lee et al. |
| 2009/0028890 A1 | 1/2009 | Karp |
| 2009/0053186 A1 | 2/2009 | Hu et al. |
| 2009/0068226 A1 | 3/2009 | Ulrich et al. |
| 2009/0068705 A1 | 3/2009 | Drapeau et al. |
| 2009/0117047 A1 | 5/2009 | Szalay et al. |
| 2009/0117048 A1 | 5/2009 | Szalay et al. |
| 2009/0117049 A1 | 5/2009 | Szalay et al. |
| 2009/0123382 A1 | 5/2009 | Szalay et al. |
| 2009/0123426 A1 | 5/2009 | Li et al. |
| 2009/0123565 A9 | 5/2009 | Maciag et al. |
| 2009/0136542 A1 | 5/2009 | Karp |
| 2009/0169517 A1 | 7/2009 | Bermudes et al. |
| 2009/0175829 A1 | 7/2009 | Forbes et al. |
| 2009/0180955 A1 | 7/2009 | Stritzker et al. |
| 2009/0208534 A1 | 8/2009 | Xu et al. |
| 2009/0215754 A1 | 8/2009 | Hochman et al. |
| 2009/0220540 A1 | 9/2009 | Marshall |
| 2009/0226372 A1 | 9/2009 | Ruoslahti et al. |
| 2009/0271163 A1 | 10/2009 | Ngo et al. |
| 2009/0297538 A1 | 12/2009 | Bush et al. |
| 2009/0300779 A1 | 12/2009 | Zhao et al. |
| 2009/0311680 A1 | 12/2009 | Nakao et al. |
| 2009/0317404 A1 | 12/2009 | Markham |
| 2009/0317487 A1 | 12/2009 | Hall et al. |
| 2010/0017918 A1 | 1/2010 | Brown et al. |
| 2010/0024074 A1 | 1/2010 | Budwoth et al. |
| 2010/0063161 A1 | 3/2010 | Miller et al. |
| 2010/0064393 A1 | 3/2010 | Berka et al. |
| 2010/0092438 A1 | 4/2010 | Fruehauf et al. |
| 2010/0120124 A1 | 5/2010 | Fernandez Herrero et al. |
| 2010/0125042 A1 | 5/2010 | Geschwind et al. |
| 2010/0129790 A1 | 5/2010 | Sawada et al. |
| 2010/0135961 A1 | 6/2010 | Bermudes |
| 2010/0135973 A1 | 6/2010 | Eisenstark et al. |
| 2010/0136048 A1 | 6/2010 | Bermudes |
| 2010/0172976 A1 | 7/2010 | Satishchandran et al. |
| 2010/0189691 A1 | 7/2010 | Fruehauf et al. |
| 2010/0216775 A1 | 8/2010 | Goel |
| 2010/0233195 A1 | 9/2010 | Delisa et al. |
| 2010/0239546 A1 | 9/2010 | Fruehauf et al. |
| 2010/0255118 A1 | 10/2010 | Kanzer |
| 2010/0287671 A1 | 11/2010 | Harper et al. |
| 2010/0312139 A1 | 12/2010 | Dash et al. |
| 2011/0027337 A1 | 2/2011 | Nielsen et al. |
| 2011/0027349 A1 | 2/2011 | Sable et al. |
| 2011/0045589 A1 | 2/2011 | Peled et al. |
| 2011/0091493 A1 | 4/2011 | Moahamadzadeh et al. |
| 2011/0104196 A1 | 5/2011 | Karp |
| 2011/0111481 A1 | 5/2011 | Li |
| 2011/0111496 A1 | 5/2011 | Li |
| 2011/0151022 A1 | 6/2011 | Ternansky et al. |
| 2011/0162107 A1 | 6/2011 | Inze et al. |
| 2011/0165680 A1 | 7/2011 | Blattner et al. |
| 2011/0184333 A1 | 7/2011 | Franz et al. |
| 2011/0213126 A1 | 9/2011 | Gonzalez et al. |
| 2011/0223241 A1 | 9/2011 | Tardi et al. |
| 2011/0262347 A1 | 10/2011 | Ruoslahti et al. |
| 2011/0268661 A1 | 11/2011 | Markiv et al. |
| 2011/0274719 A1 | 11/2011 | Marshall |
| 2011/0275585 A1 | 11/2011 | Brahmbhatt et al. |
| 2011/0296555 A1 | 12/2011 | Ivashuta et al. |
| 2011/0306035 A1 | 12/2011 | Arad et al. |
| 2011/0318308 A1 | 12/2011 | Ragolia |
| 2011/0319282 A1 | 12/2011 | Garcia Bilbao et al. |
| 2012/0020883 A1 | 1/2012 | Stritzker et al. |
| 2012/0021517 A1 | 1/2012 | Jin et al. |
| 2012/0034594 A1 | 2/2012 | Semrau et al. |
| 2012/0034674 A1 | 2/2012 | Grillberger et al. |
| 2012/0035110 A1 | 2/2012 | Grillberger et al. |
| 2012/0041066 A1 | 2/2012 | Lombard |
| 2012/0083587 A1 | 4/2012 | Gallo et al. |
| 2012/0093773 A1 | 4/2012 | Li et al. |
| 2012/0108640 A1 | 5/2012 | Hochman et al. |
| 2012/0110696 A1 | 5/2012 | Wan et al. |
| 2012/0122969 A1 | 5/2012 | Miller |
| 2012/0128594 A1 | 5/2012 | Choy et al. |
| 2012/0142080 A1 | 6/2012 | Bermudes |
| 2012/0144509 A1 | 6/2012 | Benghezal et al. |
| 2012/0148601 A1 | 6/2012 | Ulrich et al. |
| 2012/0151635 A1 | 6/2012 | Coruzzi et al. |
| 2012/0156259 A1 | 6/2012 | Rau et al. |
| 2012/0164687 A1 | 6/2012 | Bereta et al. |
| 2012/0177682 A1 | 7/2012 | Marshall |
| 2012/0189572 A1 | 7/2012 | Wei et al. |
| 2012/0190623 A1 | 7/2012 | Kaufman et al. |
| 2012/0225454 A1 | 9/2012 | Benghezal et al. |
| 2012/0244621 A1 | 9/2012 | Weiss et al. |
| 2012/0258168 A1 | 10/2012 | Montesinos |
| 2012/0270940 A1 | 10/2012 | Behnken et al. |
| 2012/0284878 A1 | 11/2012 | Brown et al. |
| 2012/0284881 A1 | 11/2012 | Brown et al. |
| 2013/0023491 A1 | 1/2013 | Annes et al. |
| 2013/0035635 A1 | 2/2013 | Rau et al. |
| 2013/0053301 A1 | 2/2013 | Rau et al. |
| 2013/0053450 A1 | 2/2013 | Miller et al. |
| 2013/0072434 A1 | 3/2013 | Kaufman et al. |
| 2013/0078275 A1 | 3/2013 | Tao |
| 2013/0116182 A1 | 5/2013 | Pratt et al. |
| 2013/0123181 A1 | 5/2013 | Pratt et al. |
| 2013/0130292 A1 | 5/2013 | Szalay et al. |
| 2013/0164307 A1 | 6/2013 | Markham |
| 2013/0164380 A1 | 6/2013 | Durum et al. |

(56) References Cited

U.S. PATENT DOCUMENTS

| | | |
|---|---|---|
| 2013/0202596 A1 | 8/2013 | Salas et al. |
| 2013/0203101 A1 | 8/2013 | Bren et al. |
| 2013/0209405 A1 | 8/2013 | Curtiss et al. |
| 2013/0210650 A1 | 8/2013 | Geschwind et al. |
| 2013/0210793 A1 | 8/2013 | Franz et al. |
| 2013/0216513 A1 | 8/2013 | Salas et al. |
| 2013/0224281 A1 | 8/2013 | Montesinos et al. |
| 2013/0232647 A1 | 9/2013 | Brown |
| 2013/0237511 A1 | 9/2013 | Manning et al. |
| 2013/0251630 A1 | 9/2013 | Petersen et al. |
| 2013/0287810 A1 | 10/2013 | Mohamadzadeh et al. |
| 2013/0295054 A1 | 11/2013 | Huang et al. |
| 2013/0309687 A1 | 11/2013 | Henderson |
| 2013/0330824 A1 | 12/2013 | Li |
| 2013/0337516 A1 | 12/2013 | Herrema |
| 2013/0345114 A1 | 12/2013 | Williams et al. |
| 2014/0023701 A1 | 1/2014 | Montesinos et al. |
| 2014/0086950 A1 | 3/2014 | Pascual et al. |
| 2014/0090106 A1 | 3/2014 | Wan et al. |
| 2014/0093885 A1 | 4/2014 | Hua et al. |
| 2014/0112951 A1 | 4/2014 | Tang et al. |
| 2014/0140959 A1 | 5/2014 | Szalay et al. |
| 2014/0148582 A1 | 5/2014 | Gallo et al. |
| 2014/0155343 A1 | 6/2014 | Brahmbhatt et al. |
| 2014/0178341 A1 | 6/2014 | Zhao et al. |
| 2014/0186401 A1 | 7/2014 | Diamond et al. |
| 2014/0205538 A2 | 7/2014 | Wei et al. |
| 2014/0206772 A1 | 7/2014 | Miller et al. |
| 2014/0212396 A1 | 7/2014 | Newman |
| 2014/0220661 A1 | 8/2014 | Bermudes |
| 2014/0243254 A1 | 8/2014 | Hersel et al. |
| 2014/0249093 A1 | 9/2014 | Vetter et al. |
| 2014/0256922 A1 | 9/2014 | David et al. |
| 2014/0296257 A1 | 10/2014 | Hersel et al. |
| 2014/0303109 A1 | 10/2014 | Sarkar et al. |
| 2014/0323402 A1 | 10/2014 | Hersel et al. |
| 2014/0343255 A1 | 11/2014 | Gonzalez et al. |
| 2014/0363874 A1 | 12/2014 | Yao et al. |
| 2015/0018525 A1 | 1/2015 | Grillberger et al. |
| 2015/0045535 A1 | 2/2015 | Berka et al. |
| 2015/0056657 A1 | 2/2015 | Grillberger et al. |
| 2015/0067923 A1 | 3/2015 | Coruzzi et al. |
| 2015/0104854 A1 | 4/2015 | Singh et al. |
| 2015/0147346 A1 | 5/2015 | Bogoch et al. |
| 2015/0184142 A1 | 7/2015 | Hong et al. |
| 2015/0202317 A1 | 7/2015 | Rau et al. |
| 2015/0218614 A1 | 8/2015 | Henderson et al. |
| 2015/0239818 A1 | 8/2015 | Miller et al. |
| 2015/0247154 A1 | 9/2015 | Ivashuta et al. |
| 2015/0247172 A1 | 9/2015 | Herrema |
| 2015/0259389 A9 | 9/2015 | Berka et al. |
| 2015/0275241 A1 | 10/2015 | Herrema |
| 2015/0354024 A1 | 12/2015 | Wyatt et al. |
| 2015/0359909 A1 | 12/2015 | OSullivan et al. |
| 2016/0074373 A1 | 3/2016 | He et al. |
| 2016/0082123 A1 | 3/2016 | Rau et al. |
| 2016/0108160 A1 | 4/2016 | Xu et al. |
| 2016/0115499 A1 | 4/2016 | Cui et al. |
| 2016/0158392 A1 | 6/2016 | Petersen et al. |
| 2016/0186168 A1 | 6/2016 | Konieczka et al. |
| 2016/0201103 A1 | 7/2016 | Yamazaki et al. |
| 2016/0220500 A1 | 8/2016 | Huang et al. |
| 2016/0287554 A1 | 10/2016 | Guida et al. |
| 2019/0055569 A1 | 2/2019 | Lesser et al. |

FOREIGN PATENT DOCUMENTS

| | | |
|---|---|---|
| EP | 1270730 A1 | 1/2003 |
| EP | 1270730 A1 | 1/2003 |
| EP | 1402036 B1 | 2/2008 |
| EP | 1402036 B1 | 2/2008 |
| EP | 1068339 B1 | 7/2008 |
| EP | 1068339 B1 | 7/2008 |
| EP | 1407052 B1 | 12/2008 |
| EP | 1407052 B1 | 12/2008 |
| WO | 0047222 A2 | 8/2000 |
| WO | WO0047222 | 8/2000 |
| WO | WO2000047222 | 8/2000 |
| WO | 0125397 A2 | 4/2001 |
| WO | WO0125397 | 4/2001 |
| WO | 02067983 A1 | 9/2002 |
| WO | 02074336 A2 | 9/2002 |
| WO | 2002070645 | 9/2002 |
| WO | WO02067983 | 9/2002 |
| WO | WO02074336 | 9/2002 |
| WO | WO2002070645 | 9/2002 |
| WO | 02083214 A1 | 10/2002 |
| WO | WO02083214 | 10/2002 |
| WO | WO2002083214 | 10/2002 |
| WO | 02087494 A2 | 11/2002 |
| WO | WO02087494 | 11/2002 |
| WO | 03014380 A2 | 2/2003 |
| WO | WO03014380 | 2/2003 |
| WO | 2004016281 A1 | 2/2004 |
| WO | WO2004016281 A1 | 2/2004 |
| WO | 2005005630 A2 | 1/2005 |
| WO | WO2005005630 | 1/2005 |
| WO | 2005018332 A1 | 3/2005 |
| WO | WO2005018332 | 3/2005 |
| WO | 2005054477 A1 | 6/2005 |
| WO | WO2005054477 | 6/2005 |
| WO | 2006017929 A1 | 2/2006 |
| WO | WO2006017929 A1 | 2/2006 |
| WO | 2006048344 A1 | 5/2006 |
| WO | WO2006048344 | 5/2006 |
| WO | 2006103118 A2 | 10/2006 |
| WO | WO2006103118 | 10/2006 |
| WO | 2008073148 A2 | 6/2008 |
| WO | WO2008073148 | 6/2008 |
| WO | 2008089132 A2 | 7/2008 |
| WO | WO2008089132 A2 | 7/2008 |
| WO | 2009021548 A1 | 2/2009 |
| WO | WO2009021548 A1 | 2/2009 |
| WO | 2009111177 A2 | 9/2009 |
| WO | WO2009111177 | 9/2009 |
| WO | 2009126189 A1 | 10/2009 |
| WO | WO2009126189 | 10/2009 |
| WO | 2009152480 A2 | 12/2009 |
| WO | WO2009152480 | 12/2009 |

OTHER PUBLICATIONS

Pawelek et al. ("Bacteria as tumor-targeting vectors," The Lancet, Oncology 4:548-556, 2003).*

* cited by examiner

Methylosinus trichosporium methanobactin operon

Methanobactin

*Yersinia pestis* Yersiniabactin synthase

Yersiniabactin

COPPER CHELATION THERAPEUTICS

CROSS REFERENCE TO RELATED APPLICATIONS

The present application claims benefit of priority under 35 U.S.C. § 119(e) from, and is a non-provisional of, U.S. Provisional Patent Application No. 62/895,961, filed Sep. 4, 2019, and U.S. Provisional Patent Application No. 62/817,970, filed Mar. 13, 2019, each of which is expressly incorporated herein by reference in its entirety.

FIELD OF THE INVENTION

This invention is generally in the field of live bacteria, and use thereof, for the treatment of disease associated with excess heavy metals, or the treatment of which benefits from reduction in heavy metals.

BACKGROUND OF THE INVENTION

Citation or identification of any reference herein, or any section of this application shall not be construed as an admission that such reference is available as prior art to the present application. The disclosures of each of these publications and patents are hereby expressly incorporated by reference in their entirety in this application, and shall be treated as if the entirety thereof forms a part of this application. Such references are provided for their disclosure of technologies to enable practice of the present invention, to provide basis for claim language, to make clear applicant's possession of the invention with respect to the various aggregates, combinations, and subcombinations of the respective disclosures or portions thereof (within a particular reference or across multiple references). The citation of references is intended to be part of the disclosure of the invention, and not merely supplementary background information. The incorporation by reference does not extend to teachings which are inconsistent with the invention as expressly described herein, and is evidence of a proper interpretation by persons of ordinary skill in the art of the terms, phrase and concepts discussed herein, without being limiting as the sole interpretation available.

Copper is a transition metal important in biology. Tisato, Francesco, Cristina Marzano, Marina Porchia, Maura Pellei, and Carlo Santini. "Copper in diseases and treatments, and copper-based anticancer strategies." Medicinal research reviews 30, no. 4 (2010): 708-749.

The term heavy metal refers to any metallic chemical element that has a relatively high density and is toxic or poisonous at low concentrations. Examples of heavy metals include mercury (Hg), cadmium (Cd), arsenic (As), chromium (Cr), thallium (Tl), and lead (Pb). Iron (Fe), copper (Cu), Chromium (Cr), and zinc (Zn) are also heavy metals, though with some beneficial biological activity at normal environmental concentrations.

See, www.lenntech.com/processes/heavy/heavy-metals/heavy-metals.htm; en.wikipedia.org/wiki/Heavy_metals; en.wikipedia.org/wiki/Toxic_heavy_metal; Tchounwou, Paul B et al. "Heavy metal toxicity and the environment." Experientia supplementum (2012) vol. 101 (2012): 133-64. doi:10.1007/978-3-7643-8340-4_6.

Copper is found in all living organisms and is a crucial trace element in redox chemistry, growth and development. It is important for the function of several enzymes and proteins involved in energy metabolism, respiration, and DNA synthesis, notably cytochrome oxidase, superoxide dismutase, ascorbate oxidase, and tyrosinase. The major functions of copper-biological molecules involve oxidation-reduction reactions in which they react directly with molecular oxygen to produce free radicals. Therefore, copper requires tightly regulated homeostatic mechanisms to ensure adequate supplies without any toxic effects. Overload or deficiency of copper is associated, respectively, with Wilson disease (WD) and Menkes disease (MD), which are of genetic origin. Therapies based on metal supplementation with copper histidine or removal of copper excess by means of specific copper chelators are currently effective in treating MD and WD, respectively. Copper chelation therapy is now attracting much attention for the investigation and treatment of various neurodegenerative disorders such as Alzheimer, Parkinson and Creutzfeldt-Jakob's Disease. An excess of copper appears to be an essential co-factor for angiogenesis. Moreover, elevated levels of copper have been found in many types of human cancers, including prostate, breast, colon, lung, and brain. On these bases, the employment of copper chelators has been reported to be of therapeutic value in the treatment of several types of cancers as anti-angiogenic molecules. More recently, mixtures of copper chelators with copper salts have been found to act as efficient proteasome inhibitors and apoptosis inducers, specifically in cancer cells. Moreover, following the worldwide success of platinum(II) compounds in cancer chemotherapy, several families of individual copper complexes have been studied as potential antitumor agents. These investigations, revealing the occurrence of mechanisms of action quite different from platinum drugs, head toward the development of new anticancer metallodrugs with improved specificity and decreased toxic side effects.

Copper is a micronutrient essential to all organisms living in oxygen-rich environments. It is a redox-active metal that easily switches from the reduced Cu(I) to oxidized Cu(II) oxidation state or vice-versa both in conventional bench chemical reactions and in physiological conditions. With these accessible changes in redox state, copper can coordinate a variety of ligands including carboxylate oxygen, imidazole nitrogen, cysteine thiolate, and methionine thio-ether sulfurs, and less common phosphine phosphorus. In biology, copper is crucial for the function of several enzymes and proteins involved, among others, in energy metabolism, mitochondrial respiration (e.g. cytochrome oxidase; Cco), antioxidation (e.g. Zn,Cu-superoxide dismutase; SOD), collagen cross-linking (e.g. lysil oxidase), pigmentation (e.g. tyrosinase), and catecholamine biosynthesis (e.g. dopamine-b-monooxygenase). I The major functions of copper compounds involve oxidation-reduction reactions in which copper containing biological molecules react directly with molecular oxygen to produce free radicals. For this reason, free cellular copper concentrations are maintained at extremely low levels. Copper homeostasis in living organisms is actually highly regulated by both transcriptional control and selective transport mechanisms through a conserved group of proteins that contain unique cysteine-, methionine- and histidine-rich domains.

Altered levels of copper are associated with disease states, as established in the case of MD and WD, which are characterized by a deficiency or an overload of copper in the organism, respectively. The abnormal accumulation of copper by cancer cells might prove to be a distinguishing characteristic of transformed vs. healthy cells that can be targeted by novel chemotherapeutic agents.

Moreover, there is now increasing evidence that, among others, altered metal homeostasis may be involved in the progression of neurodegenerative diseases. Protein-metal interactions appear to play a critical role in protein aggregation and are therefore likely to provide a link between the accumulation of aggregated proteins, oxidative damage of the brain, and neuronal cell loss in an age-dependent manner. Copper is also implicated in Creutzfeldt-Jakob (prion) disease whereas recent studies emphasize the role of copper, iron, and zinc as contributors to both amyloid Ab assembly in vitro and the neuropathology of Alzheimer disease (AD). Furthermore, coordination environments for copper(II) complexes in the amyloid precursor protein (APP), amyloid Ab peptide, and prion protein have been very well characterized by several biophysical and structural studies.

These chelating agents may work as metal scavengers, for instance to remove copper excess in local districts to prevent angiogenesis, mimicking the copper chelation approach utilized in the treatment of WD. Copper chelators may be also combined with copper salts to generate mixtures of the so-called "organic copper compounds" capable to either remove excess of copper and promote proteasome inhibition followed by apoptosis or discrete copper complexes may be employed directly as anticancer metallodrugs, resembling the behavior of the current clinically used cis-diamminedichloroplatinum(II) (cisplatin), but likely adopting different cytotoxic mechanisms.

A diverse variety of copper-containing metalloenzymes occurs in plants and animals. They are utilized for electron transfer (azurin, plastocyanin, laccase), for oxygenation reactions (tyrosinase, ascorbate oxidase), and for oxygen transport (hemocyanin). Copper-containing metalloproteins and enzymes may contain Cu(I) d10, Cu(II) d9, and Cu(III) d8 ions. A relatively high redox potential for the Cu(II)/Cu(I) system is found in copper enzymes, most of them working between 10.25 and 10.75 V. This high potential can be utilized for a direct oxidation of certain substrates, easy to oxidize, such as superoxide in SOD, ascorbate in ascorbate oxidase and catechols in tyrosinase or in laccases. During the few C—H bond oxidations by copper enzymes such as those catalyzed by dopamine b-hydroxylase, containing a mononuclear active Cu site, or by tyrosinase, containing a dinuclear Cu site, an intermediate copper peroxo Cu—OOH or $Cu(O_2)Cu$ complex, in which the bound peroxide is highly activated has been suggested to be the oxidizing reagent.

Copper, like many other essential metals, becomes toxic when it is allowed to rise above relatively low concentration levels. This simple fact has required the development of quite sophisticated mechanisms able to control and regulate copper levels in the cell and in the different organs. The distribution of copper in the cell involves entry and exit mechanisms as well as specific pathways that ensure that this essential enzymatic co-factor is delivered to its required targets. The identification of many of the elements involved in this network has only recently been achieved, but the current picture is still partial.

The first systematic investigations on the basis of copper entry into eukaryotic cells were performed in the nineties on the yeast *Saccharomyces cerevisiae*. Researchers identified the proteins that mediate copper transport, CTR1 and CTR3, which constitute the first members of a widely conserved family of high affinity copper transporters, then recognized in plants, and mammals. All these proteins contain many copper-coordinating residues, notably histidine, cysteine, and methionine. Human copper transporters (hCTR1) contain three transmembrane segments with amino and carboxyl termini located on opposite sides of the plasma membrane. An extracellular amino-terminal domain contains 66 amino acid residues with a series of four histidine-rich and methionine-rich sequences, an intracellular loop of 46 amino acid residues (poorly conserved among various species), an intramembrane domain consisting of the three transmembrane segments, and a relatively short carboxyl-terminal tail of 15 amino acids that ends in His-Cys-His, a putative metal binding site. Recently, experimental evidence that CTR1 has a homotrimeric organization in the membrane was provided, also suggesting that a central pore is formed by transmembrane helices in the trimer. CTR1 transports copper with high affinity in a time-dependent and saturable manner. Copper is delivered to the extracellular histidine-rich N-terminal domain of CTR1 where it is driven into a pore; once there, the metal ion traverses the pore and exits at the inner surface, perhaps bound at the carboxyl terminus for delivery to its target protein.

Metal-trafficking proteins should bind their cargo ions tightly enough to prevent adventitious reactions or easy release of the ions, but this coordination environment has also to allow for metal transfer to the target. In this light, it is not surprising that such trafficking proteins often make use of uncommon coordination chemistry. If we consider copper-binding sites in proteins from the broader perspective of inorganic chemistry, the number of amino acid functional groups that may bind copper ions is rather limited. The list includes the cysteine thiolate, the histidine imidazole, the carboxylate group of aspartate and glutamate, the methionine thioether and, much less frequently, the serine or tyrosine hydroxyl groups, the deprotonated peptide amide nitrogen or the N-terminal amine. Although the protein-based ligand set seems limited, these biopolymers possess complex architectures that can tune coordination sites to achieve exquisite selectivity and proper affinity.

Studies concerning metal concentrations reveal that, for example, *Escherichia coli* concentrate Zn and Fe to about 100 mM, whereas Cu, Mo, and Mn are maintained in the 10 to 100 mM range. Therefore, many transition metals are really abundant in the cell, but they are usually confined in the copious number of metalloproteins having high metal ion affinity or in small molecules responsive to the changing metabolic needs of the cell. In the complex cellular copper-trafficking machinery, the continuous interplay between thermodynamic and kinetic factors is driven by the intimate coordination chemistry of each family of copper sites in several proteins ensuring an extremely low level of free metal in the cell. Disruptions to normal copper homeostasis are evident in three human genetic disorders: MD, occipital horn syndrome (OHS), and WD. Each disease results from the absence or dysfunction of homologous copper transporting ATPases. The responsible gene for MD and OHS is the ATP7A gene, whereas the ATP7B gene is responsible for WD. ATP7A is expressed in most tissues other than liver, whereas ATP7B is expressed predominantly in the liver and also in several types of neoplastic cells. Recently, ATP7A and ATP7B were found to be involved in drug resistance. A relationship between the expression of ATP7A and ATP7B in malignant cells and cisplatin resistance has been confirmed by clinical studies. ATP7A-overexpressing cells exhibited elevated resistance to a variety of anticancer drugs including CPT-11 (7-ethyl10-[4-(1-piperidino)-1-piperidino]carbonyloxycamptothecin) and its active metabolite SN-38 (7-ethyl-10-hydroxycamptothecin), vincristine, paclitaxel, etoposide, doxorubicin, and mitoxantron. It seems that ATP7A confers multidrug resistance to cancer cells by modulating drug cellular localization in the Golgi apparatus and by enhancing drug efflux.

Copper has also been reported to play a role in the pathogenesis of neurodegenerative diseases, including amyotrophic lateral sclerosis (ALS), AD, and the prion-mediated encephalopathies. Genetic disorders of the proteins involved in the copper machinery have long been known, and related diseases caused by deficiency (MD) or accumulation (WD) of the metal are now under pharmacological treatment.

Menkes Disease, also called the kinky hair disease or Menkes kinky hair syndrome is a fatal X-linked disorder caused by diverse mutations in a copper-transporter gene, ATP7A (often called the Menkes protein). The ATP7A gene (chromosome location Xq12-q13, OMIM 309400) codes for a P-type ATPase that is responsible for excretion of copper from cells and delivery of the metal to enzymes in the trans-Golgi (TG) network.

Historically, the treatment of MD required subcutaneous or intravenous administration of copper salts. Later, the identification of the copper-histidine system in normal human serum and the knowledge gained from the studies of its chemistry and physiological significance led to treatment of MD by copper-histidine formulations. Although most of copper in normal human serum is bound to Cp, but in a not-exchangeable form, the formation of the albumin-copper-histidine ternary complex provides the actual carrier necessary for the regulation and control of copper transport across the cell membrane.

Wilson Disease, or hepatolenticular degeneration, first described by the American neurologist Samuel Wilson in 1912, is an autosomal recessive disorder of copper transport involving accumulation of copper in the liver and brain of affected individuals. WD is caused by a defect in the ATP7B gene (chromosome location 13q140.3-q21.1 OMIM: 277900) that codes for a copper transport gene required for copper excretion via the bile. In patients affected by WD liver copper levels rise and serum Cp levels decrease because of the diminished function of the ATP7B protein, which is directly involved in the vesicular pathway of hepatic copper transport from the liver to bile canaliculi. Pathologic manifestations include liver failure, tremors, slurred speech, and other neurological impairments. The age of onset for WD ranges from 5 years to mid-50s, with age 17 considered to be the average age a diagnosis is made, with an incidence of approximately 1 in 30-40,000 people worldwide.

Treatment of WD consists on orally administered pharmacological agents. It is generally agreed that patients with symptoms or signs of hepatic insufficiency or chronic active hepatitis with or without neurologic manifestations should be offered chelation therapy with D-penicillamine (D-Pen; Cuprimine, Depen), trientine hydrochloride (trien; Syprine) or tetrathiomolybdate (TM). After adequate treatment with a chelator stable patients may continue with a lower dose of a chelating agent or shifted to treatment with zinc salts.

Neurodegeneration is a complex and multifaceted process that leads to many chronic disease states. Among the factors that underlie neurodegeneration (genetic, environmental, biological, metabolic, autoimmunity, ageing) the role played by intrinsic neurotoxins such as metals and excitatory amino acids are under continuous scrutiny. Protein aggregation and oxidative-stress-induced damage represent a recurring phenomenon in all the pathologies, notably in AD, Parkinson (PD), and prion diseases. Several functions that eventually lead to neurodegeneration appear to be induced and/or mediated by metals thus rendering chelation therapy a sensible strategy. The interesting feature of a suitable chelating agent would be the ability firstly to scavenge the free redox-active metal present in excess in the brain to form a nontoxic metal complex, which is then excreted, and secondly to cap the metal at its labile binding site preventing any mediated toxic action.

Alzheimer's Disease is a progressive neurodegeneration disease characterized by extra cellular deposition of Ab peptides in senile plaques and intracellular accumulation of hyperphosphorylated t protein in neuronal cells as neurofibrillary tangles. Potentially toxic Ab peptides are generated from the copper-binding APP, which is actively involved in balancing copper concentration in cells. The N-terminus copper binding domain (CuBD-I) of APP shows structural homology to the CuBD of Cu chaperons binding Cu with nanomolar affinity. PD, the second most common neurodegenerative disorder, is associated with the degeneration of dopaminergic neurons in the substantia nigra pars compacta. One of the pathological hallmarks of PD and related synucleinopathies is the presence of intracellular inclusions called Lewy bodies that consist of aggregates of the pre-synaptic soluble 140 amino acids protein a-synuclein (AS). Since this discovery, the process of AS aggregation has been proposed to underlie dopaminergic degeneration in PD. Altered metal homeostasis has been described as an important cofactor in the progression of PD. Analogously, copper has been implicated in Creutzfeldt-Jakob disease.

An attractive advancement in the field of AD treatment with copper chelators has recently been proposed by Meunier et al. They have linked two 8-OHQ monomers with a methylene carbon chain in order to increase the affinity of the chelate toward divalent metal ions including Cu(II) and Zn(II). The resulting tetradentate, poly-hydroxyquinoline ligands (P-OHQ) proved to be 10000 times more efficient in metal complexation than the corresponding 8-OHQ monomer. These chelates have been evaluated as potential metal-chelating agents in the treatment of AD.

In a recent study, it has been suggested that P-OHQ chelates can dissolve Ab-deposits (in particular the most toxic Ab1-42 peptide) by removing copper from the amyloid aggregates. P-OHQ ligands can also inhibit the production of $H_2O_2$ induced by the copper-Ab1-42 complexes and involved in the toxicity of the peptide.

By using a diametrically opposite approach, other researchers observed that increased Cu levels were shown to reduce Ab peptides production in APP transgenic mouse models. They consequently speculated that Cu intake might stabilize cognitive decline in AD patients.

The remarkable metabolic changes that have long been known to occur in cancer cells have been associated, among other factors, with copper handling and copper utilizing proteins. Since the discovery that respiratory capacity is down-regulated in many cancer cell types, mechanisms underlying this metabolic switch continue to be investigated. A number of copper-dependent roles in angiogenesis have been proposed, but the range of functions important for efficient angiogenesis that requires copper is still under scrutiny. Potent copper chelators as TM or 8-OHQ utilized as copper scavengers in the cure for WD have been reported to be of therapeutic value in the treatment of several types of cancers as antiangiogenic and anticancer molecules.

Moreover, mixtures constituted by the combination of copper(II) salts and specific copper chelators have been shown to suppress proliferation and clonogenicity of different types of human cancer cells. And since the seventies, a great variety of copper complexes including classes of therapeutic ligands, such as thiosemicarbazones (TSCs), imidazoles, phosphines, etc., have been proposed as potential anticancer agents.

Angiogenesis is the process that generates new blood vessels from the existing vascular bed. Generally, this phenomenon occurs under strict control in particular phases of the life and in specific actions such as embryonic and postembryonic development, reproductive cycle, and wound repair. Persistent upregulated angiogenesis is a signal of a pathological condition as it happens, among others, in the case of arthritis and atherosclerosis, and, notably, in solid tumor progression and metastasis. Tumors are therefore dependent on angiogenesis for their growth, invasion, and metastasis, an idea first proposed by Folkman in the seventies. In this connection, it has been shown that tumors cannot grow larger than 1 to 2 mm$^3$ without forming new blood vessels.

In 1980, it was also postulated that copper played a significant role in angiogenesis. In particular, researchers found that three copper-binding proteins Cp, heparin, and glycyl-L-hystidyl-L-lysine were essential factors for angiogenesis in the cornea of rabbit's eyes. Moreover, results from cell culture studies showed that copper could stimulate proliferation and migration of human endothelial cells. Specifically copper, but not other transition metals, was found to be a co-factor required for several angiogenic mediators including vascular endothelial growth factor (VEGF), basic fibroblast growth factor (bFGF), interleukin-1 (IL-1) and IL-8, which are essential for tumor angiogenesis processes. Copper also increases the affinity with which angiogenin, a potent angiogenic molecule, binds to high-affinity endothelial receptors. Based on these copper-mediated findings, significant efforts were undertaken aiming at the control of the angiogenesis process by means of the regulation of the copper levels. Obviously, copper chelators utilized in WD were first checked as anti-angiogenic drugs. Trien and D-pen were used to treat mice bearing hepatocellular carcinoma xenografts showing significant inhibition of the tumor growth associated with suppression of tumor angiogenesis. Analogously, TM displayed encouraging anti-angiogenic and antitumor effects in animal models bearing human squamous cell carcinoma xenografts. TM was then selected for clinical trials in humans. In a Phase I study, patients having metastatic cancer were administrated with TM. The copper chelator was found to be nontoxic since when serum Cp level was reduced to 15-20% of baseline and, contemporarily, the hematocrit was maintained higher than 80% of baseline. In a following Phase II clinical trial, 34 patients with cytoreduced malignant pleural mesothelioma underwent treatment with TM (180 mg/day) for 34 days. In all these patients the level of Cp was reduced from 4572 to 1372 mg/dl and VEGF decreased significantly from an average of 2086 to 1250 pg/ml. Studies in the field of medicinal inorganic chemistry have established a link among proteasome inhibition, copper and cancer.

Adams J. Preclinical and clinical evaluation of proteasome inhibitor PS-341 for the treatment of cancer. Curr Opin Chem Biol 2002; 6:493-500.

Adams J. The proteasome: Structure, function, and role in the cell. Cancer Treat Rev 2003; 29:3-9.

Adsule S, Barve V, Chen D, Ahmed F, Dou Q P, Padhye S, Sarkar F H. Novel Schiff base copper complexes of quinoline-2 carboxaldehyde as proteasome inhibitors in human prostate cancer cells. J Med Chem 2006:49:7242-7246.

Adwankar M K, Wycliff C, Samuelson A. In vitro cytotoxic effect of new diphenylphosphinoethane-copper(I) complexes on human ovarian carcinoma cells. Indian J Exp Biol 1997; 35:810-814.

Ahmed F, Adsule S, Ali A S, Banerjee S, Ali S, Kulkarni S, Padhye S, Sarkar F H. A novel copper complex of 3-benzoyl-alpha methyl benzene acetic acid with antitumor activity mediated via cyclooxygenase pathway. Int J Cancer 2007; 120:734-742.

Alemon-Medina R, Brena-Valle M, Munoz-Sanchez J L, Gracia-Mora M I, Ruiz-Azuara L Induction of oxidative damage by copper-based antineoplastic drugs (Casiopeinas). Cancer Chemother Pharmacol 2007; 60:219-228.

Aller S G, Unger V M. Projection structure of the human copper transporter CTR1 at 6-A resolution reveals a compact trimer with a novel channel-like architecture. Proc Natl Acad Sci USA 2006; 103:3627-3632.

Ambike V, Adsule S, Ahmed F, Wang Z, Afrasiabi Z, Sinn E, Sarkar F, Padhye S. Copper conjugates of nimesulide Schiff bases targeting VEGF, COX and Bcl-2 in pancreatic cancer cells. J Inorg Biochem 2007; 101:1517-1524.

An B, Goldfarb R H, Siman R, Dou Q P. Novel dipeptidyl proteasome inhibitors overcome Bcl-2 protective function and selectively accumulate the cyclin-dependent kinase inhibitor p27 and induce apoptosis in transformed, but not normal, human fibroblasts. Cell Death Differ 1998; 5:1062-1075.

Aust S D, Morehouse L A, Thomas C E. Role of metals in oxygen radical reactions. J Free Radic Biol Med 1985; 1:3-25.

Balatri E, Banci L, Bertini I, Cantini F, Ciofi-Baffoni S. Solution Structure of ScoI: A thioredoxin-like protein involved in cytochrome c Oxidase assembly. Structure 2003; 11:1431-1443.

Baldini M, Belicchi-Ferrari M, Bisceglie F, Pelosi G, Pinelli S, Tarasconi P. Cu(II) complexes with heterocyclic substituted thiosemicarbazones: The case of 5-formyluracil. synthesis, characterization, X-ray structures, DNA interaction studies, and biological activity. Inorg Chem 2003; 42:2049-2055.

Bales B C, Kodama T, Weledji Y N, Pitie M, Meunier B, Greenberg M M. Mechanistic studies on DNA damage by minor groove binding copper-phenanthroline conjugates. Nucleic Acids Res 2005; 33:5371-5379.

Barcelo-Oliver M, Garcia-Raso A, Terron A, Molins E, Prieto M J, Moreno V, Martinez J, Llado V, Lopez I, Gutierrez A, Escriba P V. Synthesis and mass spectroscopy kinetics of a novel ternary copper(II) complex with cytotoxic activity against cancer cells. J Inorg Biochem 2007; 101:649-659.

Barnham K J, McKinstry W J, Multhaup G, Galatis D, Morton C J, Curtain C C, Williamson N A, White A R, Hinds M G, Norton R S, Beyreuther K, Masters C L, Parker M W, Cappai R. Structure of the Alzheimer's disease amyloid precursor protein copper binding domain. J Biol Chem 2003; 278:17401-17407.

Barve V, Ahmed F, Adsule S, Banerjee S, Kulkarni S, Katiyar P, Anson C E, Powell A K, Padhye S, Sarkar F H. Synthesis, molecular characterization, and biological activity of novel synthetic derivatives of chromen-4-one in human cancer cells. J Med Chem 2006; 49: 3800-3808.

Bayer T A, Wirths O, Majtenyi K, Hartmann T, Multhaup G, Beyreuther K, Czech C. Key factors in Alzheimer's disease: Beta-amyloid precursor protein processing, metabolism and intraneuronal transport. Brain Pathol 2001; 11:1-11.

Belicchi Ferrari M, Bisceglie F, Leporati E, Pelosi G, Tarasconi P. Synthesis, solution chemistry, X-ray structure and biological activity of novel pyridoxal thiosemicarbazone derivatives. Bull Chem Soc Jpn 2002; 75:781-788.

Belicchi Ferrari M, Bisceglie F, Pelosi G, Sassi M, Tarasconi P, Cornia M, Capacchi S, Albertini R, Pinelli S. Synthesis, characterization and X-ray structures of new antiproliferative and proapoptotic natural aldehyde thiosemicarbazones and their nickel(II) and copper(II) complexes. J Inorg Biochem 2002; 90:113-126.

Belicchi Ferrari M, Bisceglie F, Pelosi G, Tarasconi P, Albertini R, Bonati A, Lunghi P, Pinelli S. Synthesis, characterization, X-ray structure and biological activity of three new 5-formyluracil thiosemicarbazone complexes. J Inorg Biochem 2001; 83:169-179.

Belicchi Ferrari M, Capacchi S, Pelosi G, Reffo G, Tarasconi P, Albertini R, Pinelli S, Lunghi P. Synthesis, structural characterization and biological activity of helicin thiosemicarbazone monohydrate and a copper(II) complex of salicylaldehyde thiosemicarbazone. Inorg Chim Acta 1999; 286:134-141.

Belicchi Ferrari M, Fava G G, Leporati E, Pelosi G, Rossi R, Tarasconi P, Albertini R, Bonati A, Lunghi P, Pinelli S. Synthesis, characterization and biological activity of three copper(II) complexes with a modified nitrogenous base: 5-Formyluracil thiosemicarbazone. J Inorg Biochem 1998; 70:145-154.

Belicchi Ferrari M, Gasparri Fava G, Tarasconi P, Albertini R, Pinelli S, Starcich R. Synthesis, spectroscopic and structural characterization, and biological activity of aquachloro(pyridoxal thiosemicarbazone)copper(II) chloride. J Inorg Biochem 1994; 53:13-25.

Berners-Price S J, Johnson R K, Mirabelli C K, Faucette L F, McCabe F L, Sadler P J. Copper(I) complexes with bidentate tertiary phosphine ligands: Solution chemistry and antitumor activity. Inorg Chem 1987; 26:3383-3387.

Berners-Price S J, Mirabelli C K, Johnson R K, Mattern M R, McCabe F L, Faucette L F, Sung C M, Mong S M, Sadler P J, Crooke S T. In vivo antitumor activity and in vitro cytotoxic properties of bis[1,2-bis(diphenylphosphino)ethane]gold(I) chloride. Cancer Res 1986; 46:5486-5493.

Berners-Price S J, Sadler P J. Phosphines and metal phosphine complexes: Relationship of chemistry to anticancer and other biological activity. Structure & Bonding. Bioinorganic Chemistry. Berlin, Germany: Springer. Vol. 70; 1988. pp 27-102.

Bertini I, Rosato A. Menkes disease. Cell Mol Life Sci 2008; 65:89-91.

Bisceglie F, Baldini M, Belicchi-Ferrari M, Buluggiu E, Careri M, Pelosi G, Pinelli S, Tarasconi P. Metal complexes of retinoid derivatives with antiproliferative activity: Synthesis, characterization and DNA interaction studies. Eur J Med Chem 2007; 42:627-634.

Booth B A, Agrawal K C, Moore E C, Sartorelli A C. Alpha-(N)-heterocyclic carboxaldehyde thiosemicarbazone inhibitors of ribonucleoside diphosphate reductase. Cancer Res 1974; 34:1308-1314.

Brewer G J, Dick R D, Grover D K, LeClaire V, Tseng M, Wicha M, Pienta K, Redman B G, Jahan T, Sondak V K, Strawderman M, LeCarpentier G, Merajver S D. Treatment of metastatic cancer with tetrathiomolybdate, an anticopper, antiangiogenic agent: Phase I study. Clin Cancer Res 2000; 6:1-10.

Brewer G J, Johnson V D, Dick R D, Hedera P, Fink J K, Kluin K J. Treatment of wilson's disease with zinc. XVII: Treatment during pregnancy. Hepatology 2000; 31:364-370.

Brewer G J. Copper control as an antiangiogenic anticancer therapy: Lessons from treating Wilson's disease. Exp Biol Med 2001; 226:665-673.

Brewer G J. Recognition, diagnosis, and management of Wilson's disease. Proc Soc Exp Biol Med 2000; 223:39-46.

Brockman R W, Thomson J R, Bell M J, Skipper H E. Observations on the antileukemic activity of pyridine-2-carboxaldehyde thiosemicarbazone and thiocarbohydrazone. Cancer Res 1956; 16:167-170.

Bull P C, Cox D W. Wilson disease and Menkes disease: New handles on heavy-metal transport. Trends Genet 1994; 10:246-252.

Bull P C, Thomas G R, Rommens J M, Forbes J R, Cox D W. The Wilson disease gene is a putative copper transporting P-type ATPase similar to the Menkes gene. Nat Genet 1993; 5: 327-337.

Bush A I. Metals and neuroscience. Curr Opin Chem Biol 2000; 4:184-191.

Cai X, Pan N, Zou G. Copper-1,10-phenanthroline-induced apoptosis in liver carcinoma Bel-7402 cells associates with copper overload, reactive oxygen species production, glutathione depletion and oxidative DNA damage. Biometals 2007; 20:1-11.

Chaka G, Sonnenberg Jason L, Schlegel H B, Heeg Mary J, Jaeger G, Nelson Timothy J, Ochrymowycz L A, Rorabacher D B. A definitive example of a geometric "entatic state" effect: Electron-transfer kinetics for a copper(II/I) complex involving A quinquedentate macrocyclic trithiaether-bipyridine ligand. J Am Chem Soc 2007; 129: 5217-5227.

Chelly J, Tuemer Z, Toennesen T, Petterson A, Ishikawa-Brush Y, Tommerup N, Horn N, Monaco A P. Isolation of a candidate gene for Menkes disease that encodes a potential heavy metal binding protein. Nat Genet 1993; 3:14-19.

Chen D, Cui Q C, Yang H, Dou Q P. Disulfiram, a clinically used anti-alcoholism drug and copper-binding agent, induces apoptotic cell death in breast cancer cultures and xenografts via inhibition of the proteasome activity. Cancer Res 2006; 66:10425-10433.

Chen D, Dou Q P. New uses for old copper-binding drugs: converting the pro-angiogenic copper to a specific cancer cell death inducer. Expert Opin Ther Targets 2008; 12:739-748.

Chen K, Yuldasheva S, Penner-Hahn J E, O'Halloran T V. An atypical linear Cu(I)-S2 center constitutes the high-affinity metal-sensing site in the CueR metalloregulatory protein. J Am Chem Soc 2003; 125:12088-12089.

Chen R, Liu C-S, Zhang H, Guo Y, Bu X-H, Yang M. Three new Cu(II) and Cd(II) complexes with 3-(2-pyridyl)pyrazole-based ligand: Syntheses, crystal structures, and evaluations for bioactivities. J Inorg Biochem 2007; 101: 412-421.

Chu F, Koomen J M, Kobayashi R, O'Brian C A. Identification of an inactivating cysteine switch in protein kinase Ce, a rational target for the design of protein kinase Ce-inhibitory cancer therapeutics. Cancer Res 2005; 65:10478-10485.

Conry R. Copper: Inorganic & coordination chemistry. In: King R, editor. Encyclopedia of inorganic chemistry. Chichester, United Kingdom: John Wiley & Sons Ltd; 2005.

Cotton F A, Wilkinson G, Murillo C A, Bochmann M. Copper. Group II. Advanced inorganic chemistry. 6th ed. New York: Wiley Interscience; 1999. pp 854-876.

Crane B R, Di Bilio A J, Winkler J R, Gray H B. Electron tunneling in single crystals of *Pseudomonas aeruginosa* azurins. J Am Chem Soc 2001: 123:11623-11631.

Crim J A, Petering H G. The antitumor activity of Cu(II) KTS, the copper (II) chelate of 3-ethoxy-2-oxobutyraldehyde bis(thiosemicarbazone). Cancer Res 1967; 27:1278-1285.

Culotta V C, Yang M, O'Halloran T V. Activation of superoxide dismutases: Putting the metal to the pedal. Biochim Biophys Acta, Mol Cell Res 2006; 1763:747-758.

Cvek B, Milacic V, Taraba J, Dou Q P. Ni(II), Cu(II), and Zn(II) Diethyldithiocarbamate Complexes Show Various Activities Against the Proteasome in Breast Cancer Cells. J Med Chem 2008; 51:6256-6258.

Dallavalle F, Gaccioli F, Franchi-Gazzola R, Lanfranchi M, Marchio L, Pellinghelli M A, Tegoni M. Synthesis, molecular structure, solution equilibrium, and antiproliferative activity of thioxotriazoline and thioxotriazole complexes of copper(II) and palladium(II). J Inorg Biochem 2002; 92:95-104.

Dancis A, Yuan D S, Haile D, Askwith C, Eide D, Moehle C, Kaplan J, Klausner R D. Molecular characterization of a copper transport protein in *S. cerevisiae*: An unexpected role for copper in iron transport. Cell 1994; 76:393-402.

Daniel K G, Gupta P, Harbach R H, Guida W C, Dou Q P. Organic copper complexes as a new class of proteasome inhibitors and apoptosis inducers in human cancer cells. Biochem Pharmacol 2004; 67:1139-1151.

Daniel K G, Harbach R H, Guida W C, Dou Q P. Copper storage diseases: Menkes, Wilson's, and cancer. Front Biosci 2004; 9:2652-2662.

Danks D M, Campbell P E, Stevens B J, Mayne V, Cartwright E. Menkes's kinky hair syndrome. An inherited defect in copper absorption with widespread effects. Pediatrics 1972; 50.188-201.

Das S, Levinson B, Vulpe C, Whitney S, Gitschier J, Packman S. Similar splicing mutations of the Menkes/mottled copper-transporting ATPase gene in occipital horn syndrome and the blotchy mouse. Am J Hum Genet 1995; 56:570-576.

Davis A V, O'Halloran T V. A place for thioether chemistry in cellular copper ion recognition and trafficking. Nat Chem Biol 2008: 4:148-151.

de Bie P, Muller P, Wijmenga C, Klomp L W J. Molecular pathogenesis of Wilson and Menkes diseases: Correlation of mutations with molecular defects and disease phenotypes. J Med Genet 2007; 44:673-688.

de Hoog P, Boldron C, Gamez P, Sliedregt-Bol K, Roland I, Pitie M, Kiss R, Meunier B, Reedijk J. New approach for the preparation of efficient DNA cleaving agents: Ditopic copper-platinum complexes based on 3-clip-phen and cisplatin. J Med Chem 2007; 50:3148-3152.

Deegan C, McCann M, Devereux M, Coyle B, Egan D A. In vitro cancer chemotherapeutic activity of 1,10-phenanthroline (phen), [Ag$_2$(phen)$_3$(mal)] 2H$_2$O, [Cu(phen)$_2$(mal)] 2H$_2$O and [Mn(phen)$_2$(mal)] 2H$_2$O (malH$_2$ 5 malonic acid) using human cancer cells. Cancer Lett 2007; 247:224-233.

Dennison C. Investigating the structure and function of cupredoxins. Coord Chem Rev 2005; 249:3025-3054.

Deraeve C, Boldron C, Maraval A, Mazarguil H, Gomitzka H, Vendier L, Pitie M, Meunier B. Preparation and study of new poly-8-hydroxyquinoline chelators for an anti-Alzheimer strategy. Chem Eur J 2008; 14:682-696.

Deraeve C, Pitie M, Mazarguil H, Meunier B. Bis-8-hydroxyquinoline ligands as potential anti-Alzheimer agents. New J Chem 2007; 31:193-195.

Devereux M, O'Shea D, O'Connor M, Grehan H, Connor G, McCann M, Rosair G, Lyng F, Kellett A, Walsh M, Egan D, Thati B. Synthesis, catalase, superoxide dismutase and antitumour activities of copper(II) carboxylate complexes incorporating benzimidazole, 1,10-phenanthroline and bipyridine ligands: X-ray crystal structures of [Cu(BZA)$_2$(bipy)(H$_2$O)], [Cu(SalH)$_2$(BZDH)$_2$] and [Cu(CH$_3$COO)$_2$(5,6-DMBZDH)$_2$] (SalH$_2$ 5 salicylic acid; BZAH 5 benzoic acid; BZDH 5 benzimidazole and 5,6-DMBZDH 5 5,6-dimethylbenzimidazole). Polyhedron 2007; 26:4073-4084.

Dou Q P, Goldfarb R H. Bortezomib millennium pharmaceuticals. Drugs 2002; 5:828-834.

Dou Q P, Smith David M, Daniel Kenyon G, Kazi A. Interruption of tumor cell cycle progression through proteasome inhibition: Implications for cancer therapy. Prog Cell Cycle Res 2003; 5:441-446.

Dutta S, Padhye S, Ahmed F, Sarkar F. Pyridazolate-bridged dicopper (II) SOD mimics with enhanced antiproliferative activities against estrogen and androgen independent cancer cell lines. Inorg Chim Acta 2005; 358:3617-3624.

Easmon J, Heinisch G, Holzer W, Rosenwirth B. Synthesis and antiviral activity of thiosemicarbazone derivatives of pyridazinecarbaldehydes and alkyl pyridazinyl ketones. Arzneim-Forsch 1989; 39:1196-1201.

Easmon J, Puerstinger G, Heinisch G, Roth T, Fiebig H H, Holzer W, Jaeger W, Jenny M, Hofmann J. Synthesis, cytotoxicity, and antitumor activity of copper(II) and iron(II) complexes of 4N-azabicyclo[3.2.2]nonane thiosemicarbazones derived from acyl diazines. J Med Chem 2001; 44:2164-2171.

Eisses J F, Stasser J P, Ralle M, Kaplan J H, Blackburn N J. Domains I and III of the human copper chaperone for superoxide dismutase interact via a cysteine-bridged dicopper(I) cluster. Biochemistry 2000; 39:7337-7342.

Fenteany G, Standaert R F, Reichard G A, Corey E J, Schreiber S L. A beta-lactone related to lactacystin induces neurite outgrowth in a neuroblastoma cell line and inhibits cell cycle progression in an osteosarcoma cell line. Proc Natl Acad Sci USA 1994; 91:3358-3362.

Feun L, Modiano M, Lee K, Mao J, Marini A, Savaraj N, Plezia P, Almassian B, Colacino E, Fischer J, MacDonald S. Phase I and pharmacokinetic study of 3-aminopyridine-2-carboxaldehyde thiosemicarbazone (3-AP) using a single intravenous dose schedule. Cancer Chemother Pharmacol 2002; 50:223-229.

Filomeni G, Cerchiaro G, Da Costa Ferreira A M, De Martino A, Pedersen J Z, Rotilio G, Ciriolo M R. Pro-apoptotic activity of novel isatin-Schiff base copper(II) complexes depends on oxidative stress induction and organelle-selective damage. J Biol Chem 2007; 282: 12010-12021.

Finney L, Vogt S, Fukai T, Glesne D. Copper and angiogenesis: Unraveling a relationship key to cancer progression. Clin Exp Pharmacol Physiol 2009; 36:88-94.

Finney L A, O'Halloran T V. Transition Metal Speciation in the Cell: Insights from the chemistry of metal ion receptors. Science 2003; 300:931-936.

Folkman J. Tumor angiogenesis: Therapeutic implications. N Engl J Med 1971; 285: 1182-1186.

Fontecave M, Pierre J-L Oxidations by copper metalloenzymes and some biomimetic approaches. Coord Chem Rev 1998; 170:125-140.

Forno L S. Neuropathology of Parkinson's disease. J Neuropathol Exp Neurol 1996; 55: 259-272.

Frausto Da Silva J J R, Williams R J P. The biological chemistry of elements. The inorganic chemistry of life: Oxford: Clarendon Press; 1994.

Furukawa T, Komatsu M, Ikeda R, Tsujikawa K, Akiyama S-i. Copper transport systems are involved in multidrug resistance and drug transport. Curr Med Chem 2008; 15: 3268-3278.

Gaeta A, Hider R C. The crucial role of metal ions in neurodegeneration: The basis for a promising therapeutic strategy. Br J Pharmacol 2005; 146:1041-1059.

Gaggelli E, Bernardi F, Molteni E, Pogni R, Valensin D, Valensin G, Remelli M, Luczkowski M, Kozlowski H. Interaction of the human prion PrP(106-126) sequence with copper(II), manganese(II), and zinc(II): NMR and EPR studies. J Am Chem Soc 2005; 127: 996-1006.

Gaggelli E, Kozlowski H, Valensin D, Valensin G. Copper homeostasis and neurodegenerative disorders (Alzheimer's, prion, and Parkinson's diseases and amyotrophic lateral sclerosis). Chem Rev 2006; 106:1995-2044.

Gamica A, Chan W Y, Rennert O. Copper-histidine treatment of Menkes disease. J Pediatr 1994: 336-338.

Goedert M. Alpha-synuclein and neurodegenerative diseases. Nat Rev Neurosci 2001; 2:492-501.

Goldberg A L. Functions of the proteasome: The lysis at the end of the tunnel. Science 1995; 268:522-523.

Goodyer I D, Jones E E, Monaco A P, Francis M J. Characterization of the Menkes protein copper-binding domains and their role in copper-induced protein re-localization. Hum Mol Genet 1999; 8:1473-1478.

Gray H B, Malmstrom B G, Williams R J P. Copper coordination in blue proteins. J Biol Inorg Chem 2000; 5:551-559.

Greenwood N N, Earnshaw A. Chemistry of the elements. 2nd ed. Oxford: Butterworth-Heinemann; 1998. pp 1173-1200.

Gu Y H, Kodama H, Murata Y, Mochizuki D, Yanagawa Y, Ushijima H, Shiba T, Lee C C. ATP7A gene mutations in 16 patients with Menkes disease and a patient with occipital horn syndrome. Am J Med Genet 2001; 99:217-222.

Gullino P M. Considerations on the mechanism of the angiogenic response. Anticancer Res 1986; 6:153-158.

Gupte A, Mumper R J. Elevated copper and oxidative stress in cancer cells as a target for cancer treatment. Cancer Treat Rev 2009; 35:32-46.

Habib N S, Rida S M, Badawey E A, Fahmy H T, Ghozlan H A. Synthesis and biological investigations of some novel thiazolylbenzimidazoles, and benzimidazolyl-thiazolo[4,5-d]pyrimidines. Pharmazie 1997; 52:346-350.

Halliwell B, Gutteridge J M. Role of free radicals and catalytic metal ions in human disease: An overview. Methods Enzymol 1990; 186:1-85.

Handsley M M, Edwards D R. Metalloproteinases and their inhibitors in tumor angiogenesis. Int J Cancer 2005; 115:849-860.

Hesse L, Beher D, Masters C L, Multhaup G. The beta A4 amyloid precursor protein binding to copper. FEBS Lett 1994; 349:109-116.

Ho Y-P, Au-Yeung S C F, To K K W. Platinum-based anticancer agents: Innovative design strategies and biological perspectives. Med Res Rev 2003; 23:633-655.

Hoke G D, Macia R A, Meunier P C, Bugelski P J, Mirabelli C K, Rush G F, Matthews W D. In vivo and in vitro cardiotoxicity of a gold-containing antineoplastic drug candidate in the rabbit. Toxicol Appl Pharmacol 1989; 100:293-306.

Horn N. Menkes' X-linked disease: Prenatal diagnosis and carrier detection. J Inherit Metab Dis 1983; 6:59-62.

Hu G-F. Copper stimulates proliferation of human endothelial cells under culture. J Cell Biochem 1998; 69:326-335.

Huffman D L, O'Halloran T V. Function, structure, and mechanism of intracellular copper trafficking proteins. Annu Rev Biochem 2001; 70:677-701.

Huster D, Lutsenko S. Wilson disease: not just a copper disorder. Analysis of a Wilson disease model demonstrates the link between copper and lipid metabolism. Mol Biosyst 2007; 3:816-824.

Inoue T, Nishio N, Suzuki S, Kataoka K, Kohzuma T, Kai Y. Crystal structure determinations of oxidized and reduced pseudoazurins from *Achromobacter cycloclastes*. Concerted movement of copper site in redox forms with the rearrangement of hydrogen bond at a remote histidine. J Biol Chem 1999; 274:17845-17852.

Kaim W, Rall J. Copper-A "modern" bioelement. Angew Chem Int Ed Engl 1996; 35:43-60.

Kaler S G, Goldstein D S, Holmes C, Salerno J A, Gahl W A. Plasma and cerebrospinal fluid neurochemical pattern in Menkes disease. Ann Neurol 1993; 33:171-175.

Kaler S G, Holmes C S, Goldstein D S, Tang J, Godwin S C, Donsante A, Liew C J, Sato S, Patronas N. Neonatal diagnosis and treatment of Menkes disease. N Engl J Med 2008; 358.605-614.

Kaler S G. Menkes disease. Adv Pediatr 1994: 41:263-304.

Karr J W, Szalai V A. Cu(II) binding to monomeric, oligomeric, and fibrillar forms of the alzheimer's disease amyloid-beta peptide. Biochemistry 2008; 47:5006-5016.

Katoh R, Takebayashi Y, Takenoshita S. Expression of copper-transporting P-type adenosine triphosphatase (ATP7B) as a chemoresistance marker in human solid carcinomas. Ann Thorac Cardiovasc Surg 2005; 11:143-145.

Kelland L R. Preclinical perspectives on platinum resistance. Drugs 2000; 59:1-8.

Kessler H, Bayer T A, Bach D, Schneider-Axmann T, Supprian T, Herrmann W, Haber M, Multhaup G, Falkai P, Pajonk F-G. Intake of copper has no effect on cognition in patients with mild Alzheimer's disease: A pilot phase 2 clinical trial. J Neural Transm 2008; 115:1181-1187.

Khan G N, Merajver S D. Modulation of angiogenesis for cancer prevention: strategies based on antioxidants and copper deficiency. Curr Pharm Des 2007; 13:3584-3590.

Kitajima N, Moro-oka Y. Copper-dioxygen complexes. Inorganic and Bioinorganic Perspectives. Chem Rev 1994; 94:737-757.

Klewpatinond M, Davies P, Bowen S, Brown D R, Viles J H. Deconvoluting the Cu21 binding modes of full-length prion protein. J Biol Chem 2008; 283:1870-1881.

Klinman J P. Mechanisms whereby mononuclear copper proteins functionalize organic substrates. Chem Rev 1996; 96:2541-2561.

Kodama H, Fujisawa C. Copper metabolism and inherited copper transport disorders: Molecular mechanisms, screening, and treatment. Metallomics 2009; 1:42-52.

Kodama H, Murata Y, Kobayashi M. Clinical manifestations and treatment of Menkes disease and its variants. Pediatr Int 1999; 41:423-429.

Komatsu M, Sumizawa T, Mutoh M, Chen Z-S, Terada K, Furukawa T, Yang X-L, Gao H, Miura N, Sugiyama T, Akiyama S-I. Copper-transporting P-type adenosine triphosphatase (ATP7B) is associated with cisplatin resistance. Cancer Res 2000; 60:1312-1316.

Kutko K V, Kaplienko A I, Nikolova E P, Anders A G. EPR spectrum of copper orotate. Czech J Phys 2004; 54:D591-D594.

La Fontaine S, Mercer J F B. Trafficking of the copper-ATPases, ATP7A and ATP7B: Role in copper homeostasis. Arch Biochem Biophys 2007; 463:149-167.

Langner C, Denk H. Wilson disease. Virchows Arch 2004: 445:111-118.

Lau S-J, Kruck T P A, Sarkar B. Peptide molecule mimicking the copper(II) transport site of human serum albumin. Comparative study between the synthetic site and albumin. J Biol Chem Lazoff S G, Rybak J J, Parker B R, Luzzatti L. Skeletal dysplasia, occipital horns, diarrhea and obstructive uropathy—a new hereditary syndrome. Birth Defects Orig Artic Ser 1975; 11:71-74.

Lee J, Pena M M O, Nose Y, Thiele D J. Biochemical characterization of the human copper transporter CtrI. J Biol Chem 2002; 277:4380-4387.

Linder M C, Wooten L, Cerveza P, Cotton S, Shulze R, Lomeli N. Copper transport. Am J Clin Nutr 1998; 67:965S-971S.

Linder M C. Biochemistry of copper. New York: Plenum Press; 1991.

Lingnau R, Straehle J. 2,4,6-Ph3C6H2M [M 5 copper(I), silver(I)] monomeric complexes with the coordination number of 1. Angew Chem 1988; 100:409-410.

Lodish H, Berk A, Matsudaira P, Kaiser C A, Krieger M, Scott M P, Zipursky S L, Darnell J. Molecular cell biology. 5th ed. New York: W.H. Freeman and CO; 2004. pp 66-72.

Lowndes S A, Adams A, Timms A, Fisher N, Smythe J, Watt S M, Joel S, Donate F, Hayward C, Reich S, Middleton M, Mazar A, Harris A L Phase I study of copper-binding agent ATN-224 in patients with advanced solid tumors. Clin Cancer Res 2008; 14:7526-7534.

Lutsenko S, Barnes N L, Bartee M Y, Dmitriev O Y. Function and regulation of human copper-transporting ATPases. Physiol Rev 2007; 87:1011-1046.

Lutsenko S, LeShane E S, Shinde U. Biochemical basis of regulation of human copper-transporting ATPases. Arch Biochem Biophys 2007; 463:134-148.

Mak C M, Lam C-W. Diagnosis of Wilson's Disease: A comprehensive review. Crit Rev Clin Lab Sci 2008: 45:263-290.

Malmstrom B G. Rack-induced bonding in blue-copper proteins. Eur J Biochem 1994; 223:711-718.

Marques A J, Palanimurugan R, Matias A C, Ramos P C, Dohmen R J. Catalytic mechanism and assembly of the proteasome. Chem Rev 2009; 109:1509-1536.

Maryon E B, Molloy S A, Zimnicka A M, Kaplan J H. Copper entry into human cells: Progress and unanswered questions. Biometals 2007; 20:355-364.

Marzano C, Gandin V, Pellei M, Colavito D, Papini G, Gioia Lobbia G, Del Giudice E, Porchia M, Tisato F, Santini C. In vitro antitumor activity of the water soluble copper(I) complexes bearing the tris(hydroxymethyl)phosphine ligand. J Med Chem 2008; 51:798-808.

Marzano C, Pellei M, Alidori S, Brossa A, Gioia Lobbia G, Tisato F, Santini C. New copper(I) phosphane complexes of dihydrobis(3-nitro-1,2,4-triazolyl)borate ligand showing cytotoxic activity. J Inorg Biochem 2006; 100:299-304.

Marzano C, Pellei M, Colavito D, Alidori S, Gioia Lobbia G, Gandin V, Tisato F, Santini C. Synthesis, characterization, and in vitro antitumor properties of tris(hydroxymethyl) phosphine copper(I) complexes containing the new bis(1,2,4-triazol-1-yl)acetate ligand. J Med Chem 2006: 49:7317-7324.

Marzano C, Pellei M, Tisato F, Santini C. Copper complexes as anticancer agents. Anti-Canc Agents in Med Chem 2009; 9:185-211.

McAuslan B R, Reilly W. Endothelial cell phagokinesis in response to specific metal ions. Exp Cell Res 1980; 130:147-157.

Meijler M M, Zelenko O, Sigman D S. Chemical mechanism of DNA scission by (1,10-phenanthroline)copper. Carbonyl oxygen of 5-methylenefuranone is derived from water. J Am Chem Soc 1997; 119:1135-1136.

Menkes J H, Alter M, Steigleder G K, Weakley D R, Sung J H. A sex-linked recessive disorder with retardation of growth, peculiar hair, and focal cerebral and cerebellar degeneration. Pediatrics 1962: 764-779.

Mercer J F B, Livingston J, Hall B, Paynter J A, Begy C, Chandrasekharappa S, Lockhart P, Grimes A, Bhave M, Siemieniak D, Glover T W. Isolation of a partial candidate gene for Menkes disease by positional cloning. Nat Genet 1993; 3:20-25.

Milacic V, Chen D, Giovagnini L, Diez A, Fregona D, Dou Q P. Pyrrolidine dithiocarbamate-zinc(II) and -copper(II) complexes induce apoptosis in tumor cells by inhibiting the proteasomal activity. Toxicol Appl Pharmacol 2008; 231:24-33.

Milne D B. Copper intake and assessment of copper status. Am J Clin Nutr 1998; 67:1041S-1045S.

Molina-Holgado F, Hider R C, Gaeta A, Williams R, Francis P. Metals ions and neurodegeneration. Biometals 2007; 20:639-654.

Moriguchi M, Nakajima T, Kimura H, Watanabe T, Takashima H, Mitsumoto Y, Katagishi T, Okanoue T, Kagawa K. The copper chelator trientine has an antiangiogenic effect against hepatocellular carcinoma, possibly through inhibition of interleukin-8 production. Int J Cancer 2002; 102:445-452.

Mukherjee R. Copper. In: McCleverty J A, Meyer T J, editors. Comprehensive coordination chemistry II-from biology to nanotechnology. Vol. 6. Oxford (UK): Elsevier Ltd.; 2004. pp 747-910.

Murphy B, Hathaway B. The stereochemistry of the copper (II) ion in the solid-state-some recent perspectives linking the Jahn-Teller effect, vibronic coupling, structure correlation analysis, structural pathways and comparative X-ray crystallography. Coord Chem Rev 2003; 243:237-262.

Murugkar A, Unnikrishnan B, Padhye S, Bhonde R, Teat S, Triantafillou E, Sinn E. Hormone anchored metal complexes. I. Synthesis, structure, spectroscopy and in vitro antitumor activity of testosterone acetate thiosemicarbazone and its metal complexes. Met-Based Drugs 1999; 6:177-182.

Nakagawa T, Inoue Y, Kodama H, Yamazaki H, Kawai K, Suemizu H, Masuda R, Iwazaki M, Yamada S, Ueyama Y, Inoue H, Nakamura M. Expression of copper-transporting P-type adenosine triphosphatase (ATP7B) correlates with cisplatin resistance in human non-small cell lung cancer xenografts. Oncol Rep 2008; 20:265-270.

Nasulewicz A, Mazur A, Opolski A. Role of copper in tumor angiogenesis-clinical implications. J Trace Elem Med Biol 2004; 18:1-8.

Ochiai E. Iron versus copper. II. Principles and applications in bioinorganic chemistry. J Chem Educ 1986; 63:942-944.

Ohtsu H, Shimazaki Y, Odani A, Yamauchi O, Mori W, Itoh S, Fukuzumi S. Synthesis and characterization of imidazolate-bridged dinuclear complexes as active site models of Cu,Zn-SOD. J Am Chem Soc 2000; 122:5733-5741.

Ott I, Gust R. Non platinum metal complexes as anti-cancer drugs. Arch Pharm Chem Life Sci 2007; 340:117-126.

Owatari S, Akune S, Komatsu M, Ikeda R, Firth S D, Che X F, Yamamoto M, Tsujikawa K, Kitazono M, Ishizawa T, Takeuchi T, Aikou T, Mercer J F B, Akiyama S, Furukawa T. Copper-transporting P-type ATPase, ATP7A, confers multidrug resistance and its expression is related to resistance to SN-38 in clinical colon cancer. Cancer Res 2007; 67:4860-4868.

Pass H I, Brewer G J, Dick R, Carbone M, Merajver S. A phase II trial of tetrathiomolybdate after surgery for malignant mesothelioma: final results. Ann Thorac Surg 2008; 86:383-389; discussion 390.

Peters J M, Franke W W, Kleinschmidt J A. Distinct 19 S and 20 S subcomplexes of the 26 S proteasome and their distribution in the nucleus and the cytoplasm. J Biol Chem 1994; 269:7709-7718.

Petrukhin K, Fischer S G, Pirastu M, Tanzi R E, Chernov I, Devoto M, Brzustowicz L M, Cayanis E, Vitale E, Russo J J, Matseoane D, Boukhgalter B, Wasco W, Figus A L, Loudianos J, Cao A, Sternlieb I, Evgrafov O, Parano E, Pavone L, Warburton D, Ott J, Penchaszadeh G K, Scheinberg I H, Gilliam T C. Mapping, cloning and genetic characterization of the region containing the Wilson disease gene. Nat Genet 1993; 5:338-343.

Pierrel F, Cobine P A, Winge D R. Metal ion availability in mitochondria. BioMetals 2007; 20:675-682.

Pitie M, Boldron C, Gornitzka H, Hemmert C, Donnadieu B, Meunier B. DNA cleavage by copper complexes of 2- and 3-Clip-Phen derivatives. Eur J Inorg Chem 2003:528-540.

Pitie M, Burrows C J, Meunier B. Mechanisms of DNA cleavage by copper complexes of 3-clip-phen and of its conjugate with a distamycin analogue. Nucleic Acids Res 2000; 28:4856-4864.

Pitie M, Donnadieu B, Meunier B. Preparation of the new bis(phenanthroline) ligand "Clip-Phen" and evaluation of the nuclease activity of the corresponding copper complex. Inorg Chem 1998; 37:3486-3489.

Pitie M, Meunier B. Preparation of a spermine conjugate of the bis-phenanthroline ligand Clip-Phen and evaluation of the corresponding copper complex. Bioconjugate Chem 1998; 9:604-611.

Pitie M, Sudres B, Meunier B. Dramatic increase of the DNA cleavage activity of Cu(Clip-Phen) by fixing the bridging linker on the C3 position of the phenanthroline units. Chem Commun 1998: 2597-2598.

Popova T V, Aksenova N V. Complexes of copper in unstable oxidation states. Russ J Coord Chem 2003; 29:743-765.

Prohaska J R, Gybina A A. Intracellular copper transport in mammals. J Nutr 2004; 134:1003-1006.

Pufahl R A, Singer C P, Peariso K L, Lin S J, Schmidt P J, Fahrni C J, Cizewski Culotta V, Penner-Hahn J E, O'Halloran T V. Metal ion chaperone function of the soluble Cu(I) receptor Atx1. Science 1997; 278:853-856.

Puig S, Lee J, Lau M, Thiele D J. Biochemical and genetic analyses of yeast and human high affinity copper transporters suggest a conserved mechanism for copper uptake. J Biol Chem 2002; 277:26021-26030.

Quesada A R, Munoz-Chapuli R, Medina M A. Anti-angiogenic drugs: From bench to clinical trials. Med Res Rev 2006; 26:483-530.

Rae T D, Schmidt P J, Pufahl R A, Culotta V C, O'Halloran T V. Undetectable intracellular free copper. The requirement of a copper chaperone for superoxide dismutase. Science 1999; 284:805-808.

Rajendiran V, Karthik R, Palaniandavar M, Stoeckli-Evans H, Periasamy V S, Akbarsha M A, Srinag B S, Krishnamurthy H. Mixed-ligand Copper(II)-phenolate complexes: Effect of coligand on enhanced DNA and protein binding, DNA cleavage, and anticancer activity. Inorg Chem 2007; 46:8208-8221.

Ranford J D, Sadler P J, Tocher D A. Cytotoxicity and antiviral activity of transition-metal salicylato complexes and crystal structure of bis(diisopropylsalicylato)(1,10-phenanthroline)copper(II). J Chem Soc, Dalton Trans 1993:3393-3399.

Raptopoulou C P, Paschalidou S, Pantazaki A A, Terzis A, Perlepes S P, Lialiaris T, Bakalbassis E G, Mrozinski J, Kyriakidis D A. Bis(acetato)bis(1-methyl-4,5-diphenylimidazole)copper(II): Preparation, characterization, crystal structure, DNA strand breakage and cytogenetic effect. J Inorg Biochem 1998; 71:15-27.

Reedy B J, Blackburn N J. Preparation and characterization of half-apo dopamine-beta-hydroxylase by selective removal of CuA. Identification of a sulfur ligand at the dioxygen binding site by EXAFS and FTIR spectroscopy. J Am Chem Soc 1994; 116:1924-1931.

Requena J R, Groth D, Legname G, Stadtman E R, Prusiner S B, Levine R L. Copper-catalyzed oxidation of the recombinant SHa(29-231) prion protein. Proc Natl Acad Sci USA 2001; 98:7170-7175.

Richardson Paul G, Hideshima T, Anderson Kenneth C. Bortezomib (PS-341): A novel, first-in-class proteasome inhibitor for the treatment of multiple myeloma and other cancers. Cancer Control 2003; 10:361-369.

Riordan S M, Williams R. The Wilson's disease gene and phenotypic diversity. J Hepatol 2001; 34:165-171.

Roat-Malone R M. Bioinorganic chemistry. Hoboken, N.J.: Wiley; 2002. pp 187-230.

Roberts E A, Schilsky M L. A practice guideline on Wilson disease. Hepatology 2003; 37:1475-1492.

Roberts E A, Schilsky M L. Diagnosis and treatment of Wilson disease: An update. Hepatology 2008: 47:2089-2111.

Roychaudhuri R, Yang M, Hoshi M M, Teplow D B. Amyloid beta-protein assembly and Alzheimer disease. J Biol Chem 2009; 284:4749-4753.

Ryan C J, Wilding G. Angiogenesis inhibitors: New agents in cancer therapy. Drugs Aging 2000; 17:249-255.

Ryde U, Olsson M H M, Roos B O, Borin A C. A theoretical study of the copper-cysteine bond in blue copper proteins. Theor Chem Acc 2001; 105:452-462.

Saczewski F, Dziemidowicz-Borys E, Bednarski P J, Gruenert R, Gdaniec M, Tabin P. Synthesis, crystal structure and biological activities of copper(II) complexes with chelating bidentate 2-substituted benzimidazole ligands. J Inorg Biochem 2006; 100:1389-1398.

Saha D K, Padhye S, Padhye S. Targeting estrogen receptor sites in human breast cancer cell line T47D with copper conjugates of nonsteroidal antiinflammatory drug derivatives: Antiproliferative activity of ketoprofen derivative and its copper complex. Met-Based Drugs 2001; 8:73-77.

Samimi G, Varki N M, Wilczynski S, Safaei R, Alberts D S, Howell S B. Increase in expression of the copper transporter ATP7A during platinum drug-based treatment is associated with poor survival in ovarian cancer patients. Clin Cancer Res 2003; 9:5853-5859.

Sanghamitra N J, Phatak P, Das S, Samuelson A G, Somasundaram K. Mechanism of cytotoxicity of copper(I) complexes of 1,2-Bis(diphenylphosphino)ethane. J Med Chem 2005;48:977-985.

Sarkar B, Kruck T P A. Copper-amino acid complexes in human serum. Biochemistry of Copper, Proc Symp; Toronto, Canada: Univ. Toronto; 1966. pp 183-196.

Sarkar B. Treatment of Wilson and Menkes diseases. Chem Rev 1999; 99:2535-2544.

Scovill J P, Klayman D L, Franchino C F. 2-Acetylpyridine thiosemicarbazones. 4. Complexes with transition metals as antimalarial and antileukemic agents. J Med Chem 1982; 25:1261-1264.

Sen C K, Khanna S, Venojarvi M, Trikha P, Ellison E C, Hunt T K, Roy S. Copper-induced vascular endothelial growth factor expression and wound healing. Am J Physiol 2002; 282:H1821-H1827.

Shaw C F. Gold-based therapeutic agents. Chem Rev 1999; 99:2589-2600.

Shyamal D K, Ray K. Wilson's disease: an update. Nat Clin Pract Neurol 2006; 2:482-493.

Sigman D S, Graham D R, D'Aurora V, Stern A M. Oxygen-dependent cleavage of DNA by the 1,10-phenanthroline-cuprous complex. Inhibition of *E. coli* DNA polymerase I. J Biol Chem 1979; 254:12269-12272.

Sigman D S, Landgraf R, Perrin D M, Pearson L. Nucleic acid chemistry of the cuprous complexes of 1,10-phenanthroline and derivatives. Met Ions Biol Syst 1996; 33:485-513.

Solomon E I, Baldwin M J, Lowery M D. Electronic structures of active sites in copper proteins: Contributions to reactivity. Chem Rev 1992; 92:521-542.

Solomon E I, Szilagyi R K, DeBeer George S, Basumallick L. Electronic structures of metal sites in proteins and models: Contributions to function in blue copper proteins. Chem Rev 2004; 104:419-458.

Soncin F, Guitton J-D, Cartwright T, Badet J. Interaction of human angiogenin with copper modulates angiogenin binding to endothelial cells. Biochem Biophys Res Commun 1997; 236:604-610.

Spillantini M G, Schmidt M L, Lee V M Y, Trojanowski J Q, Jakes R, Goedert M. alpha-synuclein in Lewy bodies. Nature 1997; 388:839-840.

Syme C D, Viles J H. Solution 1H NMR investigation of Zn21 and Cd21 binding to amyloid-beta peptide (Abeta) of Alzheimer's disease. Biochim Biophys Acta, Proteins Proteomics 2006; 1764:246-256.

Tamura H, Imai H, Kuwahara J, Sugiura Y. A new antitumor complex: bis(acetato)bis(imidazole)copper(II). J Am Chem Soc 1987; 109:6870-6871.

Tanzi R E, Petrukhin K, Chernov I, Pellequer J L, Wasco W, Ross B, Romano D M, Parano E, Pavone L, Brzustowicz L M. The Wilson disease gene is a copper transporting ATPase with homology to the Menkes disease gene. Nat Genet 1993; 5:344-350.

Tapiero H, Townsend D M, Tew K D. Trace elements in human physiology and pathology. Copper. Biomed Pharmacother 2003; 57:386-398.

Tardito S, Bussolati O, Gaccioli F, Gatti R, Guizzardi S, Uggeri J, Marchio L, Lanfranchi M, Franchi-Gazzola R. Non-apoptotic programmed cell death induced by a copper(II) complex in human fibrosarcoma cells. Histochem Cell Biol 2006; 126:473-482.

Tardito S, Bussolati O, Maffini M, Tegoni M, Giannetto M, Dall'Asta V, Franchi-Gazzola R, Lanfranchi M, Pellinghelli M A, Mucchino C, Mori G, Marchio L. Thioamido coordination in a thioxo-1,2,4-triazole copper(II) complex enhances non-apoptotic programmed cell death associated with copper accumulation and oxidative stress in human cancer cells. J Med Chem 2007; 50:1916-1924.

Teknos Theodoros N, Islam M, Arenberg Douglas A, Pan Q Carskadon Shannon L, Abarbanell Aaron M, Marcus B, Paul S, Vandenberg Curtis D, Carron M, Nor Jacques E, Merajver Sofia D. The effect of tetrathiomolybdate on cytokine expression, angiogenesis, and tumor growth in squamous cell carcinoma of the head and neck. Arch Otolaryngol Head Neck Surg 2005; 131:204-211.

Thati B, Noble A, Creaven B S, Walsh M, Kavanagh K, Egan D A. Apoptotic cell death: A possible key event in mediating the in vitro anti-proliferative effect of a novel copper(II) complex, [Cu(4-Mecdoa)(phen)2] (phen 5 phenanthroline, 4-Mecdoa 5 4-methylcoumarin-6, 7-dioxactetate), in human malignant cancer cells. Eur J Pharmacol 2007; 569:16-28.

Thati B, Noble A, Creaven B S, Walsh M, Kavanagh K, Egan D A. An in vitro investigation of the induction of apoptosis and modulation of cell cycle events in human cancer cells by bisphenanthro-line-coumarin-6,7-dioxacetatocopper(II) complex. Chem Biol Interact 2007; 168: 143-158.

Thederahn T B, Kuwabara M D, Larsen T A, Sigman D S. Nuclease activity of 1,10-phenanthro-line-copper: kinetic mechanism. J Am Chem Soc 1989; 11:4941-4946.

Trejo-Solis C, Palencia G, Zuniga S, Rodriguez-Ropon A, Osorio-Rico L, Luvia S T, Gracia-Mora I, Marquez-Rosado L, Sanchez A, Moreno-Garcia M E, Cruz A, Bravo-Gomez M E, Ruiz-Ramirez L, Rodriguez-Enriquez S, Sotelo J. Cas IIgly induces apoptosis in glioma C6 cells in vitro and in vivo through caspase-dependent and caspase-independent mechanisms. Neoplasia 2005; 7:563-574.

Turnlund J R, Keyes W R, Anderson H L, Acord L L. Copper absorption and retention in young men at three levels of dietary copper by use of the stable isotope copper-65. Am J Clin Nutr 1989; 49:870-878.

Turski M L, Thiele D J. New roles for copper metabolism in cell proliferation, signaling, and disease. J Biol Chem 2009; 284:717-721.

Twombly R. First proteasome inhibitor approved for multiple myeloma. J Natl Cancer Inst 2003; 95:845.

Uversky V N, Li J, Fink A L. Metal-triggered structural transformations, aggregation, and fibrillation of human alpha-synuclein. A possible molecular link between Parkinson's disease and heavy metal exposure. J Biol Chem 2001; 276:44284-44296.

Veal J M, Rill R L Noncovalent DNA binding of bis(1,10-phenanthroline)copper(I) and related compounds. Biochemistry 1991; 30:1132-1140.

Vulpe C, Levinson B, Whitney S, Packman S, Gitschier J. Isolation of a candidate gene for Menkes disease and evidence that it encodes a copper-transporting ATPase. Nat Genet 1993; 3:7-13.

Walshe J M. Wilson's disease; new oral therapy. Lancet 1956; 270:25-26.

Wang T, Guo Z J. Copper in medicine: Homeostasis, chelation therapy and antitumor drug design. Curr Med Chem 2006; 13:525-537.

Warburg O. The metabolism of tumors. London: Constable and Company Ltd; 1930.

Weder J E, Dillon C T, Hambley T W, Kennedy B J, Lay P A, Biffin J R, Regtop H L, Davies N M. Copper complexes of non-steroidal anti-inflammatory drugs: An opportunity yet to be realized. Coord Chem Rev 2002; 232:95-126.

West D X, Liberta A E, Padhye S B, Chikate R C, Sonawane P B, Kumbhar A S, Yerande R G. Thiosemicarbazone complexes of copper(II): Structural and biological studies. Coord Chem Rev 1993; 123:49-71.

Williams R J P. Energized (entatic) states of groups and of secondary structures in proteins and metalloproteins. Eur J Biochem 1995; 234:363-381.

Xue Y, Davis A V, Balakrishnan G, Stasser J P, Staehlin B M, Focia P, Spiro T G, Penner-Hahn J E, O'Halloran T V. Cu(I) recognition via cation-pi and methionine interactions in CusF. Nat Chem Biol 2008; 4:107-109.

Yamaguchi Y, Heiny M E, Gitlin J D. Isolation and characterization of a human liver cDNA as a candidate gene for Wilson disease. Biochem Biophys Res Commun 1993; 197:271-277.

Yoshii J, Yoshiji H, Kuriyama S, Ikenaka Y, Noguchi R, Okuda H, Tsujinoue H, Nakatani T, Kishida H, Nakae D, Gomez D E, De Lorenzo M S, Tejera A M, Fukui H. The copper-chelating agent, trientine, suppresses tumor development and angiogenesis in the murine hepatocellular carcinoma cells. Int J Cancer 2001; 94:768-773.

Zambre A P, Kulkarni V M, Padhye S, Sandur S K, Aggarwal B B. Novel curcumin analogs targeting TNF-induced NF-kB activation and proliferation in human leukemic KBM-5 cells. Bioorg Med Chem 2006; 14:7196-7204.

Zhang C X, Lippard S J. New metal complexes as potential therapeutics. Curr Opin Chem Biol 2003; 7:481-489.

Zhang H, Liu C-S, Bu X-H, Yang M. Synthesis, crystal structure, cytotoxic activity and DNA-binding properties of the copper(II) and zinc(II) complexes with 1-[3-(2-pyridyl)pyrazol-1-ylmethyl]naphthalene. J Inorg Biochem 2005; 99:1119-1125.

Zhou H, Zheng C, Zou G, Tao D, Gong J. G I-phase specific apoptosis in liver carcinoma cell line induced by copper-1,10-phenanthroline. Int J Biochem Cell Biol 2002; 34:678-684.

Copper participates in processes that promote cancer growth and metastasis through angiogenesis. Angiogenesis is the process of recruiting new blood vessels to a site, a process strongly correlated with the growth of tumors which are fed by the neovasculature; copper serves to promote both endothelial cell proliferation and migration which are major elements in angiogenesis. See:

Antoniades V, Sioga A, Dietrich E M, Meditskou S, Ekonomou L, Antoniades K., "Is copper chelation an effective anti-angiogenic strategy for cancer treatment?", Med Hypotheses. 2013 December; 81(6):1159-63. doi: 10.1016/j.mehy.2013.09.035. Epub 2013 Oct. 11. PMID: 24210000.

Bicknell, Roy, and Adrian L. Harris. "Novel growth regulatory factors and tumour angiogenesis." European Journal of Cancer and Clinical Oncology 27.6 (1991): 781-785.

Brem "Angiogenesis and Cancer Control: From Concept to Therapeutic Trail," Cancer Control, 6(5):436-458, 1999.

Brem et al., "Anticopper Treatment Inhibits Pseudopodial Protrusion and the Invasive Spread of 9L Gliosarcoma Cells in the Rat Brain," Neurosurgery, 26:391-396, 1990.

Brem et al., "Inhibition of Angiogenesis and Tumor Growth in the Brain. Suppression of Endothelial Cell Turnover by Penicillamine and the Depletion of Copper, an Angiogenic Cofactor," Am. J. Pathol., 137(5):1121-1142, 1990.

Brem et al., "Tetrathiomolybdate, A Chelator of Copper, Reduces Intracerebral Peritumoral Edema in Rats," Proc. Amer. Assoc. Cancer Res., 33:76, Abstract 455, 1992.

Brem, Steven, et al. "Phase 2 trial of copper depletion and penicillamine as antiangiogenesis therapy of glioblastoma." Neuro-oncology 7.3 (2005): 246-253.

Brewer and Merajver, "Treatment of Metastatic Cancer with the Anticopper Antiangiogenic Drug Tetrathiomolybdate," J. Invest. Med., 47(7):223A, 1999.

Brewer et al., "Treatment of Metastatic Cancer with Tetrathiomolybdate, an Anticopper, Antiangiogenic Agent: Phase I Study," Clin. Canc. Res., 6(1):1-10, 2000.

Brewer, G. J. "Tetrathiomolybdate anticopper therapy for Wilson's disease inhibits angiogenesis, fibrosis and inflammation." Journal of cellular and molecular medicine 7.1 (2003): 11-20.

Brewer, George J. "Copper control as an antiangiogenic anticancer therapy: lessons from treating Wilson's disease." Experimental Biology and Medicine 226.7 (2001): 665-673.

Brewer, George J. "Copper lowering therapy with tetrathiomolybdate as an antiangiogenic strategy in cancer." Current cancer drug targets 5.3 (2005): 195-202.

Camphausen K, Sproull M, Tantama S, Sankineni S, Scott T, Ménard C, Coleman C N, Brechbiel M W., "Evaluation of copper chelation agents as anti-angiogenic therapy", Bioorg Med Chem. 2003 Sep. 15; 11 (19):4287-93.

Camphausen K, Sproull M, Tantama S, Venditto V, Sankineni S, Scott T, Brechbiel M W., "Evaluation of chelating agents as anti-angiogenic therapy through copper chelation", Bioorg Med Chem. 2004 Oct. 1; 12(19):5133-40. PMID: 15351396.

Chen, Di, and Q. Ping Dou. "New uses for old copper-binding drugs: converting the pro-angiogenic copper to a specific cancer cell death inducer." Expert opinion on therapeutic targets 12.6 (2008): 739-748.

Chen, Di, et al. "Inhibition of prostate cancer cellular proteasome activity by a pyrrolidine dithiocarbamate-copper complex is associated with suppression of proliferation and induction of apoptosis." Front Biosci 10.2 (2005): 2932-9.

Cox, Claudell, et al. "The role of copper suppression as an antiangiogenic strategy in head and neck squamous cell carcinoma." The Laryngoscope 11.4 (2001): 696-701.

D'amore, P. A., and R. W. Thompson. "Mechanisms of angiogenesis." Annual review of physiology 49.1 (1987): 453-464.

Daniel K G, Harbach R H, Guida W C, Dou Q P., "Copper storage diseases: Menkes, Wilsons, and cancer", Front Biosci. 2004 Sep. 1; 9:2652-62.

Daniel, Kenyon G., et al. "Clioquinol and pyrrolidine dithiocarbamate complex with copper to form proteasome inhibitors and apoptosis inducers in human breast cancer cells." Breast Cancer Research 7.6 (2005): 1.

Engleka and Maciag, "Inactivation of Human Fibroblast Growth Factor-I (FGF-I) Activity by Interaction with Copper Ions Involves FGF-I Dimer Formation Induced by Copper-Catalyzed Oxidation," J. Biol. Chem., 267: 11307-11315, 1994.

Fatfat M, Merhi R A, Rahal O, Stoyanovsky D A, Zaki A, Haidar H, Kagan V E, Gali-Muhtasib H, Machaca K., "Copper chelation selectively kills colon cancer cells through redox cycling and generation of reactive oxygen species", BMC Cancer. 2014 Jul. 21; 14:527. doi: 10.1186/1471-2407-14-527. PMID: 25047035.

Finney L, Vogt S, Fukai T, Glesne D., "Copper and angiogenesis: unravelling a relationship key to cancer progression", Clin Exp Pharmacol Physiol. 2009 January; 36(1): 88-94. doi: 10.1111/j.1440-1681.2008.04969.x. Epub 2008 May 23. Review. PMID: 18505439.

Finney, Lydia, et al. "X-ray fluorescence microscopy reveals large-scale relocalization and extracellular translocation of cellular copper during angiogenesis." Proceedings of the National Academy of Sciences 104.7 (2007): 2247-2252.

Goodman, V. L., G. J. Brewer, and S. D. Merajver. "Copper deficiency as an anti-cancer strategy." Endocrine-related cancer 11.2 (2004): 255-263.

Goodman, Vicki L., George J. Brewer, and Sofia D. Merajver. "Control of copper status for cancer therapy." Current cancer drug targets 5.7 (2005): 543-549.

Gupte A, Mumper R J., "Copper chelation by D-penicillamine generates reactive oxygen species that are cytotoxic to human leukemia and breast cancer cells", Free Radic Biol Med. 2007 Nov. 1: 43(9):1271-8. Epub 2007 Jul. 13, PMID: 17893040.

Harris, Edward D. "A requirement for copper in angiogenesis." Nutrition reviews 62.2 (2004): 60-64.

Hassouneh, Basil, et al. "Tetrathiomolybdate promotes tumor necrosis and prevents distant metastases by suppressing angiogenesis in head and neck cancer." Molecular cancer therapeutics 6.3 (2007): 1039-1045.

Hordyjewska, Anna, Łukasz Popiołek, and Joanna Kocot. "The many "faces" of copper in medicine and treatment." Biometals 27.4 (2014): 611-621.

Juarez, Jose C., et al. "Copper binding by tetrathiomolybdate attenuates angiogenesis and tumor cell proliferation through the inhibition of superoxide dismutase I." Clinical Cancer Research 12.16 (2006): 4974-4982.

Khan G, Merajver S., "Copper chelation in cancer therapy using tetrathiomolybdate: an evolving paradigm", Expert Opin Investig Drugs. 2009 April; 18(4):541-8. doi: 10.1517/13543780902845622. Review. PMID: 19335282.

Krupanidhi, S., Arun Sreekumar, and C. B. Sanjeevi. "Copper & biological health." Indian Journal of Medical Research 128.4 (2008): 448.

Liang Z D, Long Y, Tsai W B, Fu S, Kurzrock R, Gagea-Iurascu M, Zhang F, Chen H H, Hennessy B T, Mills G B, Savaraj N, Kuo M T., "Mechanistic basis for overcoming platinum resistance using copper chelating agents", Mol Cancer Ther. 2012 November; 11(11):2483-94. doi: 10.1158/1535-7163.MCT-12-0580. Epub 2012 Aug. 21. PMID: 22914438.

Lowndes S A, Adams A, Timms A, Fisher N, Smythe J, Watt S M, Joel S, Donate F, Hayward C, Reich S, Middleton M, Mazar A, Harris A L, "Phase I study of copper-binding agent ATN-224 in patients with advanced solid tumors", Clin Cancer Res. 2008 Nov. 15; 14(22):7526-34. doi: 10.1158/1078-0432.CCR-08-0315. PMID: 19010871.

Lowndes S A, Harris A L, "Copper chelation as an antiangiogenic therapy", Oncol Res. 2004; 14(11-12):529-39. Review. PMID: 15666995.

Lowndes S A, Sheldon H V, Cai S, Taylor J M, Harris A L, "Copper chelator ATN-224 inhibits endothelial function by multiple mechanisms", Microvasc Res. 2009 May; 77(3):314-26. doi: 10.1016/j.mvr.2009.01.003. Epub 2009 Jan. 27. PMID: 19323979.

Lowndes, Sarah A., and Adrian L. Harris. "The role of copper in tumour angiogenesis." Journal of mammary gland biology and neoplasia 10.4 (2005): 299-310.

Mandinov et al., Copper Chelation Represses the Vascular Response To Injury" PNAS, 100:6700-6705, 2003.

Marikovsky, Moshe, et al. "Cu/Zn superoxide dismutase plays a role in angiogenesis." International journal of cancer 97.1 (2002): 34-41.

Marzano, Cristina, et al. "Copper complexes as anticancer agents." Anti-Cancer Agents in Medicinal Chemistry (Formerly Current Medicinal Chemistry-Anti-Cancer Agents) 9.2 (2009): 185-211.

Merajver et al., "Copper Depletion as an Anti-Angiogenic Strategy in HER2-neu Transgenic Mice," Proceedings of Special AACR Conference on Angiogenesis and Cancer, Abstract #B-II, Jan. 22-24, 1998.

Merajver, "A Phase I study of Oral Tetrathiomolybdate (TM) as a Decoppering and Anti-Angiogenesis Agent for Metastatic Cancer," www.cancer.med.umich.edu/cgi-bin/protocol?9708_701, 1998.

Merajver, "Phase I Study of Tetrathiomolybdate in Metastatic Cancer," NIH Grant No. 5R03CA77122-02, 1998.

Morier-Teissier et al. "Synthesis and Anti-Tumor Properties of an Anthraquinone Bisubstituted by the Copper Chelating Peptide Gly-Gly-L-His." J. Med. Chem. 36(1993): 2084-2090.

Nagai, M. et al., Abstract #CII: The Oxidative Stress Inducer Elesclomol Requires Copper Chelation for its Anticancer Activity, AACR-NCI-EORTC Molecular Targets and Cancer Therapeutics, Nov. 15, 2009, XP002641815.

Narayanan, Gomathy, et al. "CTR1 silencing inhibits angiogenesis by limiting copper entry into endothelial cells." PloS one 8.9 (2013): e71982.

Nasulewicz, Anna, Andrzej Mazur, and Adam Opolski. "Role of copper in tumour angiogenesis-clinical implications." J. of Trace Elements in Medicine and Bio. 18.1 (2004): 1-8.

Oikawa, Tsutomu, et al. "Inhibition of angiogenesis by bleomycin and its copper complex." Chemical and Pharmaceutical Bulletin 38.6 (1990): 1790-1792.

Omoto A, Kawahito Y, Prudovsky I, Tubouchi Y, Kimura M, Ishino H, Wada M, Yoshida M, Kohno M, Yoshimura R, Yoshikawa T, Sano H., "Copper chelation with tetrathiomolybdate suppresses adjuvant-induced arthritis and inflammation-associated cachexia in rats", Arthritis Res Ther. 2005; 7(6): R1174-82. Epub 2005 Aug. 8. PMID: 16277669.

Pan, Quintin, Li Wei Bao, and Sofia D. Merajver. "Tetrathiomolybdate Inhibits Angiogenesis and Metastasis Through Suppression of the NFκB Signaling CascadeI I NIH grants R01CA77612 (SDM), P30CA46592, and M01-RR00042, Head and Neck SPORE P50CA97248, Susan G. Komen Breast Cancer Foundation, NIH Cancer Biology Postdoctoral Fellowship T32 CA09676 (QP), Department of Defense Breast Cancer Research Program Postdoctoral Fellowship (QP), and Tempting Tables Organization, Muskegon, Mich." Molecular cancer research 1.10 (2003): 701-706.

Rabinovitz, Marco. "Angiogenesis and its inhibition: the copper connection." Journal of the National Cancer Institute 91.19 (1999): 1689-1690.

Schuschke et al., "Short-Term Dietary Copper Deficiency does not Inhibit Angiogenesis in Tumours Implanted in Striated Muscle," Br. J. Cancer, 66:1059-1064, 1992.

Sergeant et al. "Iron and Copper Requirements for Proliferation and Differentiation of a Human Promyelocytic Leukemia Cell Line (HL-60)." J. Cell. Physiol. 163.3 (1995):477-485.

Sigurdsson et al. Copper Chelation Delays the Onset of Prion Disease." J. Biol. Chem. 278.47 (2003):46199-46202.

Sproull M, Brechbiel M, Camphausen K., "Antiangiogenic therapy through copper chelation", Expert Opin Ther Targets. 2003 June; 7(3):405-9. Review. PMID: 12783576

Tashiro-Itoh et al. "Metallothionein Expression and Concentrations of Copper and Zinc are Associated with Tumor Differentiation in Hepatocellular Carcinoma." Liver. 17(1997):300-306.

Tisato F, Marzano C, Porchia M, Pellei M, Santini C., "Copper in diseases and treatments, and copper-based anticancer strategies", Med Res Rev. 2010 July; 30(4): 708-49. doi: 10.1002/med.20174. Review. PMID: 19626597.

Tisato, Francesco, et al. "Copper in diseases and treatments, and copper-based anticancer strategies." Med Res Rev 30.4 (2010): 708-749.

Wadas T J, Wong E H, Weisman G R, Anderson C J. Copper chelation chemistry and its role in copper radiopharmaceuticals. Current pharmaceutical design. 2007; 13:3-16.

Yoo J Y, Pradarelli J, Haseley A, Wojton J, Kaka A, Bratasz A, Alvarez-Breckenridge C A, Yu J G, Powell K, Mazar A P, Teknos T N, Chiocca E A, Glorioso J C, Old M, Kaur B., "Copper chelation enhances antitumor efficacy and systemic delivery of oncolytic HSV", Clin Cancer Res. 2012 Sep. 15; 18(18):4931-41.

Yoshii, Junichi, et al. "The copper-chelating agent, trientine, suppresses tumor development and angiogenesis in the murine hepatocellular carcinoma cells." International journal of cancer 94.6 (2001): 768-773.

Zagzag, David. The Effects of Copper Depletion on Intracerebral Angiogenesis and Growth of Experimental Brain Tumors. 1988.

U.S. Pat. Nos. 4,678,667; 6,703,050; 7,189,865; 7,758, 898; 7,888,389; 8,163,494; 8,168,180; 8,815,823; 8,815, 945; 9,255,271; 5,023,237; 5,039,529; 5,145,838; 5,164, 367; 6,441,009; 6,610,693; 6,703,050; 6,855,340; 6,897, 243; 6,951,890; 6,962,698; 7,169,605; 7,189,865; 7,312, 078; 7,344,881; 7,416,741; 7,429,489; 7,438,931; 7,459, 446; 7,601,525; 7,655,225; 7,758,898; 7,816,403; 7,851, 505; 7,855,075; 7,888,389; 7,893,289; 7,928,094; 8,034, 799; 8,202,724; 8,852,888; 8,987,244; 9,012,180; 9,226, 984; 9,339,479; 9,402,911; 9,409,971; 9,458,222; 20020114789; 20030087830; 20040009237; 20040019087; 20040019102; 20040138103; 20040229796; 20040259945; 20050031595; 20050058720; 20050118150; 20050147694; 20050159364; 20050196423; 20050214262; 20060040980; 20060147512; 20060148891; 20060160805; 20060210647; 20070248689; 20070292533; 20070298030; 20070298122; 20080003301; 20080031817; 20080031975; 20080118519; 20090004158; 20090068705; 20090123565; 20100216775; 20100312139; 20110045589; 20110151022; 20120034674; 20120035110; 20130237511; 20130251630; 20140303109; 20150018525; 20150056657; 20160074373; 20160108160; 20160158392; 20160220500; and 20160287554.

Cancer or neoplastic diseases including solid tumors, lymphomas, leukemias or leukemic bone marrow, is a devastating condition of uncontrolled cell growth, which often has the ability to spread throughout the body (metastases) resulting in death. Tumor-targeted bacteria offer tremendous potential advantages for the treatment of solid tumors, including the targeting from a distant inoculation site and the ability to express therapeutic agents directly within the tumor (Pawelek et al., 1997, Tumor-targeted Salmonella as a novel anticancer agent, Cancer Research 57: 4537-4544; Low et al., 1999, Lipid A mutant Salmonella with suppressed virulence and TNF-alpha induction retain tumor-targeting in vivo, Nature Biotechnol. 17: 37-41).

YS1646 is a highly attenuated *Salmonella enterica* serovar *typhimurium* carrying mutations in the msbB (LPS) and purI (purine biosynthesis pathway) genes that was originally developed as a possible cancer therapeutic (Toso, 2002). Although its development was halted when it failed to provide any benefit in a large phase I trial in subjects with advanced cancers, possibly due to sensitivity to physiologic levels of CO2 (Karsten, 2009), it was safe when administered at doses of up to $1.0 \times 10^9$ intravenously (Chen, 2009). See, Pawelek, Low, and Bermudes, 2003. Salmonella as an Anticancer Agent. Lancet Oncology Reviews, 4: 548-556.

Tumor-targeted bacteria, especially those derived from wild type samples, are typically capable of producing a chronic infection without strong acute response. That is, these bacteria seem to have evolved to avoid triggering a debilitating immune response in the host while at the same time establishing long term colonization of tissues, in the case of tumor targeting bacteria, tissues which may include necrotic regions. According to some evolutionary theories, the attenuated host response to these bacteria may result from a survival benefit for the host in permitting the colonization. Indeed, there are at least anecdotal reports of successful eradication of tumors by bacterial therapy. This implies that bacteria derived from these strains can be pharmaceutically acceptable, for administration through various routes of administration.

The primary shortcoming of tumor-targeted bacteria investigated in the human clinical trials (Salmonella strain VNP20009 and its derivative TAPET-CD; Toso et al., 2002, Phase I study of the intravenous administration of attenuated *Salmonella typhimurium* to patients with metastatic melanoma, J. Clin, Oncol. 20: 142-152; Meir et al., 2001, Phase I trial of a live, attenuated *Salmonella typhimurium* (VNP20009) administered by direct Intra-tumoral (IT) injection, Proc Am Soc Clin Oncol 20: abstr 1043); Nemunaitis et al., 2003, Pilot trial of genetically modified, attenuated Salmonella expressing the *E. coli* cytosine deaminase gene in refractory cancer patients, Cancer Gene Therapy 10: 737-744) was that no significant antitumor activity was observed, even in patients where the bacteria was documented to target the tumor. In addition, an important factor was also that bacterial colonization of tumors, both in the form of the percentage of tumors that were colonized and amount of the bacteria that accumulated within the tumors, was usually lower compared to the preclinical studies using mice. One method of increasing the ability of the bacteria to expand their numbers within tumors is to kill tumor cells by engineering the bacteria to express conventional bacterial toxins (e.g., WO2009/126189, WO2003/014380, WO2005/ 018332, WO2008/073148, US 2003/0059400, U.S. Pat. Nos. 7,452,531, 7,354,592, 6,962,696, 6,923,972, 6,863, 894, 6,685,935, 6,475,482, 6,447,784, 6,190,657 and 6,080, 849).

In recent years, live attenuated Salmonella has been increasingly used to express foreign antigens against infectious diseases and cancers. *Salmonella enterica* is a facultative intracellular pathogen that replicates in a unique membrane-bound host cell compartment, the Salmonella-containing vacuole. Although this location limits exposure of both Salmonella and foreign proteins produced by the bacterium to the immune system, the organism's type III secretion systems (T3SS) can be exploited to translocate heterologous antigens into the host cell cytoplasm. *Salmonella enterica* encodes two distinct T3SS within the Salmonella pathogenicity islands 1 and 2 (SPI-I and SPI-II) that become active at different phases of infection. The SPI-I T3SS translocates effector proteins upon first contact of the bacterium with epithelium cells through to the stage of early cell invasion. In contrast, SPI-II expression is induced when the bacterium has been phagocytosed. Several effector proteins translocated by these T3SSs have been tested in the promotion of heterologous antigen expression in Salmonella-based vaccine development programs but how effector protein-mediated secretion of heterologous antigens affects immune responses is still poorly understood. The T3SS secretion system is discussed in U.S. 2019/0055569, 2010/

0120124, 2012/0021517, 2015/0359909, U.S. Pat. Nos. 9,951,340, and 6,306,387. Some bacterial pathogens comprise a type three secretion system (T3SS), which serves as a needle-like system for delivering bacterial polypeptides (effectors) into host cells. These effector polypeptides typically contribute to the virulence of the bacterial cell. In contrast, commensal microbes have not been described to comprise a T3SS.

A T3SS is a multi-protein structure found in gram negative bacteria. It moves polypeptides from the cytoplasm of the bacterial cell through the interior of the T3SS "needle" into the cytoplasm of a target cell. T3SS's are found in pathogenic strains and have been observed in pathogenic isolates of, e.g., *Shigella, Salmonella, E. coli, Burkholderia, Yersinia, Chlamydia, Pseudomonas, Erwinia, Ralstonia, Rhizobium, Vibrio*, and *Xanthamonas*. Further discussion of T3SS's can be found, e.g. in Izore et al. Structure 2011 19:603-612; Korotkov et al. Nature Rev. Microbio. 2012 10:336-351; Wooldridge, K. (ed) Bacterial Secreted Proteins. Caster Ac. Press 2009; Snyder & Champness (eds.) Mol. Gen. of Bacteria. 3rd Ed. ASM Press: 2007.

The suite of T3SS-related proteins in a given wild-type cell is typically divided into structural proteins (those proteins which form the needle itself), substrate proteins (those proteins which are transported through the needle to the host), and chaperones (those proteins that bind effectors in the cytoplasm to protect, process, and/or shuttle the effectors to the needle). As used herein, a "functional T3SS" refers, minimally, to the set of structural proteins which are required in order to transfer at least one polypeptide to a target cell. A functional T3SS system can comprise one or more chaperone proteins, e.g., two, three, or four, substrates which are not virulence factor (e.g. certain translocators). A functional T3SS may avoid having a virulence factor which is delivered to the target cell.

As used herein, a "virulence factor" refers to those substrates which affect and/or manipulate a target cell in a manner which is beneficial to infection and deleterious to the target cell, i.e. they perturb the normal function of the target cell. Examples of actions of virulence factors include, but are not limited to, modulation of actin polymerization, induction of apoptosis, modulation of the cell cycle, modulation of gene transcription. Not all substrates are necessarily virulence factors. By way of non-limiting example, a T3SS (and a functional T3SS) can comprise proteins referred to as translocators. These substrates are secreted by the T3SS as it nears a complete form and create a pore in the target cell membrane, allowing further substrates to be delivered into the cytoplasm of the target cell, i.e. translocators are substrates in that they travel through the needle to the target cell and are also structural proteins in that they form part of the structure through which other substrates are delivered into the target cell. A single polypeptide can be both a translocator and a virulence factor (e.g. IpaB of Shigella). A functional T3SS system can be introduced into a non-pathogenic bacterial cell.

Homologs of any given polypeptide or nucleic acid sequence can be found using, e.g., BLAST programs (freely available on the world wide web at blast.ncbi.nlm.nih.gov/), e.g. by searching freely available databases of sequence for homologous sequences, or by querying those databases for annotations indicating a homolog (e.g. search strings that comprise a gene name or describe the activity of a gene). The homologous amino acid or DNA sequence can be at least 90%, at least 95%, at least 96%, at least 97%, at least 98%, at least 99%, or more, identical to a reference sequence. The degree of homology (percent identity) between a reference and a second sequence can be determined, for example, by comparing the two sequences using freely available computer programs commonly employed for this purpose on the world wide web.

Examples of T3SS secretion signals and chaperone-binding domains are known in the art, see, e.g. Schmitz et al. Nat Methods 2009 6:500-2; which described the signals and domains of Shigella effectors. Additional examples are known in the art, e.g. Sory et al. PNAS 1995 92:11998-20002. A T3SS signal may reduce the activity of the non-T3SS signal portion of the T3SS-compatible polypeptide once it is delivered to the target cell. The T3SS-compatible polypeptide can comprise a cleavage site after the T3SS signal sequence. The cleavage site may be a site recognized by an endogenous component of the target cell, e.g. a calpain, sumo, and/or furin cleavage site. Instead of a cleavage site, the T3SS-compatible polypeptide can comprise an ubiquitin molecule after the T3SS signal sequence such that the ubiquitin molecule and the sequence N-terminal of it is removed from the remainder of the polypeptide by a eukaryotic target cell. The first amino acid C-terminal of the ubiquitin molecule can be a methionine.

Promoters, i.e., genetic regulatory elements that control the expression of the genes encoding the therapeutic molecules described above that are useful in the present technology, and may include constitutive and inducible promoters. A preferred constitutive promoter is that from the vector pTrc99a (Promega). Preferred inducible promoters include the tetracycline inducible promoter (TET promoter), colicin promoters, sulA promoters and hypoxic-inducible promoters including but not limited to the PepT promoter (Bermudes et al., WO 01/25397), the arabinose inducible promoter (AraBAD) (Lossner et al., 2007, Cell Microbiol. 9: 1529-1537; WO/2006/048344) the salicylate (aspirin) derivatives inducible promoter (Royo et al., 2007, Nature Methods 4: 937-942; WO2005/054477), or a quorum-sensing (autoinduction) promoter Anerson et al., 2006 Environmentally controlled invasion of cancer cells by engineered bacteria, J. Mol. Biol. 355: 619-627.

A single promoter may be used to drive the expression of more than one gene, such as an antigen and a protease inhibitor. The genes may be part of a single synthetic operon (polycistronic), or may be separate, monocistronic constructs, with separate individual promoters of the same type used to drive the expression of their respective genes. The promoters may also be of different types, with different genes expressed by different constitutive or inducible promoters. Use of two separate inducible promoters for more than one antigen or other effector type peptide allows, when sufficient tetracycline, arabinose or salicylic acid is administered following administration of the bacterial vector, their expression to occur simultaneously, sequentially, or alternatingly (i.e., repeated). An inducible promoter is not required, and a constitutive promoter may be employed. Promoters, i.e., genetic regulatory elements that control the expression of the genes encoding the therapeutic molecules described above that are useful and may include constitutive and inducible promoters. A preferred constitutive promoter is that from the vector pTrc99a (Promega). Preferred inducible promoters include the tetracycline inducible promoter (TET promoter), colicin promoters, sulA promoters and hypoxic-inducible promoters including but not limited to the PepT promoter (Bermudes et al., WO 01/25397), the arabinose inducible promoter (AraBAD) (Lossner et al., 2007, Cell Microbiol. 9: 1529-1537; WO/2006/048344) the salicylate (aspirin) derivatives inducible promoter (Royo et al., 2007, Nature Methods 4: 937-942; WO2005/054477), or a quorum-sensing (autoinduction) promoter Anerson et al., 2006 Environmentally controlled invasion of cancer cells by engineered bacteria, J. Mol. Biol. 355: 619-627.

Clairmont C, Lee K C, Pike J, Ittensohn M, Low K B, Pawelek J, Bermudes D, Brecher S M, Margitich D, Tumier J, Li Z, Luo X, King I, Zheng L M. 2000. Biodistribution and genetic stability of the novel antitumor agent VNP20009, a genetically modified strain of *Salmonella typhimurium*. The Journal of infectious diseases 181:1996-2002.

Galen J E, Buskirk A D, Tennant S M, Pasetti M F. 2016. Live Attenuated Human Salmonella Vaccine Candidates: Tracking the Pathogen in Natural Infection and Stimulation of Host Immunity. EcoSal Plus 7.

Gerlach R G, Hensel M. 2007. Salmonella pathogenicity islands in host specificity, host pathogen-interactions and antibiotics resistance of *Salmonella enterica*. Berl Munch Tierarztl Wochenschr 120:317-327.

Haselbeck A H, Panzner U, Im J, Baker S, Meyer C G, Marks F. 2017. Current perspectives on invasive nontyphoidal Salmonella disease. Curr Opin Infect Dis 30:498-503.

Hayashi F, Smith K D, Ozinsky A, Hawn T R, Yi E C, Goodlett D R, Eng J K, Akira S, Underhill D M, Aderem A. 2001. The innate immune response to bacterial flagellin is mediated by Toll-like receptor 5. Nature 410:1099-1103.

Hindle Z, Chatfield S N, Phillimore J, Bentley M, Johnson J, Cosgrove C A, Ghaem Maghami M, Sexton A, Khan M, Brennan F R, Everest P, Wu T, Pickard D, Holden D W, Dougan G, Griffin G E, House D, Santangelo J D, Khan S A, Shea J E, Feldman R G, Lewis D J. 2002. Characterization of *Salmonella enterica* derivatives harboring defined aroC and Salmonella pathogenicity island 2 type III secretion system (ssaV) mutations by immunization of healthy volunteers. Infect Immun 70:3457-3467.

Jepson M A, Clark M A. 2001. The role of M cells in Salmonella infection. Microbes Infect 3:1183-1190.

Karsten V, Murray S R, Pike J, Troy K, Ittensohn M, Kondradzhyan M, Low K B, Bermudes D. 2009. msbB deletion confers acute sensitivity to $CO_2$ in *Salmonella enterica* serovar *typhimurium* that can be suppressed by a loss-of-function mutation in zwf. BMC Microbiol 9:170.

Panthel K, Meinel K M, Sevil Domenech V E E, Trilzsch K, Russmann H. 2008. Salmonella type III-mediated heterologous antigen delivery: a versatile oral vaccination strategy to induce cellular immunity against infectious agents and tumors. International journal of medical microbiology: IJMM 298:99-103.

Prisco A, De Berardinis P. 2012. Memory immune response: a major challenge in vaccination. Biomol Concepts 3:479-486.

Toso J F, Gill V J, Hwu P, Marincola F M, Restifo N P, Schwartzentruber D J, Sherry R M, Topalian S L, Yang J C, Stock F, Freezer L J, Morton K E, Seipp C, Haworth L, Mavroukakis S, White D, MacDonald S, Mao J, Sznol M, Rosenberg S A. 2002. Phase I study of the intravenous administration of attenuated *Salmonella typhimurium* to patients with metastatic melanoma. Journal of clinical oncology: official journal of the American So. of Clin. Oncology 20:142-152.

Xiong G, Husseiny M I, Song L, Erdreich-Epstein A, Shackleford G M, Seeger R C, Jackel D, Hensel M, Metelitsa L S. 2010. Novel cancer vaccine based on genes of Salmonella pathogenicity island 2. Int J Cancer 126: 2622-2634.

Much research has been performed on bacterial therapies and bacterial delivery vectors. For example, tumor targeting bacteria offer tremendous potential advantages for the treatment of solid tumors, including the targeting from a distant inoculation site and the ability to express therapeutic agents directly within the tumor (Pawelek et al., 1997, Tumor-targeted Salmonella as a novel anticancer agent, Cancer Research 57: 4537-4544; Low et al., 1999, Lipid A mutant Salmonella with suppressed virulence and TNF-alpha induction retain tumor-targeting in vivo, Nature Biotechnol. 17: 37-41). However, the primary shortcoming of tumor-targeted bacteria investigated in the human clinical trials (Salmonella strain VNP20009 also known as YS1646, and its derivative TAPET-CD; Toso et al., 2002, Phase I study of the intravenous administration of attenuated *Salmonella typhimurium* to patients with metastatic melanoma, J. Clin, Oncol. 20: 142-152; Meir et al., 2001, Phase I trial of a live, attenuated Salmonella *typhimurium* (VNP20009) administered by direct Intra-tumoral (IT) injection, Proc Am Soc Clin Oncol 20: abstr 1043); Nemunaitis et al., 2003, Pilot trial of genetically modified, attenuated Salmonella expressing the *E. coli* cytosine deaminase gene in refractory cancer patients, Cancer Gene Therapy 10: 737-744) is that no significant antitumor activity has been observed, even in patients where the bacteria was documented to target the tumor. One method of increasing the ability of the bacteria to kill tumor cells is to engineer the bacteria to express conventional bacterial toxins (e.g., WO2009/126189, WO2003/014380, WO2005/018332, WO2008/073148, US 20030059400 U.S. Pat. Nos. 7,452,531, 7,354,592, 6,962, 696, 6,923,972, 6,863,894, 6,685,935, 6,475,482, 6,447,784, 6,190,657, 6,080,849, 8,241,623, 8,524,220 8,771,669, and 8,524,220).

Use of secreted proteins in live bacterial vectors has been demonstrated by several authors. Holland et al. (U.S. Pat. No. 5,143,830) have illustrated the use of fusions with the C-terminal portion of the hemolysin A (hlyA) gene, a member of the type I secretion system. When co-expressed in the presence of the hemolysin protein secretion channel (hlyBD) and a functional TolC, heterologous fusions are readily secreted from the bacteria. The type I secretion system that has been utilized most widely, and although it is currently considered the best system available, is thought to have limitations for delivery by attenuated bacteria (Hahn and Specht, 2003, FEMS Immunology and Medical Microbiology, 37: 87-98). Those limitations include the amount of protein secreted and the ability of the protein fused to it to interfere with secretion. Improvements of the type I secretion system have been demonstrated by Sugamata and Shiba (2005 Applied and Environmental Micobiology 71: 656-662), using a modified hlyB, and by Gupta and Lee (2008 Biotechnology and Bioengineering, 101: 967-974), by addition of rare codons to the hlyA gene. Fusion to the gene ClyA (Galen et al., 2004, Infection and Immunity, 72: 7096-7106 and Type III secretion proteins have also been used. Surface display has been used to export proteins outside of the bacteria. For example, fusion of the Lpp protein amino acids 1-9 with the transmembrane region B3-B7 of OmpA has been used for surface display (Samuelson et al., 2002, Display of proteins on bacteria, J. Biotechnology 96: 129-154). The autotransporter surface display has been described by Berthet et al., WO/2002/070645.

Other heterologous protein secretion systems utilizing the autotransporter family can be modulated to result in either surface display or complete release into the medium (see Henderson et al., 2004, Type V secretion pathway: the autotransporter story, Microbiology and Molecular Biology Reviews 68: 692-744; Jose, 2006 Applied Microbiol. Biotechnol. 69: 607-614; Jose J, Zangen D (2005) Autodisplay of the protease inhibitor aprotinin in *Escherichia coli*. Biochem Biophys Res Commun 333:1218-1226 and Rutherford and Mourez 2006 Microbial Cell Factories 5: 22). For example, Veiga et al. (2003 Journal of Bacteriology 185: 5585-5590 and Klauser et al., 1990 EMBO Journal 9: 1991-1999), demonstrated hybrid proteins containing the b-autotransporter domain of the immunoglobulin A (IgA) protease of *Neisseria gonorrhea*. Fusions to flagellar proteins have been demonstrated. The peptide, usually of 15 to 36 amino acids in length, is inserted into the central, hypervariable region of the FliC gene such as that from *Salmonella muenchen* (Verma et al. 1995 Vaccine 13: 235-24; Wu et al., 1989 Proc. Natl. Acad. Sci. USA 86: 4726-4730; Cuadro et al., 2004 Infect. Immun. 72: 2810-2816; Newton et al., 1995, Res. Microbiol. 146: 203-216). Multihybrid FliC insertions of up to 302 amino acids have also been prepared (Tanskanen et al. 2000, Appl. Env. Microbiol. 66: 4152-4156). Trimerization of antigens and functional proteins can be achieved using the T4 fibritin foldon trimerization sequence (Wei et al. 2008 J. Virology 82: 6200-6208) and VASP tetramerization domains (Kühnel et al., 2004 PNAS 101: 17027-17032). The multimerization domains are used to create, bi-specific, tri-specific, and quadra-specific targeting agents, whereby each individual agent is expressed with a multimerization tag, each of which may have the same or separate targeting peptide, such that following expression, surface display, secretion and/or release, they form multimers with multiple targeting domains. Other secretion systems include C-terminal fusions to the protein YebF (Zhang et al., 2006, Extracellular accumulation of recombinant proteins fused to the carrier protein YebF in *Escherichia coli*, Nat Biotechnol 24: 100-104), which is commercially available as a kit (pAES40; AthenaES, Baltimore, Md.). Fusions to OmsY and other proteins are also capable of secreting proteins into the medium (Zian et al., 2008, Proteome-Based Identification of Fusion Partner for High-Level Extracellular Production of Recombinant Proteins in *Escherichia coli*, Biotechnol Bioengineer 101: 587-601). Other secretions systems include that of Kotzsch et al. 2011 (A secretory system for bacterial production of high-profile protein targets, Protein Science 20: 597-609) using OmpA, OmpF, YebF and OsmY, or those described by Yoon et al., 2010 (Secretory production of recombinant proteins in *Escherichia coli*, Recent Patents on Biotechnology 4: 23-29, See, US 20040005695; 20046673569; 20060270043; 20067094579; 20070287171; 20080064062; 20080076157; 20080166757; 20080166764; 20080182295; 20080193974; 20080206814; 20080206818; 20080254511; 20080280346; 20080280346; 20090011995; U.S. Pat. Nos. 5,470,719; 5,508,192; 5,824,502; 5,989,868; 6,083,715; 6,309,861; 6,329,172; 6,455,279; 6,596,509; 6,596,510; 6,605,697; 6,642,027; 6,828,121; 6,852,512; 6,861,403; 6,919,198; 6,921,659; 7,052,867; 7,056,732; 7,070,989; 7,105,327; 7,112,434; 7,202,059; 7,202,059; 7,202,059; 7,202,059; 7,291,325; 7,410,788; 7,491,528; EP1068339; EP1270730; EP1402036; EP1407052; EP786009; EP866132; WO2006017929; WO2008089132; and WO2009021548.

Salmonella are also encompassed that are, for example, attenuated in virulence by mutations in a variety of metabolic and structural genes. The technology therefore may provide a live composition for treating cancer comprising a live attenuated bacterium that is a serovar of *Salmonella enterica* comprising an attenuating mutation in a genetic locus of the chromosome of said bacterium that attenuates virulence of said bacterium and wherein said attenuating mutation is a combinations of other known attenuating mutations. Other attenuating mutation useful in the Salmonella bacterial strains described herein may be in a genetic locus selected from the group consisting of phoP, phoQ edt, cya, crp, poxA, rpoS, htrA, nuoG, pmi, pabA, pts, damA, met, cys, pur, purA, purB, purI, purF, leu, ilv, arg, lys, zwf, aroA, aroB, aroC, aroD, serC, gua, cadA, rfc, rjb, rfa, ompR, msbB, pfkAB, crr, glk, ptsG, ptsHI, manXYZ and combinations thereof. The strain may also contain a mutation known as "Suwwan", which is an approximately 100 kB deletion between two IS200 elements. The strain may also carry a defective thioredoxin gene (trxA-; which may be used in combination with a TrxA fusion), a defective glutathione oxidoreductase (gor-) and optionally, overexpress a protein disulfide bond isomerase (DsbA). The strain may also be engineered to express invasion and/or escape genes dyA, dyC patI and pld from Rickettsia, whereby the bacteria exhibit enhanced invasion and/or escape from the phagolysosome (Witworth et al., 2005, Infect. Immun. 73:6668-6673), thereby enhancing the activity of the effector genes described below. The strain may also be engineered to be deleted in an avirulence (anti-virulence) gene, such as zirTS, grvA and/or pcgL, or express the *E. coli* lac repressor, which is also an avirulence gene in order to compensate for over-attenuation. The strain may also express SlyA, a known transcriptional activator. The Salmonella strains may be msbB mutants (msbB-). The strains may be msbB- and Suwwan. The strains may be msbB-, Suwwan and zwf-. Zwf has recently been shown to provide resistance to CO2, acidic pH and osmolarity (Karsten et al., 2009, BMC Microbiology August 18; 9:170). Use of the msbB zwf genetic combination is also particularly preferred for use in combination with administered carbogen (an oxygen carbon dioxide mixture that may enhance delivery of therapeutic agents to a tumor). The strains may be msbB-, Suwwan, zwf- and trxA-. The strains may be msbB-, Suwwan, zwf-, trxA- and gor-.

SUMMARY AND OBJECTS OF THE INVENTION

Reduced Copper Availability for Tumor Growth

Copper chelation has been shown to have clinical effects on cancer. See:

Garber, 2015, Targeting copper to treat breast cancer, Science 349: 128-129; Haas 2008; Cancer grows on SODI, SciBX I (18): 1-3).

Fatfat et al., 2014, Copper chelation selectively kills colon cancer cells through redox cycling and generation of reactive oxygen species, BMC Cancer, 21:14:527;

Antoniades et al., 2013, Is copper chelation an effective anti-angiogenic strategy for cancer treatment? Med Hypotheses 81:1159-63;

Liang et al., 2012, Mechanistic basis for overcoming platinum resistance using copper chelating agents, Mol Cancer Ther. 11 (11):2483-94;

Yoo et al., 2012, Copper chelation enhances antitumor efficacy and systemic delivery of oncolytic HSV, Clin Cancer Res. 18(18):4931-41;

Tisato et al., 2010, Copper in diseases and treatments, and copper-based anticancer strategies, Med Res Rev. 30(4): 708-49;

Khan and Merajver 2009, Copper chelation in cancer therapy using tetrathiomolybdate: an evolving paradigm, Expert Opin Investig Drugs, 18(4):541-8;

Lowndes et al., 2009, Copper chelator ATN-224 inhibits endothelial function by multiple mechanisms, Microvasc Res 77(3): 314-26;

Lowndes et al., 2008, Phase I study of copper-binding agent ATN-224 in patients with advanced solid tumors, Clin Cancer Res. 14(22):7526-34;

Finney et al., 2009, Copper and angiogenesis: unravelling a relationship key to cancer progression, Clin Exp Pharmacol Physiol 36(1):88-94;

Gupte and Mumper, 2007, Copper chelation by D-penicillamine generates reactive oxygen species that are cytotoxic to human leukemia and breast cancer cells, Free Radic Biol Med 43(9):1271-8;

Omota et al., 2005, Copper chelation with tetrathiomolybdate suppresses adjuvant-induced arthritis and inflammation-associated cachexia in rats, Arthritis Res Ther 7(6): R1174-82;

Lowndes and Harris 2004, Copper chelation as an antiangiogenic therapy, Oncol Res 14(11-12):529-39;

Daniel et al., 2004, Copper storage diseases: Menkes, Wilsons, and cancer, Front Biosci 9:2652-62; Camphausen et al., 2004, Evaluation of chelating agents as anti-angiogenic therapy through copper chelation, Bioorg Med Chem, 12(19):5133-40;

Camphausen et al., 2003, Evaluation of copper chelation agents as anti-angiogenic therapy, Bioorg Med Chem 11(19):4287-93;

Sproull et al., 2003, Antiangiogenic therapy through copper chelation, Expert Opin Ther Targets, 7(3):405-9; U.S. Pat. No. 9,255,271, Compositions and methods for treating tumors, fibrosis, and pulmonary alveolar proteinosis;

U.S. Pat. Nos. 8,815,945, 8,815,823, 8,168,180, 8,163,494, 7,888,389, 7,758,898, 7,189,865, 6,703,050, and 4,678,667.

Bacterial metabolites such as methanobactin have previously been recognized for their ability to chelate copper, and that they therefore have a therapeutic potential (U.S. Pat. Nos. 7,932,052; 8,735,538, 7,199,099; Lichtmannegger et al., 2016, Methanobactin reverses acute liver failure in a rat model of Wilson disease, J Clin Investigation, 126: 2721-2735). The presence of siderophores in probiotic bacteria such as the Nissle 1917 has also been suggested for their ability to take up iron (U.S. Pat. No. 8,859,256, Method for detecting replication or colonization of a biological therapeutic).

However, it has not been suggested that a live therapeutic bacterium could be engineered to express a heterologous copper-chelating agent that would have a therapeutic effect against tumors. Furthermore, live therapeutic bacteria require attenuating mutations that limit their pathogenesis, whereas bacterial acquisition of metal ions such as copper is considered essential for pathogenesis (e.g., Tesio 2012, Chelating copper to be virulent, ChemViews, Aug. 6, 2012). In addition, means to mitigate the toxicity of copper chelation by a therapeutic bacterium to the bacterium itself have not been suggested. The present technology provides appropriately attenuated bacteria that chelate copper through expression of heterologous copper chelating agents, are resistant to copper, and have therapeutic effects against cancer.

The present technology provides compositions and methods to reduce the availability of copper to cancer cells, endothelial cells, cancer associated and tumor stromal cells. Reduction in copper availability, alone or in combination, results in an overall decrease in copper availability through 1) copper sequestration, including binding, chelating or internalizing copper, 2) locally precipitating copper, and/or 3) oxidizing or reducing copper into a form that cannot be utilized by cancerous cells, cancer associated cells or endothelial cells.

The compositions or genetically engineered bacteria may comprise at least one of 1) bacteria capable of expression, including over-expression of one or more copper binding proteins that reduces availability of copper for cancerous cells, cancer associated cells or endothelial cells, 2) bacteria capable of expression, including over-expression of genes that encode a copper binding siderophore such as yersiniabactin (Koh and Henderson 2015, Microbial copper-binding siderophores at the host-pathogen interface. J. Biol. Chem 290: 18967-18974; Pfeifer et al., 2003, Biosynthesis of yersiniabactin, a complex polyketide-non-ribosomal peptide, using *Escherichia coli* as a heterologous host, Applied and Environmental Microbiology 69: 6698-6702; Miller et al., 2002, Yersiniabactin synthetase: A four-protein assembly line producing the non-ribosomal peptide/polyketide hybrid siderophore of *Yersinia pestis*. Chemistry & Biology 9: 333-344) including but not limited to yersiniabactin homologues from pathogenic *E. coli* UT189, or methanobactins (Kenney and Rosenzweig 2013, Genome mining for methanobactins, BMC Biology 2013, 11:17), including but not limited to methanobactins from, *Methylosinus trichosporium* OB3b; *Photorhabdus* and other species (*P. luminscens* sub. *Laumondii* TT01, *V. caribbenthicus* BAA-2122, *G. oboediens* 174bp2, *Gluconacetobacter* sp. SXCC-I, *Azospirillum* sp. B510, *Methylobacterium* sp. B34, *Azospirillum* sp. B506, *P. fluorescens* NZ17, *P. extremaustrahs* 14-3 sub. 14-3b, *C. basilensis* B-8, *T. mobilis* KA081020-065, *Methylocystis* sp. SC2, *M. rosea* SV97T, *M. parvus* OBBP, ctg3 *Methylosinus* sp. LW3, v2 Bioreactormetagenome PBDCA2, *M. trichosporium* OB3b, *Methylosinus* sp. LW3, v1 *Methylosinus* sp. LW4, *M. parvus* OBBP, ctg41) and those described by Ghazouani et al., 2012 (Variations in methanobactin structure influences copper utilization by methane-oxidizing bacteria, Proc Natl Acad Sci USA 109: 8400-8404; *M. hirsute* CSC1 mb; *M. hirsute* CSC1 mb (SO3); *M. hirsute* CSC1 mb Thr SO3) (Ghazouani et al, 2012) that thereby reduces availability of copper for cancerous cells, cancer associated cells or endothelial cells (Ahmadi et al., 2015, Total biosynthesis and diverse applications of the non-ribosomal peptide-polyketide siderophore yersiniabactin, Applied and Environmental Microbiology 81: 5290-5298). Copper binding and/or storage proteins also include those described by Dennison et al., 2018 (J. Biol. Chem. 293: 4616-4627) and Inesi 2016 (Molecular features of copper binding proteins involved in copper homeostasis, IUBMB Life. doi.org/10.1002/iub.1590, including but not limited to those in the genus *Methylosinus*, including *Methylosinus trichosporium* OB3b *M. hirsute* CSC1 and others and their genes Csp1 (Csp1a), Csp2 (Csp1b), Csp3, and homologues and CXXXC and CXXC motif proteins, or those Cu-ATPases in humans (ATP7A and ATP7B) of humans, and *Escherichia coli* CopZ derived from CopA. The host may be supplemented with salicylate (e.g., aspirin) to initiate production and/or optionally, the irp9 gene from *Yersinia enterocolitica*, *Escherichia coli* or homologue may be co-expressed, and the ybtT auxiliary protein may also be co-expressed.

Bacteria producing cytotoxic proteins with reduced elimination and enhanced tumor selectivity and enhanced tumor penetration.

Therapeutic combinations with and without copper inactivating bacteria are also provided, which include liposomes and nanoparticles, including but not limited to abraxane (paclitaxel albumen stabilized nanoparticle), doxorubicin liposome, irinotechan liposomes, vincristine liposomes, and cytarabine and daunorubicin combination liposomes. Therapeutic combinations with cytotoxic therapeutics are also encompassed, including but not limited to cisplatin, carboplatin, taxol, daunorubicin, cyclophosphamide, irinotechan, gemcitabine, vincristine, vinorelbine, thalidomide, temsirolimus, and others. Therapeutic combinations with antibodies are also encompassed, including but not limited to humira (anti TNF-alpha), bevacizumab, cetuximab, ipilimumab (anti-CLTA4), atezolizumab (anti-PD-L1) and others. Specific kinase inhibitors including but not limited to imatinib and pazopanib and others are included. Novel modifications of the bacteria to express and surface display, secrete and/or release peptides that have the effect of reducing the antibacterial effects of complement (Rooijakkers et al., Therapeutic use of scin, a staphylococcal complement inhibitor in inflammatory diseases, WO2006/103118) or the lectin binding pathway (Van Wamel et al., WO 2005/005630 Therapeutic use of lpi, a staphylococcal lectin pathway inhibitor in inflammatory diseases) are also encompassed. Novel modifications of the bacteria to express and surface display, secrete and/or release peptides that have the effect of enhancing tumor penetration are also encompassed. Tumor and lymphatic vessel targeting includes peptides previously described (Teesalu et al, 2013, Tumor-penetrating peptides, Frontiers in Oncology 2013/Vol. 3/Article 216/1-8; Sugahara et al. 2010, Coadministration of a tumor-penetrating peptide enhances the efficacy of cancer drugs, Science 328: 1031-1035; U.S. Pat. No. 8,367,621 Ruoslahti et al., Methods and compositions related to internalizing RGD peptides; U.S. Pat. No. 8,753,604 Ruoslahti et al., Methods and compositions for synaptically-targeted treatment for cancer; United States Patent Application 20090226372, Ruoslahti et al, Methods And Compositions Related To Peptides And Proteins With C-Terminal Elements; United States Patent Application 20110262347, Ruoslahti et al., Methods And Compositions For Enhanced Delivery Of Compounds) which includes lymphatic vessels and hypoxic portions of tumors targeting peptide, LyP-I CGNKRTRGC (SEQ ID NO: 54), as well as tripartite peptides containing a vascular homing motif (e.g., RGD), a CendR peptide (e.g., R/KXXR/K SEQ ID NO: 55) and a protease recognition site (e.g., K) such as the peptide CRGDKGPDC (SEQ ID NO: 56) (or other variants including but not limited to CR/KGDR/KGPDC. Such peptides first bind through the RGD motif to alpha-v integrins that are over expressed on tumor endothelial cells, followed by proteolytic cleavage leaving the CendR peptide R/KXXR/K (SEQ ID NO: 55). Other preferred peptides include CRGDRGPDC (SEQ ID NO: 30) and CRGDKGPEC (SEQ ID NO: 31). Other examples of this class of peptides include CRGDRGPEC (SEQ ID NO: 32), RGD(R/K/H) (SEQ ID NO: 33), CRGD (R/K/H)GP(D/H)C (SEQ ID NO: 34), CRGD(R/K/H)GP(D/E/H)C (SEQ ID NO: 35), CRGD(R/K/H)G(P/V)(D/E/H)C (SEQ ID NO: 36), CRGDHGPDC (SEQ ID NO: 37), CRGDHGPEC (SEQ ID NO: 38), CRGDHGPHC (SEQ ID NO: 39), CRGDHGVDC (SEQ ID NO: 40), CRGDHGVEC (SEQ ID NO: 41), CRGDHGVHC (SEQ ID NO. 42), CRGDKGPHC (SEQ ID NO: 43), CRGDKGVDC (SEQ ID NO: 44), CRGDKGVEC (SEQ ID NO: 45), CRGDKGVHC (SEQ ID NO: 46), CRGDRGPEC (SEQ ID NO:47), CRGDRGPHC (SEQ ID NO: 48), CRGDRGVDC (SEQ ID NO: 49), CRGDRGVEC (SEQ ID NO: 50), or CRGDRGVHC (SEQ ID NO: 51). Alternatively, peptides that bind other receptors such as aminopeptidase N (e.g., and CRNGRGPDC; SEQ ID NO: 52) may be used. These peptides may be secreted, released or surface displayed by tumor-targeting bacteria, and thereby penetrate tumors more efficiently.

Compositions described in accordance with various embodiments herein include, without limitation, *Salmonella enterica* serovar *typhimurium* ("*S. typhimurium*"), *Salmonella montevideo, Salmonella enterica* serovar *typhi* ("*S. typhi*"), *Salmonella enterica* serovar *paratyphi* A, *paratyphi* B ("*S. paratyphi* 13"), *Salmonella enterica* serovar *paratyphi* C ("*S. paratyphi* C"), *Salmonella enterica* serovar *hadar* ("*S. hadar*"), *Salmonella enterica* serovar *enteriditis* ("*S. enteriditis*"), *Salmonella enterica* serovar *kentucky* ("*S. kentucky*"), *Salmonella enterica* serovar *infantis* ("*S. infantis*"), *Salmonella enterica* serovar *pullorum* ("*S. pullorum*"), *Salmonella enterica* serovar *gallinarum* ("*S. gallinarum*"), *Salmonella enterica* serovar Muenchen ("*S. muenchen*"), *Salmonella enterica* serovar *anatum* ("*S. anatum*"), *Salmonella enterica* serovar *dublin* ("*S. dublin*"), *Salmonella enterica* serovar *derby* ("*S. derby*"), *Salmonella enterica* serovar *choleraesuis* var. *kunzendorf* ("*S. cholerae kunzendorf*"), and *Salmonella enterica* serovar *minnesota* (*S. minnesota*). A preferred serotype for the treatment of bone marrow related diseases is *S. dublin*.

By way of example, live bacteria in accordance with aspects of the technology include known strains of *S. enterica* serovar *typhimurium* (*S. typhimurium*) and *S. enterica* serovar *typhi* (*S. typhi*) which are further modified as provided by various embodiments of the technology. Such strains include Ty21a, CMV906, CMV908, CMV906-htr, CMV908-htr, Ty800, aroA-/serC-, holavax, M01ZH09, VNP20009. These strains contain defined mutations within specific serotypes of bacteria. The technology also includes the use of these same (or different) mutational combinations contained within alternate serotypes or strains in order to avoid immune reactions which may occur in subsequent administrations. For example, *S. typhimurium, S. montevideo*, and *S. typhi* which have non-overlapping O-antigen presentation (e.g., *S. typhimurium* is O-1, 4, 5, 12 and *S. typhi* is Vi, *S. montevideo* is O-6, 7) may be used. Thus, for example, *S. typhimurium* is a suitable serotype for a first administration and another serotype such as *S. typhi* or *S. montevideo* are used for a second administration and third administration. Likewise, the flagellar antigens are also selected for non-overlapping antigenicity between different administrations. The flagellar antigen may be H1 or H2 or no flagellar antigen, which, when combined with the three different O-antigen serotypes, provides three completely different antigenic profiles. See also, U.S. Pat. No. 6,548,287, and EP0973911. See also: US 20140256922; 20120108640; 20110318308; 20090215754; 20090169517; 20070298012; 20070110752; 20070004666; 20060115483; 20060104955; 20060089350; 20060025387; 20050267103; 20050249706; 20050112642; 20050009750; 20040229338; 20040219169; 20040058849; 20030143676; 20030113293; 20030031628; 20030022835; 20020151063; 20140220661; 20140212396; 20140186401; 20140178341; 20140155343; 20140093885; 20130330824; 20130295054; 20130209405; 20130130292; 20120164687; 20120142080; 20120128594; 20120093773; 20120020883; 20110275585; 201111496; 201111481; 20100239546; 20100189691; 20100136048; 20100135973; 20100135961; 20100092438; 20090300779; 20090180955; 20090175829; 20090123426; 20090053186; 20080311681; 20080124355; 20080038296; 20070110721; 20070104689; 20060083716; 20050026866; 20050008618; 20040202663; 20050255088; 20030109026; 20020026655; 20110223241; 20070009489; 20050036987; 20030170276; 20140148582; 20130345114; 20130287810; 20130164380;

20130164307; 20130078275; 20120225454; 20120177682; 20120148601; 20120144509; 20120083587; 20120021517; 20110274719; 20110268661; 20110165680; 20110091493; 20110027349; 20100172976; 20090317404; 20090220540; 20090123382; 20090117049; 20090117048; 20090117047; 20090068226; 20080249013; 20080206284; 20070202591; 20070191262; 20070134264; 20060127408; 20060057152; 20050118193; 20050069491; 20050064526; 20040234455; 20040202648; 20040054142; 20030170211; 20030059400; 20030036644; 20030009015; 20030008839; 20020176848; 20020102242; 20140205538; 20140112951; 20140086950; 20120244621; 20120189572; 20110104196; 20100233195; 20090208534; 20090136542; 20090028890; 20080260769; 20080187520; 20070031382; 20060140975; 20050214318; 20050214317; 20050112140; 20050112139; 20040266003; 20040115174; 20040009936; 20030153527; 20030125278; 20030045492; U.S. Pat. Nos. 8,828,681; 8,822,194; 8,784, 836; 8,771,669; 8,734,779; 8,722,668; 8,715,641; 8,703, 153; 8,685,939; 8,663,634; 8,647,642; 8,642,257; 8,623, 350; 8,604,178; 8,591,862; 8,586,022; 8,568,707; 8,551, 471; 8,524,220; 8,440,207; 8,357,486; 8,343,509; 8,323, 959; 8,282,919; 8,241,623; 8,221,769; 8,198,430; 8,137, 904; 8,066,987; 8,021,662; 8,008,283; 7,998,461; 7,955, 600; 7,939,319; 7,915,218; 7,887,816; 7,842,290; 7,820, 184; 7,803,531; 7,790,177; 7,786,288; 7,763,420; 7,754, 221; 7,740,835; 7,736,898; 7,718,180; 7,700,104; 7,691, 383; 7,687,474; 7,662,398; 7,611,883; 7,611,712; 7,588, 771; 7,588,767; 7,514,089; 7,470,667; 7,452,531; 7,404, 963; 7,393,525; 7,354,592; 7,344,710; 7,247,296; 7,195, 757; 7,125,718; 7,084,105; 7,083,791; 7,015,027; 6,962, 696; 6,923,972; 6,916,918; 6,863,894; 6,770,632; 6,685, 935; 6,682,729; 6,506,550; 6,500,419; 6,475,482; 6,447, 784; 6,207,648; 6,190,657; 6,150,170; 6,080,849; 6,030, 624; and 5,877,159. Novel strains are also encompassed that are, for example, attenuated in virulence by mutations in a variety of metabolic and structural genes. The technology therefore may provide a live composition for treating cancer comprising a live attenuated bacterium that is a serovar of *Salmonella enterica* comprising an attenuating mutation in a genetic locus of the chromosome of said bacterium that attenuates virulence of said bacterium and wherein said attenuating mutation is the Suwwan deletion (Murray et al., 2004. Hot spot for a large deletion in the 18-19 Cs region confers a multiple phenotype in *Salmonella enterica* serovar typhimurium strain ATCC 14028. Journal of Bacteriology 186: 8516-8523 (2004)) or combinations with other known attenuating mutations. Other attenuating mutation useful in the Salmonella bacterial strains described herein may be in a genetic locus selected from the group consisting of phoP, phoQ edt, cya, crp, poxA, rpoS, htrA, nuoG, pmi, pabA, pts, damA, pur, purA, purB, purl, purF, zwf, aroA, aroB, aroC, aroD, serC, gua, cadA, rfc, rjb, rfa, ompR, msbB, leucine and arginine, and combinations thereof.

The technology also encompasses attenuated gram-positive bacteria. For example, *Staphylococcus epidermidis* group B *Streptococcus* including *S. agalaciae*, and *Listeria* species including *L. monocytogenes* and *Erysipelothrix rhusiopathiae* may be employed. It is known to those skilled in the art that variations in molecular biology techniques such as use of gram-positive origins of replication, gram-positive signal sequences and gram-positive promoters and filamentous phage (e.g., phage B5; Chopin et al., 2002 J. Bacteriol. 184: 2030-2033, described further below) may be employed and substituted as needed. Other bacterial strains may also be encompassed, including non-pathogenic bacteria of the gut skin (such as *Staphylococcus epidermidis*; Propionibacteria) and other body locations known as the human microbiome (Grice et al., Topographical and temporal diversity of the human skin microbiome, Science 324: 1190-1192; A framework for human microbiome research; The Human Microbiome Project Consortium, 14 Jun. 2012 Nature 486, 215-221; Spor et al., 2011, Unravelling the effects of the environment and host genotype on the gut microbiome, Nature Reviews Microbiology 9: 279-290) such as *E. coli* strains, Bacteriodies, *Bifidobacterium* and *Bacillus*, attenuated pathogenic strains of *E. coli* including enteropathogenic and uropathogenic isolates, *Enterococcus* sp. and *Serratia* sp. as well as attenuated *Neisseria* sp., *Shigella* sp., *Staphylococcus* sp., *Staphylococcus carnosis*, *Yersinia* sp., *Streptococcus* sp. and *Listeria* sp. including *L. monocytogenes*. Bacteria of low pathogenic potential to humans and other mammals or birds or wild animals, pets and livestock, such as insect pathogenic *Xenorhabdus* sp., *Photorhabdus* sp. and human wound *Photorhabdus* (*Xenorhabdus*) are also encompassed. Probiotic strains of bacteria are also encompassed, including *Lactobacillus* sp. (e.g., *Lactobacillus acidophilus, Lactobacillus salivarius*) *Lactococcus* sp., (e.g., *Lactococcus lacris, Lactococcus casei*) *Leuconostoc* sp., *Pediococcus* sp., *Streptococcus* sp. (e.g., *S. salivariu, S. thermophilus*), *Bacillus* sp., *Bifidobacterium* sp. (including but not limited to *B. angulaum, B. asteroids, B. boum, B. adolescentis B. animalis, B. bifidum, B. breve, B. catenulatum, B. choeinum, B. coryneforme, B. cuniculi, B. dentium, B. gallicum, B. gallinarum, B. indicum, B. infantis, B. lacris, B. lactis* DN-173 101, *B. lactis* DR10, *B. lactis* HN019, *B. longum, B. magnum, B. merycicum, B. minimum, B. pseudocatenulatum, B. pseudolongum, B. psychraerophilum, B. pullorum, B. regulars, B. ruminatium, B. Saeculare, B. scadovii, B. simiae, B. subtlile, B. thermacidophilum, B. termophilum, B. urinalis*), *Bacteroides* sp., and *Escherichia coli* such as the 1917 Nissel strain. It is known to those skilled in the art that minor variations in molecular biology techniques such as use of gram-positive origins of replication, gram-positive signal sequences gram-positive promoters (e.g., *Lactococcus* expression, Mohamadzadeh et al., PNAS Mar. 17, 2009 vol. 106 no. 11 4331-4336) may be used and substituted as needed. The bacteria may be further modified to be internalized into the host cell (Guimaraes et al., 2006, Use of Native Lactococci as Vehicles for Delivery of DNA into Mammalian Epithelial Cells, Appl Environ Microbiol. 2006 November; 72(11): 7091-7097; Innocentin et al., 2009, *Lactococcus lactis* Expressing either *Staphylococcus aureus* Fibronectin-Binding Protein A or *Listeria monocytogenes* Internalin A Can Efficiently Internalize and Deliver DNA in Human Epithelial Cells Appl Environ Microbiol. 2009 July; 75(14): 4870-4878).

The technology also encompasses combinations with known agents, including imatinib, pazopanib, bevacizumab (anti-VEGF antibody), bradykinin, angiotensin II receptor agonists, hyperthermia, carbogen+/−nicotinomide, hyaluronidase or pegylated hyaluronidase which improve tumor permeability and penetration and may result in what is known as "vacular normalization". Other agents that dilate vasculature directly or indirect, such as angiotensin converting enzyme (ACE) inhibitors are also encompassed. Additionally, reticuloendothelial system (RES) blocker such as clodronate (dichloromethylene-bisphosphonate; Compositions and methods comprising genetically enhanced obligate and facultative anaerobic bacteria for oncopathic cancer therapy, WO2009/111177) which have the potential to improve the circulation time of the bacteria, are also employed. Agents that reduced autophagy such as chloroquine (Zhang et al., 2016, Chloroquine enhanced the anticancer capacity of VNP20009 by inhibiting autophagy, Scientific Reports 6:29774) are also encompassed.

The technology also encompasses combinations with protease inhibitors and targeted toxins and chimeric toxins (e.g., Quintero et al., 2016, EGFR-targeted chimeras of Pseudomonas ToxA released into the extracellular milieu by attenuated Salmonella selectively kill tumor cells. Biotechnology and Bioengineering doi: 10.1002/bit.26026) and antitumor enzymes and/or genetically engineered phage and phagemids (Bermudes, U.S. Pat. Nos. 8,524,220, 8,241,623, 8,623,350).

The technology also encompasses combinations with antivascular agents, such as platelet factor 4 and thrombospondin, alone or in combination (Bermudes et al., U.S. Pat. Nos. 6,962,696, 7,452,531).

Resistance of Bacterial Vectors to Copper

Copper is required by all living organisms, but high concentrations are toxic. In another embodiment, the present technology provides compositions and methods to reduce the toxicity of copper to the bacterial vector sequestering copper. Reduction of copper sensitivity facilitates reduction in copper availability by:

1) copper sequestration, including binding, chelating or internalizing copper, 2) locally precipitating copper, and/or 3) chemically oxidizing or reducing copper into a form that cannot be utilized by cancerous cells, cancer associated cells or endothelial cells.

The compositions or genetically engineered bacteria may comprise at least one of 1) bacteria capable of expression, including over-expression of genes that encode copper resistance proteins that reduces their sensitivity to copper, 2) bacteria capable of expression, including over-expression of genes that encode copper sensitivity suppressor proteins that reduces their sensitivity to copper, 3) bacteria capable of expression, including over-expression of genes that encode copper oxidizing proteins that reduces their sensitivity to copper, 4) bacteria capable of expression, including over-expression of genes that encode copper reducing proteins or siderophores that reduces their sensitivity to copper.

The types of cancers or neoplasias to which the present technology is directed include all neoplastic malignancies, including solid tumors such as those of colon, lung, breast, prostate, sarcomas, carcinomas, head and neck tumors, melanoma, as well as hematological, non-solid or diffuse cancers such as leukemia and lymphomas, myelodysplastic cells, plasma cell myeloma, plasmacytomas, and multiple myelomas. Specific types of cancers include acute lymphoblastic leukemia, acute myeloid leukemia, adrenocortical carcinoma adrenocortical carcinoma, adult (primary) liver cancer, adult acute myeloid leukemia, aids-related cancers, aids-related lymphoma, anal cancer, appendix cancer, astrocytomas, basal cell carcinoma, bile duct cancer, bladder cancer, bone cancer, brain stem glioma, brain tumor, breast cancer (female), breast cancer (male), bronchial tumors, burkitt lymphoma, carcinoid tumor, carcinoma of ureter and renal pelvis, central nervous system atypical teratoid/rhabdoid tumor, central nervous system embryonal tumors, central nervous system lymphoma, central nervous system tumors, cervical cancer, childhood acute myeloma, childhood astrocytomas, childhood multiple myeloma/plasma cell neoplasm, childhood teratoid/rhabdoid tumor, chordoma, chronic lymphocytic leukemia, chronic myelogenous leukemia, chronic myeloid leukemia, chronic myeloproliferative disorders, colon cancer, colorectal cancer, craniopharyngioma, cutaneous T-cell lymphoma, embryonal tumors, endometrial cancer, endometrial uterine sarcoma, ependymoblastoma, ependymoma, esophageal cancer, ewing sarcoma family of tumors, extracranial germ cell tumor, extragonadal germ cell tumor, extrahepatic bile duct cancer, extrahepatic bladder cancer, eye cancer, gallbladder cancer, gastric (stomach) cancer, gastrointestinal carcinoma, gastrointestinal carcinoid tumor, gastrointestinal stromal cell tumor, gastrointestinal stromal tumor (gist), germ cell tumor, glioma, hairy cell leukemia, head and neck cancer, hepatocellular (liver) cancer, hodgkin lymphoma, hypopharyngeal cancer, intraocular melanoma, islet cell tumors, kaposi sarcoma, kidney (renal cell) cancer, langerhans cell histiocytosis, laryngeal cancer, leukemia, lip and oropharyngeal cancer, liver cancer, macroglobulinemia, medulloblastoma, medulloepithelioma, melanoma, merkel cell carcinoma, mesothelioma, metastatic squamous neck cancer with occult primary, metastatic stomach (gastric) cancer, multiple endocrine neoplasia syndrome, multiple myeloproliferative disorders, mycosis fungoides and Sézary syndrome, myelodysplastic/myeloproliferative diseases, myelogenous leukemia, nasal cavity and paranasal sinus cancer, nasopharyngeal cancer, nervous system atypical teratoid/rhabdoid tumor, neuroblastoma, non-hodgkin lymphoma, non-small cell lung cancer, osteosarcoma and malignant fibrous histiocytoma of bone, ovarian cancer, ovarian epithelial cancer, ovarian germ cell tumor, ovarian gestational trophoblastic tumor, ovarian low malignant potential tumor, pancreatic cancer, papillomatosis, paranasal sinus and nasal cavity cancer, parathyroid cancer, penile cancer, pharyngeal cancer, pineal parenchymal tumors, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, primary cervical cancer, primary hepatocellular (liver) cancer, primary lung cancer, prostate cancer, rectal cancer, renal cell (kidney) cancer, renal pelvis and ureter cancer, respiratory tract carcinoma involving the nut gene on chromosome 15, retinoblastoma, retinoblastoma, rhabdomyosarcoma, salivary gland cancer, sarcoma, skin cancer (nonmelanoma), small cell lung cancer, small cell lymphoma, small intestine cancer, soft tissue sarcoma, spinal cord tumors, squamous cell carcinoma, squamous neck cancer with occult primary, stomach (gastric) cancer, supratentorial primitive neuroectodermal tumors and pineoblastoma, T-cell lymphoma, testicular cancer, throat cancer, thymoma and thymic carcinoma, thyroid cancer, transitional cell cancer of the renal pelvis and ureter, trophoblastic tumor (gestational) unknown primary site, unknown primary site carcinoma, urethral cancer, uterine cancer, uterine sarcoma, vaginal cancer, vulvar cancer, Waldenström macroglobulinemia, Waldenström malignant fibrous histiocytoma of bone and osteosarcoma, and Wilms tumor.

Issues related to bacterial targeting and efficacy have previously been address by Bermudes (U.S. Pat. No. 8,241,623). Survival under $CO_2$ conditions, high osmolarity and acidic conditions has also been addressed (Bermudes U.S. Pat. No. 8,647,642).

It is one object to generate tumor-targeted bacteria that reduce the availability of copper to tumor cells, tumor associated cells and endothelial cells by sequestration of copper.

Sequestration of copper may be achieved by expression or overexpression of copper siderophores such as methanylobactin from *Methylosinus trichosprium*, yersiniabactin from *Yersinia pestis* or pathogenic *E. coli* such as strain UT189, or other known copper binding siderophores including aerobactin, salmonchelin, ceruloplasmin, (Koh and Henderson 2015, Microbial copper-binding siderophores at the host-pathogen interface. J. Biol. Chem 290. 18967-18974). Siderophores that result in copper toxicity, such as catecholate siderophores, are avoided. See, Balasubramanian, Ramakrishnan, and Amy C. Rosenzweig. "Copper methanobactin: a molecule whose time has come." Current opinion in chemical biology 12.2 (2008): 245-249.

Bandow, Nathan, et al. "Spectral and copper binding properties of methanobactin from the facultative methanotroph *Methylocystis* strain SB2." Journal of inorganic biochemistry 110 (2012): 72-82.

Baral, Bipin S., et al. "Mercury binding by methanobactin from *Methylocystis* strain SB2." Journal of inorganic biochemistry 141 (2014): 161-169.

Behling, Lee A., et al. "NMR, mass spectrometry and chemical evidence reveal a different chemical structure for methanobactin that contains oxazolone rings." Journal of the American Chemical Society 130.38 (2008): 12604-12605.

Choi, Dong W., et al. "Oxidase, superoxide dismutase, and hydrogen peroxide reductase activities of methanobactin from types I and II methanotrophs." Journal of inorganic biochemistry 102.8 (2008): 1571-1580.

Choi, Dong W., et al. "Spectral and thermodynamic properties of Ag (I), Au (III), Cd (II), Co (II), Fe (III), Hg (II), Mn (II), Ni (II), Pb (II), U (IV), and Zn (II) binding by methanobactin from *Methylosinus trichosporium* OB3b." Journal of inorganic biochemistry 100.12 (2006): 2150-2161.

Choi, Dong W., et al. "Spectral and thermodynamic properties of methanobactin from γ-proteobacterial methane oxidizing bacteria: A case for copper competition on a molecular level." Journal of inorganic biochemistry 104.12 (2010): 1240-1247.

Choi, Dong W., et al. "Spectral, kinetic, and thermodynamic properties of Cu (I) and Cu (II) binding by methanobactin from *Methylosinus trichosporium* OB3b." Biochemistry 45.5 (2006): 1442-1453.

El Ghazouani, Abdelnasser, et al. "Variations in methanobactin structure influences copper utilization by methane-oxidizing bacteria." Proceedings of the National Academy of Sciences 109.22 (2012): 8400-8404.

Hakemian, Amanda S., et al. "The Copper Chelator Methanobactin from *Methylosinus trichosporium* OB3b Binds Copper (I)." Journal of the American Chemical Society 127.49 (2005): 17142-17143.

Jahnke, Ann Christin, et al. "Oxazolone copper (I) complexes inspired by the methanobactin active site." Inorganica Chimica Acta 374.1 (2011): 601-605.

Kalidass, Bhagyalakshmi, et al. "Competition between metals for binding to methanobactin enables expression of soluble methane monooxygenase in the presence of copper." Applied and environmental microbiology 81.3 (2015): 1024-1031.

Kenney, Grace E., and Amy C. Rosenzweig. "Chemistry and biology of the copper chelator methanobactin." ACS chemical biology 7.2 (2011): 260-268.

Kenney, Grace E., and Amy C. Rosenzweig. "Chemistry and biology of the copper chelator methanobactin." ACS chemical biology 7.2 (2011): 260-268.

Kim, Hyung J., et al. "Methanobactin, a copper-acquisition compound from methane-oxidizing bacteria." Science 305.5690 (2004): 1612-1615.

Kim, Hyung J., et al. "Purification and physical-chemical properties of methanobactin: a chalkophore from *Methylosinus trichosporium* OB3b." Biochemistry 44.13 (2005): 5140-5148.

Knapp, Charles W., et al. "Methane monooxygenase gene expression mediated by methanobactin in the presence of mineral copper sources." Proceedings of the National Academy of Sciences 104.29 (2007): 12040-12045.

Pesch, M-L., et al. "Competitive ligand exchange between Cu-humic acid complexes and methanobactin." Geobiology 11.1 (2013): 44-54.

Summer, Karl H., et al. "The biogenic methanobactin is an effective chelator for copper in a rat model for Wilson disease." Journal of Trace Elements in Medicine and Biology 25.1 (2011): 36-41.

Vorobev, Alexey, et al. "Detoxification of mercury by methanobactin from *Methylosinus trichosporium* OB3b." Applied and environmental microbiology 79.19 (2013): 5918-5926.

U.S. Pat. Nos. 7,199,099; 7,932,052; 8,629,239; 8,673,980; 8,735,538; 9,017,953; 9,040,267; 9,062,094; 9,085,784; 20040171519; 20120034594; 20120156259; 20120270940; 20130035635; 20130053301; 20130309687; 20130337516; 20140243254; 20140249093; 20140296257; 20140323402; 20150104854; 20150202317; 20150218614; 20150247172; 20150275241; 20150354024; 20160082123; and 20160186168.

Other methanobactin-related chelators and the genes encoding their sequence are also encompassed, such as those described by Kenney and Rosenzweig 2013 (Genome mining for methanobactins, BMC Biology 2013, 11:17) which includes *T. mobilis* KA081020-065, *C. basilensis* B-8, *Azospirillum* sp. B510, *Azospirillum* sp. B506, *P. extremaustralis* 14-3 sub. 14-3b, *P. fluorescens* NZ17, *M. trichosporium* OB3b, *M. parvus* OBBP ctg. 41, *Methylosinus* sp. LW4, *Methylosinus* sp. LW2 v. 1, *M. parvus* OBBP, ctg. 3, *Methylosinus* sp. LW2 v. 2, *Methylocystis* sp. SC2, *M. rosea* SV97T, *P. luminescens* TT01, *V. caribbenthicus* BAA-2122, *Gluconacetobacter* sp. SXCC-I, *G. oboediens* 174bp2. Methanobactins derived from *M. hirsute* CSC1 mb; *M. hirsute* CSC1 mb (SO3); *M. hirsute* CSC1 mb Thr SO3) (Ghazouani et al, 2012, Variations in methanobactin structure influences copper utilization by methane-oxidizing bacteria, Proc Natl Acad Sci USA 109: 8400-8404) are also especially preferred.

Copper binding proteins (Cops) of *Pseudomonas* and *Xanthomonas* are also encompassed. Behlau, Franklin, Blanca I. Canteros, Gerald V. Minsavage, Jeffrey B. Jones, and James H. Graham. "Molecular characterization of copper resistance genes from *Xanthomonas citri* subsp. *citri* and *Xanthomonas alfalfae* subsp. *citrumelonis*." Appl. Environ. Microbiol. 77, no. 12 (2011): 4089-4096).

See, U.S. Pat. Nos. 5,523,215; 5,681,746; 5,736,119; 5,854,023; 5,866,362; 5,922,302; 6,124,271; 6,193,891; 6,372,262; 6,576,672; 6,783,775; 6,800,437; 6,838,437; 7,041,449; 7,045,312; 7,060,458; 7,109,033; 7,199,099; 7,312,078; 7,320,988; 7,344,881; 7,429,489; 7,459,534; 7,557,081; 7,615,624; 7,618,634; 7,652,037; 7,655,225; 7,692,065; 7,754,765; 7,847,156; 7,855,075; 7,855,274; 7,897,836; 8,039,690; 8,080,417; 8,097,771; 8,173,369; 8,183,344; 8,202,724; 8,314,153; 8,318,171; 8,426,576; 8,436,162; 8,440,827; 8,558,056; 8,653,144; 8,772,461; 8,815,533; 8,846,393; 8,895,610; 8,969,420; 9,040,774; 9,175,266; 9,284,535; 9,365,593; 9,399,612; 20020023281; 20020040489; 20020054916; 20020098519; 20020132306; 20020160378; 20030032030; 20030055113; 20030115639;

20030130797; 20030135888; 20030148953; 20030232799; 20030233670; 20030233681; 20040009476; 20040013680; 20040049350; 20040078852; 20040092442; 20040171519; 20050037341; 20050171150; 20060014683; 20060021088; 20060068438; 20060134708; 20060183137; 20060293238; 20060293505; 20070207191; 20070265199; 20070280927; 20070299002; 20080031817; 20080057093; 20080069874; 20080120750; 20080200502; 20080256665; 20090271163; 20090297538; 20090311680; 20090317487; 20100017918; 20100024074; 20100063161; 20100064393; 20100125042; 20100129790; 20100255118; 20100287671; 20110027337; 20110162107; 20110184333; 20110213126; 20110296555; 20110306035; 20110319282; 20120041066; 20120110696; 20120122969; 20120151635; 20120190623; 20120258168; 20120284878; 20120284881; 20130023491; 20130053450; 20130072434; 20130116182; 20130123181; 20130202596; 20130203101; 20130210650; 20130210793; 20130216513; 20130224281; 20130232647; 20140023701; 20140090106; 20140140959; 20140206772; 20140343255; 20140363874; 20150045535; 20150067923; 20150147346; 20150184142; 20150239818; 20150247154; 20150259389; 20160074373; 20160115499; and 20160201103.

Sequestration of copper may be achieved by expression or overexpression of copper binding proteins such as those from *Vibrio alginolyticus*, or the plastocyanin family of copper-binding proteins, which include plastocyanins, amicyanin, auracyanins A and B, blue copper protein from *Alcaligenes* cupredoxin, halocyanin, rusticyaninstellacyanin, and umecyanin.

Short copper binding peptides are also encompassed, including those described by Khoury et al., 2014 (Formation constants of copper (II) complexes with tripeptides containing glu, gly and his: Potentiometric measurements and modeling by generalized multiplicative analysis of variance, Inorg Chem 53: 1278-1287) which include 27 tripeptides (EEE, EEG, EEH, EGE, EGG, EGH, EHE, EHG, EHH, GEE, GEG, GEH, GGE, GGG, GGH, GHE, GHG, GHH, HEE, HEG, HEH, HGE, HGG, HGH, HHE, HHG, HHH). In addition to the tripeptide GGH, GHK is also especially preferred. Dimer, trimer and multimers of these peptides are also encompassed, and may be operably linked to a secretion signal or surface display protein.

The present technology may also encompass resistance of the bacteria to copper. Resistance to copper may be achieved by expression or overexpression of known copper resistance genes (see Orell et al., 2010, Life in blue: Copper resistance mechanisms of bacteria and Archeae used in industrial biomining of minerals, Biotechnology Advances 28: 839-848), such as CueO which oxidizes Cu(I) to Cu(II) and Cop proteins that participate in copper efflux. Resistance to copper may also be simultaneously achieved by expression of a copper siderophore. Optionally, the bacteria may be resistant to copper by deficiency in copper siderophore import, through mutation or deletion of a siderophore import protein, such as the yersiniabactin import gene fyuA or its homologues. The inorganic polyphosphate (polyP)-copper resistance mechanism may be employed using the genes identified by Vera et al., 2003 (Proteomic and genomic analysis of the phosphate starvation response of *Acidithiobacillus ferrooxidans*. Hydrometallurgy 71: 125-132). Resistance to copper may also be achieved by expression of copper resistance proteins and copper sensitivity suppressors from *Vibrio alginolyticus*.

A preferred bacterial strain comprises a bacterium of genus Salmonella, e.g., VNP 20009/YS1646 or a CO2 and acid resistant derivative.

Administration of the genetically engineered bacterium to the human or animal may result in at least one of: decreased serum copper; decreased copper availability within the cancerous tissue; or reduction in the metastatic spread of the disease.

A still further object provides a method for treating a neoplastic disease in a living human or animal, comprising: administering a pharmaceutically acceptable formulation containing a genetically engineered bacterium to the living human or animal having the neoplastic disease, the genetically engineered bacterium having the ability to reduce the amount of available copper, and may optionally be genetically engineered or selected to be resistant to copper while retaining antibiotic sensitivity, permitting the genetically engineered bacterium to grow within the tumor causing antitumor effects and then be cleared from the living human or animal, which are non-lethal to the living human or animal.

The live genetically engineered bacterium may have a selective tropism for at least one type of tumor in a human or animal, and the functional gene product is effective for treating the at least one type of tumor, the live genetically engineered bacterium being provided within a pharmaceutically acceptable formulation for administration to the human or animal.

When administering self-replicating organisms, the minimum dose approximates a single in vivo replication competent organism or minimum infectious dose, which itself is approximated by an in vitro determined colony forming unit (CFU). Suitable dosage ranges are generally from about 1.0 cfu/kg to about $1 \times 10$ cfu/kg; optionally from about 1.0 cfu/kg to about $1 \times 10^8$ cfu/kg; optionally from about $1 \times 10^2$ cfu/kg to about $1 \times 10^8$ cfu/kg; optionally from about $1 \times 10^4$ cfu/kg to about $1 \times 10^8$ cfu/kg; and optionally from about $1 \times 10^4$ cfu/kg to about $1 \times 10^{10}$ cfu/kg. Effective doses may be extrapolated from dose-response curves derived from in vitro or animal model test systems. However, higher doses are preferred, in order to permit prompt initiation of therapeutic effect and avoid host immune response suppression of the organisms before they reach full therapeutic potential. In some cases, replication incompetent organisms may be used, e.g., where the organisms remain competent to produce biologically active products as discussed herein while not being able to replicate, in which case a dose may be, for example, in the range $10^8$ to $10^{10}$ organisms and determined by non-culture-based methods (e.g., hemocytometer). The maximum dose of preferred organisms which display low toxicity and pathogenicity is in excess of $10^{10}$, and for orally or dermally administered probiotic species, gram scale doses may be administered.

The bacterial delivery vector may be attenuated, non-pathogenic, low pathogenic (including wild type), or a probiotic bacterium. The bacteria are introduced either systemically (e.g., parenteral, intravenous (IV), intramuscular (IM), intralymphatic (IL), intradermal (ID), subcutaneously (sub-q), local-regionally (e.g., intralesionally, intratumorally (IT), intraperitoneally (IP), topically, intrathecally (intrathecal), by inhaler or nasal spray) or to the mucosal system through oral, nasal, pulmonary intravessically, enema or suppository administration. The terms "oral", "enteral", "enterally", "orally", "non-parenteral", "non-parenterally", and the like, refer to administration of a compound or composition to an individual by a route or mode along the alimentary canal. Examples of "oral" routes of administration include, without limitation, swallowing liquid or solid forms by the mouth, administration of a composition through a nasojejunal or gastrostomy tube, intraduodenal administration of a composition, and rectal administration, e.g., using suppositories that release a live bacterial strain described herein to the lower intestinal tract of the alimentary canal. Upon administration, the bacteria are able to undergo limited or unlimited replication, express, surface display, secrete and/or release the effector molecules and/or protease inhibitors with anti-cancer thereby providing a therapeutic benefit by reducing or eliminating the malignancy and/or neoplasia.

Toxins, therapeutic cytokines and other molecules, homologues or fragments thereof useful in conjunction with the present technology include small lytic peptides, larger lytic peptides, pore-forming toxins, protein inhibitors, extracellular DNAases (DNase), intracellular DNAases, apoptosis inducing peptides, cytokines, prodrug converting enzymes, metabolite destroying enzymes, ribonucleases, antibody inactivating toxins and other anticancer peptides. In a preferred embodiment, the toxins include those that are naturally secreted, released and/or surface displayed, or heterologously secreted, released and/or surface displayed, and that can be modified uniquely to suit the delivery by a bacterium and may be further engineered to have the tumor, lymphoma, leukemic bone marrow or proximity-selective targeting system described herein, including but not limited to the proteins azurin, truncated azurins (e.g., p18 azurin amino acids 50-67 and P28 azurin amino acids 50-77 Chakrabarty et al., 2014 Bacterial proteins and peptides in cancer therapy: today and tomorrow, Bioengineered 5:234-242); Pep27anal2: Lee et al., 2005, Functional and structural characteristics of anticancer peptide Pep27 analogues, Cancer Cell International 2005 5:21) entap from *Enterococcus* (Karpinski and Szkaradkiewicz 2013 Anticancer peptides from bacteria, Bangladesh J Pharmacol 8:343-348), carboxylesterase Est55 (a prodrug converting enzyme from *Geobacillus* that activates CPT-11 to SN-38), thiaminase (e.g., from *Bacillus*), methionase (methioninase), asparaginase, tryptophanase, apoptin, Torquetnovirus (TTV) derived apoptosis-inducing protein TAIP and with gyrovirus VP3 bax, bim, p53, BAK, BH3 peptide (BCL2 homology domain 3), cytochrome C, thrombospondin, platelet factor 4 (PF4) peptide, *Bacillus* sp. cytolysins, *Bacillus* sp. nheABC toxins, cytolethal distending toxins (cldt) including those cldts from *Haemophilus, Aggregaribacter, Salmonella, Escherichia, Shigella, Campylobacter, Helicobacter, Hahella* and *Yersinia*, typhoid toxins (pertussis like toxin) (pltAB), pertussis toxin, cldt:plt hybrids, actAB, cytotoxic necrotic factor (cnf), dermonecrotic factor (dnf), shiga toxins and shiga-like toxins, bacteriocins, (colicins and microcins; Hen and Jack, Chapter 13 Microcins, in Kastin (ed), 2006, Handbook of Biologically Active Peptides, Academic Press; Nes et al., Chapter 17, The nonlantibiotic heat-stable bacteriocins in gram-positive bacteria, in Kastin (ed), 2006, Handbook of Biologically Active Peptides, Academic Press; Sharma et al., Chapter 18 in Kastin (ed), 2006, Handbook of Biologically Active Peptides, Academic Press) including membrane depolarizing (or pore-forming), DNAases (including colicin DNase, Staphylococcal Nuclease A:OmpA fusions (Takahara et al., 1985 J. Biol. Chem 260: 2670-2674), *Serratia marcescens* DNase (Clegg and Allen, 1985, FEMS Microbiology Letters 27: 257-262; *Vibrio* DNase Newland et al., 1985 Infect Immun 47: 691-696) or other bacterial DNase), RNAases, and tRNAases, including but not limited colicin A, colicin D, colicin E5, colicin E492, microcin M24, colE1, colE2, colE3, colE5 colE7, coleE8, colE9, col-1a, colicin N and colicin B, membrane lytic peptides from *Staphylococcus* (listed below) and sea anemones, P15 peptide and other TGF-beta mimics, repeat in toxin (RTX) family members (together with the necessary acylation and secretion genes) including *Actinobacillus* leucotoxins, a leuckotoxin: *E. coli* HlyA hybrid, *E. coli* HlyA hemolysin, *Bordetella* adenylate cyclase toxin, heat stable enterotoxins from *E. coli* and *Vibrio* sp. (Dubreuil 2006, Chapter 48, *Escherichia coli, Vibrio* and *Yersinia* species heat stable enterotoxins, Alouf and Popoff (eds), 2006, Comprehensive Sourcebook of Bacterial Protein Toxins, Third Edition, Academic Press), autotransporter toxins including but not limited to IgA protease, picU espC, and sat, *Staphylococcus* protein A, clostridium enterotoxin, *Clostridium difficile* toxin A, scorpion chlorotoxin, aerolysin, subtilase, cereolysin, *Staphylococcus* leukotoxins (e.g. LukF-PV, LukF-R, LukF-I, LukM, HlgB) and the other, to class S (e.g. LukS-PV, LukS-R, LukS-I, HlgA, HlgC). Best known are the toxins produced by *S. aureus*: γ-haemolysins, HlgA/HlgB and HlgC/HlgB and leukocidin Panton-Valentine, LukS-PV/LukF-PV (Luk-PV, PVL)) TRAIL, fasL, IL-18, CCL-21, human cytokine LIGHT, agglutinins (*Maackia amurensis*, wheat germ, *Datura stramonium, Lycopersicon* (tomato) plant lectin, leukoagglutinin (L-PHA, *Helix pomaria*) saporin, ricin, pertussis toxin, and porB, as well as other toxins and peptides (Kastin (ed), 2006, Handbook of Biologically Active Peptides, Academic Press; Alouf and Popoff (eds), 2006, Comprehensive Sourcebook of Bacterial Protein Toxins, Third Edition, Academic Press).

The bacteria may produce bacteriocins (including lactococcins, colicins and microcins), and would typically have the accompanying immunity factors. (Riley and Chavan 2006, Bacteriocins: Ecology and Evolution, Springer; de Vuyst and Vandamme 2012, Bacteriocins of lactic acid bacteria; Microbiology, genetics and applications, Blackie Ac. & Prof. Press).

In one embodiment, the probiotic bacteria express one or more bacteriocins and one or more bacteriocin immunity proteins. Bacteriocins (bacterially produced antibacterial agents that inhibit other strains of bacteria but not the host strain that produces them), such as lactococcins, microcins or colicins (Riley and Chavan 2006, Bacteriocins: Ecology and Evolution, Springer; de Vuyst and Vandamme 2012, Bacteriocins of lactic acid bacteria; Microbiology, genetics and applications, Blackie Academic & Professional Press). The bacteriocin may be the acnecin from *Propionibacterium acnes* (Fujimura and Nakamura 1978) or the bacteriocin from *Propionibacterium shermanii* (Ayers et al., Propionibacteria peptide microcin U.S. Pat. No. 5,635,484 A), the bacteriocin from *Streptococcus salivarius* (Bowe et al., 2006, J. Drugs Dermatol 5: 868-870), the bacteriocin from *Lactococcus* sp. HY 449 (Oh et al., 2006. Effect of bacteriocin produced by *Lactococcus* sp HY 449 on skin inflammatory bacteria, Food Chem Toxicol 44: 1184-1190) or the bacteriocin from *Lactococcus* sp. HY 49 or *Lactobacillus casei* HY 2782 described by Kim et al., U.S. Pat. No. 6,329,002. The bacteriocin acts, for example to stabilize the colonization of the enteric tissue by the bacteria by suppressing growth of other bacteria. A suitable probiotic will typically not disrupt native intestinal flora to cause persistent digestive disease.

The bacteria may be further selected for enhanced bacteriocin production using standard methods for visualizing production of bacteriocins which uses an indicator strain usually embedded in a soft agar overlay, and a test strain, or library or mixed population of strains, applied to the surface. The production of the bacteriocin is then visualized as an increased zone of inhibition of the indicator strain. Using methods known to those skilled in the arts which include various mutagenesis methods such as exposure to ultraviolet light, chemical mutagens such as nitrosoguanidine, or genetic methods such as over expression on plasmids, insertion of strong promoters, transposon mutagenesis, organisms with improved production of bacteriocins are visualized as producing wider zones of bacterial inhibition.

Resistance to phage by the *Propionibacteria acnes* RT6, and many other bacteria species, is already understood to occur, at least in part, by the CRISPER (Clustered Regularly Interspaced Short Palindromic Repeats) systems, but the "immunity" may be incomplete, and could allow phage from resident pathogenic bacteria to kill the probiotic bacterium, preventing it from having as fully effective therapeutic action. The bacteria of the technology may be further engineered to have phage resistance proteins, such as phage repressor proteins related to lambda phage cI repressor, including those identified by Marinelli, et al., 2012 (*Propionibacterium acnes* Bacteriophages Display Limited Genetic Diversity and Broad Killing Activity against Bacterial Skin Isolates, mBio 3(5) doi:10.1128/mBio.00279-1). These authors suggest the possible use of the phage as a form of "phage therapy", i.e., to kill *Propionibacterium acnes*, but do not propose or suggest the use of the *Propionibacterium acnes*, or phage-resistant bacteria, or bacteria with bacteriocins, or bacteria with bacteriocins and protease inhibitors as an effective form of therapy for acne. Use of standard methods of isolating and/or identifying phage resistant strains is also encompassed. It is of importance that the therapeutic bacterial strain, such as the RT6 strain of *Propionibacterium acnes*, be resistant to the resident, disease-associated organisms such as pathogenic ribotypes RT4, 5, 7, 8, 9 & 10 of *Propionibacterium acnes* (Fitz-Gibbon et al., 2013) or bacteria such as *Staphylococcus aureus* or *Streptomyces pyogenes*. Methods for selecting resistant strains selection for spontaneous resistance by exposure of the strain such as RT6 to the phage such as those described by Marinelli, et al., 2012 (*Propionibacterium acnes* Bacteriophages Display Limited Genetic Diversity and Broad Killing Activity against Bacterial Skin Isolates, mBio 3(5) doi: 10.1128/mBio.00279-1), and recovery of the survivors, or the strain can be initially modified by chemical, ultraviolet or transposon mutagenesis, to create a mixed genetic population followed by exposure to the phage, and selection of survivors (Levin, 1994, Isolating multiple strains of *Escherichia coli* for coliphage isolation, phage typing, and mutant recovery, Chapter 4 pages 63-72, in Tested studies for laboratory teaching, Volume 15 (C. A. Goldman, Editor). Proceedings of the 15th Workshop/Conference of the Association for Biology Laboratory Education (ABLE), 390 pages; Exploitation of a new flagellatropic phage of *Erwinia*.

Metabolite toxins such as the *Chromobacterium violaceum* depsipeptides (Shigeatsu et al., 1994, FR901228, a novel antitumor bicyclic depsipeptide produced by *Chromobacterium violaceum* No. 968. 11. Structure determination. J Antibiot (Tokyo) 47(3):311-4) or those from *Serratia* are also of use in the present technology.

Tumor specificity of the therapeutic peptides listed above are further enhanced by insertion, in-frame into the amino acid sequence of the above proteins, of two separate classes of inteins, alone or in combination (self-splicing protein intervening sequences; Green and Belfort 2016, Microbes as intein havens, Microbe 11: 388-393). One class of inteins are sensitive to oxidative and nitrosative stresses (Topilina et al., 2015 SufB intein of *Mycobacterium tuberculosis* as a sensor for oxidative and nitrosative stresses, Proc Natl Acad Sci USA 112: 10348-10353). Topilina et al. demonstrate that oxidative and nitrosative stresses turn off self-splicing in their presence, and suggest that this mechanism is important for Mycobacterial dormancy. However, Topilina et al. did not suggest the utility for this intein by way of activation of therapeutic proteins with the amino acid sequence disrupted by the presence of an oxidatively or nitrosatively inactivated intein, and that such an insertion would become active under the hypoxic conditions of the tumor. When administered systemically (e.g., by intravenous administration) as purified proteins or when delivered by tumor-targeted bacteria, such proteins selectively become active inside the hypoxic portion of the tumor, and thereby selectively become toxic to tumor cells within the tumor itself, thereby limiting toxicity to normal oxygenated cells.

A second, novel class of inteins, uses protease inhibitors inserted into or exchanged for the homing endonuclease portion of inteins. The protease inhibitors are those that inhibit proteases that are known to be preferentially overexpressed in tumors. Such inteins, for example the *M tuberculosis* RecA intein, genetically engineered to contain a protease inhibitor, for example the matrix metalloprotease inhibitor peptide CTTHWGFTLC (SEQ ID NO: 53) exchanged for the intein homing endonuclease domain, is then triggered by tumor proteases, such as matrix metalloproteases, causing self protein splicing of the intein rather than proteolytic cleavage by the protease, resulting in activating the therapeutic proteins listed above in a tumor-selective fashion and thereby limiting toxicity to normal tissues that do not over-express tumor proteases. Enhanced protease triggered self-splicing may be further enhanced by the simple directed evolution method described by Peck et al. 2011 (Directed evolution of small molecule-triggered intein with improved splicing properties in mammalian cells, Chem Biol 18: 619-630), which selects for increased kanamycin resistance reflected by self-splicing of the RecA intein that has been inserted into the kanamycin gene and selecting for increased splicing among high error rate PCR mutants of the intein in the presence of the desired triggering molecule. However, Peck et al. did not suggest the use of a protease inhibitor insertion into the intein nor did they suggest the use in the treatment of cancer.

Tumor associated proteases with known protease inhibitors suitable for insertion into inteins include but are not limited to cysteine cathepsins (e.g., cathepsin K, cathepsin B, cathepsin L) aspartic cathepsins (e.g., cathepsin E, Cathepsin D), kalikrens (e.g., general intracellular or secreted kalikrens, hK1, PSA (hK3), hK10, hK15), serine proteases (e.g., uPA, uPAR, matriptase), caspases, matrix metalloproteases (e.g., MMP-1, -2, -8, -9, -13, -14) (see Edwards et al (Eds), The Cancer Degradome, Proteases and Cancer Biology, Springer, N Y, 926 pp).

Promoters, i.e., genetic regulatory elements that control the expression of the genes encoding the therapeutic molecules described above that are useful in the present technology include constitutive and inducible promoters. A preferred constitutive promoter is that from the vector pTrc99a (Promega). Preferred inducible promoters include the tetracycline inducible promoter (TET promoter), SOS-response promoters responsive to DNA damaging agents such as mitomycin, alkylating agents, X-rays and ultraviolet (UV) light such as the recA promoter, colicin promoters, sulA promoters and hypoxic-inducible promoters including but not limited to the PepT promoter (Bermudes et al., WO2001/025397), the arabinose inducible promoter (Ara$_{BAD}$) (Lossner et al., 2007, Cell Microbiol. 9: 1529-1537; WO2006/048344) the salicylate (asprin) derivatives inducible promoter (Royo et al., 2007, Nature Methods 4: 937-942; WO2005/054477), a tumor-specific promoter (Arrach et al., 2008, Cancer Research 68: 4827-4832; WO/2009/152480) or a quorum-sensing (autoinduction) promoter (Anerson et al., 2006 Environmentally controlled invasion of cancer cells by engineered bacteria, J. Mol. Biol. 355: 619-627; Bhushan et al., Construction of an inducible cell-communication system that amplifies Salmonella gene expression in tumor tissue, Biotechnology and Bioengineering 11): 1769-1781; Swofford et al., 2015, Quorum-sensing Salmonella selectively trigger protein expression within tumors, Proc Natl Acad Sci USA 112: 3457-3462; Din et al., 2016, Synchronized cycles of bacterial lysis for in vivo delivery, Nature 536: 81-85).

Gene expression that induces autolysis may also be used (e.g., Chang et al., 2011, Engineering of *Escherichia coli* for targeted delivery of transgenes to HER2/neu-Positive tumor cells, Biotechnology and Bioengineering 108: 1662-1672 which uses phiX174 lysin gene E-mediated autolysis; Camacho et al., 2016 Engineering of Salmonella as intracellular factory for effective killing of tumor cells. Scientific reports 6, Article number 30591 which uses lambda phage lysis; Din et al., 2016, Synchronized cycles of bacterial lysis for in vivo delivery, Nature 536: 81-85; other similar autolytic proteins may be used). Autolytic delivery is used for therapeutic proteins that are poorly soluble, secreted and/or released, such as parasporin (A total of 13 Parasporin proteins have been isolated from 11 strains of *Bacillus*, with 8 proteins allied to PS1, 2 to PS2, 2 to PS3 and 1 to PS4; Ohba et al., 2009, Parasporin, a new anticancer protein group from *Bacillus thuringiensis* Anticancer Research 29: 4247-434; Okassov et al., 2015, Parasporins as new natural anticancer agents: a review, JBUON 2015; 20(1):5-16; Mizuki et al., 2000, Parasporin, a human leukemic cell-recognizing parasporal protein of *Bacillus thuringiensis*, Clinical and Diagnostic Laboratory Immunology 7: 625-634).

Expression and delivery of the therapeutic proteins described above may be accompanied by co-expression with an apoptosis inducing protein construct that is expressed, surface displayed, secreted and/or released, such that it enhances the overall activity of the therapeutic protein or may have activity that is at least additive to the activity of those therapeutic proteins. Such a construct may consist of, for example, a secretion signal or fusion (e.g., OmpA signal sequence, OmpF signal sequence, YebF, ice nucleation protein with a secretory (release intein)), a ferry peptide (MacEwan and Chilkoti 2013, Harnessing the power of cell-penetrating peptides: Activatable carriers for targeting systemic delivery of cancer therapeutics and imaging agents, Interdisicip Rev Nanomed Nanobiotechnol 5: 31-48; Raucher and Ryu, 2015, Cell penetrating peptides: strategies for anticancer treatment, Trends in Molecular Medicine 21: 560-570; e.g., HIV TAT protein, the antennapedia homeodomain (penetraxin), Kaposi fibroblast growth factor (FGF) membrane-translocating sequence (MTS), herpes simplex virus VP22, hexahistidine, hexalysne, or hexaarginine, and may also include the cell penetrating protease inhibitor sunflower trypsin inhibitor; SFTI; Cascales et al., 2011, Identification and characterization of a new family of cell penetrating peptides: Cyclic cell-penetrating peptides. J Biol Chem 286: 36932-36943), and an apoptosis inducing, anticancer cytotoxicity enhancing protein (apoptin; Noteborn, 2009, Proteins selectively killing tumor cells, European Journal of Pharmacology 625: 165-173; Los et al., 2009, Apoptin, a tumor-selective killer, Biochimica et Biophysica Acta 1793: 1335-1342; and/or HAMLET (human alpha-lactalbumin made lethal to tumor cells, also known as MAL; U.S. Pat. Nos. 7,713,533; 9,085,643; 9487561; Svensson et al., 2000, Proc, Natl Acad Sci USA 97, 4221-4226). See FIGS. 3A-3C and 4A-4C.

Chimeras of effector proteins may be further modified by addition of one or more multimerization domains, such as the T4 foldon trimerization domain (Meier et al., 2004, Journal of Molecular Biology, 344: 1051-1069; Bhardwaj et al., Protein Sci. 2008 17: 1475-1485) or tetramerization domains such as VASP (Kühnel et al., 2004 PNAS 101: 17027-17032). Chimeric toxins may be further modified by the addition of known cell penetrating (ferry) peptide which further improves their entry into target cells (e.g., TAT-apoptin, TAT-bim, TAT-p53). Nuclear localization signals (NLSs) may also be added, including but not limited to that from herpes simplex virus thymidine kinase, the SV40 large T antigen monopartite NLS, or the nucleoplasmin bipartite NLS or more preferably, the NLS from apoptin, a tumor associated (tumor-selective) NLS. The tumor-selective nuclear export signal from apoptin may be used alone or together with NLS from apoptin (Heckl et al., 2008, Value of apoptin's 40-amino-acid C-terminal fragment for the differentiation between human tumor and non-tumor cells, Apoptosis 13: 495-508; Backendor et al., 2008, Apoptin: Therapeutic potential of an early sensor of carcinogenic transformation, Ann Rev Pharmacol Toxicol 48: 143-69). Fragments of apoptin may also be used, as described in FIGS. 3A-3C and 4A-4C. In a preferred embodiment, fusions such as those with cytolethal distending toxin B, have as the final amino acid, cysteine, in order to provide a disulfide bond with the appropriate subunit (e.g., with PltA).

Regarding use of tumor-targeted bacteria expressing wild type cytolethal distending toxin and chimeras including those with apoptin, there have been several earlier descriptions (U.S. Pat. Nos. 6,962,696, 7,452,531, 8,241,623, 8,524,220, 8,623,350, 8,771,669). Cytolethal distending toxins (CLDTs) comprise a family of heterotrimeric holotoxins produced by bacteria that are internalized into mammalian cells and translocated into the nucleus. CLDTs are known to occur in a number of bacterial genera including *Haemophilus, Agregatibacter, Salmonella, Escherichia, Shigella, Campylobacter, Helicobacter, Hahella* and *Yersinia* (Gargi et al., 2012 Bacterial toxin modulation of the eukaryotic cell cycle: are all cytolethal distending toxins created equally? Frontiers in Cellular and Infection Microbiol. 2:124. doi: 10.3389/fcimb.2012.00124), however CLDT does not exist in the VNP20009 strain of Salmonella used in human clinical studies (Toso et al. 2002. Phase I Study of the Intravenous Administration of Attenuated *Salmonella typhimurium* to Patients With Metastatic Melanoma. J. Clin. Oncol. 20, 142-152; Low et al., 2004, Construction of VNP20009, a novel, genetically stable antibiotic sensitive strain of tumor-targeting Salmonella for parenteral administration in humans. Methods Mol Med 90. 47-60).

Depending upon both the specific CLDT and the mammalian cells type, different effects have been documented. All CLDTs have homology to exonuclease III and several have been directly shown to exhibit DNase activity in vitro (Ewell and Dreyfus 2000 DNase I homologous residues in CdtB are critical for cytolethal distending toxin-mediated cell cycle arrest. Mol Microbiol 37, 952-963; Lara-Tejero and Galán, 2000 A bacterial toxin that controls cell cycle progression as a deoxyribonuclease I-like protein. Science 290, 354-357), which is believed to be the primary effect of the toxin. The DNase activity results in double-stranded DNA breaks that activates the cell's DNA damage response and interrupts the cell cycle at G2M. Non-hemopoietic cells tend to enlarge, hence part of the toxin name distending, and in many cases the cells subsequently undergo apoptosis. In hemopoietic cells apoptosis is more rapidly produced (Jinadasa et al., 2011, Cytolethal distending toxin: a conserved bacterial genotoxin that blocks cell cycle progression, leading to apoptosis of a broad range of mammalian cell lineages. Microbiology 157: 1851-1875; Gargi et al., 2012).

Most of the CLDTs are organized in a unidirectional operon of cldtA, cldtB and cldrC genes, where the cldtB encodes the active subcomponent, and cldtA and cldtC encode peptides that are involved in cell binding and translocation. In Salmonella however, the genes exist as a bidirectional operon consisting of cldtB together with a two pertussis like toxin subunits oriented in the opposite direction, pltA and pltrB as well as sty and ttsA, also in opposing directions, that are reported to be required for secretion of the toxin (Hodak and Galan 2013. A *Salmonella typhi* homologue of bacteriophage muramidase controls typhoid toxin secretion. EMBO Reports 14: 95-102). However, in the present technology, the presence of sty and ttsA are not required for secretion of the active toxin when the operon is reorganized into a unidirectional operon of cldtB, pltB and pltA.

Translocation of *E. coli* CLDTs to the nucleus, which constitutes the target location for the endonuclease activity, requires the presence of a nuclear localization signal (NLS). In *Escherichia coli* CLDT-II for example, the NLS is bipartite and located at the C-terminus (McSweeney and Dreyfus, 2004). Nishikubo et al., 2003 identified an NLS occurring in the 48-124 amino acid region in *Actinobacillus actinomycetemcomitans.*

Apoptins are a family of viral genes that were first discovered in chicken anemia virus. Apoptin is the product of the VP3 gene that is involved in lymphoid atrophy and anemia in infected chickens (Peñaloza et al., 2014 Apoptins: selective anticancer agents, Trends in Molecular Medicine 20: 519-528; Los et al., 2009 Apoptin, a tumor selective killer, Biochimica et Biophysica Acta 1793: 1335-1342). Apoptin was subsequently found to selectively induce apoptosis in cancer cells (Danen-Van Oorschot et al., 1997 Apoptin induces apoptosis in human transformed and malignant cells but not in normal cells. Proc. Natl. Acad. Sci. USA 94: 5843-5847). Apoptin shares similarity with Torquetnovirus (TTV) derived apoptosis-inducing protein TAIP and with gyrovirus VP3. Apoptin consists of several different domains including a leucine rich sequence (LRS) which is involved in binding to the promyelocytic leukemia (PML) protein of nuclei and in apoptin multimerization, an SRC homology 3 (SH3) binding domain with is part of a bipartite nuclear localization signal (NLS), a nuclear export sequence (NES) that promotes egress of apoptin from normal cell nuclei, a set of threonines of which T108 must be phosphorylated for full apoptin activity, the C-terminal portion of the bipartite NLS and an anaphase promoting complex/cyclosome I (APC/CI) binding domain that consists of approximately one third of the C-terminus.

According to one embodiment, the present technology provides cysteine-terminated fusions that are modified Salmonella CLDT operon and forms of cytolethal distending toxins that are chimeric with apoptin and other peptide moieties including peptide linkers that improve activity and peptide blocking moieties that must be specifically cleaved to activate the protein. The present technology may incorporate deletions in the CLDT nuclear localization signals which are then complemented by N- or C-terminal fusions with apoptin, or apoptin fragments, which supply its nuclear localization signal in trans as a fusion peptide, followed by a cysteine. It is noted that the copper sequestering proteins may be used in conjunction with a variety of therapies, including other bacterially secreted peptides and factors, heterologous peptides, chimeric peptides, etc.

A single promoter may be used to drive the expression of more than one gene, such as a protease sensitive toxin and a protease inhibitor. The genes may be part of a single synthetic operon (polycistronic), or may be separate, monocistronic constructs, with separate individual promoters of the same type used to drive the expression of their respective genes. The promoters may also be of different types, with different genes expressed by different constitutive or inducible promoters. Use of two separate inducible promoter for more than one cytotoxin or other effector type peptide allows, when sufficient X-ray, tetracycline, arabinose or salicylic acid is administered following administration of the bacterial vector, their expression to occur simultaneously, sequentially, or alternatingly (i.e., repeated).

Bacteria useful in accordance with various aspects of the technology may have recognizable attributes in regard to their ability to sequester, chelate, bind, oxidize or reduce copper in a manner that lessens the availability of copper to cancer cells, cancer associated cells and/or endothelial cells. For example, in vitro, a copper detecting electrode can be used to measure the quantity of Cu(II), the primary form that is transferred to cancerous tissues. Cu(II) in solution, in the presence of the bacteria of the present technology, when given sufficient nutrients for growth, will reduce the measurable Cu(II) compared to the unengineered parental form of the bacteria. In animals and humans in vivo, copper in the blood can be measured by a serum or plasma copper test for free copper (copper not bound to ceruloplasmin). Other methods such as inductively coupled mass spectrometry of ultrafiltrated plasma may also be used (McMillin et al., 2009, Direct measurement of free copper in serum or plasma ultrafiltrate, American Journal of Clinical Pathology 131: 160-165). Thus, the bacteria of the technology can be measured in vitro, and subsequently tested in vivo for the ability to remove copper from the blood. The bacteria can also be evaluated in a tumor model for increased antitumor effects (Teicher (ed) 2011, Tumor Models in Cancer Research, Springer Science and Business Media).

Bacteria useful in accordance with various aspects of the technology may have recognizable attributes in regard to their ability to resist the toxic effects of sequestering, chelating, binding, oxidizing or reducing copper in a manner that lessens the availability of copper to cancer cells. For example, in vitro, the level of copper toxicity/resistance is assessed using the Kirby-Bauer method of disc diffusion known to those skilled in the art, in order to establish the level of copper in solution that is toxic to the parental strain of the bacteria. The bacteria of the present technology have at least a 1.8 fold increase in resistance compared to the parental strain. Thus, the bacteria of the technology are more able to sequester, chelate, bind, oxidize or reduce copper in a manner that lessens the availability of copper to cancer cells, cancer associated cells and/or endothelial cells.

The bacteria may be engineered to produce various factors, including ATN-224, ISIS 333611, RTA 801, Lencota sodium stibogluconate, and other known copper chelating, sequestering, or SODI interacting drugs. These may be peptides, antibodies, small molecules produced by systems of enzymes, microcins, bacteriocins, etc.

The technology also provides, according to one embodiment, a process for preparing genetically stable therapeutic bacterial strains comprising genetically engineering the therapeutic genes of interest into a bacterially codon optimized expression sequence within a bacterial plasmid expression vector, endogenous virulence (VIR) plasmid (of Salmonella sp.), or chromosomal localization expression vector for any of the deleted genes or IS200 genes, defective phage or intergenic regions within the strain and further containing engineered restriction endonuclease sites such that the bacterially codon optimized expression gene contains subcomponents which are easily and rapidly exchangeable, and the bacterial strains so produced.

The present technology provides, for example, and without limitation, live bacterial compositions that are genetically engineered to express one or more protease inhibitors combined with antigens.

According to various embodiments, the technology provides pharmaceutical compositions comprising pharmaceutically acceptable carriers and one or more bacterial mutants. The technology also provides pharmaceutical compositions comprising pharmaceutically acceptable carriers and one or more bacterial mutants comprising nucleotide sequences encoding one or more peptides. Preferably, the bacterial mutants are attenuated by introducing one or more mutations in one or more genes in the lipopolysaccharide (LPS) biosynthetic pathway (for gram-negative bacteria), and optionally one or more mutations to auxotrophy for one or more nutrients or metabolites.

In one embodiment, a pharmaceutical composition comprises a pharmaceutically acceptable carrier and one or more bacterial mutants, wherein said attenuated bacterial mutants are facultative anaerobes or facultative aerobes. In another embodiment, a pharmaceutical composition comprises a pharmaceutically acceptable carrier and one or more attenuated bacterial mutants, wherein said attenuated bacterial mutants are facultative anaerobes or facultative aerobes. In one embodiment, a pharmaceutical composition comprises a pharmaceutically acceptable carrier and one or more bacterial mutants, wherein said attenuated bacterial mutants are facultative anaerobes or facultative aerobes. In another embodiment, a pharmaceutical composition comprises a pharmaceutically acceptable carrier and one or more attenuated bacterial mutants, wherein said attenuated bacterial mutants are facultative anaerobes or facultative aerobes.

A pharmaceutically effective dosage form may comprise between about 105 to 1012 live bacteria, within a lyophilized medium for oral administration. In some embodiments, about 109 live bacteria are administered.

Pharmaceutically Acceptable Formulations

Pharmaceutically acceptable formulations may be provided for delivery by other various routes e.g. by intramuscular injection, subcutaneous delivery, by intranasal delivery (e.g. WO2000/047222, U.S. Pat. No. 6,635,246), intradermal delivery (e.g. WO2002/074336, WO2002/067983, WO2002/087494, WO2002/0832149 WO2004/016281) by transdermal delivery, by transcutaneous delivery, by topical routes, etc. Injection may involve a needle (including a microneedle), or may be needle-free. See, e.g., U.S. Pat. Nos. 7,452,531, 7,354,592, 6,962,696, 6,923,972, 6,863,894, 6,685,935, 6,475,482, 6,447,784, 6,190,657, 6,080,849 and US Pub. 2003/0059400.

The bacteria are generally administered along with a pharmaceutically acceptable carrier and/or diluent. The particular pharmaceutically acceptable carrier and/or diluent employed is not critical to the present technology unless otherwise specific herein (or in a respective incorporated referenced relevant to the issue). Examples of diluents include a phosphate buffered saline, buffer for buffering against gastric acid in the stomach, such as citrate buffer (pH 7.0) containing sucrose, bicarbonate buffer (pH 7.0) alone (Levine et al, J. Clin. Invest., 79:888-902 (1987); and Black et al J. Infect. Dis., 155:1260-1265 (1987)), or bicarbonate buffer (pH 7.0) containing ascorbic acid, lactose, and optionally aspartame (Levine et al, Lancet, 11:467-470 (1988)). Examples of carriers include proteins, e.g., as found in skim milk, sugars, e.g., sucrose, or polyvinylpyrrolidone. Typically, these carriers would be used at a concentration of about 0.1-30% (w/v) but preferably at a range of 1-10% (w/v).

Set forth below are other pharmaceutically acceptable carriers or diluents which may be used for delivery specific routes. Any such carrier or diluent can be used for administration of the bacteria of the technology, so long as the bacteria are still capable of invading a target cell. In vitro or in vivo tests for invasiveness can be performed to determine appropriate diluents and carriers. The compositions of the technology can be formulated for a variety of types of administration, including systemic and topical or localized administration. Lyophilized forms are also included, so long as the bacteria are invasive upon contact with a target cell or upon administration to the subject. Techniques and formulations generally may be found in Remington's Pharmaceutical Sciences, Meade Publishing Co., Easton, Pa. For systemic administration, injection is preferred, including intramuscular, intravenous, intraperitoneal, and subcutaneous. For injection, the composition, e.g., bacteria, of the technology can be formulated in liquid solutions, preferably in physiologically compatible buffers such as Hank's solution or Ringer's solution.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner.

For administration by inhalation, the pharmaceutical compositions for use according to the present technology are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the composition, e.g., bacteria, and a suitable powder base such as lactose or starch.

The pharmaceutical compositions may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The pharmaceutical compositions may also be formulated in rectal, intravaginal or intraurethral compositions such as suppositories or retention enemas, e.g., containing conventional suppository bases such as cocoa butter or other glycerides. See also U.S. Pat. No. 6,962,696.

The present technology provides a pharmaceutical composition comprising a pharmaceutically acceptable carrier and an attenuated tumor-targeted bacteria comprising one or more nucleic acid molecules encoding one or more primary effector molecules operably linked to one or more appropriate promoters. The present technology provides a pharmaceutical composition comprising a pharmaceutically acceptable carrier and an attenuated tumor-targeted bacteria comprising one or more nucleic acid molecules encoding one or more primary effector molecules and one or more secondary effector molecules operably linked to one or more appropriate promoters.

The present technology provides a pharmaceutical composition comprising a pharmaceutically acceptable carrier and a bacterium.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil, olive oil, and the like. Saline is a preferred carrier when the pharmaceutical composition is administered intravenously. Saline solutions and aqueous dextrose and glycerol solutions can also be employed as liquid carriers, particularly for injectable solutions. Suitable pharmaceutical excipients include non-cytotoxic amounts and types of starch, glucose, lactose, sucrose, gelatin, malt, rice, flour, chalk, silica gel, sodium stearate, glycerol monostearate, talc, sodium chloride, dried skim milk, glycerol, propylene, glycol, water, dilute ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic attenuated tumor-targeted bacteria, in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a suspending agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The amount of the pharmaceutical composition of the technology which will be effective in the vaccination of a subject can be determined by standard clinical techniques. In addition, in vitro assays may optionally be employed to help identify optimal dosage ranges. The precise dose to be employed in the formulation will also depend on the route of administration, and should be decided according to the judgment of the practitioner and each patient's circumstances. However, suitable dosage ranges are generally from about 1.0 cfu/kg to about $1\times10^{10}$ cfu/kg; optionally from about 1.0 cfu/kg to about $1\times10^{8}$ cfu/kg; optionally from about $1\times10^{2}$ cfu/kg to about $1\times10^{8}$ cfu/kg; optionally from about 1 $10^{4}$ cfu/kg to about $1\times10^{8}$ cfu/kg; and optionally from about $1\times10^{4}$ cfu/kg to about $1\times10^{10}$ cfu/kg. Effective doses may be extrapolated from dose-response curves derived from in vitro or animal model test systems. In some cases, replication incompetent microbes (which do not form colonies) may be provided, either as the entirety of a dose or some portion of it. These microbes may interact with replication competent organisms, and be complementary, antagonistic, synergistic, etc.

Various delivery systems are known and can be used to administer a pharmaceutical composition of the present technology. Methods of introduction include but are not limited to intradermal, intramuscular, intraperitoneal, intravenous, subcutaneous, intranasal, and oral routes. Methods of introduction may also be intra-tumoral (e.g., by direct administration into the area of the tumor).

The compositions may be administered by any convenient route, for example by infusion or bolus injection, by absorption through epithelial or mucocutaneous linings (e.g., oral mucosa, rectal and intestinal-mucosa, etc.) and may be administered together with other biologically active agents. Administration can be systemic or local. In addition, it may be desirable to introduce the pharmaceutical compositions of the technology into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

The technology also provides a pharmaceutical pack or kit comprising one or more containers filled with one or more of the ingredients of the pharmaceutical compositions of the technology. Optionally associated with such container(s) can be a notice in the form prescribed by governmental agency regulating the manufacture, use or sale of pharmaceuticals or biological products, which notice reflects approval by the agency of manufacture, use or sale for human administration.

The compositions and methods described herein can be administered to a subject in need of treatment, e.g. in need of treatment for inflammation or cancer. In some embodiments, the methods described herein comprise administering an effective amount of compositions described herein, e.g. engineered microbial cells to a subject in order to alleviate a symptom. As used herein, "alleviating a symptom" is ameliorating any condition or symptom associated with a given condition. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, subcutaneous, transdermal, airway (aerosol), cutaneous, topical, or injection administration. Administration can be local or systemic.

The term "effective amount" as used herein refers to the amount of engineered microbial cells needed to alleviate at least one or more symptom of the disease or disorder, and relates to a sufficient amount of pharmacological composition to provide the desired effect. The term "therapeutically effective amount" therefore refers to an amount of engineered microbial cells that is sufficient to effect a particular effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the $ED_{50}$ (the dose therapeutically effective in 50% of the population). The dosage can vary depending upon the dosage form employed and the route of administration utilized. The dose ratio between toxic and therapeutic effects is the therapeutic index and can be expressed as the ratio $ED_{50}$. Compositions and methods that exhibit large therapeutic indices are preferred. A therapeutically effective dose can be estimated initially from cell culture assays. Also, a dose can be formulated in animal models to achieve a circulating plasma concentration range that includes the $IC_{50}$ (i.e., the concentration of an engineered microbial cell which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for inflammation, among others. The dosage can be determined by a physician and adjusted, as necessary, to suit observed effects of the treatment.

In some embodiments, the technology described herein relates to a pharmaceutical composition comprising an engineered microbial cell as described herein, and optionally a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

Pharmaceutical compositions comprising an engineered microbial cell can be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

In certain embodiments, an effective dose of a composition comprising engineered microbial cells as described herein can be administered to a patient once. In certain embodiments, an effective dose of a composition comprising engineered microbial cells can be administered to a patient repeatedly. In some embodiments, the dose can be a daily administration, for example oral administration, of, e.g., a capsule comprising bacterial cells as described herein. In some embodiments, the dose can be, e.g. an injection or gavage of bacterial cells. In some embodiments, the dose can be administered systemically, e.g. by intravenous injection. In some embodiments, a dose can comprise from $10^6$ to $10^{12}$ cells. In some embodiments, a dose can comprise from about $10^8$ to $10^{10}$ cells. A composition comprising engineered microbial cells can be administered over a period of time, such as over a 5-minute, 10-minute, 15-minute, 20-minute, 25-minute period, 30-minute period, 45-minute period, 60-minute period, 90-minute period, 120-minute period, etc. The administration can be repeated, for example, on a regular basis, such as every few days, once a week, or biweekly (i.e., every two weeks) for one month, two months, three months, four months or longer.

In some embodiments, after an initial treatment regimen, the treatments can be administered on a less frequent basis. For example, after treatment biweekly for three months, treatment can be repeated once per month, for six months or a year or longer.

The efficacy of engineered microbial cells in, e.g. the raising of an appropriate immune response to a specified disease, e.g., schistosomiasis, can be determined by the skilled clinician. However, a treatment is considered "effective treatment," as the term is used herein, clinically useful partial or complete immunity is achieved. Efficacy can be assessed, for example, by measuring a marker, indicator, population statistic, or any other measurable parameter appropriate.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed technology, because the scope of the technology is limited only by the claims. Unless otherwise defined, all technical and scientific terms used herein have the same meaning as commonly understood by one of ordinary skill in the art to which this technology belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, the terms "reduced", "reduction", "decrease", or "inhibit" can mean a decrease by at least 10% as compared to a reference level, for example a decrease by at least about 20%, or at least about 30%, or at least about 40%, or at least about 50%, or at least about 60%, or at least about 70%, or at least about 80%, or at least about 90% or more or any decrease of at least 10% as compared to a reference level. In some embodiments, the terms can represent a 100% decrease, i.e. a non-detectable level as compared to a reference level. In the context of a marker or symptom, a "decrease" is a statistically significant decrease in such level. The decrease can be, for example, at least 10%, at least 20%, at least 30%, at least 40% or more, and is preferably down to a level accepted as within the range of normal for an individual without such disorder. In some instances, the symptom can be essentially eliminated which means that the symptom is reduced, i.e. the individual is in at least temporary remission.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or non-human animal. Usually the non-human animal is a vertebrate such as a primate, rodent, domestic animal or game animal. Primates include chimpanzees, cynomolgus monkeys, spider monkeys, and macaques, e.g., Rhesus. Rodents include mice, rats, woodchucks, ferrets, rabbits and hamsters. Animals also include armadillos, hedgehogs, and camels, to name a few. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, cow, or pig, but is not limited to these examples. Mammals other than humans can be advantageously used as subjects that represent animal models of a given condition. A subject can be male or female.

A subject can be one who has been previously diagnosed with or identified as suffering from or having a condition in need of treatment, and optionally, have already undergone treatment. Alternatively, a subject can also be one who has not been previously diagnosed as having a condition. For example, a subject can be one who exhibits one or more risk factors or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operatively linked to appropriate regulatory sequences. A gene may or may not include regions preceding and following the coding region, e.g. 5' untranslated (5'UTR) or "leader" sequences and 3' UTR or "trailer" sequences.

The term "operatively linked" includes having an appropriate start signal (e.g., ATG) in front of the polynucleotide sequence to be expressed, and maintaining the correct reading frame to permit expression of the polynucleotide sequence under the control of the expression control sequence, and, optionally, production of the desired polypeptide encoded by the polynucleotide sequence. In some examples, transcription of a nucleic acid is under the control of a promoter sequence (or other transcriptional regulatory sequence) which controls the expression of the nucleic acid in a cell-type in which expression is intended. It will also be understood that the nucleic acid can be under the control of transcriptional regulatory sequences which are the same or which are different from those sequences which control transcription of the naturally-occurring form of a protein.

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated."

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. cancer or inflammation. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present technology was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Bio., Vol. 57, Jennie P. Mather and David Barnes editors, Academic Press, 1st edition, 1998). Other terms are defined herein within the description of the various aspects of the technology.

All patents and other publications; including literature references, issued patents, published patent applications, and co-pending patent applications; cited throughout this application are expressly incorporated herein by reference for all purposes, including, but not limited to, describing and disclosing, for example, the methodologies described in such publications that might be used in connection with the technology described herein. The technologies and techniques provide written description for details of elements mentioned in this disclosure, enablement for their manufacture and use, and their citation is intended to reflect a possession of the content of those mentioned works as being an integral part of the present technology. The incorporations are not intended to be limiting with respect to alternates outside of the respective incorporated disclosures, except where adoption of the respective disclosure for the intended purpose is restrictive in nature.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

It is therefore an object to provide a genetically engineered bacterium, comprising: at least one heterologous copper binding protein gene which results in expression of a copper binding protein and is capable of reducing copper availability external to the live, replication competent genetically engineered bacterium, in a neoplastic tissue. The bacterium is preferably a live, replication competent bacterium. The bacterium preferably is tumor targeting, i.e., having a selective tropism for tumors over normal gut tissues and liver.

The live genetically engineered may be adapted to colonize a mammalian tissue where the copper binding protein is derived from *Vibrio alginolyticus*. The genetically engineered bacterium may be adapted to selectively colonize a mammalian neoplastic tissue. The genetically engineered may be adapted to selectively colonize metastatic cancerous mammalian tissue, wherein the reduction of copper availability reduces angiogenesis. The genetically engineered bacterium may produce a copper binding protein derived from *Vibrio alginolyticus*. The genetically engineered bacterium may further express a copper resistance protein.

It is also an object to provide a live genetically engineered bacterium comprising at least one genetic operon resulting in expression of a heterologous copper binding siderophore, the live genetically engineered bacterium being capable of colonizing and reducing copper availability to cancerous tissue. The bacterium may further express a copper resistance protein. The siderophore may be selected from the group consisting of methanobactin and yersiniabactin.

It is a further object to provide a method of treating a neoplasm, comprising pretreating a patient with an ACE inhibitor and/or chloroquine followed by a tumor-targeted bacterium. The tumor-targeted bacterium may express a copper-binding protein. The tumor-targeted bacteria may express a cytotoxic protein. The cytotoxic protein may be selected from the group consisting of: small lytic peptides, larger lytic peptides, pore-forming toxins, protein inhibitors, extracellular DNAases (DNase), intracellular DNAases, apoptosis inducing peptides, cytokines, prodrug converting enzymes, metabolite destroying enzymes, ribonucleases, antibody inactivating toxins and other anticancer peptides including those that are naturally secreted, released and/or surface displayed, or heterologously secreted, released and/or surface displayed, and that can be modified uniquely to suit the delivery by a bacterium and may be further engineered to have the tumor, lymphoma, leukemic bone marrow or proximity-selective targeting system including but not limited to the proteins azurin, carboxylesterase Est55 (a prodrug converting enzyme from *Geobacillus* that activates CPT-11 to SN-38), thiaminase (e.g., from *Bacillus*), methionase (methioninase), asparaginase, tryptophanase, apoptin, Torquetnovirus (TTV) derived apoptosis-inducing protein TAIP and with gyrovirus VP3 bax, bim, p53, BAK, BH3 peptide (BCL2 homology domain 3), cytochrome C, thrombospondin, platelet factor 4 (PF4) peptide, *Bacillus* sp. cytolysins, *Bacillus* sp. nheABC toxins, cytolethal distending toxins (cldt) including those cldts from *Hemophilus, Aggregatibacter, Salmonella, Escherichia, Shigella, Campylobacter, Helicobacter, Hahella* and *Yersinia*, typhoid toxins (pertussis like toxin) (pltAB), pertussis toxin, cldt:plt hybrids, cldt:apoptin N terminal fusion, cldt:apoptin C-terminal fusions, actAB, cytotoxic necrotic factor (cnf), dermonecrotic factor (dnf), shiga toxins and shiga-like toxins, bacteriocins, (colicins and microcins; Hen and Jack, Chapter 13 Microcins, in Kastin (ed), 2006, Handbook of Biologically Active Peptides, A. Press; Nes et al., Ch. 17, The nonlantibiotic heat-stable bacteriocins in gram-positive bacteria, in Kastin (ed), 2006, Handbook of Biologically Active Peptides, Ac. Press; Sharma et al., Ch. 18 in Kastin (ed), 2006, Handbook of Biologically Active Peptides, Ac. Press) including membrane depolarizing (or pore-forming), DNAases (including colicin DNase, Staphylococcal Nuclease A:OmpA fusions (Takahara et al., 1985 J. Biol. Chem 260: 2670-2674), *Serratia marcescens* DNase (Clegg and Allen, 1985, FEMS Microbiology Letters 27: 257-262; *Vibrio* DNase Newland et al., 1985 Infect Immun 47: 691-696) or other bacterial DNase), RNAases, and tRNAases, including but not limited colicin A, colicin D, colicin E5, colicin E492, microcin M24, colE1, colE2, colE3, colE5 colE7, coleE8, colE9, col-1a, colicin N and colicin B, membrane lytic peptides from *Staphylococcus* (listed below) and sea anemones, P15 peptide and other TGF-beta mimics, repeat in toxin (RTX) family members (together with the necessary acylation and secretion genes) including *Actinobacillus* leucotoxins, a leuckotoxin: *E. coli* HlyA hybrid, *E. coli* HlyA hemolysin, *Bordetella* adenylate cyclase toxin, heat stable enterotoxins from *E. coli* and *Vibrio* sp. (Dubreuil 2006, Chapter 48, *Escherichia coli*, *Vibrio* and *Yersinia* species heat stable enterotoxins, Alouf and Popoff (eds), 2006, Comprehensive Sourcebook of Bacterial Protein Toxins, $3^{rd}$ Edition, Ac. Press), autotransporter toxins including but not limited to IgA protease, picU espC, and sat, *Staphylococcus* protein A, *clostridium* enterotoxin, *Clostridium difficile* toxin A, scorpion chlorotoxin, aerolysin, subtilase, cereolysin, *Staphylococcus* leukotoxins (e.g. LukF-PV, LukF-R, LukF-I, LukM, HlgB) and the other, to class S (e.g. LukS-PV, LukS-R, LukS-I, HlgA, HlgC). Best known are the toxins produced by *S. aureus*: γ-haemolysins, HlgA/HlgB and HlgC/HlgB and leukocidin Panton-Valentine, LukS-PV/LukF-PV (Luk-PV, PVL)) TRAIL, fasL, IL-18, CCL-21, human cytokine LIGHT, agglutinins (*Maackia amurensis*, wheat germ, *Datura stramonium*, *Lycopersicon* (tomato) plant lectin, leukoagglutinin (L-PHA, *Helix pomatia*) saporin, ricin, pertussis toxin, porB, Pseudomonas ToxA and modified Pseudomonas ToxA+/−a colicin or phage lysis protein such as ColE3 lysis (e.g., Pseudomonas ToxA KDEL, O-T-G-PE38R, O-T-G-PE38K, O-T-G-D111R, O-T-G-D111K, O-T-G-D1bR, O-T-G-D1bK).

It is a still further object to provide a pharmaceutically acceptable formulation, comprising: a live genetically engineered bacterium, having at least one heterologous copper binding protein gene which results in expression of a copper binding protein, the live genetically engineered bacterium being capable of reducing copper availability in its environment, the live genetically engineered bacterium being a tumor targeting bacterium adapted to replicate in a neoplastic tissue; and a pharmaceutically acceptable excipient, provided in unit dosage form for administration to a human. At least a portion of the live genetically engineered bacterium may be replication competent. The live genetically engineered bacterium may be a Salmonella, e.g., *Salmonella enterica* serovar *typhimurium.*

The copper binding protein may be a chimeric protein comprising a copper binding portion and a secretion peptide portion that interacts with a secretion system of the live genetically engineered bacterium to promote secretion of the chimeric protein from the live genetically engineered bacterium.

The bacterium to be administered may be selected from the group consisting of: *Lactobacillus acidophilus, Bifidus breve, Enteroccus faecium, Bacillus cereus, Lactobacillus casei, Lactobacillus paracasei, Bifidus longum* ssp. *infantis, Enteroccus faecalis, Bacillus coagulans, Lactobacillus delbrueckii* ssp. *bulgaricus, Bifidus longum* ssp. *longum, Lactococcus lactis, Clostridium butyricum, Lactobacillus johnsonii, Bifidus adolescentis, Streptococcus thermophilus, Escherichia coli, Lactobacillus reuterii, Bifidus animalis* ssp. *lactis, Propionibacterium freudenreichii, Lactobacillus rhamnosus, Bifidus bifidum, Saccharomyces boulardii, Lactobacillus salivarius, Lactobacillus fermentum, Lactobacillus plantarum, Lactobacillus crispatus, Lactobacillus gasseri*, and *Lactobacillus amylovorus*. The bacterium may also be attenuated Salmonella, e.g., YS1646 or YS1646 zwf-.

Another object provides a method of treating a genetic defect of copper metabolism, comprising administering a non-pathogenic bacteria which colonizes an enteric tissue of a host animal and sequesters copper from its environment, in such an amount and in such dosage form, to effectively reduce availability of copper from dietary sources to the host animal, to thereby reduce excess copper in tissues of the host animal and effectively treat the genetic defect of copper metabolism of the host animal. The non-pathogenic bacteria preferably persists in the enteric tissue of the host animal for at least one day, permitting i.d. or b.i.d. dosage regimen.

The dosage form may be a dairy food product, e.g., liquid, yogurt or cheese. The dosage form may also comprise lyophilized bacteria, e.g., in an enteric dissolution capsule which delivers the bacteria to the gut while protecting them from stomach acid. The non-pathogenic bacteria may be probiotic. The non-pathogenic bacteria may produce a copper-sequestering peptide, and/or secrete a heterologous copper-binding peptide, and/or a heterologous or homologous siderophore. The enteric tissue is, e.g., the colon.

The non-pathogenic bacteria may further produce at least one bacteriocin or microcin.

The animal host may have Wilson's disease, Menke's disease, or a neurological disorder associated with copper toxicity.

A further object provides a heavy metal toxicity treatment for a host animal, by colonizing an enteric tissue after administering a non-pathogenic bacteria to the host animal, which sequesters the heavy metal in the tissue, the non-pathogenic bacteria being provided in such an amount and in such dosage form, to deplete heavy metal in tissues of the host animal outside the enteric tissue, and effectively treat the heavy metal toxicity of the host animal.

It is an object to provide a live, replication competent genetically engineered bacterium, comprising at least one heterologous copper binding protein gene which causes the live, replication competent genetically engineered bacterium to express a copper binding protein and is capable of reducing copper availability external to the live, replication competent genetically engineered bacterium.

The live, replication competent genetically engineered bacterium may be adapted to colonize a mammal, e.g., a mammalian tissue and/or a mammalian neoplastic tissue.

The bacteria may be adapted to selectively colonize a mammalian metastatic cancerous tissue, wherein the reduction of copper availability reduces angiogenesis in the colonized mammalian metastatic cancerous tissue.

The copper binding protein may be derived from *Vibrio alginolyticus* The bacteria may further express a heterologous *Vibrio alginolyticus* copper resistance protein, or a heterologous copper resistance protein.

The copper binding protein may be a copper-binding siderophore, and the live, replication competent genetically engineered bacterium may be adapted to colonize and persist within a host organism, and reduce copper availability to the host organism.

The host organism may have a defect of copper metabolism, and the live, replication competent genetically engineered bacterium may be effective to treat a disease associated with the defect of copper metabolism. The host organism may have a defect in ATP7A or ATP7B, and the live, replication competent genetically engineered bacterium may be effective to treat a disease associated with the defect in ATP7A or ATP7B.

The bacteria may further comprise at least one gene which causes the live, replication competent genetically engineered bacterium to express a cytotoxic protein.

The live, replication competent genetically engineered bacterium may be of species *E. coli*, genus/species *Salmonella*, or at least one of *Lactobacillus acidophilus, Bifidus breve, Enteroccus faecium, Bacillus cereus, Lactobacillus casei, Lactobacillus paracasei, Bifidus longum* ssp. *infantis, Enteroccus faecalis, Bacillus coagulans, Lactobacillus delbrueckii* ssp. *bulgaricus, Bifidus longum* ssp. *longum, Lactococcus lacus, Clostridium butyricum, Lactobacillus johnsonii, Bifidus adolescentis, Streptococcus thermophilus. Escherichia coli, Lactobacillus reuterii, Bifidus animalis* ssp. *lactis, Propionibacterium freudenreichii, Lactobacillus rhamnosus, Bifidus bifidum, Saccharomyces boulardii, Lactobacillus salivarius, Lactobacillus fermentum, Lactobacillus plantarum, Lactobacillus crispatus, Lactobacillus gasseri*, and *Lactobacillus amylovorus*.

The copper binding protein may be selected from the group consisting of methanobactin, yersiniabactin, *Vibrio alginolyticus* copper binding protein, plastocyanin, amicyanin, auracyanin A, auracyanin B, *Alcaligenes* blue copper protein, cupredoxin, halocyanin, rusticyaninstellacyanin, umecyanin, aerobactin, salmonchelin, and ceruloplasmin.

It is another object to provide a pharmaceutically acceptable formulation, comprising: a live replication competent genetically engineered bacterium, having at least one heterologous copper binding protein gene which results in expression of a copper binding protein, the live genetically engineered bacterium being capable of reducing copper availability in its environment, the live genetically engineered bacterium being a probiotic bacterium adapted to replicate in an enteric organ of a human; and a pharmaceutically acceptable excipient, provided in unit dosage form for administration to the human.

The copper binding protein may be a chimeric protein comprising a copper binding portion and a secretion peptide portion that interacts with a secretion system of the live replication competent genetically engineered bacterium to promote secretion of the chimeric protein from the live genetically engineered bacterium into the environment.

It is a further object to provide a method of treating a patient having an excess of transition metals in tissue, comprising: administering a non-pathogenic live bacteria to the patient, the non-pathogenic live bacteria being genetically engineered to express a heterologous transition metal binding protein which sequesters transition metals in an environment of the non-pathogenic live bacteria; colonizing an enteric tissue of the patient with the non-pathogenic live bacteria; effectively reducing availability of the transition metal from dietary sources to the patient, to thereby treat the excess of transition metals.

The excess of transition metals may comprise an excess of copper, the heterologous transition metal binding protein may comprise a copper binding peptide, and the non-pathogenic live bacteria may be effective to reduce availability of copper from dietary sources to the patient, to thereby treat Wilson disease or Menke's disease.

The live genetically engineered bacterium may be an antibiotic-sensitive bacteria selected from the group consisting of: *Salmonella, E. coli, Lactobacillus acidophilus, Bifidus breve, Enteroccus faecium, Bacillus cereus, Lactobacillus casei, Lactobacillus paracasei, Bifidus longum* ssp. *infantis, Enteroccus faecalis, Bacillus coagulans, Lactobacillus delbrueckii* ssp. *bulgaricus, Bifidus longum* ssp. *longum, Lactococcus lacus, Clostridium butyricum, Lactobacillus johnsonii, Bifidus adolescentis, Streptococcus thermophilus, Escherichia coli, Lactobacillus reuterii, Bifidus animalis* ssp. *lactis, Propionibacterium freudenreichii, Lactobacillus rhamnosus, Bifidus bifidum, Saccharomyces boulardii, Lactobacillus salivarius, Lactobacillus fermentum, Lactobacillus plantarum, Lactobacillus crispatus, Lactobacillus gasseri*, and *Lactobacillus amylovorus*.

The technology described herein is further illustrated by the following examples which in no way should be construed as being further limiting.

DETAILED DESCRIPTION OF THE PREFERRED EMBODIMENTS

Figure 2:
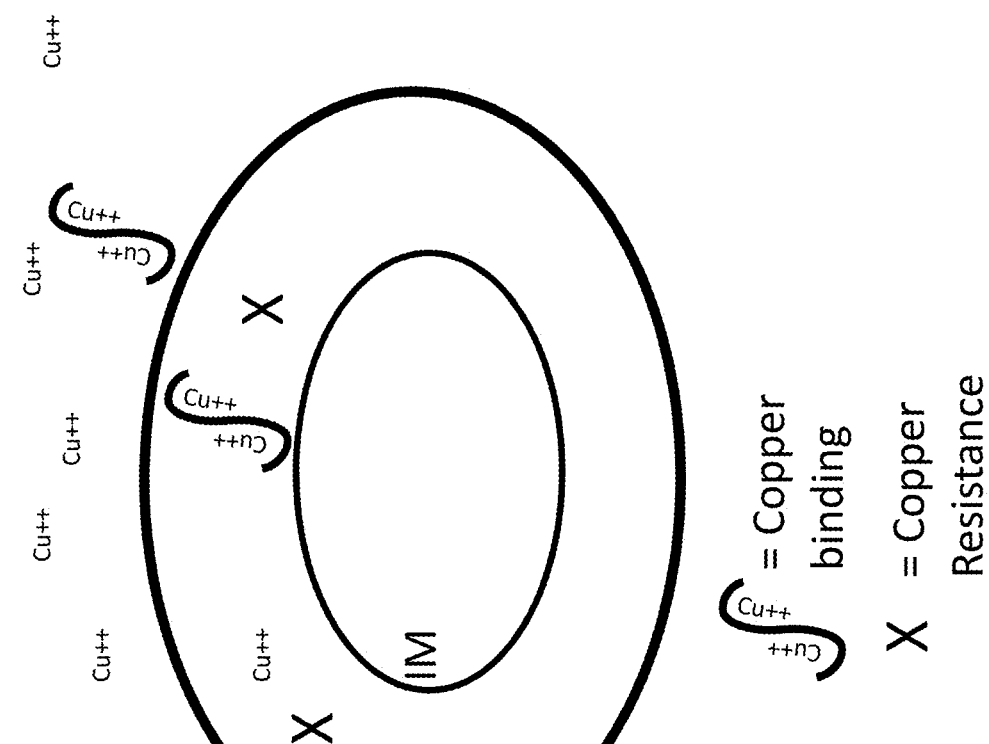
FIG. 2 shows a Salmonella expressing a copper binding protein and a copper resistance protein.

The present technology provides, according to various embodiments, bacteria with the ability to reduce the availability of copper to cancer cells, endothelial cells, cancer associated and tumor stromal cells. Reduction in copper availability, alone or in combination, results in an overall decrease in copper availability through 1) copper sequestration, including binding, chelating or internalizing copper, 2) locally precipitating copper, and/or 3) oxidizing or reducing copper into a form that cannot be utilized by cancerous cells, cancer associated cells or endothelial cells.

For reasons of clarity, the detailed description is divided into the following subsections: 1) bacteria that sequester copper, and 2) bacteria resistant to copper.

The present technology provides, according to various embodiments, improved live attenuated therapeutic bacterial strains that express one or more therapeutic molecules that exert their therapeutic effect through reducing the availability of copper. The primary characteristic of the bacteria of certain embodiments of the technology is to reduce the availability of copper to cancerous tissue, which thereby have enhanced antitumor activity. A secondary effect of the bacteria is to normalize tumor vasculature and increase the availability of anticancer agents to the tumor. In one embodiment, the percent increase in effect is approximately 2% to approximately 95%, approximately 2% to approximately 75%, approximately 2% to approximately 50%, approximately 2% to about 40%, approximately 2% to about 30%, approximately 2% to about 25%, approximately 2% to about 20% or about 2% to approximately 10% greater than the parental strain of bacteria without expressing one or more of the modifications described herein under the same conditions.

According to other embodiments, compositions derived from bacteria are employed as useful therapies in a pharmaceutically acceptable formulation, in some cases in unit dose form.

Tumor-targeted bacteria that sequester copper.

Typical Salmonella are gram-negative rods that require minimal amounts of copper for survival, an essential nutrient that is required by all organisms. Salmonella and other bacteria of the technology have the ability to bind or sequester higher amounts of copper by several different means. Bacteria that sequester greater than normal amounts of copper are generated by cloning copper binding proteins, copper siderophores, or enzymes that chemically oxidize or reduce copper thereby making it unavailable for cancerous tissue. The effect of these bacteria on copper-containing solutions can be measured in vitro, and the effect of these bacteria can be measured in vivo.

Tumor-targeted bacteria that are resistant to copper.

Typical Salmonella and other bacteria of the technology are sensitive to high levels of copper. Bacteria resistant to copper may be isolated by random mutagenesis using UV and nitrosoguanidine, or by transposon mutagenesis and selected for smaller size as described above. Alternatively, unsuppressed msbB strains (YSI; Murray et al., 2001, Extragenic suppressors of msbB growth defects in Salmonella. J. Bacteriol. 183: 5554-5561) or partially suppressed msbB strains (Murray et al., 2007. PmrA(Con) Confers pmrHFIJKL-Dependent EGTA and Polymyxin Resistance on msbB Salmonella by Decorating Lipid A with Phosphoethanolamine. J. Bacteriology, 189: 5161-5169; Murray et. al., 2004 Hot spot for a large deletion in the 18-19 Cs region confers a multiple phenotype in *Salmonella enterica* serovar *typhimurium* strain ATCC 14028, J. Bacteriol, 186: 8516-8523) may be used to selected for spontaneous mutations or combination of selections thereof. The mutations can be identified by methods known to those skilled in the art including genome sequencing.

Bacteria resistant to copper may also be generated by heterologous expression or overexpression of copper resistance proteins. It is understood that the sequences are publicly available (e.g., Stein et al., 2010, Genome Sequence of the Obligate Methanotroph *Methylosinus trichosporium* Strain OB3b *J. Bacteriol. December* 2010 vol. 192 no. 24 6497-6498, Genbank ADVE00000000; Hurst et al., 2014, Draft Genome Sequence of *Photorhabdus temperata* Strain MegI, an Entomopathogenic Bacterium Isolated from *Heterorhabditis megidis* Nematodes, Genome Announce 2(6): e01273-14, and many others).

The figures show compositions and methods to modify bacteria of the present technology.

Figure 1:
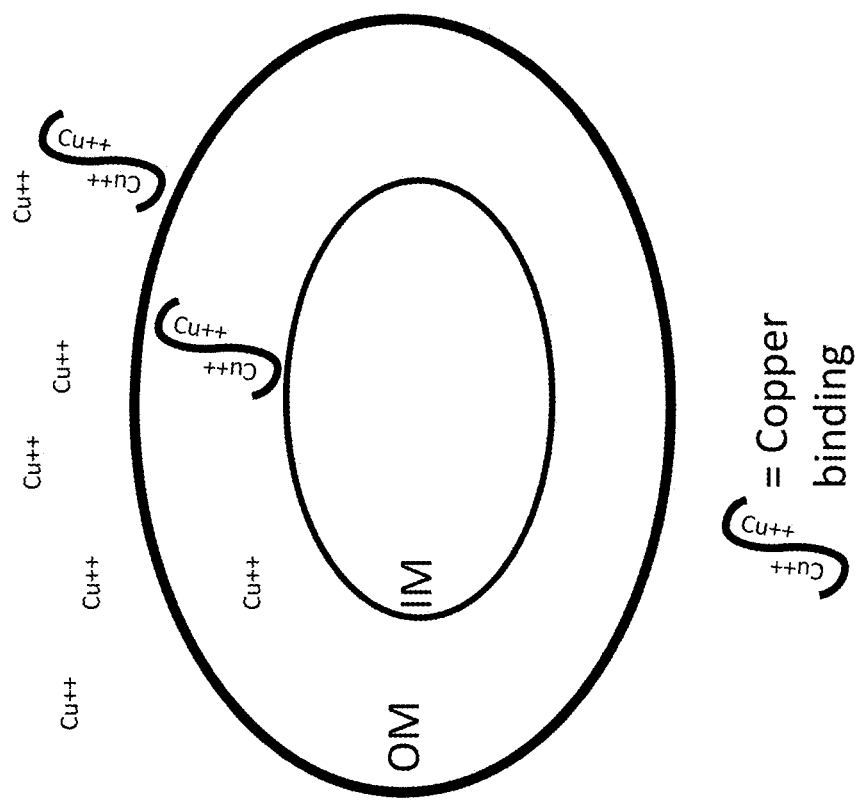
FIG. 1 shows a Salmonella expressing a copper binding protein and binding copper in the periplasm.

FIG. 1 shows a tumor-targeted bacteria expressing a copper binding protein. The figure shows a gram-negative bacterium with an inner membrane (IM) and outer membrane (OM), and a copper binding protein in the periplasmic space, as well as secreted. External copper binds externally and/or enters into the periplasmic space and is trapped by the copper-binding protein.

FIG. 2 shows a tumor-targeted bacteria expressing a copper binding protein and a copper-resistance protein. The figure shows a gram-negative bacterium with an inner membrane (IM) and outer membrane (OM), and a copper binding protein in the periplasmic space interspersed with a copper resistance protein. External copper binds externally and/or enters into the periplasmic space and is trapped by the copper-binding protein (X) while the resistance protein protects the bacterium form copper toxicity.

Figure 3A:
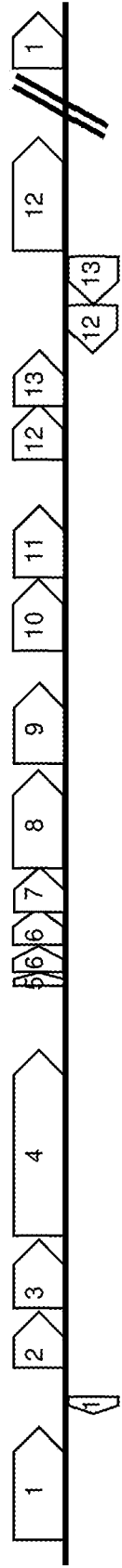
FIGS. 3A-3C shows the methanobactin operon (FIG. 3A), a Salmonella expressing methanobactin (FIG. 3B), and methanobactin (FIG. 3C)
Figure 3B:
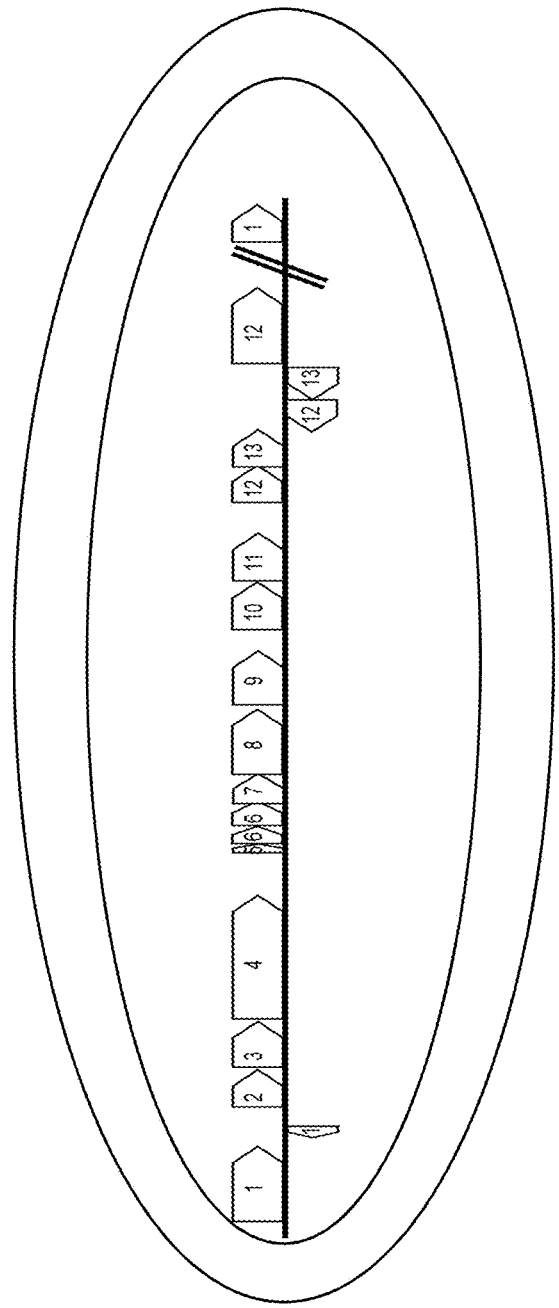
Figure 3C:
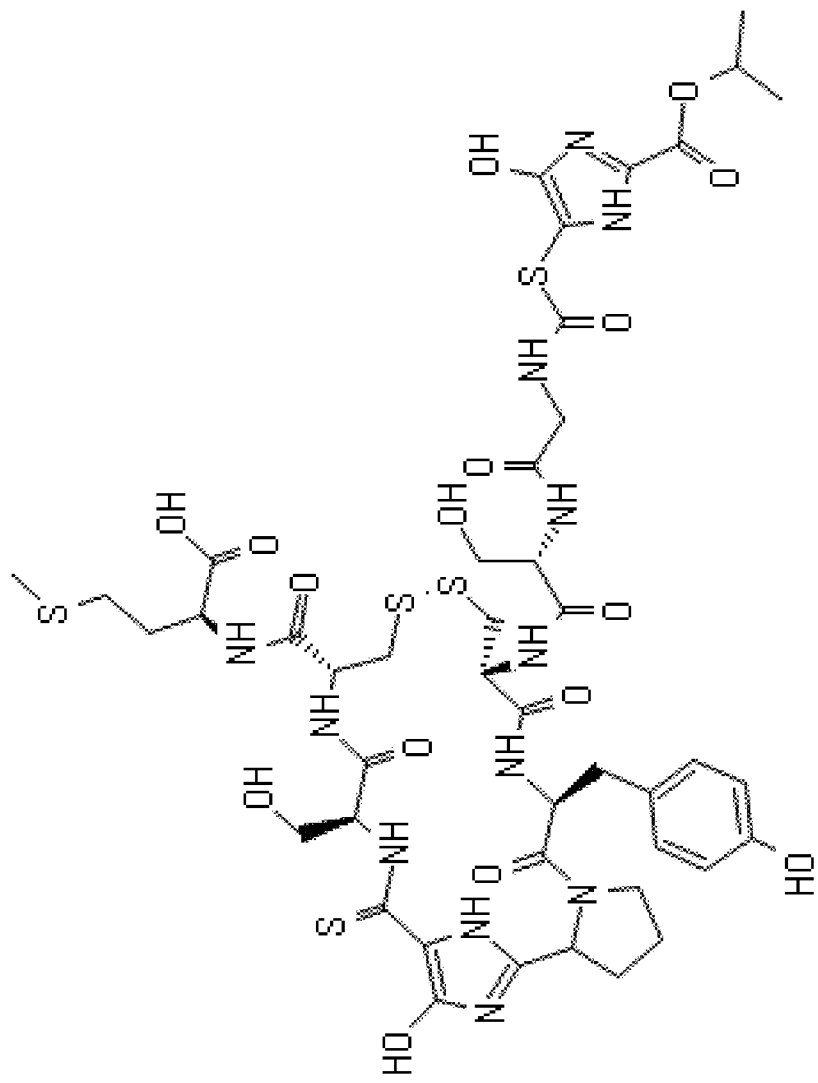
Figure 4A:
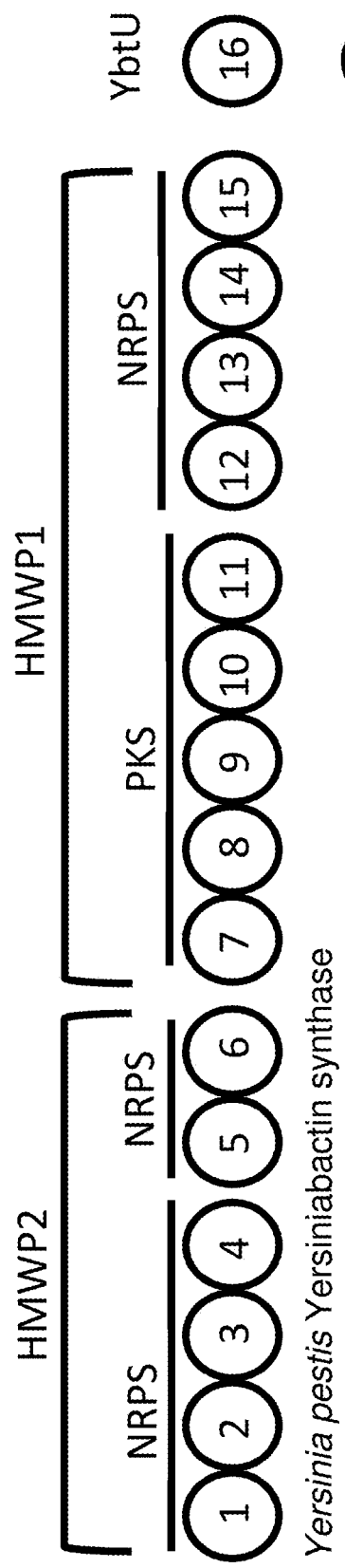
FIGS. 4A-4C show the yersiniabactin operon (FIG. 4A), a Salmonella expressing yersiniabactin (FIG. 4B), and yersiniabactin (FIG. 4C).
Figure 4B:
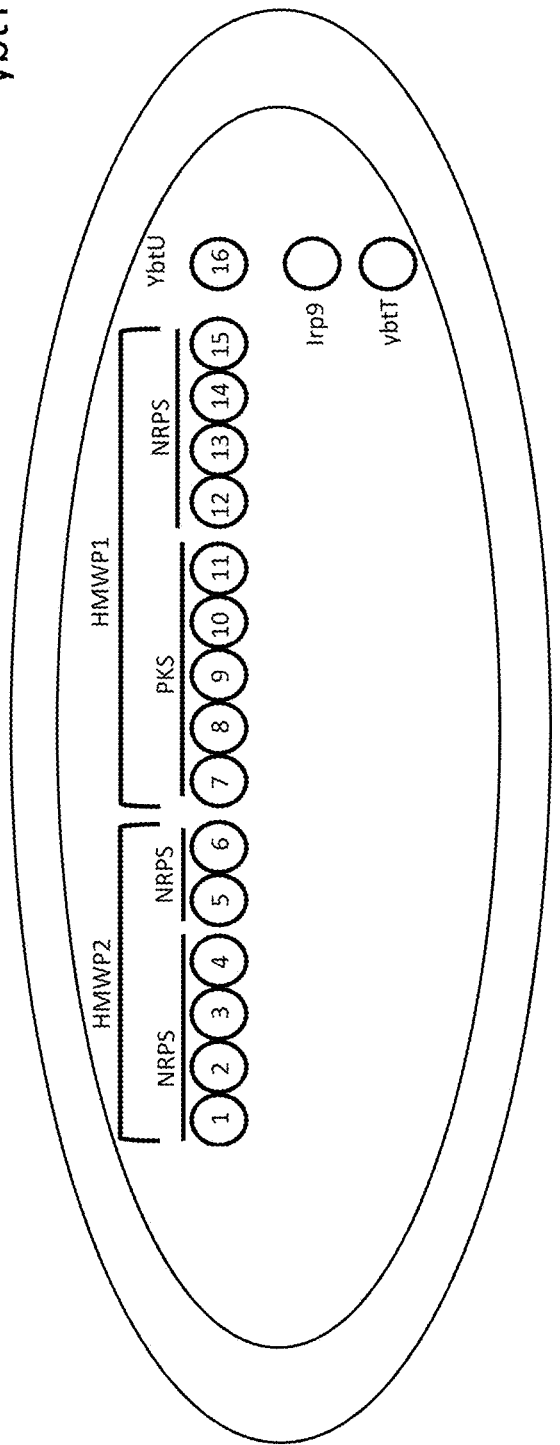
Figure 4C:
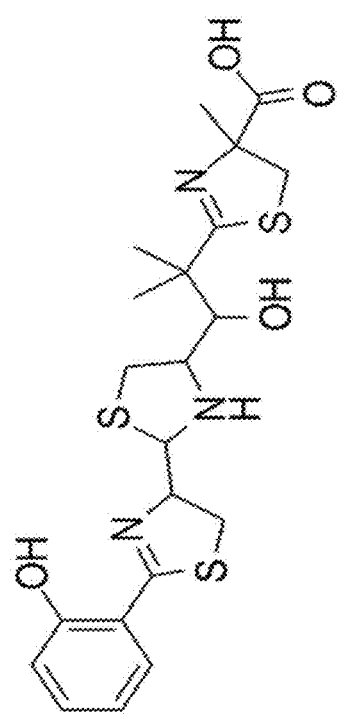

FIGS. 3A-3C show a tumor-targeted Salmonella expression of methanobactin. FIG. 3A shows the methanobactin operon (redrawn from Kenny and Rosenzweig 2013, Genome mining for methanobactins. BMC Biology 2013, 11:17 doi.org/10.1186/1741-7007-11-17). 1—mobile genetic element; 2—ECF s70 factor FecI-like=MbnI; 3—FecR-like membrane sensor (MbnR); 4—TonB-dependent transporter (MbnT); 5—MbnA (Mbn precursor); 6—MbnB (unknown Mbn biosynthesis protein 1); 7—MbnC (unknown Mbn biosynthesis protein 2); 8—MATE efflux pump (MbnM); 9—Periplasmic binding protein; 10—Partner of MbnH (MbnP); 11 Di-heme cytochrome c peroxidase (MbnH); 12—Annotated proteins of unknown relevance; 13—Putative/hypothetical protein (includes ECF s70 and ATP/Zn protease and Type I restriction modifying enzyme). FIG. 3B shows Salmonella VNP20009 containing the Mbn operon on an expression plasmid, or inserted into the chromosome. FIG. 3C shows methanobactin (see, Krentz et al. (2010) A comparison of methanobactins from *Methylosinus trichosporium* OB3b and *Methylocystis* strain SB2 predicts methanobactins are synthesized from diverse peptide precursors modified to create a common core for binding and reducing copper ions. Biochemistry 49: 10117-10130.) FIGS. 4A-4C show the Ybt synthetase organized into non-ribosomal peptide synthesis (NRPS) and polypeptide synthesis (PKS) domains that results in yersiniabactin production from tumor-targeted Salmonella. FIG. 4A shows the polyketide synthase, non-ribosomal peptide synthase complex) YbtE (activation); HMWP2 (1, aryl carrier protein; 2, cyclization protein 1; 3, adenylation; 4, peptidyl carrier protein; 5, cyclization protein 2; 6, peptidyl carrier protein 2); HMWP1 (7, ketosynthase; 8, acyltransferase; 9, methyltransferase 1; 10, NADPH-dependent ketoreductase; 11, acyl carrier protein; 12; cyclization protein 3; 13, methyltransferase 2; 14, peptidyl carrier protein 3; 15, thioesterase); 16, the YbtU reductase; irp9 from *Yersinia enterocolitica* converts chorismate from the shikimate pathway into salicylate; ybt T accessory protein. FIG. 4B shows Salmonella (e.g., tumor targeted Salmonella VNP20009) with the polyketide synthase non-ribosomal synthase complex either on one or more expression plasmids or inserted into the chromosome. FIG. 4C shows the yersiniabactin produced by tumor-targeted Salmonella.

EXAMPLES

In order to more fully illustrate the technology, the following examples are provided.

Example 1: A Tumor-Targeted Bacterium Expressing a *Vibrio alginolyticus* Copper Sensitivity Suppressor Protein Inducible expression vectors for *E. coli* and Salmonella, such as arabinose inducible expression vectors, are widely available and known to those skilled in the art. By way of example, an expression vector typically contains a promoter which functions to generate an mRNA from the DNA, such as an inducible arabinose promoter with a functional ribosomal binding site (RBS) an initiation codon (ATG) and suitable cloning sites for operable insertion of the functional DNA encoding the effector proteins described below into the vector, followed by a transcriptional termination site, plasmid origin of replication, and an antibiotic resistance factor that allows selection for the plasmid. Vectors that lack antibiotic resistance such as asa(−) balanced lethal vectors (Galan et al., 1990 cloning and characterization of the asd gene of *Salmonella Typhimurium* use in stable maintenance of recombinant Salmonella vaccine strains, Gene 94: 29-35) may also be used, or insertion into the chromosome.

The *Vibrio alginolyticus* chromosome 2 copper sensitivity suppressor protein A has the amino acid sequence

SEQ ID NO: 1:
MVCLSQNSGFSKSCPKAHQIQSQQNESVNLSPSCDLSEKLVQAYQHQFDH

ILIPFFLFALIVALPMASTAIRYLEYTEPIREKYRVHLKLCVFRE and is encoded by the DNA

SEQ ID NO: 2:
atggtatgataagccaaaactccggcactcgaaaagctgccctaaggctc accaaatacagagtcagcaaaatgaaagcgtgaatttatcaccatcttgc gaccatcagagaagctggttcaagcgtaccaacaccagatgatcatattc ttattccattattctgatgctttgattgtggcgctgccgatggcatccac agcaattcgttatctggaatacacagaaccgatacgggaaaagtatcggg ttcacctaaaactagcgtgatagagaataa The complete sequence of the arabinose inducible plasmid capable of expressing the copper sensitivity suppressor protein with a start codon at 35I is constructed using methods known to those skilled in the art including PCR and synthetic biology in order to generate SEQ ID NO: 3:
ggGGCGGCCGCaagaaaccaattgtccatattgcatcagacattgccgt cactgcgtcattactggctcttctcgctaaccaaaccggtaacccgctt attaaaagcattctgtaacaaagcgggaccaaagccatgacaaaaacgcg taacaaaagtgtctataatcacggcagaaaagtccacattgattatttgc acggcgtcacactagctatgccatagcattatatccataagattagcga tcctacctgacgcatttatcgcaactctctactgatctccatacccgata ttgggctagcgaattcgagctCGGTACCCAGGAGGAATTCACCATGgtat gtttaagcc aaaac tccggc ttc tcgaaaagctgccctaaggctca ccaaatacagagtcagcaaaatgaaagcgtgaatttatcaccatcttgcg acctttcagagaagctggttcaagcgtaccaacaccagatgatcatattc ttattccattttttctgtttgctttgattgtggcgctgccgatggcACCC

CATGCCGAACTCAGAAGTGAAACGCCGTAGCGCCGATGGTAGTGTGGGT

CTCCCCATGCGAGAGTAGGGAACTGCCAGGCATCAAATAAAACGAAAGGC

TCAGTCGAAAGACTGGGCCTTTCGTTTTATCTGTTGTTTGTCGGTGAACG

CTCTCCTGAGTAGGACAAATCCGCCGGGAGCGGATTTGAACGTTGCGAAG

CAACGGCCCGGAGGGTGGCGGGCAGGACGCCCGCCATAAACTGCCAGGCA

TCAAATTAAGCAGAAGGCCATCCTGACGGATGGCCTTTTTGCGTTTCTAC

AAACTCTTTTTGTTTATTTTTCTAAATACATTCAAATATGTATCCGCTCA

TGAGACAATAACCCTGATAAATGCTTCAATAATATTGAAAAAGGAAGAGT

ATGAGTATTCAACATTTCCGTGTCGCCCTTATTCCCTTTTTTGCGGCATT

TTGCCTTCCTGTTTTTGCTCACCCAGAAACGCTGGTGAAAGTAAAAGATG

CTGAAGATCAGTTGGGTGCACGAGTGGGTTACATCGAACTGGATCTCAAC

AGCGGTAAGATCCTTGAGAGTTTTCGCCCCGAAGAACGTTTTCCAATGAT

GAGCACTTTTAAAGTTCTGCTATGTGGCGCGGTATTATCCCGTGTTGACG

CCGGGCAAGAGCAACTCGGTCGCCGCATACACTATTCTCAGAATGACTTG

GTTGAGTACTCACCAGTCACAGAAAAGCATCTTACGGATGGCATGACAGT

AAGAGAATTATGCAGTGCTGCCATAACCATGAGTGATAACACTGCGGCCA

ACTTACTTCTGACAACGATCGGAGGACCGAAGGAGCTAACCGCTTTTTTG

-continued
CACAACATGGGGGATCATGTAACTCGCCTTGATCGTTGGGAACCGGAGCT

GAATGAAGCCATACCAAACGACGAGCGTGACACCACGATGCCTACAGCAA

TGGCAACAACGTTGCGCAAACTATTAACTGGCGAACTACTTACTCTAGCT

TCCCGGCAACAATTAATAGACTGGATGGAGGCGGATAAAGTTGCAGGACC

ACTTCTGCGCTCGGCCCTTCCGGCTGGCTGGTTTATTGCTGATAAATCTG

GAGCCGGTGAGCGTGGGTCTCGCGGTATCATTGCAGCACTGGGGCCAGAT

GGTAAGCCCTCCCGTATCGTAGTTATCTACACGACGGGGAGTCAGGCAAC

TATGGATGAACGAAATAGACAGATCGCTGAGATAGGTGCCTCACTGATTA

AGCATTGGTAACTGTCAGACCAAGTTTACTCATATATACTTTAGATTGAT

TTAAAACTTCATTTTTAATTTAAAAGGATCTAGGTGAAGATCCTTTTTGA

TAATCTCATGACCAAAATCCCTTAACGTGAGTTTTCGTTCCACTGAGCGT

CAGACCCCGTAGAAAGATCAAAGGATCTTCTTGAGATCCTTTTTTTCTG

CGCGTAATCTGCTGCTTGCAAACAAAAAAACCACCGCTACCAGCGGTGGT

TTGTTTGCCGGATCAAGAGCTACCAACTCTTTTTCCGAAGGTAACTGGCT

TCAGCAGAGCGCAGATACCAAATACTGTCCTTCTAGTGTAGCCGTAGTTA

GGCCACCACTTCAAGAACTCTGTAGCACCGCCTACATACCTCGCTCTGCT

AATCCTGTTACCAGTGGCTGCTGCCAGTGGCGATAAGTCGTGTCTTACCG

GGTTGGACTCAAGACGATAGTTACCGGATAAGGCGCAGCGGTCGGGCTGA

ACGGGGGGTTCGTGCACACAGCCCAGCTTGGAGCGAACGACCTACACCGA

ACTGAGATACCTACAGCGTGAGCTATGAGAAAGCGCCACGCTTCCCGAAG

GGAGAAAGGCGGACAGGTATCCGGTAAGCGGCAGGGTCGGAACAGGAGAG

CGCACGAGGGAGCTTCCAGGGGGAAACGCCTGGTATCTTTATAGTCCTGT

CGGGTTTCGCCACCTCTGACTTGAGCGTCGATTTTTGTGATGCTCGTCAG

GGGGGCGGAGCCTATGGAAAAACGCCAGCAACGCGGCCTTTTTACGGTTC

CTGGCCTTTTGCTGGCCTTTTGCTCACATGTTCTTTCCTGCGTTATCCCC

TGATTCTGTGGATAACCGTATTACCGCCTTTGAGTGAGCTGATACCGCTC

GCCGCAGCCGAACGACCGAGCGCAGCGAGTCAGTGAGCGAGGAAGCGGAA

GAGCGCCTGATGCGGTATTTTCTCCTTACGCATCTGTGCGGTATTTCACA

CCGCATATG

Determination of copper sensitivity can be performed by any of the means known to those skilled in the art, such as the methods of Achard et al., 2010 (The multi-copper-ion oxidase CueO of *Salmonella enterica* serovar *typhimurium* is required for systemic virulence. Infect Immun 78: 2312-2319) or de A. Ramos and Rosato 1996 (Copper accumulation in *Xanthomonas campestris* pv. Vesicatorai, Brazilain Journal of Genetics 19: 551-554).

Example 2. A Tumor-Targeted Bacterium Expressing the *Vibrio alginolyticus* Putative Suppressor for Copper-Sensitivity B Protein The expression plasmid of Example 1 above is used to operably link a DNA encoding the amino acid sequence

SEQ ID NO: 4:
MNQIIKLTQFAFMFFMTLALSLLSLSISAQTTDIGWITNPQHPPVQTRFV

LIGQQDPQAKTLTGYLDVKLTGDWKTYWRSPGEGGVAPSIDWQNSQNLSK

VDWQWPHPQKFELLGIETLGYKGDTLFPMILHVEDMSKPVTIDAVLILSS

CITICVLIDYQIQLTFLPSDLTVDEGVMFSYAQAVSNVPQPSPFIDVTQA

SWDVNQSKLQIKLQNSQGWQQPQVLVDGVDEATRDYSFKLEGMHQEGNIV

TASYIVDTWLGDVELDGQSLFVTIKDTNLLAEETTQATAEAIVEPLPSTS

LTSVFLFALLGGLILNIMPCVLPVLGMKLSSIVAAQGIERRQIRAQFVAS

SLGILTSFWILAGFILVLKLIGNAIGWGVQFQSPWFLGLMVLVITLFGAN

MLGLFEVRLSSGINTWLASKGDNSLAGHYVQGMFAILLATPCSAPFLGTA

VAFALGADVLTLFATFTALALGMALPWLLVAVFPNIALKLPKPGSWMNVV

KIVFGIMMLATSIWLLSLMANHVPMLWIALIAVVAFVVMMARVKKVYGEK

ALAVSGTASLVLIAGGLLLGSVTADQWATPLPEDLAWQKLSNSAIEDHVN

NGRVVFVDVTADWCVTCKANKIGVIWQDPVYSLLQSPNVATLKGDWTHPD

GSVTDFLRAHGRYGVPFNIVYGPAAPQGIPLPVILTDDVVLSAVKQASGG

AIQ

Determination of copper sensitivity can be performed by any of the means known to those skilled in the art, such as the methods of Achard et al., 2010 (The multi-copper-ion oxidase CueO of *Salmonella enterica* serovar *typhimurium* is required for systemic virulence. Infect Immun 78: 2312-2319 or de A. Ramos and Rosato 1996 (Copper accumulation in *Xanthomonas campestris* pv. Vesicatorai, Brazilain Journal of Genetics 19: 551-554).

Example 3: A Tumor-Targeted Bacterium Expressing the *Vibrio alginolyticus* Copper Binding Protein The expression plasmid of Example 1 above is used to operably link a DNA encoding the amino acid sequence

SEQ ID NO: 5:
MKKT LIT LALALTTTTAFAQMDHSNMDHANMDHSNMKHENMDHGSMKM

DHSKMDHSNMMDMPGMSAVGMPAKGAKPDKVVHVILGDDMTIKFKKDVKI

EPNDVVQFVVMNTGKINHEFTIGSAKEQLEHREMMKTMSGDHMHDSGNAV

TVEPGKAKQLLWHFHGDNKVEFACNIPGHAESGMVKKIEL

Measurement of copper accumulation can utilize any of the methods known to those skilled in the art, such as atomic absorption spectrophotometry (de A. Ramos and Rosato 1996, Copper accumulation in *Xanthomonas campestris* pv. Vesicatorai, Brazilain Journal of Genetics 19: 551-554), copper selective electrodes and mass spectroscopy (Berson and Lidstrom 1996, Study of copper accumulation by the Type I methanotroph *Methylomicrobium albus* BG8, Environ. Sci. Technol 30: 802-809.

Example 4: A Tumor-Targeted Bacterium Expressing a *Vibrio alginolyticus* Copper Homeostasis Protein The expression plasmid of Example 1 above is used to operably link a DNA encoding the amino acid sequence

SEQ ID NO: 6:
MNVVTHLEVCIDNIESLHYAIAGGATRIELCSSLALGGLTPSYGFMQQAA

KLSSVPVYAMIRPRQGDFFYNEEEIEMMRWDIEAAHQSGLSGVVFGVLIQ

DGDIHMPYAAALCEFAQALGLGVTFHRAFDQCRDAEKTLEELISLGCERI

LTSGLAPSAPQGIDVLRALVKQAQGRIAIMAGAGVNASNVRALVEDTQVP

EIHLSGKTTRPSQMTFVAEQSKMGASDVDDFLIPITSTQAITDVVATLK

Determination of copper sensitivity can be performed by any of the means known to those skilled in the art, such as the methods of Achard et al., 2010 (The multi-copper-ion oxidase CueO of *Salmonella enterica* serovar *typhimurium* is required for systemic virulence. Infect Immun 78: 2312-2319) or de A. Ramos and Rosato 1996 (Copper accumulation in *Xanthomonas campestris* pv. Vesicatorai, Brazilain Journal of Genetics 19: 551-554).

Example 5: A Tumor-Targeted Bacterium Expressing a *Vibrio alginolyticus* Multicopper Oxidase Protein The expression plasmid of Example 1 above is used to operably link a DNA encoding the amino acid sequence

SEQ ID NO: 7:
MDISRRRFLQSSLAISALTVLPACSLSRSTNKQGQYIYDITAEPSTAELV

PGFNTDVLAFNGSIPAPTIRCRQGEKVIIRFINKLSEPTTIHWHGLRIPI

EMDGVPFLSQPPIMPGETFVYEFTPPDAGTFWYHPHMNSVKQLGMGLVGL

IIVEEAEPVLFDEEQEIVLKHWHLDKQGQWKNLMVPRLSARMGTPGEWSS

VNGVHEPVYALKQNATTRLRIANVDNTITYPIAIEGAEAWVIAIDGNPVK

APYKLIQHKIGPGMRLDVGLIAPKAGTRVYVRRMKGRFPFPLCEFDVVES

DLPSNQKLPLLPLNPVPALDLKNAEQIDYVFEWEGAITPADKSGKAIPQF

WLMNKRAWEGMSKDNIPAPLSTLEMGKTYIFNLKNVTQYHHPIHLHGHTF

TVLELDGKKLDEPFHTDTVLLGKSGSAKAAFVADNPGRWMYHCHVIEHMK

TGLMGYIEVK

Measurement of copper accumulation can utilize any of the methods known to those skilled in the art, such as atomic absorption spectrophotometry (de A. Ramos and Rosato 1996, Copper accumulation in *Xanthomonas campestris* pv. Vesicatorai, Brazilain Journal of Genetics 19: 551-554), copper selective electrodes and mass spectroscopy (Berson and Lidstrom 1996, Study of copper accumulation by the Type I methanotroph *Methylomicrobium albus* BG8, Environ. Sci. Technol 30: 802-809.

Example 6: A Tumor-Targeted Bacterium Expressing a *Vibrio alginolyticus* Copper/Silver Resistance Protein The expression plasmid of Example 1 above is used to operably link a DNA encoding the amino acid sequence

SEQ ID NO: 8:
MKTLKIATIALIVGGALGFGANHFLAGSTHDMSAMGGESAASSNDPLYWV

APMDPNYKRDKPGKSPMGMDLIPVYAEDLSGEQDAPGTVTIDPSVENNLG

VKTANATLQQLSPRIETVGYIAFDESLLWQTNVRVAGWVEKLYINAVGEK

Example 7: A Tumor-Targeted Bacterium Expressing the *Pseudomonas syringae* Copper Resistance Proteins The expression plasmid of Example 1 above is used to operably link a DNA encoding the amino acid sequences below. It is understood that the sequences may be expressed as a polycistronic construct, whereby following each of the stop codons, a ribosomal binding site is positioned appropriately before the start codon for the next sequence using methods known to those skilled in the art.

SEQ ID NO: 9:
CopA
MESRTSRRTFVKGLAAAGVLGGLGLWRSPSWAASGSPALSVLSGTEFDLS
IGEMPVNITGRRRTAMAINGGLPGPLLRWKEGDTVTLRVRNRLDAATSIH
WHGIILPPNMDGVPGLSFAGIEPGGVVYQFKVQQNGTYWYHSHSGFQEQ
VGVYGPLVIEAKEPEPFKYDSEHVVMLTDWIDEDPVSLMRTLKKQSDYYN
FHKRTVGDFVNDVADKGWAATVADRKMWAEMKMNPTDLADVSGATYTYLL
NGQAPNMNWTGLFRPGEKLRLRFINGSAMTYFDIRIPGLKMTVVASDGQF
VNPVEVDELRIAVAETFDVIVEPTAEAYTVFAQSMDRTGYARGTLAVREG
LVAQVPPLDPRPLVTMDDMGMGGMDHGSMDGMSGMDSGADDGMQTMSSMG
GDSMPAMDHSKMSTMQGMDHGAMSGMDHGAMGGMVMQSHPASENDNPLVD
MQAMSPTAKLNDPGLGLRNNGRKVLTYADLKSTFEDPDGREPSRTIELHL
TGHMEKFAWSFDGIKFADAQPLILKYGERVRIVLVNDTMMTHPIHLHGMW
SDLEDEDGNFRVRKHTIDMPPGSKRSYRVTADALGRWAYHCHLLYHMEMG
MFREVRVEE

SEQ ID NO: 10:
CopB
MTVLNRLHVCSLLAVSSLGMLPVGVFAAEAAMPGVDHSQMQGMDHSKMQG
MDHSQMQGMDHSKMQGMDHSQMQGMDSDMITMAPSKPAAPTQSRTPIAPV
TDANRAAVYRSAKGHTVHDEAANYFLLFDQLEWQDADNGSVLNWDVNGWV
GGDIDRLWIRSEGERTNGKTFSAELQALWGHAISPWWDLVGGVRQDFKPG
SPQTWAAFGLQGLALYNFEAEATAFLGEGGQTGLRLEGDYDILLTNRLIL
QPTAEVNFYGQSDPQRGIGSGLSETEVGVRLRYEIRREFAPYIGVTWNRS
YGNTADFAREEGEDRSEARLVLGVRMWF
VKKGDVLFTLYSPELVKAQEELLNAYRTGRKGLVKGATERLVTLGVDRAQ
IKSITRSGKASQTIEIKAPADGVIASLNVREGGYLSPAQAVISAGPLDNV
WVDAEVFERQAHWMKAGSQATMILDAIPGNEWQGVVDYVYPILDPKTRTL
RVRLKFPNPDGALKPNMFANIALQPVTDHAVLTIPKSSVIRSGGMTRVVL
AEGEGKYRSARIEVGREAGEQIEVLQGLKQGDKIVISSHFMLDSESSQSA
DLSRINGVEAAAETAWAKGEITDVMKDHRMLTINHQPVPEWDWPGMVMNF
TFADGVEMGDLKKGQAIEFEMQKTESGQYQIIDYKADNSVIAAEVWLIGD
ISMLMTDFGMITLNHLPVAEWNWDAGEMNFSVGEDVDLSGFEEGQKVRFL
VEKQGSDYVLKQLVPATIAVEG

SEQ ID NO: 11:
CopC
MLLNRTSFVTLFAAGMLVSALAQAHPKLVSSTPAEGSEGAAPAKIELHFS
ENLVTQFSGAKLVMTAMPGMEHSPMAVKAAVSGGGDPKTMVITPASPLTA
GTYKVDWRAVSSDTHPITGSVTFKVK

SEQ ID NO: 12:
CopD
MEDPLSIAVRFALYTDLMMLFGLALFGLYSLRGAERRSGAVLPFRPLLSA
TALIGLLLSVVSIVLMAKAMSGASEWLEAVPHAEMMVTQTELGTAWLIRM
AALVGAAVTIAFNLRVPMASLLMVSLLGGVALATLAWIGHGAMDEGSRRF
WHFSADILHLWSSGGWFGALVAFALMLRPNKVETLQSVQVLSRTLSGFER
AGAVIVAFIVLSGVVNYLFIVGPQVSGVVESTYGVLLLGKLALFGLMVGL
ASANRFVLSPAFERAVHRGEYARAARSIRYSMALELGAAVLVLGLIAWLG
TLSPEMEAGM

These peptides are known to be encoded by the following sequence GenBank: M19930.1 (Mellano and Cooksey 1988, Nucleotide sequence and organization of copper resistance genes from *Pseudomonas syringae* pv. tomato J. Bacteriol. 170: 2879-2883).

SEQ ID NO: 13:
ctgcagatactaaaaaaactgaaagctctaaggcatgttgctaaccaacg
caggattcaagcttacagaaatgtaatcgcgccgcttacgatgctgtgac
atcgtccactccagtaccttaaacccagtacacggcttaaatgccgtcct
tgcctacctggacccgcgcgtatggaatcaagaacttctcgacgtacttt
cgtcaaaggcctcgcggctgccggcgtgctaggtgggctaggcttgtggc
gttcgcccagctgggcggcgtccggctcgccggcgctcagcgtgagagcg
gtacggagttcgacctgtctattggcgagatgccggtaaacatcaccggc
aggcgtcgcacagcgatggcgatcaatggcgggctgccgggcccctgct
gcgctggaaagagggtgacactgtcacgctccgggtacgcaaccggctcg
acgctgcaacctccatacactggcacggcattatcctgccgccgaacatg
gacggcgttccaggactgagcttcgcgggcatcgagccgggtggcgtgta
cgtctaccagttcaaggtccaacagaacgggacgtactggtaccacagcc
actccggatttcaggagcaggtggggtgtatggcccgctcgtcatcgag
gcgaaagagcccgagccttcaagtacgacagtgaacatgtggtgatgct
gaccgactggacggatgaagatcccgtctcgctgatgcgtaccctcaaaa
agcagtccgattactacaacttccacaagcgcacagtcggtgacttcgtc
aacgatgtggctgataagggctgggccgcaaccgtcgcggatcgcaagat
gtgggccgagatgaagatgaacccacggaccttgcggacgtgagcgggg
ccacctacacgtacctgctcaatggtcaggccccaatatgaactggacc
ggcttgttccgtcctggcgaaaagctgcgcctgcggttcatcaacggctc
ggctatgacgtacttcgacatccgtattccaggcctgaaaatgaccgtgg
tagcttcggatggccagttcgtgaacccggttgaggtcgatgaattacgc
attgccgtggccgaaaccttcgatgtgatcgttgagcccactgccgaggc
gtatacggtcatgctcaatccatggatcgcacgggctacgcccgcggcac -continued
```
cctagccgtgcgggaaggcttggtagcccaggtcccccccttgatcctc
gtccgctggtcacgatggacgatatgggcatgggtggtatggaccatggc
agcatggatggcatgagcggcatggattcgggtgccgacgacggcatgca
gaccatgagcagcatgggggcgactccatgcccgccatggaccatagca
aaatgtctaccatgcagggtatggaccacggcgctatgtcgggcatggac
catggtgcgatgggcggcatggtgatgcagagccaccctgccagcgagaa
cgacaacccgctggtggacatgcaggccatgagccctaccgccaagctga
acgatcctggcctgggcctgcgtaataacgggcgcaaggtgctcacctat
gccgaccttaaaagcaccttcgaagaccctgacgggcgtgagccgagccg
gaccattgagctgcacctgaccgggcacatggaaaaatttgcatggtcgt
ttgacggcatcaaattcgcggacgcccaacctctgatactcaaatacggc
gaacgggtaagaatcgtgctggtgaatgacacgatgatgactcacccgat
ccatctgcatggatgtggagtgacttggaggacgaggacggaaacttca
gggtgcgcaagcacaccattgatatgccgccaggctccaagcgcagctac
cgtgtcaccgctgatgcctggggcgctgggcctatcactgtcacctgct
ctaccacatggagatgggtatgttccgcgaagttcgggtagaggagtgag
gccaatgactgattgaatagactccacgtagttcactgctcgcggtcagc
agcctgggaatgctcccagtgggcgtgtagcggcagaggccgctatgccg
ggcgtggaccacagccagatgcaaggcatggatcattccaagatgcaggg
tatggaccacagccagatgcagggcatggatcattccaaaatgcaggta
tggaccatagccagatgcagggcatggactcggacatgacgaccatggcc
cccagcaagcctgcggcaccgacacaaagccgcacgcctattgcgcctgt
caccgatgccaatcgggctgcggtctaccgaagtgccaaaggccacactg
tccatgacgaagcagctaattatacctgctcttcgatcaactcgaatggc
aggacgccgacaacggcagcgtccttaattgggacgttaacggctgggtg
ggtggtgacatcgaccggctctggattcgctccgagggcgaacgtaccaa
cggcaagaccgaatcggccgagctgcaagcgctgtggggccatgcgatca
gtccaggtgggacctggtcggcggcgtccggcaggacttcaagccaggct
cgccgcaaacctgggctgcatttggcctccagggcctcgctttatacaac
ttcgaagccgaagcgactgcgtacttggtgaaggcggccaaaccgggtta
aggctggaaggcgactacgacattagctgactaaccggctgatatacagc
ccacggctgaggttaatactacggtcagagcgatcctcagcgcggcatcg
gctctggcctgtctgaaaccgaagtcggcgtacgactgcgctacgaaatc
cgccgcgagtagcccgtacattggcgtcacctggaaccgctcctacggc
aatacagccgactagcccgcgaggaaggcgaggaccgcagcgaggcccgc
ttagtcctgggcgtgcgcatgtggactgagccgactagtctgaaaatctg
atccccacgaacggccatttgggctgtaaggagttcgcatgagttgaac
cgcacaagatcgtcacgctcatgccgctgggatgctggtcagcgcattgg
cccaagcccaccccaagctggtgtcttcgactccggctgaaggtagtgaa
ggcgcggcccctgccaagatcgagctgcatactccgaaaacctggttacc
caattaccggcgcgaagctggtcatgacggcgatgccaggcatggaacac
```
-continued
```
tcaccgatggcagtcaaagccgcggtatcgggcgggggtgaccccaagac
catggtgattacccggcctcacctctgacggcaggcacctacaaggtcg
attggcgggcagtgtcaccgatacccacccgattaccggtagcgtgacga
taaggtcaagtaaacatggaagatccgctcagcatcgcagttcgatcgcg
ctgtataccgatttgatgatgctgacgggctggccctctaggccatacag
cctacgcggcgcagaacgccgttcgggcgctgtattgccatcaggcccca
ctgagcgcgaccgctttgatcggcctgctgagtcggagtctccattgtgc
tcatggccaaagccatgagcggtgcgtctgaatggctagaggctgtgcct
cacgccgagatgatggtgacgcagacggagcaggcactgcctggctcatc
cgcatggccgcactggtgggggctgctgtgaccatcgccttcaaccttcg
ggtgcccatggcaagcctgctgatggatcgctgctgggaggcgtggccct
ggcgaccttggcctggacgggccacggggccatggacgaaggctcccggc
gcttaggcacttcagcgcggacatccttcatctgtggtcctcgggcggct
ggttcggcgcgctggtggcgtagcactgatgctgcggcccaacaaggtcg
aaaccctacagtcagtccaggtgctgtcgcgcacgctcagcggatcgaac
gggccggcgcggtgatcgtggcatcatcgtcctctcgggcgtggtgaact
atctgacatcgtcggccccaggtcagtggtgtggtggaaagcacctacg
gggtgagctgctgggcaagctggcactgtaggccttatggtcggattggc
ctcagctaaccgctagtcctgagcccggcgatgaacgggcggtccaccgg
ggcgagtacgcgcgagcggcccgctcgatccgctacagcatggccctgga
actgggcgccgccgtcaggtgagggcctgattgcctggcttggcacactg
tcccctgagatggaagcggggatgtgagtgtgcctgaccctgattaccgt
cacactgggccggtgccgtggagggtcgaacatgaaactgctggtagccg
aagacgaacctaaaactggaatctatctgcag
```

Determination of copper sensitivity can be performed by any of the means known to those skilled in the art, such as the methods of Achard et al., 2010 (The multi-copper-ion oxidase CueO of *Salmonella enterica* serovar *typhimurium* is required for systemic virulence. Infect Immun 78: 2312-2319) or de A. Ramos and Rosato 1996 (Copper accumulation in *Xanthomonas campestris* pv. Vesicatorai, Brazilain Journal of Genetics 19: 551-554).

Example 8: A Tumor-Targeted Bacterium Expressing the *Xanthomonas* Copper Resistance Proteins The expression plasmid of Example 1 above is used to operably link a DNA encoding the amino acid sequences of genes copL, copA, copB, copM copG copC, copD, and copF described by (Behlau 2011, Molecular Characterization of Copper Resistance Genes from *Xanthomonas citri* subsp. *citri* and *Xanthomonas alfalfae* subsp. *citrumelonis,* 77: 4089-4096) may be expressed as a polycistronic construct, whereby following each of the stop codons, a ribosomal binding site is positioned appropriately before the start codon for the next sequence using methods known to those skilled in the art. Alternatively, the promoter and genes from the inducible plasmid may be inserted into the chromosome using methods known to those skilled in the art.

Determination of copper sensitivity can be performed by any of the means known to those skilled in the art, such as the methods of Achard et al., 2010 (The multi-copper-ion oxidase CueO of *Salmonella enterica* serovar *typhimurium* is required for systemic virulence. Infect Immun 78: 2312-2319) or de A. Ramos and Rosato 1996 (Copper accumulation in *Xanthomonas campestris* pv. Vesicatorai, Brazilain Journal of Genetics 19: 551-554).

Example 9: A Tumor-Targeted Bacterium Expressing the Yersiniabactin Biosynthesis Genes The expression plasmid of Example 1 above is used to operably link a DNA encoding the amino acid sequences of genes ybtE (irp5), ybtT, irp1 (HLMWP1), irp2 (HLMWP2), and ybrS (Irp9) described by (Parkhill et al., 2001, Genome sequence of *Yersinia pestis*, the causative agent of plague Nature 413 (6855), 523-527) may be expressed as a polycistronic construct, whereby following each of the stop codons, a ribosomal binding site is positioned appropriately before the start codon for the next sequence using methods known to those skilled in the art. Alternatively, the promoter and genes from the inducible plasmid may be inserted into the chromosome using methods known to those skilled in the art.

SEQ ID NO: 14:
YbtE
MNSSFESLIEQYPLPIAEQLRHWAARYASRIAVVDAKGSLTYSALDAQVD
ELAAGLSSLGLRSGEHVIVQLPNDNAFVTLLFALLRLGVIPVLAMPSQRA
LDIDALIELAQPVAYVIHGENHAELARQMAHKHACLRHVLVAGETVSDDF
TPLFSLHGERQAWPQPDVSATALLLLSGGITGTPKLIPRRHADYSYNFSA
SAELCGISQQSVYLAVLPVAHNFPLACPGILGTLACGGKVVLTDSASCDE
VMPLIAQERVTHVALVPALAQLWVQAREWEDSDLSSLRVIQAGGARLDPT
LAEQVIATFDCTLQQVFGMAEGLLCFTRLDDPHATILHSQGRPLSPLDEI
RIVDQDENDVAPGETGQLLTRGPYTISGYYRAPAHNAQAFTAQGFYRTGD
NVRLDEVGNLHVEGRIKEQINRAGEKIAAAEVESALLRLAEVQDCAVVAA
PDILLGERICAFIIAQQVPTIDYQQLRQQLTRMGLSAWKIPDQIEFLDHW
PLTAVGKIDKKRLTALAVDRYRHSAQ

SEQ ID NO: 15:
YbtT
MIQSAMCIPLWPARNGNTAHLVMCPFAGGSSSAFRHWQAEQLTDCALSLV
IWPGRDRLRHLEPLRSITQLAALLANELEASVSPDTPLLLAGHSMGAQVA
FETCRLLEQRGLAPQGLIISGCHAPHLHSERQLSHRDDADFIAELIDIGG
CSPELRENQELMSLFLPLLRADFYATESYHYDSPDVCPPLRIPALLLCGS
HDREASWQQVDAWRQWLSHVIGPVVIDGDHFYPIQQARSFFTQIVRHFPH
AFSAMTALQKQPSTSER

SEQ ID NO: 16:
YbtU
MMPSASPKQRVLIVGAKFGEMYLNAFMQPPEGLELVGLLAQGSARSRELA
HAFGIPLYTSPEQIIRMPDIACIVVRSTVAGGTGTQLARHFLTRGVHVIQ
EHPLHPDDISSLQTLAQEQGCCYWVNTFYPHTRAGRTWLRDAQQLRRCLA
KTPPVVHATTSRQLLYSTLDLLLLALGVDAAAVECDVVGSFSDFHCLRLF
WPEGEACLLLQRYLDPDDPDMHSLIMHRLLLGWPEGHLSLEASYGPVIWS
SSLFVADHQENAHSLYRRPEILRDLPGLIRSAAPLSWRDCCETVGPEGVS
WLLHQLRSHLAGEHPPAACQSVHQIALSRLWQQILRKIGNAEIRRLIPPH
HDRLAGFYNDDDKEAL

SEQ ID NO: 17:
IrpI
MDNLRFSSAPTADSIDASIAQHYPDCEPVAVIGYACHFPESPDGETFWQN
LLEGRECSRRFTREELLAVGLDAAIIDDPHYVNIGTVLDNADCFDATLFG
YSRQEAESMDPQQRLFLQAVWHALEHAGYAPGAVPHKTGVFASSRMSTYP
GREALNVTEVAQVKGLQSLMGNDKDYIATRAAYKLNLHGPALSVQTACSS
SLVAVHLACESLRAGESDMAVAGGVALSFPQQAGYRYQPGMIFSPDGHCR
PFDASAEGTWAGNGLGCVVLRRLRDALLSGDPIISVILSSAVNNDGNRKV
GYTAPSVAGQQAVIEEALMLAAIDDRQVGYIETHGTGTPLGDAIEIEALR
NVYAPRPQDQRCALGSVKSNMGHLDTAAGIAGLLKTVLAVSRGQIPPLLN
FHTPNPALKLEESPFTIPVSAQAWQDEMRYAGVSSFGIGGINCHMIVASL
PDALNRARLPNIDSGRKSTALLLSAASDSALRRLATDYAGALRENADASSL
AFTALHARRLDLPFRLAAPLNRETAEALSAWAGEKSGALVYSGHGASGKQ
VWLFTGQGSHWRIMGQIMYQHSTAFADTLDRCFSACSEMLIPSLREAMFN
PDSAQLDNMAWAQPAIVAFEIAMAAHWRAEGLKPDFAIGHSVGEFAAAVV
CGHYTIEQVMPLVCRRGALMQQCASGAMVAVFADEDTLMPLARQFELDLA
ANNGTQHTVFSGPEARLAVFCATLSQHDINYRRLSVTGAAHSALLEPILD
RFQDACAGLHAEPGQIPIISTLTADVIDESTLNQADYWRRHMRQPVRFIQ
SIQVAHQLGARVFLEMGPDAQLVACGQREYRDNAYWIASARRNKEASDVL
NQALLQLYAAGVALPWADLLAGDGQRIAAPCYPFDTERYWKERVSPACEP
ADAALSAGLEVASRAATALDLPRLEALKQCATRLHAIYVDQLVQRCTGDA
IENGVDAMTIMRRGRLLPRYQQLLQRLLNNCVVDGDYRCTIDGRYVRARP
IEHQQRESLLTELAGYCEGFQAIPDTIARAGDRLYEMMSGAEEPVAIIFP
QSASDGVEVLYQEFSFGRYFNQIAAGVLRGIVQTRQPRQPLRILEVGGGT
GGTTAWLLPELNGVPALEYHFTDISALFTRRAQQKFADYDFVKYSELDLE
KEAQSQGFQAQSYDLIVAANVIHATRHIGRILDNLRPLLKPGGRLLMREI
TQPMRLFDFVFGPLVLPLQDLDAREGELFLTTAQWQQQCRHAGFSKVAWL
PQDGSPTAGMSEHIILATLPGQAVSAVTFTAPSEPVLGQALTDNGDYLAD
WSDCAGQPERFNARWQEAWRLLSQRHGDALPVEPPPVAAPEWLGKVRLSW
QNEAFSRGQMRVEARHPTGEWLPLSPAAPLPAPQTHYQWRWTPLNVASID
HPLIFSFSAGTLARSDELAQYGIIHDPHASSRLMIVEESEDTLALAEKVI
AALTASAAGLIVVIRRAWRVEENEALSASHHALWALLRVAANEQPERLLA
AIDLAENTPWETLHQGLSAVSLSQRWLAARGDTLWLPSLAPNTGCAAELP
ANVFTGDSRWHLVTGAFGGLGRLAVNWLREKGARRIALLAPRVDESWLRD
VEGGQTRVCRCDVGDAGQLATVLDDLAANGGIAGAIHAAGVLADAPLQEL
DDHQLAAVFAVKAQAASQLLQTLRNHDGRYLILYSSAAATLGAPGQSAHA
LACGYLDGLAQQFSTLDAPKTLSVAWGAWGESGRAATPEMLATLASRGMG
ALSDAEGCWHLEQAVMRGAPWRLAMRVFTDKMPPLQQALFNISATEKAAT

```
PVIPPADDNAFNGSLSDETAVMAWLKKRIAVQLRLSDPASLHPNQDLLQL
GMDSLLFLELSSDIQHYLGVRINAERAWQDLSPHGLTQLICSKPEATPAA
SQPEVLRHDADERYAPFPLTPIQHAYWLGRTHLIGYGGVACHVLFEWDKR
HDEFDLAILEKAWNQUARHDMLRMVVDADGQQRILATTPEYHIPRDDLRA
LSPEEQRIALEKRRHELSYRVLPADQWPLFELVVSEIDDCHYRLHMNLDL
LQFDVQSFKVMMDDLAQVWRGETLAPLAITFRDYVMAEQARRQTSAWHDA
WDYWQEKLPQLPLAPELPVVETPPETPHFTTFKSTIGKTEWQAVKQRWQQ
QGVTPSAALLTLFAATLERWSRTTTFTLNLTFFNRQPIHPQINQLIGDFT
SVTLVDFNFSAPVTLQEQMQQTQQRLWQNMAHSEMNGVEVIRELGRLRGS
QRQPLMPVVFTSMLGMTLEGMTIDQAMSHLFGEPCYVFTQTPQVWLDHQV
MESDGELMFSWYCMDNVLEPGAAEAMFNDYCAILQAVIAAPESLKTLASG
IAGHIPRRRWPLNAQADYDLRDIEQATLEYPGIRQARAEITEQGALTLDI
VMADDPSPSAAMPDEHELTQLALPLPEQAQLDELEATWRWLEARALQGIA
ATLNRHGLFTTPEIAHRFSAIVQALSAQASHQRLLRQWLQCLTEREWLIR
EGESWRCRIPLSEIPEPQEACPQSQWSQALAQYLETCIARHDALFSGQCS
PLELLFNEQHRVIDALYRDNPASACLNRYTAQIAALCSAERILEVGAGTA
ATTAPVLKATRNTRQSYHFTDVSAQFLNDARARFHDESQVSYALFDINQP
LDFTAHPEAGYDLIVAVNVLHDASHVVQTLRRLKLLLKAGGRLLIVEATE
RNSVFQLASVGFIEGLSGYRDFRRRDEKPMLIRSAWQEVLVQAGFANELA
WPAQESSPLRQHLLVARSPGVNRPDKKAVSRYLQQRFGTGLPILQIRQRE
ALFTPLHAPSDAPTEPAKPTPVAGGNPALEKQVAELWQSLLSRPVARHHD
FFELGGDSLMATRMVAQLNRRGIARANLQDLFSHSTLSDFCAHLQAATSG
EDNPIPLCQGDGEETLFVFHASDGDISAWLPLASALNRRVFGLQAKSPQR
FATLDQMIDEYVGCIRRQQPHGPYVLAGWSYGAFLAAGAAQRLYAKGEQV
RMVLIDPVCRQDFCCENRAALLRLLAEGQTPLALPEHFDQQTPDSQLADF
ISLAKTAGMVSQNLTLQAAETWLDNIAHLLRLLTEHTPGESVPVPCLMVY
AAGRPARWTPAETEWQGWINNADDAVIEASHWQIMMEAPHVQACAQHITR
WLCATSTQPENTL
SEQ ID NO: 18:
Irp2
MISGAPSQDSLLPDNRHAADYQQLRERLIQELNLTPQQLHEESNLIQAGL
DSIRLMRWLHWFRKNGYRLTLRELYAAPTLAAWNQLMLSRSPENAEEETP
PDESSWPNMTESTPFPLTPVQHAYLTGRMPGQTLGGVGCHLYQEFEGHCL
TASQLEQAITTLLQRHPMLHIAFRPDGQQVWLPQPYWNGVIVHDLRHNDA
ESRQAYLDALRQRLSHRLLRVEIGETFDFQLTLLPDNRHRLHVNIDLLIM
DASSFTLFFDELNALLAGESLPAIDTRYDFRSYLLHQQKINQPLRDDARA
YWLAKASTLPPAPVLPLACEPATLREVRNTRRRMIVPATRWHAFSNRAGE
YGVIPTMALATCFSAVLARWGGLTRLLLNITLFDRQPLHPAVGAMLADFT
NILLLLDTACDGDTVSNLARKNQLTFTEDWEHRHWSGVELLRELKRQQRYP
HGAPVVFTSNLGRSLYSSRAESPLGEPEWGISQTPQVWIDHLAFEHHGEV
WLQWDSNDALFPPALVETLFDAYCQLINQLCDDESAWQKPFADMMPASQR
AIRERVNATGAPIPEGLLHEGIFRIALQQPQALAVTDMRYQWNYHELTDY
ARRCAGRLIECGVQPGDNVAITMSKGAGQLVAVLAVLLAGAVYVPVSLDQ
PAARREKIYADASVRLVLICQHDASAGSDDIPVLAWQQAIEAEPIANPVV
RAPTQPAYIIYTSGSTGTPKGVVISHRGALNICCDINTRYQVGPHDRVLA
LSALHFDLSVYDIFGVLRAGGALVMVMENQRRDPHAWCELIQRHQVTLWN
SVPALFDMLLTWCEGFADATPENLRAVMLSGDWIGLDLPARYRAFRPQGQ
FIAMGGATEASIWSNACEIHDVPAHWRSIPYGFPLINQRYRVVDEQGRDC
PDWVPGELWIGGIGVAEGYFNDPLRSEQQFLTLPDERWYRTGDLGCYWPD
GTIEFLGRRDKQVKVGGYRIELGEIESALSQLAGVKQATVLAIGEKEKTL
AAYVVPQGEAFCVTDHRNPALPQAWHTLAGTLPCCAISPEISAEQVADFL
QHRLLKLKPGHTAGADPLPLMNSLAIQPRWQAVVERWLAFLVTQRRLKPA
AEGYQVCAGEEREDEHPHFSGHDLTLSQILRGARNELSLLNDAQWSPESL
AFNHPASAPYIQELATICQQLAQRLQRPVRLLEVGIRTGRAAESLLAQLN
AGQIEYVGLEQSQEMLLSARQRLAPWPGARLSLWNADTLAAHAHSADIIW
LNNALHRLLPEDPGLLATLQQLAVPGALLYVMEFRQLTPSALLSTLLLIN
GQPEALLHNSADWAALFSAAAFNCQHGDEVAGLQRFLVQCPDRQVRRDPR
QLQAALAGRLPGWMVPQRIVFLDALPLTANGKIDYQALKRRHTPEAENPA
EADLPQGDIEKQVAALWQQLLSIGNVTRETDFFQQGGDSLLATRLTGQLH
QAGYEAQLSDLFNHPRLADFAATLRKTDVPVEQPFVHSPEDRYQPFALTD
VQQAYLVGRQPGFALGGVGSHFFVEFEIADLDLTRLETVWNRLIARHDML
RAIVRDGQQQVLEQTPPWVIPAHTLHTPEEALRVREKLAHQVLNPEVWPV
FDLQVGYVDGMPARLWLCLDNLLLDGLSMQILLAELEHGYRYPQQLLPPL
PVTFRDYLQQPSLQSPNPDSLAWWQAQLDDIPPAPALPLRCLPQEVETPR
FARLNGALDSTRWHRLKKRAADAHLTPSAVLLSVWSTVLSAWSAQPEFTL
NLTLFDRRPLHPQINQILGDFTSLMLLSWHPGESWLHSAQSLQQRLSQNL
NHRDVSAIRVMRQLAQRQNVPAVPMPVVFTSALGFEQDNFLARRNLLKPV
WGISQTPQVWLDHQIYESEGELRFNWDFVAALFPAGQVERQFEQYCALLN
RMAEDESGWQLPLAALVPPVKHAGQCAERSPRVCPEHSQPHIAADESTVS
LICDAFREVVGESVTPAENFFEAGATSLNLVQLHVLLQRHEFSTLTLLDL
FTHPSPAALADYLAGVATVEKTKRPRPVRRRQRRI
EXAMPLE 9:
SEQ ID NO: 19:
Irp9 (YbtS)
MKISEFLHLALPEEQWLPTISGVLRQFAEEECYVYERQPCWYLGKGCQAR
LHINADGTQATFIDDAGEQKWAVDSIADCARRFMAHPQVKGRRVYGQVGF
NFAAHARGIAFNAGEWPLLTLTVPREELIFEKGNVTVYADSADGCRRLCE
WVKEAGTTTQNAPLAVDTALNGEAYKQQVARAVAEIRRGEYVKVIVSRAI
PLPSRIDMPATLLYGRQANTPVRSFMFRQEGREALGFSPELVMSVIGNKV
VTEPLAGTRDRMGNPEHNKAKEAELLHDSKEVLEHILSVKEAIAELEAVC
QPGSVVVEDLMSVRQRGSVQHLGSGVSGQLAENKDAWDAFTVLFPSITAS
GIPKNAALNAIMQIEKTPRELYSGAILLLDDTRFDAALVLRSVFQDSQRC
WIQAGAGIIAQSTPERELTETREKLASIAPYLMV
```

Example 10: Pharmaceutically Acceptable Formulations

Pharmaceutically acceptable formulations may be provided for delivery by other various routes e.g. by intramuscular injection, subcutaneous delivery, by intranasal delivery (e.g. WO2000/47222, U.S. Pat. No. 6,635,246), intradermal delivery (e.g. WO2002/074336, WO2002/067983, WO2002/087494, WO2002/0832149 WO2004/016281) by transdermal delivery, by transcutaneous delivery, by topical routes, etc. Injection may involve a needle (including a microneedle), or may be needle-free. See, e.g., U.S. Pat. Nos. 7,452,531, 7,354,592, 6,962,696, 6,923,972, 6,863,894, 6,685,935, 6,475,482, 6,447,784, 6,190,657, 6,080,849 and 20030059400.

Bacterial vector vaccines are known, and similar techniques may be used for the present bacteria as for bacterial vaccine vectors (U.S. Pat. No. 6,500,419, Curtiss, In: New Generation Vaccines: The Molecular Approach, Ed., Marcel Dekker, Inc., New York, N.Y., pages 161-188 and 269-288 (1989); and Mims et al, In: Medical Microbiology, Eds., Mosby-Year Book Europe Ltd., London (1993)). These known vaccines can enter the host, either orally, intranasally or parenterally. Once gaining access to the host, the bacterial vector vaccines express an engineered prokaryotic expression cassette contained therein that encodes a foreign antigen(s). Foreign antigens can be any protein (or part of a protein) or combination thereof from a bacterial, viral, or parasitic pathogen that has vaccine properties (New Generation Vaccines: The Molecular Approach, supra; Vaccines and Immunotherapy, supra; Hilleman, Dev. Biol. Stand., 82:3-20 (1994); Formal et al, Infect. Immun. 34:746-751 (1981); Gonzalez et al, J. Infect. Dis., 169:927-931 (1994); Stevenson et al, FEMS Lett., 28:317-320 (1985); Aggarwal et al, J. Exp. Med., 172:1083-1090 (1990); Hone et al, Microbial. Path., 5:407-418 (1988); Flynn et al, Mol. Microbiol., 4:2111-2118 (1990); Walker et al, Infect. Immun., 60:4260-4268 (1992); Cardenas et al, Vacc., 11:126-135 (1993); Curtiss et al, Dev. Biol. Stand., 82:23-33 (1994); Simonet et al, Infect. Immun., 62:863-867 (1994); Charbit et al, Vacc., 11:1221-1228 (1993); Turner et al, Infect. Immun., 61:5374-5380 (1993); Schodel et al, Infect. Immun., 62:1669-1676 (1994); Schodel et al, J. Immunol., 145:4317-4321 (1990); Stabel et al, Infect. Immun., 59:2941-2947 (1991); Brown, J. Infect. Dis., 155:86-92 (1987); Doggett et al, Infect. Immun., 61:1859-1866 (1993); Brett et al, Immunol., 80:306-312 (1993); Yang et al, J. Immunol., 145:2281-2285 (1990); Gao et al, Infect. Immun., 60:3780-3789 (1992); and Chatfield et al, Bio/Technology, I0:888-892 (1992)). Delivery of the foreign antigen to the host tissue using bacterial vector vaccines results in host immune responses against the foreign antigen, which provide protection against the pathogen from which the foreign antigen originates (Mims, The Pathogenesis of Infectious Disease, Academic Press, London (1987); and New Generation Vaccines: The Molecular Approach, supra). See also: Formal et al, Infect. Immun., 34:746-751 (1981); Wick et al, Infect. Immun., 62:4542-4548 (1994)); Hone et al, Vaccine, 9:810-816 (1991); Tacket et al, Infect. Immun., 60:536-541 (1992); Hone et al, J. Clin. Invest., 90:412-420 (1992); Chatfield et al, Vaccine, 10:8-11 (1992); Tacket et al, Vaccine, I0:443-446 (1992); van Damme et al, Gastroenterol., 103:520-531 (1992) (*Yersinia pestis*), Noriega et al, Infect. Immun., 62:5168-5172 (1994) (*Shigella* spp), Levine et al, In: *Vibrio cholerae*, Molecular to Global Perspectives, Wachsmuth et al, Eds, ASM Press, Washington, D.C., pages 395-414 (1994) (*Vibrio cholerae*), Lagranderie et al, Vaccine, 11:1283-1290 (1993); Flynn, Cell. Molec. Biol., 40 (Suppl.I):31-36 (1994) (*Mycobacterium* strain BCG), Schafer et al, J. Immunol., 149:53-59 (1992) (*Listeria monocytogenes*).

In a specific embodiment, it may be desirable to administer the pharmaceutical compositions of the technology locally to the area in need of treatment; this may be achieved by, for example, and not by way of limitation, local infusion during surgery, by injection, by means of a catheter, or by means of an implant, said implant being of a porous, non-porous, or gelatinous material, including membranes, such as silastic membranes, or fibers. In one embodiment, administration can be by direct injection at the site (or former site) of a malignant tumor or neoplastic or pre-neoplastic tissue.

The attenuated tumor-targeted bacteria comprising one or more primary effector molecules and optionally, one or more secondary effector molecules may be delivered in a controlled release system. The attenuated tumor-targeted bacteria comprising one or more fusion proteins of the technology and optionally, one or more effector molecules may also be delivered in a controlled release system. In one embodiment, a pump may be used (see Langer, supra; Sefton, CRC Crit. Ref. Biomed. Eng. 14:201 (1987); Buchwald et al., 1980, Surgery 88:507; and Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem: 23:61 (1983); see also Levy et al., 1985, Science 228:190; During et al., 1989, Ann. Neurol. 25:351; and Howard et al., 1989, J. Neurosurg. 71:105). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (1990, Science 249:1527-1533) and may be used in connection with the administration of the attenuated tumor-targeted bacteria comprising one or more primary effector molecule(s) and optionally, one or more secondary effector molecule(s).

The technology also provides a pharmaceutical pack or kit comprising one or more containers filled with one or more of the ingredients of the pharmaceutical compositions of the technology. Optionally associated with such container(s) can be a notice in the form prescribed by governmental agency regulating the manufacture, use or sale of pharmaceuticals or biological products, which notice reflects approval by the agency of manufacture, use or sale for human administration.

The present technology also provides methods for treating a solid tumor comprising administering to a human or animal in need thereof, a pharmaceutical composition of the technology and at least one other known cancer therapy. In a specific embodiment, a human or animal with a solid tumor cancer is administered a pharmaceutical composition of the technology and at least one chemotherapeutic agent. Examples of chemotherapeutic agents include, but are not limited to, cisplatin, ifosfamide, taxanes such as taxol and paclitaxol, topoisomerase I inhibitors (e.g., CPT-11, topotecan, 9-AC, and GG-211), gemcitabine, vinorelbine, oxaliplatin, 5-fluorouracil (5-FU), leucovorin, vinorelbine, temodal, cytochalasin B, gramicidin D, emetine, mitomycin, etoposide, tenoposide, vincristine, vinblastine, colchicin, doxorubicin, daunorubicin, dihydroxy anthracendione, mitoxantrone, mithramycin, actinomycin D, I-dehydrotestosterone, glucocorticoids, procaine, tetracaine, lidocaine, propranolol, and puromycin homologs, and cytoxan.

The present technology includes the sequential or concomitant administration of pharmaceutical composition of the technology and an anti-cancer agent such as a chemotherapeutic agent. In a specific embodiment, the pharmaceutical composition of the technology is administered prior to (e.g., 2 hours, 6 hours, 12 hours, 1 day, 4 days, 6 days, 12 days, 14 days, 1 month or several months before) the administration of the anti-cancer agent. In another specific embodiment, the pharmaceutical composition of the technology is administered subsequent to (e.g., 2 hours, 6 hours, 12 hours, 1 day, 4 days, 6 days, 12 days, 14 days, 1 month or several months after) the administration of an anti-cancer agent. In a specific embodiment, the pharmaceutical composition of the technology is administered concomitantly with an anti-cancer agent. The technology encompasses combinations of anti-cancer agents and attenuated tumor-targeted bacteria engineered to express one or more nucleic acid molecules encoding one or more effector molecules and/or fusion proteins that are additive or synergistic.

The technology also encompasses combinations of anti-cancer agents and attenuated tumor-targeted bacteria engineered to express one or more nucleic acid molecules encoding one or more effector molecules and/or fusion proteins that have different sites of action. Such a combination provides an improved therapy based on the dual action of these therapeutics whether the combination is synergistic or additive. Thus, the novel combinational therapy of the present technology yields improved efficacy over either agent used as a single-agent therapy.

In one embodiment, an animal with a solid tumor cancer is administered a pharmaceutical composition of the technology and treated with radiation therapy (e.g., gamma radiation or x-ray radiation). In a specific embodiment, the technology provides a method to treat or prevent cancer that has shown to be refractory to radiation therapy. The pharmaceutical composition may be administered concurrently with radiation therapy. Alternatively, radiation therapy may be administered subsequent to administration of a pharmaceutical composition of the technology, preferably at least an hour, five hours, 12 hours, a day, a week, a month, more preferably several months (e.g., up to three months), subsequent to administration of a pharmaceutical composition.

The radiation therapy administered prior to, concurrently with, or subsequent to the administration of the pharmaceutical composition of the technology can be administered by any method known in the art. Any radiation therapy protocol can be used depending upon the type of cancer to be treated. For example, but not by way of limitation, x-ray radiation can be administered; in particular, high-energy megavoltage (radiation of greater than 1 MeV energy) can be used for deep tumors, and electron beam and orthovoltage x-ray radiation can be used for skin cancers. Gamma ray emitting radioisotopes, such as radioactive isotopes of radium, cobalt and other elements may also be administered to expose tissues to radiation.

Additionally, the technology also provides methods of treatment of cancer with a Pharmaceutical composition as an alternative to radiation therapy where the radiation therapy has proven or may prove too toxic, i.e., results in unacceptable or unbearable side effects, for the subject being treated.

The pharmaceutical compositions of the technology are preferably tested in vitro, and then in vivo for the desired therapeutic or prophylactic activity, prior to use in humans.

For example, in vitro assays which can be used to determine whether administration of a specific pharmaceutical composition is indicated, include in vitro cell culture assays in which a patient tissue sample is grown in culture, and exposed to or otherwise administered a pharmaceutical composition, and the effect of such composition upon the tissue sample is observed.

Pharmaceutical compositions of the technology can be tested for their ability to augment activated immune cells by contacting immune cells with a test pharmaceutical composition or a control and determining the ability of the test pharmaceutical composition to modulate (e.g., increase) the biological activity of the immune cells. The ability of a test composition to modulate the biological activity of immune cells can be assessed by detecting the expression of cytokines or antigens, detecting the proliferation of immune cells, detecting the activation of signaling molecules, detecting the effector function of immune cells, or detecting the differentiation of immune cells. Techniques known to those of skill in the art can be used for measuring these activities. For example, cellular proliferation can be assayed by $^3$H-thymidine incorporation assays and trypan blue cell counts. Cytokine and antigen expression can be assayed, for example, by immunoassays including, but are not limited to, competitive and non-competitive assay systems using techniques such as western blots, immunohisto-chemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A, immunoassays and FACS analysis. The activation of signaling molecules can be assayed, for example, by kinase assays and electromobility shift assays (EMSAs). The effector function of T-cells can be measured, for example, by a 51Cr-release assay (see, e.g., Palladino et al., 1987, Cancer Res. 47:5074-5079 and Blachere et al., 1993, J. Immunotherapy 14:352-356).

Pharmaceutical compositions of the technology can be tested for their ability to reduce tumor formation in animals suffering from cancer. Pharmaceutical compositions of the technology can also be tested for their ability to alleviate of one or more symptoms associated with a solid tumor cancer. Further, pharmaceutical compositions of the technology can be tested for their ability to increase the survival period of patients suffering from a solid tumor cancer. Techniques known to those of skill in the art can be used to analyze the function of the pharmaceutical compositions of the technology in animals.

In various specific embodiments, in vitro assays can be carried out with representative cells of cell types involved in a solid tumor cancer, to determine if a pharmaceutical composition of the technology has a desired effect upon such cell types.

Pharmaceutical compositions of the technology for use in therapy can be tested in suitable animal model systems prior to testing in humans, including but not limited to rats, mice, chicken, cows, monkeys, pigs, dogs, rabbits, etc. For in vivo testing, prior to administration to humans, any animal model system known in the art may be used.

Example 11. Combinations of Tumor-Targeted Salmonella with ACE Inhibitors and Chloroquine Treatment with tumor targeted Salmonella that reduce available copper, tumor-targeted Salmonella that express a cytotoxic protein, or treatment with other tumor-targeted bacteria may be enhanced with combinations including vascular agents and autophagy inhibitors. Methods and pharmaceutical compositions of the bacteria are those described above.

Optional pretreatment or simultaneous treatment of the patient may be conducted with a vascular agent such as an ACE inhibitor (e.g., lisinopril). Pretreatment is determined by a physician based upon the initial status of blood pressure, and dosed appropriately to reduce blood pressure within a level that is safe for the patient, and of a duration necessary to reduce blood pressure, which are known to those skilled in the art and can be determined by blood pressure analysis. This pretreatment is discontinued after administration of the bacteria.

Pretreatment of a patient may further be augmented with chloroquine alone or in combination with an ACE inhibitor, which may act both as a vascular normalization agent and an anti-autophagy agent. Chloroquine is used to treat both malaria and rheumatoid arthritis, and dosage is known to those skilled in the art.

Bacterial treatment may be simultaneous or post ACE inhibitor and chloroquine treatments. Measurement of anti-tumor efficacy may be done using methods known to those skilled in the art. A second pretreatment or simultaneous alone or in combination with the first pretreatment consists of chloroquine. Chloroquine is a known anti-malarial agent, and is administered according to appropriate dosages. This pretreatment may be sustained during the course of bacterial therapy.

Example 12. Combinations of Tumor-Targeted Salmonella with a Lectin Pathway Inhibitor as a YebF Fusion Treatment with tumor targeted Salmonella that reduce available copper, tumor-targeted Salmonella that express a cytotoxic protein, or treatment with other tumor-targeted bacteria may be enhanced with combinations including lectin pathway inhibitors. Methods of expression on plasmids or inserted into the chromosome are described above.

A fusion of YebF using a commercially available yebF gene (pAES40; Athena Enzyme Systems), wherein a trypsin cleavage site of leucine and lysine amino acids (in bold) that results in release of the peptide during secretion/release is followed by the mature sequence of the lectin pathway inhibitor lpi (WO2005/005630) is inserted in-frame is shown in

SEQ ID NO: 20:
MAKKRGAFLGLLLVSACASVFAANNETSKSVTFPKCEDLDAAGIAASVKR

DYQQNRVARWADDQKIVGQADPVAWVSLQDIQGKDDKWSVPLAVRGKSAD

IHYQVSVDCKAGMAEYQRRLEDDDDKGILKSTSLPTSNEYQNEKLANELK

SLLDELNVNELATGSLNTYYKRTIKISGQKAMYALKSKDFKKMSEAKYQL

QKIYNEIDEALKSKY

Alternatively, the sequence may lack the trypsin site and remain as a YebF fusion

SEQ ID NO: 21:
MAKKRGAFLGLLLVSACASVFAANNETSKSVTFPKCEDLDAAGIAASVKR

DYQQNRVARWADDQKIVGQADPVAWVSLQDIQGKDDKWSVPLAVRGKSAD

-continued
IHYQVSVDCKAGMAEYQRRLEDDDDKGTSTSLPTSNEYQNEKLANELKSL

LDELNVNELATGSLNTYYKRTIKISGQKAMYALKSKDFKKMSEAKYQLQK

IYNEIDEALKSKY

It is understood that synthetic biology may be used for any of the sequences required, and that for example, the mature amino acid sequence may use a codon optimized nucleotide sequence that also eliminates low GC content

SEQ ID NO: 22:
TCTACCAGCCTGCCGACCTCTAACGAATATCAAAACGAGAAACTGGCAAA

CGAGCTGAAGAGTCTGCTGGATGAGCTGAACGTCAACGAGCTGGCGACCG

GCTCCCTGAACACCTATTACAAACGTACTATTAAAATCAGCGGCCAGAAA

GCAATGTATGCGCTAAAATCTAAAGACTTCAAAAAAATGTCTGAAGCTAA

ATACCAGCTGCAGAAAATCTACAACGAAATCGATGAGGCGCTGAAAAGCA

AATAT

Example 13. Combinations of Tumor-Targeted Salmonella with a Lectin Pathway Inhibitor as a Pseudomonas Ice Nucleation Protein Fusion Treatment with tumor targeted Salmonella that reduce available copper, tumor-targeted Salmonella that express a cytotoxic protein, or treatment with other tumor-targeted bacteria may be enhanced with combinations including lectin pathway inhibitors. Methods of expression on plasmids or inserted into the chromosome are described above.

A fusion with the Pseudomonas ice nucleation protein (INP), wherein the N- and C-terminus of INP are provided with an internal deletion consisting of the first 308 amino acids is followed by the mature sequence of the lectin pathway inhibitor lpi (WO2005/005630; shown in bold) is inserted in-frame to result in the amino acid sequence

SEQ ID NO: 23:
MILDKALVLRICANNMADHCGLIWPASGTVESRYWQSTRRHENGLVGLLW

GAGTSAFLSVHADARWIVCEVAVADIISLEEPGMVKFPRAEVVHVGDRIS

ASHFISARQADPASTSTSTSTSTLTPMPTAIPTPMPAVASVTLPVAEQAR

HEVFDVASVSAAAAPVNTLPVTTPQNLQTATYGSTLSGDNHSRLIAGYGS

NETAGNHSDLIGGHDCTLMAGDQSRLTAGKNSVLTAGARSKLIGSEGSTL

SAGEDSTLIFRLWDGKRYRQLVARTGENGVEADIPYYVNEDDDIVDKPDE

DDDWIEVKSTSLPTSNEYQNEKLANELKSLLDELNVNELATGSLNTYYKR

TIKISGQKAMYALKSKDFKKMSEAKYQLQKIYNEIDEALKSKY

See also, Jung et al., 1998, Surface display of *Zymomonas mobilis* levansucrase by using ice-nucleation protein of *Pseudomonas syringae*, Nature Biotechnology 16: 576-580; Kim et al., 2000, Bacterial surface display of an enzyme library for selective screening of improved cellulase variants, Applied and Environmental Microbiology 66: 788-793; Part:BBa_K811003 from www.iGEM.org.

Example 14. Combinations of Tumor-Targeted Salmonella with a Complement Pathway Inhibitor as a YebF Fusion Treatment with tumor targeted Salmonella that reduce available copper, tumor-targeted Salmonella that express a cytotoxic protein, or treatment with other tumor-targeted bacteria may be enhanced with combinations including complement pathway inhibitors. Methods of expression on plasmids or inserted into the chromosome are described above.

A fusion of YebF using a commercially available yebF gene (pAES40; Athena Enzyme Systems), wherein a trypsin cleavage site of leucine and lysine amino acids (in bold) that results in release of the peptide during secretion/release is followed by the mature sequence of the complement pathway inhibitor lpi (WO2005/005630) is inserted in-frame is shown in

SEQ ID NO: 24:
MAKKRGAFLGLLLVSACASVFAANNETSKSVTFPKCEDLDAAGIAASVKR

DYQQNRVARWADDQKIVGQADPVAWVSLQDIQGKDDKWSVPLAVRGKSAD

IHYQVSVDCKAGMAEYQRRLEDDDDKGILKSSLDKYLTESQFHDKRIAEE

LRILLNKSNVYALAAGSLNPYYKRTIMMNEYRAKAALKKNDFVSMADAKV

ALEKIYKEIDEIINR

Alternatively, the sequence may lack the trypsin site and remain as a YebF fusion

SEQ ID NO: 25:
MAKKRGAFLGLLLVSACASVFAANNETSKSVTFPKCEDLDAAGIAASVKR

DYQQNRVARWADDQKIVGQADPVAWVSLQDIQGKDDKWSVPLAVRGKSAD

IHYQVSVDCKAGMAEYQRRLEDDDDKGTSSLDKYLTESQFHDKRIAEELR

TLLNKSNVYALAAGSLNPYYKRTIMMNEYRAKAALKKNDFVSMADAKVAL

EKIYKEIDEIINR

Example 15. Combinations of Tumor-Targeted Salmonella with a Complement Pathway Inhibitor as a Pseudomonas Ice Nucleation Protein Fusion Treatment with tumor targeted Salmonella that reduce available copper, tumor-targeted Salmonella that express a cytotoxic protein, or treatment with other tumor-targeted bacteria may be enhanced with combinations including complement pathway inhibitors. Methods of expression on plasmids or inserted into the chromosome are described above.

A fusion with the Pseudomonas ice nucleation protein (INP), wherein the N- and C-terminus of INP with an internal deletion consisting of the first 308 amino acids is followed by the mature sequence of the lectin pathway inhibitor lpi (WO2005/005630; shown in bold) is inserted in-frame tor result in the amino acid sequence

SEQ ID NO: 26:
MILDKALVLRICANNMADHCGLIWPASGTVESRYWQSTRRHENGLVGLLW

GAGTSAFLSVHADARWIVCEVAVADIISLEEPGMVKFPRAEVVHVGDRIS

ASHFISARQADPASTSTSTSTSTLTPMPTAIPTPMPAVASVTLPVAEQAR

HEVFDVASVSAAAAPVNTLPVTTPQNLQTATYGSTLSGDNHSRLIAGYGS

NETAGNHSDLIGGHDCTLMAGDQSRLTAGKNSVLTAGARSKLIGSEGSTL

SAGEDSTLIFRLWDGKRYRQLVARTGENGVEADIPYYVNEDDDIVDKPDE

DDDWIEVKSSLDKYLTFSQFHDKRIAEELRTLLNKSNVYALAAGSLNPYY

KRTIMMNEYRAKAALKKNDFVSMADAKVALEKIYKEIDEIINR

Example 16. Combinations of Tumor-Targeted Salmonella with a Tumor-Penetrating Peptide as a YebF Fusion Treatment with tumor targeted Salmonella that reduce available copper, tumor-targeted Salmonella that express a cytotoxic protein, or treatment with other tumor-targeted bacteria may be enhanced with combinations including bacteria that express one or more tumor-penetrating peptides. Methods of expression on plasmids or inserted into the chromosome are described above.

A fusion of YebF using a commercially available yebF gene (pAES40; Athena Enzyme Systems), wherein a trypsin cleavage site of leucine and lysine amino acids (in bold) that results in release of the peptide during secretion/release is followed by the sequence of the tumor-penetrating peptide

SEQ ID NO: 27:
MAKKRGAFLGLLLVSACASVFAANNETSKSVTFPKCEDLDAAGIAASVKR

DYQQNRVARWADDQKIVGQADPVAWVSLQDIQGKDDKWSVPLAVRGKSAD

IHYQVSVDCKAGMAEYQRRLEDDDDKGTLKCRGDKGPDC

Alternatively, the sequence may lack the trypsin site and remain as a YebF fusion

SEQ ID NO: 28:
MAKKRGAFLGLLLVSACASVFAANNETSKSVTFPKCEDLDAAGIAASVKR

DYQQNRVARWADDQKIVGQADPVAWVSLQDIQGKDDKWSVPLAVRGKSAD

IHYQVSVDCKAGMAEYQRRLEDDDDKGTCRGDKGPDC

Example 17. Combinations of Tumor-Targeted Salmonella with a Tumor-Penetrating Peptide as a Pseudomonas Ice Nucleation Protein Fusion Treatment with tumor targeted Salmonella that reduce available copper, tumor-targeted Salmonella that express a cytotoxic protein, or treatment with other tumor-targeted bacteria may be enhanced with combinations including expression of a tumor-penetrating peptide. Methods of expression on plasmids or inserted into the chromosome are described above.

A fusion with the Pseudomonas ice nucleation protein (INP), wherein the N- and C-terminus of INP with an internal deletion consisting of the first 308 amino acids is followed by the mature sequence of the tumor-penetrating peptide is inserted in-frame to result in the amino acid sequence

SEQ ID NO: 29:
MILDKALVLRICANNMADHCGLIWPASGTVESRYWQSTRRHENGLVGLLW

GAGTSAFLSVHADARWIVCEVAVADIISLEEPGMVKFPRAEVVHVGDRIS

ASHFISARQADPASTSTSTSTSTLTPMPTAIPTPMPAVASVTLPVAEQAR

HEVFDVASVSAAAAPVNTLPVTTPQNLQTATYGSTLSGDNHSRLIAGYGS

NETAGNHSDLIGGHDCTLMAGDQSRLTAGKNSVLTAGARSKLIGSEGSTL

-continued

SAGEDSTLIFRLWDGKRYRQLVARTGENGVEADIPYYVNEDDDIVDKPDE
DDDWIEVKCRGDKGPDC

Example 18. Treatment of Wilson's Disease with Copper-Sequestering Bacteria

Treatment with attenuated Salmonella (or probiotic bacteria such as E. coli Nissle 1917) that colonize the gut, and sequester available copper, may be used to treat Wilson's Disease, Menke's Disease, or certain neurological diseases that may be associated with copper metabolism defects, such as the putative association with Alzheimer's Disease, Parkinson's Disease, Creutzfeldt-Jakob Disease and other prion-associated conditions. The probiotic bacteria may be Lactobacillus, Bifidobacterium, Saccharomyces (e.g., Saccharomyces boulardii), Enterococcus, Streptococcus, Pediococcus, Leuconostoc, Bacillus, or Escherichia coli. See, Fijan, Sabina. "Microorganisms with claimed probiotic properties: an overview of recent literature." International journal of environmental research and public health vol. 11.5 4745-67. 5 May 2014, doi:10.3390/ijerph110504745. The dosage form may be, for example, yogurt or lyophilized bacteria in capsule form.

The bacteria may produce a wild type or homologous copper-sequestering siderophores, or be genetically engineered to express a heterologous copper sequestering peptide. Bacteria having a desired growth pattern may be genetically engineered to express known heterologous copper-binding proteins or motifs from other organisms, and indeed, multiple different types of binding peptides or binding systems may be produced in the same organism. Further, compatible co-cultures of various strains of bacteria may be coadministered.

The expression plasmid of Example 1 above is used to operably link a DNA encoding the amino acid sequences of genes copL, copA, copB, copM copG, copC, copD, and copF described by (Behlau 2011, Molecular Characterization of Copper Resistance Genes from Xanthomonas citri subsp. citri and Xanthomonas alfalfae subsp. citrumelonis, 77: 4089-4096) may be expressed as a polycistronic construct, whereby following each of the stop codons, a ribosomal binding site is positioned appropriately before the start codon for the next sequence using methods known to those skilled in the art Alternatively, the promoter and genes from the inducible plasmid may be inserted into the chromosome using methods known to those skilled in the art.

Weiss, G., Carver, P. L., "Role of divalent metals in infectious disease susceptibility and outcome", Clinical Microbiology and Infection, Volume 24, Issue 1, 2018, Pages 16-23, ISSN 1198-743X, doi.org/10.1016/j.cmi.2017.01.018.

Mrvcic, Jasna, Damir Stanzer, Visnja Bacun-Druzina, and Vesna Stehlik-Tomas. "Copper binding by lactic acid bacteria (LAB)." Bioscience and microflora 28, no. 1 (2009): 1-6.

Schut, Sina, Stephan Zauner, Gabriele Hampel, Helmut König, and Harald Claus. "Biosorption of copper by wine-relevant lactobacilli." International journal of food microbiology 145, no. 1 (2011): 126-131.

Stroobants, Aurore, Jean-Marc Delroisse, Franck Delvigne, Julien Delva, Daniel Portetelle, and Micheline Vandenbol. "Isolation and biomass production of a Saccharomyces cerevisiae strain binding copper and zinc ions." Applied biochemistry and biotechnology 157, no. 1 (2009): 85-97.

Wang, Xiaoqiu, Fang Yang, Chuang Liu, Huaijun Zhou, Guoyao Wu, Shiyan Qiao, Defa Li, and Junjun Wang. "Dietary supplementation with the probiotic Lactobacillus fermentum 15007 and the antibiotic aureomycin differentially affects the small intestinal proteomes of weanling piglets." The Journal of nutrition 142, no. 1 (2011): 7-13.

Mrvčič, Jasna, Tatjana Prebeg, Lidija Baršić, Damir Stanzer, Višnja Bačun-Družina, and Vesna Stehlik-Tomas. "Zinc binding by lactic acid bacteria." Food technology and biotechnology 47, no. 4 (2009): 381-388.

Rodriguez, L Mato, and Tapani Alatossava. "Effects of copper supplement on growth and viability of strains used as starters and adjunct cultures for Emmental cheese manufacture." Journal of applied microbiology 105, no. 4 (2008): 1098-1106.

Mrvčić, Jasna, Ana Butorac, Ema Šolić, Damir Stanzer, Višnja Bačun-Družina, Mario Cindrič, and Vesna Stehlik-Tomas. "Characterization of Lactobacillus brevis L62 strain, highly tolerant to copper ions." World Journal of Microbiology and Biotechnology 29, no. 1 (2013): 75-85.

Tian, Fengwei, Yue Xiao, Xiaoxiao Li, Qixiao Zhai, Gang Wang, Qiuxiang Zhang, Hao Zhang, and Wei Chen. "Protective effects of Lactobacillus plantarum CCFM8246 against copper toxicity in mice." PloS one 10, no. 11 (2015): e0143318.

Tian, Fengwei, Qixiao Zhai, Jianxin Zhao, Xiaoming Liu, Gang Wang, Hao Zhang, Heping Zhang, and Wei Chen. "Lactobacillus plantarum CCFM8661 alleviates lead toxicity in mice." Biological trace element research 150, no. 1-3 (2012): 264-271.

Mrvčić, Jasna, Damir Stanzer, Ema Šolić, and Vesna Stehlik-Tomas. "Interaction of lactic acid bacteria with metal ions: opportunities for improving food safety and quality." World Journal of Microbiology and Biotechnology 28, no. 9 (2012): 2771-2782.

Sreevani, S., K. Chandra Sekhar, D. Esther Lebonah, and J. Pramoda Kumari. "Noxious Effect of Trace Metals on Probiotic" Lactobacillus rhamnosus". International Journal of Biological Sciences and Technology 5, no. 3 (2013): 13.

Zhai, Qixiao, Gang Wang, Jianxin Zhao, Xiaoming Liu, Fengwei Tian, Hao Zhang, and Wei Chen. "Protective effects of Lactobacillus plantarum CCFM8610 against acute cadmium toxicity in mice." Appl. Environ. Microbiol. 79, no. 5 (2013): 1508-1515.

Porcheron, Gaëlle, Amalie Garénaux, Julie Proulx, Mourad Sabri, and Charles M. Dozois. "Iron, copper, zinc, and manganese transport and regulation in pathogenic Enterobacteria: correlations between strains, site of infection and the relative importance of the different metal transport systems for virulence." Frontiers in cellular and infection microbiology 3 (2013): 90.

Frederiksen, Rikki F., Dafni K. Paspaliari, Tanja Larsen, Birgit G. Storgaard, Marianne H. Larsen, Hanne Ingmer, Monica M. Palcic, and Jørgen J. Leisner. "Bacterial chitinases and chitin-binding proteins as virulence factors." Microbiology 159, no. 5 (2013): 833-847.

Yang, Yang, Jia Yin, Jie Liu, Qi Xu, Tian Lan, Fazheng Ren, and Yanling Hao. "The copper homeostasis transcription factor CopR is involved in H2O2 stress in Lactobacillus plantarum CAUH2." Frontiers in Microbiology 8 (2017): 2015.

Patel, Ami, N. Shah, and K. D. Verma. "Lactic acid bacteria as metal quenchers to improve food safety and quality." AgroLife Sci 6 (2017): 146-154.

O'Brien, Henrik Y., Joseph W. Alvin, Sanjay V. Menghani, Koenraad Van Doorslaer, and Michael David Leslie Johnson. "Characterization of consensus operator site for *Streptococcus pneumoniae* copper repressor, CopY." bioRxiv (2019): 676700.

Finegold, Sydney M. "*Desulfovibrio* species are potentially important in regressive autism." Medical hypotheses 77, no. 2 (2011): 270-274.

Penaud, S., A. Fernandez, S. Boudebbouze, S. D. Ehrlich, E. Maguin, and M. Van De Guchte. "Induction of heavy-metal-transporting CPX-type ATPases during acid adaptation in *Lactobacillus bulgaricus*." Appl. Environ. Microbiol. 72, no. 12 (2006): 7445-7454.

Palomino, Maria Mercedes, Mariana C. Allievi, Angelika Gründling, Carmen Sanchez-Rivas, and Sandra M. Ruzal. "Osmotic stress adaptation in *Lactobacillus casei* BL23 leads to structural changes in the cell wall polymer lipoteichoic acid." Microbiology 159, no. 11 (2013): 2416-2426.

Bermudez-Brito, Miriam, Julio Plaza-Diaz, Sergio Munoz-Quezada, Carolina Gómez-Llorente, and Angel Gil. "Probiotic mechanisms of action." Annals of Nutrition and Metabolism 61, no. 2 (2012): 160-174.

Besselink, Marc G H, Hjalmar C. van Santvoort, Erik Buskens, Marja A. Boermeester, Harry van Goor, Harro M. Timmerman, Vincent B. Nieuwenhuijs et al. "Probiotic prophylaxis in predicted severe acute pancreatitis: a randomised, double-blind, placebo-controlled trial." The Lancet 371, no. 9613 (2008): 651-659.

Deriu, E., J. Z. Liu, M. Pezeshki, R. A. Edwards, R. J. Ochoa, H. Contreras, et al. Probiotic bacteria reduce *Salmonella typhimurium* intestinal colonization by competing for iron, Cell Host Microbe, 14 (2013), pp. 26-37

Dobson, Alleson, Paul D. Cotter, R. Paul Ross, and Colin Hill. "Bacteriocin production: a probiotic trait?." Appl. Environ. Microbiol. 78, no. 1 (2012): 1-6.

Donohue, D. C., and S. Salminen. "Safety of probiotic bacteria." Asia pacific journal of clinical nutrition 5 (1996): 25-28.

Farnworth, Edward R. "Kefir—a complex probiotic." Food Science and Technology Bulletin: Fu 2, no. 1 (2006): 1-17.

Holzapfel, Wilhelm H., Petra Haberer, Rolf Geisen, Johanna Björkroth, and Ulrich Schillinger. "Taxonomy and important features of probiotic microorganisms in food and nutrition." The American journal of clinical nutrition 73, no. 2 (2001): 365s-373s.

Klein, Günter, Alexander Pack, Christine Bonaparte, and Gerhard Reuter. "Taxonomy and physiology of probiotic lactic acid bacteria." International journal of food microbiology 41:2 (1998):103-125.

Lebeer, Sarah, Jos Vanderleyden, and Sigrid C J De Keersmaecker. "Genes and molecules of lactobacilli supporting probiotic action." Microbiol. Mol. Biol. Rev. 72, no. 4 (2008): 728-764.

Liyanage, S. Imindu, Prachi Vilekar, and Donald F. Weaver. "Nutrients in Alzheimer's Disease: The Interaction of Diet, Drugs and Disease." Canadian Journal of Neurological Sciences 46:1 (2019): 23-34.

Lourens-Hattingh, Analie, and Bennie C. Viljoen. "Yogurt as probiotic carrier food." International dairy journal 11, no. 1-2 (2001): 1-17;

Madsen, Karen, Anthony Cornish, Paul Soper, Conor McKaigney, Humberto Jijon, Christine Yachimec, Jason Doyle, Lawrence Jewell, and Claudio De Simone. "Probiotic bacteria enhance murine and human intestinal epithelial barrier function." Gastroenterology 121, no. 3 (2001): 580-591.

Naidu, A. S., W. R. Bidlack, and R. A. Clemens. "Probiotic spectra of lactic acid bacteria (LAB)." Critical reviews in food science and nutrition 39, no. 1 (1999): 13-126.

Oelschlaeger, Tobias A. "Mechanisms of probiotic actions—a review." International Journal of Medical Microbiology 300, no. 1 (2010): 57-62.

Reid, Gregor. "The scientific basis for probiotic strains of *Lactobacillus*." Appl. Environ. Microbiol. 65, no. 9 (1999): 3763-3766.

Rivera-Espinoza, Yadira, and Yoja Gallardo-Navarro. "Non-dairy probiotic products." Food microbiology 27, no. 1 (2010): 1-11.

Shah, N. P. "Probiotic bacteria: selective enumeration and survival in dairy foods." Journal of dairy science 83, no. 4 (2000): 894-907.

Stanton, C., G. Gardiner, P. B. Lynch, J. K. Collins, G. Fitzgerald, and R. P. Ross. "Probiotic cheese." International Dairy Journal 8, no. 5-6 (1998): 491-496.

Tillisch, Kirsten, Jennifer Labus, Lisa Kilpatrick, Zhiguo Jiang, Jean Stains, Bahar Ebrat, Denis Guyonnet et al. "Consumption of fermented milk product with probiotic modulates brain activity." Gastroenterology 144, no. 7 (2013): 1394-1401.

For example:

| Lactobacilli | Bifidobacteria | Other LAB | Non-LAB |
| --- | --- | --- | --- |
| Lactobacillus acidophilus | Bif. breve | Enteroccus faecium | Bacillus cereus |
| Lb. casei/ paracasei | Bif. longum ssp. infantis | Enteroccus faecalis | Bacillus coagulans |
| Lb. delbrueckii ssp. bulgaricus | Bif. longum ssp. longum | Lactococcus lactis | Clostridium butyricum |
| Lb. johnsonii | Bif. adolescentis | Streptococcus thermophilus | Escherichia coli |
| Lb. reuterii | Bif. animalis ssp. lactis | | Propionibacterium freudenreichii |
| Lb. rhambosus | Bif. bifidum | | Saccharomyces boulardii |
| Lb. salivarius | | | |
| Lb. paracasei | | | |
| Lb. fermentum | | | |
| Lb. plantarum | | | |
| Lb. crispatus | | | |
| Lb. gasseri | | | |
| Lb. amylovorus | | | |

Each reference cited herein is expressly incorporated herein in its entirety. Such references provide examples representing aspects of the invention, uses of the invention, disclosure of the context of the invention and its use and application. The various aspects disclosed herein, including subject matter incorporated herein by reference, may be employed, in combination or subcombination and in various permutations, consistent with the claims.

The invention may be embodied in other specific forms without departing from its spirit or essential characteristics. The described embodiment is to be considered in all respects only illustrative and not restrictive. The scope of the invention is, therefore, indicated by the appended claims rather by the foregoing description. All changes that fall within the meaning and range of equivalency of the claims are to be embraced within their scope.

What is claimed is:

1. A live, replication competent genetically engineered bacterium, comprising:
   at least one heterologous copper binding protein gene which causes the live, replication competent genetically engineered bacterium to express at least one heterologous copper binding protein, wherein the at least one heterologous copper binding protein is capable of reducing copper ion availability external to the live, replication competent genetically engineered bacterium; and
   at last one genetically engineered copper resistance or sensitivity suppressor gene which causes the live, replication competent genetically engineered bacterium to express a copper resistance or sensitivity suppressor product, the copper resistance or sensitivity suppressor product being effective to increase resistance or reduce sensitivity of the live, replication competent genetically engineered bacterium to copper ions.

2. The live, replication competent genetically engineered bacterium according to claim 1, adapted to colonize a mammalian tissue with persistence of the live, replication competent genetically engineered bacterium in the mammalian tissue for at least one day, and to accumulate copper within the live, replication competent genetically engineered bacterium.

3. The live, replication competent genetically engineered bacterium according to claim 2, adapted to selectively colonize a mammalian neoplastic tissue, wherein the of the live, replication competent genetically engineered bacterium persists in the mammalian neoplastic tissue for at least one day, and wherein the at least one heterologous copper binding protein is effective to bind copper ions in the mammalian neoplastic tissue.

4. The live, replication competent genetically engineered bacterium according to claim 3, wherein the reduction of copper ion availability by the expressed at least one heterologous copper binding protein reduces angiogenesis in the colonized mammalian metastatic cancerous tissue.

5. The live, replication competent genetically engineered bacterium according to claim 1, wherein the at least one heterologous copper binding protein is derived from *Vibrio alginolyticus*.

6. The live, replication competent genetically engineered bacterium according to claim 1, wherein the at last one genetically engineered copper resistance gene causes the live, replication competent genetically engineered bacterium to express a heterologous *Vibrio alginolyticus* copper resistance protein.

7. The live, replication competent genetically engineered bacterium according to claim 1, wherein the live, replication competent genetically engineered bacterium further expresses a heterologous copper resistance protein.

8. The live, replication competent genetically engineered bacterium according to claim 1, wherein the at least one heterologous copper binding protein is a copper-binding siderophore, and the live, replication competent genetically engineered bacterium is adapted to colonize and persist within a host organism with persistence of the live, replication competent genetically engineered bacterium in the host organism for at least one day, and reduce copper ion availability to cells of the host organism.

9. The live, replication competent genetically engineered bacterium according to claim 1, wherein the host organism has a defect of copper metabolism, and wherein the live, replication competent genetically engineered bacterium is adapted to colonize and persist within the host organism for at least one day and reduce copper ion availability to cells of the host organism, and wherein the live, replication competent genetically engineered bacterium, when administered to the host organism in a therapeutically effective amount, is effective to treat a disease associated with the defect of copper metabolism.

10. The live, replication competent genetically engineered bacterium according to claim 9, wherein the host organism has a defect in copper metabolism caused by a defect in the ATP7A or ATP7B gene, and wherein the live, replication competent genetically engineered bacterium, when administered to the host organism in a therapeutically effective amount, is effective to treat a disease associated with the defect in the ATP7A or ATP7B gene.

11. The live, replication competent genetically engineered bacterium according to claim 1, further comprising at least one gene which causes the live, replication competent genetically engineered bacterium to express a cytotoxic protein.

12. The live, replication competent genetically engineered bacterium according to claim 1, wherein the live, replication competent genetically engineered bacterium is of the species *E. coli*.

13. The live, replication competent genetically engineered bacterium according to claim 1, wherein the at least one heterologous copper binding protein is selected from the group consisting of methanobactin, yersiniabactin, *Vibrio alginolyticus* copper binding protein, plastocyanin, amicyanin, auracyanin A, auracyanin B, *Alcaligenes* blue copper protein, cupredoxin, halocyanin, rusticyaninstellacyanin, umecyanin, aerobactin, salmonchelin, and ceruloplasmin.

14. A pharmaceutically acceptable formulation for human administration, comprising:
   (a) a live replication competent genetically engineered bacterium, comprising:
      (i) at least one heterologous copper binding protein gene which results in expression of a heterologous copper binding protein, the expression of the heterologous copper binding protein by the live replication competent genetically engineered bacterium being capable of reducing copper ion availability in its environment; and
      (ii) at least one genetically engineered copper resistance or sensitivity suppressor gene which causes the live replication competent genetically engineered bacterium to express a copper resistance or sensitivity suppressor product, the copper resistance or sensitivity suppressor product being effective to increase resistance or reduce sensitivity of the live, replication competent genetically engineered bacterium to copper ions,
      the live replication competent genetically engineered bacterium being a probiotic bacterium adapted to replicate in an enteric organ of a human;
   (b) a pharmaceutically acceptable excipient; and
   (c) a sealed container,
   the live replication competent genetically engineered bacterium and the pharmaceutically acceptable excipient being provided together in the sealed container as a unit dosage form for administration to the human.

15. The pharmaceutically acceptable formulation according to claim 14, wherein the heterologous copper binding protein is a chimeric protein comprising a copper ion binding portion and a secretion peptide portion that interacts with a secretion system of the live replication competent genetically engineered bacterium to promote secretion of the chimeric protein from the live genetically engineered bacterium into the environment.

16. The pharmaceutically acceptable formulation according to claim 14, wherein the live genetically engineered bacterium is selected from the group consisting of: *Salmonella, E. coli, Lactobacillus acidophilus, Bifidus breve, Enteroccus faecium, Bacillus cereus, Lactobacillus casei, Lactobacillus paracasei, Bifidus longum* ssp. *infantis, Enteroccus faecalis, Bacillus coagulans, Lactobacillus delbrueckii* ssp. *bulgaricus, Bifidus longum* ssp. *longum, Lactococcus lactis, Clostridium butyricum, Lactobacillus johnsonii, Bifidus adolescentis, Streptococcus thermophilus, Escherichia coli, Lactobacillus reuterii, Bifidus animalis* ssp. *lactis, Propionibacterium freudenreichii, Lactobacillus rhamnosus, Bifidus bifidum, Saccharomyces boulardii, Lactobacillus salivarius, Lactobacillus fermentum, Lactobacillus plantarum, Lactobacillus crispatus, Lactobacillus gasseri,* and *Lactobacillus amylovorus.*

17. A method of treating a patient having an excess of copper in his or her tissue, comprising:
   administering a therapeutically effective amount of the live, replication competent genetically engineered bacterium according to claim 9 to the patient;
   wherein an enteric tissue of the patient is colonized by the live, replication competent genetically engineered bacterium, and wherein the live, replication competent genetically engineered bacterium persists within the enteric tissue of the patient for at least one day;
   thereby effectively reducing availability of the copper from dietary sources to the patient by chelation of the copper ions by the at least one heterologous copper binding protein, which treats the excess of copper.

18. The method according to claim 17, wherein the live, replication competent genetically engineered bacterium is effective to treat Wilson disease or Menke's disease.

19. The method according to claim 17, wherein the live, replication competent genetically engineered bacterium is an antibiotic-sensitive bacteria selected from the group consisting of: *Salmonella, E. coli, Lactobacillus acidophilus, Bifidus breve, Enteroccus faecium, Bacillus cereus, Lactobacillus casei, Lactobacillus paracasei, Bifidus longum* ssp. *infantis, Enteroccus faecalis, Bacillus coagulans, Lactobacillus delbrueckii* ssp. *bulgaricus, Bifidus longum* ssp. *longum, Lactococcus lactis, Clostridium butyricum, Lactobacillus johnsonii, Bifidus adolescentis, Streptococcus thermophilus, Escherichia coli, Lactobacillus reuterii, Bifidus animalis* ssp. *lactis, Propionibacterium freudenreichii, Lactobacillus rhamnosus, Bifidus bifidum, Saccharomyces boulardii, Lactobacillus salivarius, Lactobacillus fermentum, Lactobacillus plantarum, Lactobacillus crispatus, Lactobacillus gasseri,* and *Lactobacillus amylovorus.*

20. The live, replication competent genetically engineered bacterium according to claim 1, wherein the at least one heterologous copper binding protein comprises a chimeric protein comprising a copper binding peptide portion and a secretion peptide portion, wherein the secretion peptide portion interacts with a secretion system of the live, replication competent genetically engineered bacterium to cause secretion of the copper binding peptide portion external to the live, replication competent genetically engineered bacterium.

* * * * *

SEQUENCE LISTING

<160> NUMBER OF SEQ ID NOS: 56

<210> SEQ ID NO 1
<211> LENGTH: 95
<212> TYPE: PRT
<213> ORGANISM: Vibrio alginolyticus

<400> SEQUENCE: 1

Met Val Cys Leu Ser Gln Asn Ser Gly Phe Ser Lys Ser Cys Pro Lys
1               5                   10                  15

Ala His Gln Ile Gln Ser Gln Gln Asn Glu Ser Val Asn Leu Ser Pro
            20                  25                  30

Ser Cys Asp Leu Ser Glu Lys Leu Val Gln Ala Tyr Gln His Gln Phe
        35                  40                  45

Asp His Ile Leu Ile Pro Phe Phe Leu Phe Ala Leu Ile Val Ala Leu
    50                  55                  60

Pro Met Ala Ser Thr Ala Ile Arg Tyr Leu Glu Tyr Thr Glu Pro Ile
65                  70                  75                  80

Arg Glu Lys Tyr Arg Val His Leu Lys Leu Cys Val Phe Arg Glu
                85                  90                  95

<210> SEQ ID NO 2
<211> LENGTH: 288
<212> TYPE: DNA
<213> ORGANISM: Vibrio alginolyticus

<400> SEQUENCE: 2
atggtatgtt taagccaaaa ctccggcttc tcgaaaagct gccctaaggc tcaccaaata      60
cagagtcagc aaaatgaaag cgtgaattta tcaccatctt gcgacctttc agagaagctg     120
gttcaagcgt accaacacca gtttgatcat attcttattc cattttttct gtttgctttg     180
attgtggcgc tgccgatggc atccacagca attcgttatc tggaatacac agaaccgata     240
cgggaaaagt atcgggttca cctaaaactt tgcgtgttta gagaataa                  288

<210> SEQ ID NO 3
<211> LENGTH: 2813
<212> TYPE: DNA
<213> ORGANISM: Artificial Sequence
<220> FEATURE:
<223> OTHER INFORMATION: sequence of the arabinose inducible plasmid
      capable of expressing the copper sensitivity suppressor protein
      with a start codon at 351

<400> SEQUENCE: 3
gggggcggcc gcaagaaacc aattgtccat attgcatcag acattgccgt cactgcgtct      60
tttactggct cttctcgcta accaaaccgg taaccccgct tattaaaagc attctgtaac     120
aaagcgggac caaagccatg acaaaaacgc gtaacaaaag tgtctataat cacggcagaa     180
aagtccacat tgattatttg cacggcgtca cactttgcta tgccatagca tttttatcca     240
taagattagc ggatcctacc tgacgctttt tatcgcaact ctctactgtt tctccatacc     300
cgtttttttg ggctagcgaa ttcgagctcg tacccagga ggaattcacc atggtatgtt      360
taagccaaaa ctccggcttc tcgaaaagct gccctaaggc tcaccaaata cagagtcagc     420
aaaatgaaag cgtgaattta tcaccatctt gcgacctttc agagaagctg gttcaagcgt     480
accaacacca gtttgatcat attcttattc cattttttct gtttgctttg attgtggcgc     540
tgccgatggc accccatgcc gaactcagaa gtgaaacgcc gtagcgccga tggtagtgtg     600
gggtctcccc atgcgagagt agggaactgc caggcatcaa ataaaacgaa aggctcagtc     660

```
gaaagactgg gcctttcgtt ttatctgttg tttgtcggtg aacgctctcc tgagtaggac     720
aaatccgccg ggagcggatt tgaacgttgc gaagcaacgg cccggagggt ggcgggcagg     780
acgcccgcca taaactgcca ggcatcaaat taagcagaag gccatcctga cggatggcct     840
ttttgcgttt ctacaaactc ttttgttta tttttctaaa tacattcaaa tatgtatccg     900
ctcatgagac aataaccctg ataaatgctt caataatatt gaaaaggaa gagtatgagt     960
attcaacatt tccgtgtcgc ccttattccc tttttgcgg cattttgcct tcctgttttt    1020
gctcacccag aaacgctggt gaaagtaaaa gatgctgaag atcagttggg tgcacgagtg    1080
ggttacatcg aactggatct caacagcggt aagatccttg agagttttcg ccccgaagaa    1140
cgttttccaa tgatgagcac ttttaaagtt ctgctatgtg gcgcggtatt atcccgtgtt    1200
gacgccgggc aagagcaact cggtcgccgc atacactatt ctcagaatga cttggttgag    1260
tactcaccag tcacagaaaa gcatcttacg gatggcatga cagtaagaga attatgcagt    1320
gctgccataa ccatgagtga taacactgcg gccaacttac ttctgacaac gatcggagga    1380
ccgaaggagc taaccgcttt tttgcacaac atggggatc atgtaactcg ccttgatcgt    1440
tgggaaccgg agctgaatga agccatacca aacgacgagc gtgacaccac gatgcctaca    1500
gcaatggcaa caacgttgcg caaactatta actggcgaac tacttactct agcttcccgg    1560
caacaattaa tagactggat ggaggcggat aaagttgcag gaccacttct gcgctcggcc    1620
cttccggctg gctggtttat tgctgataaa tctggagccg gtgagcgtgg gtctcgcggt    1680
atcattgcag cactggggcc agatggtaag ccctcccgta tcgtagttat ctacacgacg    1740
gggagtcagg caactatgga tgaacgaaat agacagatcg ctgagatagg tgcctcactg    1800
attaagcatt ggtaactgtc agaccaagtt tactcatata tactttagat tgatttaaaa    1860
cttcattttt aatttaaaag gatctaggtg aagatccttt ttgataatct catgaccaaa    1920
atcccttaac gtgagttttc gttccactga gcgtcagacc ccgtagaaaa gatcaaagga    1980
tcttcttgag atcctttttt tctgcgcgta atctgctgct tgcaaacaaa aaaaccaccg    2040
ctaccagcgg tggtttgttt gccggatcaa gagctaccaa ctcttttcc gaaggtaact    2100
ggcttcagca gagcgcagat accaaatact gtccttctag tgtagccgta gttaggccac    2160
cacttcaaga actctgtagc accgcctaca tacctcgctc tgctaatcct gttaccagtg    2220
gctgctgcca gtggcgataa gtcgtgtctt accgggttgg actcaagacg atagttaccg    2280
gataaggcgc agcggtcggg ctgaacgggg ggttcgtgca cacagcccag cttggagcga    2340
acgacctaca ccgaactgag atacctacag cgtgagctat gagaaagcgc cacgcttccc    2400
gaagggagaa aggcggacag gtatccggta agcggcaggg tcggaacagg agagcgcacg    2460
agggagcttc caggggggaaa cgcctggtat ctttatagtc ctgtcgggtt cgccacctc    2520
tgacttgagc gtcgattttt gtgatgctcg tcagggggc ggagcctatg gaaaaacgcc    2580
agcaacgcgg ccttttttacg gttcctggcc ttttgctggc cttttgctca catgttcttt    2640
cctgcgttat cccctgattc tgtggataac cgtattaccg cctttgagtg agctgatacc    2700
gctcgccgca gccgaacgac cgagcgcagc gagtcagtga gcgaggaagc ggaagagcgc    2760
ctgatgcggt attttctcct tacgcatctg tgcggtattt cacaccgcat atg           2813

<210> SEQ ID NO 4
<211> LENGTH: 703
<212> TYPE: PRT
<213> ORGANISM: Vibrio alginolyticus
```

<400> SEQUENCE: 4

Met Asn Gln Ile Thr Lys Leu Thr Gln Phe Ala Phe Met Phe Phe Met
1               5                   10                  15

Thr Leu Ala Leu Ser Leu Leu Ser Leu Ser Ile Ser Ala Gln Thr Thr
            20                  25                  30

Asp Thr Gly Trp Ile Thr Asn Pro Gln His Pro Pro Val Gln Thr Arg
        35                  40                  45

Phe Val Leu Thr Gly Gln Gln Asp Pro Gln Ala Lys Thr Leu Thr Gly
    50                  55                  60

Tyr Leu Asp Val Lys Leu Thr Gly Asp Trp Lys Thr Tyr Trp Arg Ser
65                  70                  75                  80

Pro Gly Glu Gly Gly Val Ala Pro Ser Ile Asp Trp Gln Asn Ser Gln
                85                  90                  95

Asn Leu Ser Lys Val Asp Trp Gln Trp Pro His Pro Gln Lys Phe Glu
            100                 105                 110

Leu Leu Gly Ile Glu Thr Leu Gly Tyr Lys Gly Asp Thr Leu Phe Pro
        115                 120                 125

Met Thr Leu His Val Glu Asp Met Ser Lys Pro Val Thr Ile Asp Ala
    130                 135                 140

Val Leu Thr Leu Ser Ser Cys Thr Thr Ile Cys Val Leu Thr Asp Tyr
145                 150                 155                 160

Gln Ile Gln Leu Thr Phe Leu Pro Ser Asp Leu Thr Val Asp Glu Gly
                165                 170                 175

Val Met Phe Ser Tyr Ala Gln Ala Val Ser Asn Val Pro Gln Pro Ser
            180                 185                 190

Pro Phe Ile Asp Val Thr Gln Ala Ser Trp Asp Val Asn Gln Ser Lys
        195                 200                 205

Leu Gln Ile Lys Leu Gln Asn Ser Gln Gly Trp Gln Gln Pro Gln Val
    210                 215                 220

Leu Val Asp Gly Val Asp Glu Ala Thr Arg Asp Tyr Ser Phe Lys Leu
225                 230                 235                 240

Glu Gly Met His Gln Glu Gly Asn Ile Val Thr Ala Ser Tyr Ile Val
                245                 250                 255

Asp Thr Trp Leu Gly Asp Val Glu Leu Asp Gly Gln Ser Leu Phe Val
            260                 265                 270

Thr Ile Lys Asp Thr Asn Leu Leu Ala Glu Glu Thr Thr Gln Ala Thr
        275                 280                 285

Ala Glu Ala Ile Val Glu Pro Leu Pro Ser Thr Ser Leu Thr Ser Val
    290                 295                 300

Phe Leu Phe Ala Leu Leu Gly Gly Leu Ile Leu Asn Ile Met Pro Cys
305                 310                 315                 320

Val Leu Pro Val Leu Gly Met Lys Leu Ser Ser Ile Val Ala Ala Gln
                325                 330                 335

Gly Ile Glu Arg Arg Gln Ile Arg Ala Gln Phe Val Ala Ser Ser Leu
            340                 345                 350

Gly Ile Leu Thr Ser Phe Trp Ile Leu Ala Gly Phe Ile Leu Val Leu
        355                 360                 365

Lys Leu Thr Gly Asn Ala Ile Gly Trp Gly Val Gln Phe Gln Ser Pro
    370                 375                 380

Trp Phe Leu Gly Leu Met Val Leu Val Thr Thr Leu Phe Gly Ala Asn
385                 390                 395                 400

Met Leu Gly Leu Phe Glu Val Arg Leu Ser Ser Gly Thr Asn Thr Trp
                405                 410                 415

```
Leu Ala Ser Lys Gly Asp Asn Ser Leu Ala Gly His Tyr Val Gln Gly
                420                 425                 430

Met Phe Ala Thr Leu Ala Thr Pro Cys Ser Ala Pro Phe Leu Gly
                435                 440                 445

Thr Ala Val Ala Phe Ala Leu Gly Ala Asp Val Leu Thr Leu Phe Ala
450                 455                 460

Thr Phe Thr Ala Leu Ala Leu Gly Met Ala Leu Pro Trp Leu Val
465                 470                 475                 480

Ala Val Phe Pro Asn Ile Ala Leu Lys Leu Pro Lys Pro Gly Ser Trp
                485                 490                 495

Met Asn Val Val Lys Ile Val Phe Gly Ile Met Met Leu Ala Thr Ser
                500                 505                 510

Ile Trp Leu Leu Ser Leu Met Ala Asn His Val Pro Met Leu Trp Ile
                515                 520                 525

Ala Leu Ile Ala Val Val Ala Phe Val Val Met Met Ala Arg Val Lys
                530                 535                 540

Lys Val Tyr Gly Glu Lys Ala Leu Ala Val Ser Gly Thr Ala Ser Leu
545                 550                 555                 560

Val Leu Ile Ala Gly Gly Leu Leu Gly Ser Val Thr Ala Asp Gln
                565                 570                 575

Trp Ala Thr Pro Leu Pro Glu Asp Leu Ala Trp Gln Lys Leu Ser Asn
                580                 585                 590

Ser Ala Ile Glu Asp His Val Asn Asn Gly Arg Val Val Phe Val Asp
                595                 600                 605

Val Thr Ala Asp Trp Cys Val Thr Cys Lys Ala Asn Lys Ile Gly Val
                610                 615                 620

Ile Trp Gln Asp Pro Val Tyr Ser Leu Leu Gln Ser Pro Asn Val Ala
625                 630                 635                 640

Thr Leu Lys Gly Asp Trp Thr His Pro Asp Gly Ser Val Thr Asp Phe
                645                 650                 655

Leu Arg Ala His Gly Arg Tyr Gly Val Pro Phe Asn Ile Val Tyr Gly
                660                 665                 670

Pro Ala Ala Pro Gln Gly Ile Pro Leu Pro Val Ile Leu Thr Asp Asp
                675                 680                 685

Val Val Leu Ser Ala Val Lys Gln Ala Ser Gly Gly Ala Ile Gln
                690                 695                 700

<210> SEQ ID NO 5
<211> LENGTH: 188
<212> TYPE: PRT
<213> ORGANISM: Vibrio alginolyticus

<400> SEQUENCE: 5

Met Lys Lys Thr Leu Ile Thr Leu Ala Leu Ala Leu Thr Thr Thr Thr
1               5                   10                  15

Ala Phe Ala Gln Met Asp His Ser Asn Met Asp His Ala Asn Met Asp
                20                  25                  30

His Ser Asn Met Lys His Glu Asn Met Asp His Gly Ser Met Lys Met
                35                  40                  45

Asp His Ser Lys Met Asp His Ser Asn Met Met Asp Met Pro Gly Met
                50                  55                  60

Ser Ala Val Gly Met Pro Ala Lys Gly Ala Lys Pro Asp Lys Val Val
65                  70                  75                  80

His Val Ile Leu Gly Asp Asp Met Thr Ile Lys Phe Lys Lys Asp Val
```

```
                85                  90                  95
Lys Ile Glu Pro Asn Asp Val Val Gln Phe Val Val Met Asn Thr Gly
            100                 105                 110

Lys Ile Asn His Glu Phe Thr Ile Gly Ser Ala Lys Glu Gln Leu Glu
            115                 120                 125

His Arg Glu Met Met Lys Thr Met Ser Gly Asp His Met His Asp Ser
        130                 135                 140

Gly Asn Ala Val Thr Val Glu Pro Gly Lys Ala Lys Gln Leu Leu Trp
145                 150                 155                 160

His Phe His Gly Asp Asn Lys Val Glu Phe Ala Cys Asn Ile Pro Gly
                165                 170                 175

His Ala Glu Ser Gly Met Val Lys Lys Ile Glu Leu
            180                 185

<210> SEQ ID NO 6
<211> LENGTH: 249
<212> TYPE: PRT
<213> ORGANISM: Vibrio alginolyticus

<400> SEQUENCE: 6

Met Asn Val Val Thr His Leu Glu Val Cys Ile Asp Asn Ile Glu Ser
1               5                   10                  15

Leu His Tyr Ala Ile Ala Gly Gly Ala Thr Arg Ile Glu Leu Cys Ser
            20                  25                  30

Ser Leu Ala Leu Gly Gly Leu Thr Pro Ser Tyr Gly Phe Met Gln Gln
        35                  40                  45

Ala Ala Lys Leu Ser Ser Val Pro Val Tyr Ala Met Ile Arg Pro Arg
    50                  55                  60

Gln Gly Asp Phe Phe Tyr Asn Glu Glu Ile Glu Met Met Arg Trp
65                  70                  75                  80

Asp Ile Glu Ala Ala His Gln Ser Gly Leu Ser Gly Val Val Phe Gly
                85                  90                  95

Val Leu Thr Gln Asp Gly Asp Ile His Met Pro Tyr Ala Ala Ala Leu
            100                 105                 110

Cys Glu Phe Ala Gln Ala Leu Gly Leu Gly Val Thr Phe His Arg Ala
            115                 120                 125

Phe Asp Gln Cys Arg Asp Ala Glu Lys Thr Leu Glu Glu Leu Ile Ser
        130                 135                 140

Leu Gly Cys Glu Arg Ile Leu Thr Ser Gly Leu Ala Pro Ser Ala Pro
145                 150                 155                 160

Gln Gly Ile Asp Val Leu Arg Ala Leu Val Lys Gln Ala Gln Gly Arg
                165                 170                 175

Ile Ala Ile Met Ala Gly Ala Gly Val Asn Ala Ser Asn Val Arg Ala
            180                 185                 190

Leu Val Glu Asp Thr Gln Val Pro Glu Ile His Leu Ser Gly Lys Thr
        195                 200                 205

Thr Arg Pro Ser Gln Met Thr Phe Val Ala Glu Gln Ser Lys Met Gly
    210                 215                 220

Ala Ser Asp Val Asp Asp Phe Leu Ile Pro Ile Thr Ser Thr Gln Ala
225                 230                 235                 240

Ile Thr Asp Val Val Ala Thr Leu Lys
                245

<210> SEQ ID NO 7
<211> LENGTH: 460
```

<212> TYPE: PRT
<213> ORGANISM: Vibrio alginolyticus

<400> SEQUENCE: 7

```
Met Asp Ile Ser Arg Arg Phe Leu Gln Ser Ser Leu Ala Ile Ser
1               5                   10                  15

Ala Leu Thr Val Leu Pro Ala Cys Ser Leu Ser Arg Ser Thr Asn Lys
            20                  25                  30

Gln Gly Gln Tyr Ile Tyr Asp Ile Thr Ala Glu Pro Ser Thr Ala Glu
            35                  40                  45

Leu Val Pro Gly Phe Asn Thr Asp Val Leu Ala Phe Asn Gly Ser Ile
        50                  55                  60

Pro Ala Pro Thr Ile Arg Cys Arg Gln Gly Glu Lys Val Ile Ile Arg
65                  70                  75                  80

Phe Thr Asn Lys Leu Ser Glu Pro Thr Thr Ile His Trp His Gly Leu
                85                  90                  95

Arg Ile Pro Ile Glu Met Asp Gly Val Pro Phe Leu Ser Gln Pro Pro
            100                 105                 110

Ile Met Pro Gly Glu Thr Phe Val Tyr Glu Phe Thr Pro Pro Asp Ala
        115                 120                 125

Gly Thr Phe Trp Tyr His Pro His Met Asn Ser Val Lys Gln Leu Gly
        130                 135                 140

Met Gly Leu Val Gly Leu Ile Val Glu Glu Ala Glu Pro Val Leu
145                 150                 155                 160

Phe Asp Glu Glu Gln Glu Ile Val Leu Lys His Trp His Leu Asp Lys
                165                 170                 175

Gln Gly Gln Trp Lys Asn Leu Met Val Pro Arg Leu Ser Ala Arg Met
            180                 185                 190

Gly Thr Pro Gly Glu Trp Ser Ser Val Asn Gly Val His Glu Pro Val
        195                 200                 205

Tyr Ala Leu Lys Gln Asn Ala Thr Thr Arg Leu Arg Ile Ala Asn Val
    210                 215                 220

Asp Asn Thr Ile Thr Tyr Pro Ile Ala Ile Glu Gly Ala Glu Ala Trp
225                 230                 235                 240

Val Ile Ala Ile Asp Gly Asn Pro Val Lys Ala Pro Tyr Lys Leu Thr
                245                 250                 255

Gln His Lys Ile Gly Pro Gly Met Arg Leu Asp Val Gly Leu Ile Ala
            260                 265                 270

Pro Lys Ala Gly Thr Arg Val Tyr Val Arg Arg Met Lys Gly Arg Phe
        275                 280                 285

Pro Phe Pro Leu Cys Glu Phe Asp Val Val Glu Ser Asp Leu Pro Ser
        290                 295                 300

Asn Gln Lys Leu Pro Leu Leu Pro Leu Asn Pro Val Pro Ala Leu Asp
305                 310                 315                 320

Leu Lys Asn Ala Glu Gln Ile Asp Tyr Val Phe Glu Trp Glu Gly Ala
                325                 330                 335

Ile Thr Pro Ala Asp Lys Ser Gly Lys Ala Ile Pro Gln Phe Trp Leu
            340                 345                 350

Met Asn Lys Arg Ala Trp Glu Gly Met Ser Lys Asp Asn Ile Pro Ala
        355                 360                 365

Pro Leu Ser Thr Leu Glu Met Gly Lys Thr Tyr Ile Phe Asn Leu Lys
        370                 375                 380

Asn Val Thr Gln Tyr His His Pro Ile His Leu His Gly His Thr Phe
385                 390                 395                 400
```

```
Thr Val Leu Glu Leu Asp Gly Lys Lys Leu Asp Glu Pro Phe His Thr
                405                 410                 415

Asp Thr Val Leu Leu Gly Lys Ser Gly Ser Ala Lys Ala Ala Phe Val
            420                 425                 430

Ala Asp Asn Pro Gly Arg Trp Met Tyr His Cys His Val Ile Glu His
        435                 440                 445

Met Lys Thr Gly Leu Met Gly Tyr Ile Glu Val Lys
    450                 455                 460

<210> SEQ ID NO 8
<211> LENGTH: 572
<212> TYPE: PRT
<213> ORGANISM: Vibrio alginolyticus

<400> SEQUENCE: 8

Met Lys Thr Leu Lys Ile Ala Thr Ile Ala Leu Ile Val Gly Gly Ala
1               5                   10                  15

Leu Gly Phe Gly Ala Asn His Phe Leu Ala Gly Ser Thr His Asp Met
            20                  25                  30

Ser Ala Met Gly Gly Glu Ser Ala Ala Ser Ser Asn Asp Pro Leu Tyr
        35                  40                  45

Trp Val Ala Pro Met Asp Pro Asn Tyr Lys Arg Asp Lys Pro Gly Lys
    50                  55                  60

Ser Pro Met Gly Met Asp Leu Ile Pro Val Tyr Ala Glu Asp Leu Ser
65                  70                  75                  80

Gly Glu Gln Asp Ala Pro Gly Thr Val Thr Ile Asp Pro Ser Val Glu
                85                  90                  95

Asn Asn Leu Gly Val Lys Thr Ala Asn Ala Thr Leu Gln Gln Leu Ser
            100                 105                 110

Pro Arg Ile Glu Thr Val Gly Tyr Ile Ala Phe Asp Glu Ser Leu Leu
        115                 120                 125

Trp Gln Thr Asn Val Arg Val Ala Gly Trp Val Glu Lys Leu Tyr Ile
    130                 135                 140

Asn Ala Val Gly Glu Lys Val Lys Lys Gly Asp Val Leu Phe Thr Leu
145                 150                 155                 160

Tyr Ser Pro Glu Leu Val Lys Ala Gln Glu Glu Leu Leu Asn Ala Tyr
                165                 170                 175

Arg Thr Gly Arg Lys Gly Leu Val Lys Gly Ala Thr Glu Arg Leu Val
            180                 185                 190

Thr Leu Gly Val Asp Arg Ala Gln Ile Lys Ser Ile Thr Arg Ser Gly
        195                 200                 205

Lys Ala Ser Gln Thr Ile Glu Ile Lys Ala Pro Ala Asp Gly Val Ile
    210                 215                 220

Ala Ser Leu Asn Val Arg Glu Gly Gly Tyr Leu Ser Pro Ala Gln Ala
225                 230                 235                 240

Val Ile Ser Ala Gly Pro Leu Asp Asn Val Trp Val Asp Ala Glu Val
                245                 250                 255

Phe Glu Arg Gln Ala His Trp Met Lys Ala Gly Ser Gln Ala Thr Met
            260                 265                 270

Thr Leu Asp Ala Ile Pro Gly Asn Glu Trp Gln Gly Val Val Asp Tyr
        275                 280                 285

Val Tyr Pro Ile Leu Asp Pro Lys Thr Arg Thr Leu Arg Val Arg Leu
    290                 295                 300

Lys Phe Pro Asn Pro Asp Gly Ala Leu Lys Pro Asn Met Phe Ala Asn
```

```
            305                 310                 315                 320
        Ile Ala Leu Gln Pro Val Thr Asp His Ala Val Leu Thr Ile Pro Lys
                        325                 330                 335

Ser Ser Val Ile Arg Ser Gly Gly Met Thr Arg Val Val Leu Ala Glu
                        340                 345                 350

Gly Glu Gly Lys Tyr Arg Ser Arg Ile Glu Val Gly Arg Glu Ala
                        355                 360                 365

Gly Glu Gln Ile Glu Val Leu Gln Gly Leu Lys Gln Gly Asp Lys Ile
                        370                 375                 380

Val Thr Ser Ser His Phe Met Leu Asp Ser Glu Ser Ser Gln Ser Ala
        385                 390                 395                 400

Asp Leu Ser Arg Ile Asn Gly Val Glu Ala Ala Glu Thr Ala Trp
                        405                 410                 415

Ala Lys Gly Glu Ile Thr Asp Val Met Lys Asp His Arg Met Leu Thr
                        420                 425                 430

Ile Asn His Gln Pro Val Pro Glu Trp Asp Trp Pro Gly Met Val Met
                        435                 440                 445

Asn Phe Thr Phe Ala Asp Gly Val Glu Met Gly Asp Leu Lys Lys Gly
                        450                 455                 460

Gln Ala Ile Glu Phe Glu Met Gln Lys Thr Glu Ser Gly Gln Tyr Gln
        465                 470                 475                 480

Ile Ile Asp Tyr Lys Ala Asp Asn Ser Val Ile Ala Ala Glu Val Trp
                        485                 490                 495

Leu Thr Gly Asp Ile Ser Met Leu Met Thr Asp Phe Gly Met Ile Thr
                        500                 505                 510

Leu Asn His Leu Pro Val Ala Glu Trp Asn Trp Asp Ala Gly Glu Met
                        515                 520                 525

Asn Phe Ser Val Gly Glu Asp Val Asp Leu Ser Gly Phe Glu Glu Gly
                        530                 535                 540

Gln Lys Val Arg Phe Leu Val Glu Lys Gln Gly Ser Asp Tyr Val Leu
        545                 550                 555                 560

Lys Gln Leu Val Pro Ala Thr Ile Ala Val Glu Gly
                        565                 570

<210> SEQ ID NO 9
<211> LENGTH: 609
<212> TYPE: PRT
<213> ORGANISM: Pseudomonas syringae

<400> SEQUENCE: 9

Met Glu Ser Arg Thr Ser Arg Arg Thr Phe Val Lys Gly Leu Ala Ala
        1               5                   10                  15

Ala Gly Val Leu Gly Gly Leu Gly Leu Trp Arg Ser Pro Ser Trp Ala
                        20                  25                  30

Ala Ser Gly Ser Pro Ala Leu Ser Val Leu Ser Gly Thr Glu Phe Asp
                        35                  40                  45

Leu Ser Ile Gly Glu Met Pro Val Asn Ile Thr Gly Arg Arg Arg Thr
                        50                  55                  60

Ala Met Ala Ile Asn Gly Gly Leu Pro Gly Pro Leu Leu Arg Trp Lys
        65                  70                  75                  80

Glu Gly Asp Thr Val Thr Leu Arg Val Arg Asn Arg Leu Asp Ala Ala
                        85                  90                  95

Thr Ser Ile His Trp His Gly Ile Ile Leu Pro Pro Asn Met Asp Gly
                        100                 105                 110
```

```
Val Pro Gly Leu Ser Phe Ala Gly Ile Glu Pro Gly Val Tyr Val
            115                 120                 125
Tyr Gln Phe Lys Val Gln Gln Asn Gly Thr Tyr Trp Tyr His Ser His
    130                 135                 140
Ser Gly Phe Gln Glu Gln Val Gly Val Tyr Gly Pro Leu Val Ile Glu
145                 150                 155                 160
Ala Lys Glu Pro Glu Pro Phe Lys Tyr Asp Ser Glu His Val Val Met
                165                 170                 175
Leu Thr Asp Trp Thr Asp Glu Asp Pro Val Ser Leu Met Arg Thr Leu
            180                 185                 190
Lys Lys Gln Ser Asp Tyr Tyr Asn Phe His Lys Arg Thr Val Gly Asp
    195                 200                 205
Phe Val Asn Asp Val Ala Asp Lys Gly Trp Ala Ala Thr Val Ala Asp
    210                 215                 220
Arg Lys Met Trp Ala Glu Met Lys Met Asn Pro Thr Asp Leu Ala Asp
225                 230                 235                 240
Val Ser Gly Ala Thr Tyr Thr Tyr Leu Leu Asn Gly Gln Ala Pro Asn
                245                 250                 255
Met Asn Trp Thr Gly Leu Phe Arg Pro Gly Glu Lys Leu Arg Leu Arg
            260                 265                 270
Phe Ile Asn Gly Ser Ala Met Thr Tyr Phe Asp Ile Arg Ile Pro Gly
    275                 280                 285
Leu Lys Met Thr Val Val Ala Ser Asp Gly Gln Phe Val Asn Pro Val
    290                 295                 300
Glu Val Asp Glu Leu Arg Ile Ala Val Ala Glu Thr Phe Asp Val Ile
305                 310                 315                 320
Val Glu Pro Thr Ala Glu Ala Tyr Thr Val Phe Ala Gln Ser Met Asp
                325                 330                 335
Arg Thr Gly Tyr Ala Arg Gly Thr Leu Ala Val Arg Glu Gly Leu Val
            340                 345                 350
Ala Gln Val Pro Pro Leu Asp Pro Arg Pro Leu Val Thr Met Asp Asp
    355                 360                 365
Met Gly Met Gly Gly Met Asp His Gly Ser Met Asp Gly Met Ser Gly
    370                 375                 380
Met Asp Ser Gly Ala Asp Asp Gly Met Gln Thr Met Ser Ser Met Gly
385                 390                 395                 400
Gly Asp Ser Met Pro Ala Met Asp His Ser Lys Met Ser Thr Met Gln
                405                 410                 415
Gly Met Asp His Gly Ala Met Ser Gly Met Asp His Gly Ala Met Gly
            420                 425                 430
Gly Met Val Met Gln Ser His Pro Ala Ser Glu Asn Asp Asn Pro Leu
    435                 440                 445
Val Asp Met Gln Ala Met Ser Pro Thr Ala Lys Leu Asn Asp Pro Gly
    450                 455                 460
Leu Gly Leu Arg Asn Asn Gly Arg Lys Val Leu Thr Tyr Ala Asp Leu
465                 470                 475                 480
Lys Ser Thr Phe Glu Asp Pro Asp Gly Arg Glu Pro Ser Arg Thr Ile
                485                 490                 495
Glu Leu His Leu Thr Gly His Met Glu Lys Phe Ala Trp Ser Phe Asp
            500                 505                 510
Gly Ile Lys Phe Ala Asp Ala Gln Pro Leu Ile Leu Lys Tyr Gly Glu
    515                 520                 525
Arg Val Arg Ile Val Leu Val Asn Asp Thr Met Met Thr His Pro Ile
```

```
                530              535              540
His Leu His Gly Met Trp Ser Asp Leu Glu Asp Glu Asp Gly Asn Phe
545              550              555              560

Arg Val Arg Lys His Thr Ile Asp Met Pro Pro Gly Ser Lys Arg Ser
            565              570              575

Tyr Arg Val Thr Ala Asp Ala Leu Gly Arg Trp Ala Tyr His Cys His
            580              585              590

Leu Leu Tyr His Met Glu Met Gly Met Phe Arg Glu Val Arg Val Glu
        595              600              605

Glu

<210> SEQ ID NO 10
<211> LENGTH: 328
<212> TYPE: PRT
<213> ORGANISM: Pseudomonas syringae

<400> SEQUENCE: 10

Met Thr Val Leu Asn Arg Leu His Val Cys Ser Leu Leu Ala Val Ser
1               5                  10                  15

Ser Leu Gly Met Leu Pro Val Gly Val Phe Ala Ala Glu Ala Ala Met
            20                  25                  30

Pro Gly Val Asp His Ser Gln Met Gln Gly Met Asp His Ser Lys Met
        35                  40                  45

Gln Gly Met Asp His Ser Gln Met Gln Gly Met Asp His Ser Lys Met
50                  55                  60

Gln Gly Met Asp His Ser Gln Met Gln Gly Met Asp Ser Asp Met Thr
65                  70                  75                  80

Thr Met Ala Pro Ser Lys Pro Ala Ala Pro Thr Gln Ser Arg Thr Pro
                85                  90                  95

Ile Ala Pro Val Thr Asp Ala Asn Arg Ala Ala Val Tyr Arg Ser Ala
            100                 105                 110

Lys Gly His Thr Val His Asp Glu Ala Ala Asn Tyr Phe Leu Leu Phe
        115                 120                 125

Asp Gln Leu Glu Trp Gln Asp Ala Asp Asn Gly Ser Val Leu Asn Trp
130                 135                 140

Asp Val Asn Gly Trp Val Gly Gly Asp Ile Asp Arg Leu Trp Ile Arg
145                 150                 155                 160

Ser Glu Gly Glu Arg Thr Asn Gly Lys Thr Glu Ser Ala Glu Leu Gln
                165                 170                 175

Ala Leu Trp Gly His Ala Ile Ser Pro Trp Trp Asp Leu Val Gly Gly
            180                 185                 190

Val Arg Gln Asp Phe Lys Pro Gly Ser Pro Gln Thr Trp Ala Ala Phe
        195                 200                 205

Gly Leu Gln Gly Leu Ala Leu Tyr Asn Phe Glu Ala Glu Ala Thr Ala
210                 215                 220

Phe Leu Gly Glu Gly Gly Gln Thr Gly Leu Arg Leu Glu Gly Asp Tyr
225                 230                 235                 240

Asp Ile Leu Leu Thr Asn Arg Leu Ile Leu Gln Pro Thr Ala Glu Val
                245                 250                 255

Asn Phe Tyr Gly Gln Ser Asp Pro Gln Arg Gly Ile Gly Ser Gly Leu
            260                 265                 270

Ser Glu Thr Glu Val Gly Val Arg Leu Arg Tyr Glu Ile Arg Arg Glu
        275                 280                 285

Phe Ala Pro Tyr Ile Gly Val Thr Trp Asn Arg Ser Tyr Gly Asn Thr
```

```
                    290                 295                 300
Ala Asp Phe Ala Arg Glu Glu Gly Asp Arg Ser Glu Ala Arg Leu
305                 310                 315                 320

Val Leu Gly Val Arg Met Trp Phe
                325

<210> SEQ ID NO 11
<211> LENGTH: 126
<212> TYPE: PRT
<213> ORGANISM: Pseudomonas syringae

<400> SEQUENCE: 11

Met Leu Leu Asn Arg Thr Ser Phe Val Thr Leu Phe Ala Ala Gly Met
1               5                   10                  15

Leu Val Ser Ala Leu Ala Gln Ala His Pro Lys Leu Val Ser Ser Thr
            20                  25                  30

Pro Ala Glu Gly Ser Glu Gly Ala Ala Pro Ala Lys Ile Glu Leu His
        35                  40                  45

Phe Ser Glu Asn Leu Val Thr Gln Phe Ser Gly Ala Lys Leu Val Met
    50                  55                  60

Thr Ala Met Pro Gly Met Glu His Ser Pro Met Ala Val Lys Ala Ala
65                  70                  75                  80

Val Ser Gly Gly Gly Asp Pro Lys Thr Met Val Ile Thr Pro Ala Ser
                85                  90                  95

Pro Leu Thr Ala Gly Thr Tyr Lys Val Asp Trp Arg Ala Val Ser Ser
            100                 105                 110

Asp Thr His Pro Ile Thr Gly Ser Val Thr Phe Lys Val Lys
        115                 120                 125

<210> SEQ ID NO 12
<211> LENGTH: 310
<212> TYPE: PRT
<213> ORGANISM: Pseudomonas syringae

<400> SEQUENCE: 12

Met Glu Asp Pro Leu Ser Ile Ala Val Arg Phe Ala Leu Tyr Thr Asp
1               5                   10                  15

Leu Met Met Leu Phe Gly Leu Ala Leu Phe Gly Leu Tyr Ser Leu Arg
            20                  25                  30

Gly Ala Glu Arg Arg Ser Gly Ala Val Leu Pro Phe Arg Pro Leu Leu
        35                  40                  45

Ser Ala Thr Ala Leu Ile Gly Leu Leu Leu Ser Val Val Ser Ile Val
    50                  55                  60

Leu Met Ala Lys Ala Met Ser Gly Ala Ser Glu Trp Leu Glu Ala Val
65                  70                  75                  80

Pro His Ala Glu Met Met Val Thr Gln Thr Glu Leu Gly Thr Ala Trp
                85                  90                  95

Leu Ile Arg Met Ala Ala Leu Val Gly Ala Val Thr Ile Ala Phe
            100                 105                 110

Asn Leu Arg Val Pro Met Ala Ser Leu Leu Met Val Ser Leu Leu Gly
        115                 120                 125

Gly Val Ala Leu Ala Thr Leu Ala Trp Thr Gly His Gly Ala Met Asp
    130                 135                 140

Glu Gly Ser Arg Arg Phe Trp His Phe Ser Ala Asp Ile Leu His Leu
145                 150                 155                 160

Trp Ser Ser Gly Gly Trp Phe Gly Ala Leu Val Ala Phe Ala Leu Met
```

|  |  | 165 |  |  | 170 |  |  | 175 |  |  |
|---|---|---|---|---|---|---|---|---|---|---|

Leu Arg Pro Asn Lys Val Glu Thr Leu Gln Ser Val Gln Val Leu Ser
                    180                    185                    190

Arg Thr Leu Ser Gly Phe Glu Arg Ala Gly Ala Val Ile Val Ala Phe
     195                    200                    205

Ile Val Leu Ser Gly Val Val Asn Tyr Leu Phe Ile Val Gly Pro Gln
    210                    215                    220

Val Ser Gly Val Val Glu Ser Thr Tyr Gly Val Leu Leu Leu Gly Lys
225                  230                    235                240

Leu Ala Leu Phe Gly Leu Met Val Gly Leu Ala Ser Ala Asn Arg Phe
            245                    250                255

Val Leu Ser Pro Ala Phe Glu Arg Ala Val His Arg Gly Glu Tyr Ala
          260                    265                    270

Arg Ala Ala Arg Ser Ile Arg Tyr Ser Met Ala Leu Glu Leu Gly Ala
            275                    280                285

Ala Val Leu Val Leu Gly Leu Ile Ala Trp Leu Gly Thr Leu Ser Pro
    290                    295                    300

Glu Met Glu Ala Gly Met
305                  310

<210> SEQ ID NO 13
<211> LENGTH: 4478
<212> TYPE: DNA
<213> ORGANISM: Pseudomonas syringae

<400> SEQUENCE: 13

| ctgcagatac | taaaaaaact | gaaagctcta | aggcatgttg | ctaaccaacg | caggttttca | 60 |
|---|---|---|---|---|---|---|
| agcttacaga | aatgtaatcg | cgccgcttac | gatgctgtga | catcgtccac | tccagtacct | 120 |
| taaacccagt | acacggctta | aatgccgtcc | ttgcctacct | ggacccgcgc | gtatggaatc | 180 |
| aagaacttct | cgacgtactt | tcgtcaaagg | cctcgcggct | gccggcgtgc | taggtgggct | 240 |
| aggcttgtgg | cgttcgccca | gctgggcggc | gtccggctcg | ccggcgctca | gcgtgttgag | 300 |
| cggtacggag | ttcgacctgt | ctattggcga | gatgccggta | acatcaccg | gcaggcgtcg | 360 |
| cacagcgatg | gcgatcaatg | gcgggctgcc | gggcccctg | ctgcgctgga | agagggtga | 420 |
| cactgtcacg | ctccgggtac | gcaaccggct | cgacgctgca | acctccatac | actggcacgg | 480 |
| cattatcctg | ccgccgaaca | tggacggcgt | tccaggactg | agcttcgcgg | gcatcgagcc | 540 |
| gggtggcgtg | tacgtctacc | agttcaaggt | ccaacagaac | gggacgtact | ggtaccacag | 600 |
| ccactccgga | tttcaggagc | aggtgggggt | gtatggcccg | ctcgtcatcg | aggcgaaaga | 660 |
| gcccgagcct | ttcaagtacg | acagtgaaca | tgtggtgatg | ctgaccgact | ggacggatga | 720 |
| agatcccgtc | tcgctgatgc | gtaccctcaa | aaagcagtcc | gattactaca | acttccacaa | 780 |
| gcgcacagtc | ggtgacttcg | tcaacgatgt | ggctgataag | ggctgggccg | caaccgtcgc | 840 |
| ggatcgcaag | atgtgggccg | agatgaagat | gaacccacg | gaccttgcgg | acgtgagcgg | 900 |
| ggccacctac | acgtacctgc | tcaatggtca | ggcccccaat | atgaactgga | ccggcttgtt | 960 |
| ccgtcctggc | gaaagctgc | gcctgcggtt | catcaacggc | tcggctatga | cgtacttcga | 1020 |
| catccgtatt | ccaggcctga | aaatgaccgt | ggtagcttcg | gatggccagt | tcgtgaaccc | 1080 |
| ggttgaggtc | gatgaattac | gcattgccgt | ggccgaaacc | ttcgatgtga | tcgttgagcc | 1140 |
| cactgccgag | gcgtatacgg | tctttgctca | atccatggat | cgcacgggct | acgcccgcgg | 1200 |
| cacccctagcc | gtgcgggaag | gcttggtagc | ccaggtcccc | cccttgatc | ctcgtccgct | 1260 |

```
ggtcacgatg gacgatatgg gcatgggtgg tatggaccat ggcagcatgg atggcatgag    1320
cggcatggat tcgggtgccg acgacggcat gcagaccatg agcagcatgg ggggcgactc    1380
catgcccgcc atggaccata gcaaaatgtc taccatgcag ggtatggacc acggcgctat    1440
gtcgggcatg gaccatggtg cgatgggcgg catggtgatg cagagccacc ctgccagcga    1500
gaacgacaac ccgctggtgg acatgcaggc catgagccct accgccaagc tgaacgatcc    1560
tggcctgggc ctgcgtaata cgggcgcaa ggtgctcacc tatgccgacc ttaaaagcac     1620
cttcgaagac cctgacgggc gtgagccgag ccggaccatt gagctgcacc tgaccgggca    1680
catggaaaaa tttgcatggt cgtttgacgg catcaaattc gcggacgccc aacctctgat    1740
actcaaatac ggcgaacggg taagaatcgt gctggtgaat gacacgatga tgactcaccc    1800
gatccatctg catgggatgt ggagtgactt ggaggacgag gacggaaact tcagggtgcg    1860
caagcacacc attgatatgc cgccaggctc caagcgcagc taccgtgtca ccgctgatgc    1920
cctggggcgc tgggcctatc actgtcacct gctctaccac atggagatgg gtatgttccg    1980
cgaagttcgg gtagaggagt gaggccaatg actgttttga atagactcca cgtttgttca    2040
ctgctcgcgg tcagcagcct gggaatgctc ccagtgggcg tgtttgcggc agaggccgct    2100
atgccgggcg tggaccacag ccagatgcaa ggcatggatc attccaagat gcagggtatg    2160
gaccacagcc agatgcaggg catggatcat tccaaaatgc agggtatgga ccatagccag    2220
atgcagggca tggactcgga catgacgacc atggccccca gcaagcctgc ggcaccgaca    2280
caaagccgca cgcctattgc gcctgtcacc gatgccaatc gggctgcggt ctaccgaagt    2340
gccaaaggcc acactgtcca tgacgaagca gctaattatt cctgctcctt cgatcaactc    2400
gaatggcagg acgccgacaa cggcagcgtc cttaattggg acgttaacgg ctgggtgggt    2460
ggtgacatcg accggctctg gattcgctcc gagggcgaac gtaccaacgg caagaccgaa    2520
tcggccgagc tgcaagcgct gtggggccat gcgatcagtc cttggtggga cctggtcggc    2580
ggcgtccggc aggacttcaa gccaggctcg ccgcaaacct gggctgcatt tggcctccag    2640
ggcctcgctt tatacaactt cgaagccgaa gcgactgcgt ttcttggtga aggcggccaa    2700
accgggttaa ggctggaagg cgactacgac atttttgctga ctaaccggct gattttacag    2760
cccacggctg aggttaattt ctacggtcag agcgatcctc agcgcggcat cggctctggc    2820
ctgtctgaaa ccgaagtcgg cgtacgactg cgctacgaaa tccgccgcga gtttgccccg    2880
tacattggcg tcacctggaa ccgctcctac ggcaatacag ccgactttgc ccgcgaggaa    2940
ggcgaggacc gcagcgaggc ccgcttagtc tgggcgtgc catgtggtt ctgagccgtt     3000
ctagtctgaa aatctgatcc cccacgaacg gccttttgg gctgtaagga gttcgcatgt     3060
tgttgaaccg cacaagtttc gtcacgctct ttgccgctgg gatgctggtc agcgcattgg    3120
cccaagccca ccccaagctg gtgtcttcga ctccggctga aggtagtgaa ggcgcggccc    3180
ctgccaagat cgagctgcat ttctccgaaa acctggttac ccaattttcc ggcgcgaagc    3240
tggtcatgac ggcgatgcca ggcatggaac actcaccgat ggcagtcaaa gccgcggtat    3300
cgggcggggg tgaccccaag accatggtga ttaccccggc ctcacctctg acggcaggca    3360
cctacaaggt cgattggcgg gcagtgtctt ccgatacca cccgattacc ggtagcgtga     3420
cgtttaaggt caagtaaaca tggaagatcc gctcagcatc gcagttcgtt tcgcgctgta    3480
taccgatttg atgatgctgt tcgggctggc cctcttttggc ctttacagcc tacgcggcgc    3540
agaacgccgt tcgggcgctg tattgccttt caggcccctt ctgagcgcga ccgctttgat    3600
cggcctgctg ttgtcggttg tctccattgt gctcatggcc aaagccatga gcggtgcgtc    3660
```

-continued

```
tgaatggcta gaggctgtgc ctcacgccga gatgatggtg acgcagacgg agcttggcac   3720
tgcctggctc atccgcatgg ccgcactggt gggggctgct gtgaccatcg ccttcaacct   3780
tcgggtgccc atggcaagcc tgctgatggt ttcgctgctg ggaggcgtgg ccctggcgac   3840
cttggcctgg acgggccacg gggccatgga cgaaggctcc cggcgctttt ggcacttcag   3900
cgcggacatc cttcatctgt ggtcctcggg cggctggttc ggcgcgctgg tggcgtttgc   3960
actgatgctg cggcccaaca aggtcgaaac cctacagtca gtccaggtgc tgtcgcgcac   4020
gctcagcggt ttcgaacggg ccggcgcggt gatcgtggct ttcatcgtcc tctcgggcgt   4080
ggtgaactat ctgttcatcg tcggcccccca ggtcagtggt gtggtggaaa gcacctacgg   4140
ggtgttgctg ctgggcaagc tggcactgtt tggccttatg gtcggattgg cctcagctaa   4200
ccgctttgtc ctgagcccgg cgtttgaacg ggcggtccac cggggcgagt acgcgcgagc   4260
ggcccgctcg atccgctaca gcatggccct ggaactgggc gccgccgtct tggtgtttgg   4320g cctgattgcc tggcttggca cactgtcccc tgagatggaa gcggggatgt gagtgtgcct   4380
gaccctgttt taccgtcaca ctgggccggt gccgtggagg gtcgaacatg aaactgctgg   4440
tagccgaaga cgaacctaaa actggaatct atctgcag                           4478
```

<210> SEQ ID NO 14
<211> LENGTH: 525
<212> TYPE: PRT
<213> ORGANISM: Yersinia pestis

<400> SEQUENCE: 14

```
Met Asn Ser Ser Phe Glu Ser Leu Ile Glu Gln Tyr Pro Leu Pro Ile
1               5                   10                  15

Ala Glu Gln Leu Arg His Trp Ala Ala Arg Tyr Ala Ser Arg Ile Ala
            20                  25                  30

Val Val Asp Ala Lys Gly Ser Leu Thr Tyr Ser Ala Leu Asp Ala Gln
        35                  40                  45

Val Asp Glu Leu Ala Ala Gly Leu Ser Ser Leu Gly Leu Arg Ser Gly
    50                  55                  60

Glu His Val Ile Val Gln Leu Pro Asn Asp Asn Ala Phe Val Thr Leu
65                  70                  75                  80

Leu Phe Ala Leu Leu Arg Leu Gly Val Ile Pro Val Leu Ala Met Pro
                85                  90                  95

Ser Gln Arg Ala Leu Asp Ile Asp Ala Leu Ile Glu Leu Ala Gln Pro
            100                 105                 110

Val Ala Tyr Val Ile His Gly Glu Asn His Ala Glu Leu Ala Arg Gln
        115                 120                 125

Met Ala His Lys His Ala Cys Leu Arg His Val Leu Val Ala Gly Glu
    130                 135                 140

Thr Val Ser Asp Asp Phe Thr Pro Leu Phe Ser Leu His Gly Glu Arg
145                 150                 155                 160

Gln Ala Trp Pro Gln Pro Asp Val Ser Ala Thr Ala Leu Leu Leu Leu
                165                 170                 175

Ser Gly Gly Thr Thr Gly Thr Pro Lys Leu Ile Pro Arg Arg His Ala
            180                 185                 190

Asp Tyr Ser Tyr Asn Phe Ser Ala Ser Ala Glu Leu Cys Gly Ile Ser
        195                 200                 205

Gln Gln Ser Val Tyr Leu Ala Val Leu Pro Val Ala His Asn Phe Pro
    210                 215                 220
```

-continued

Leu Ala Cys Pro Gly Ile Leu Gly Thr Leu Ala Cys Gly Gly Lys Val
225                 230                 235                 240

Val Leu Thr Asp Ser Ala Ser Cys Asp Glu Val Met Pro Leu Ile Ala
            245                 250                 255

Gln Glu Arg Val Thr His Val Ala Leu Val Pro Ala Leu Ala Gln Leu
            260                 265                 270

Trp Val Gln Ala Arg Glu Trp Glu Asp Ser Asp Leu Ser Ser Leu Arg
            275                 280                 285

Val Ile Gln Ala Gly Gly Ala Arg Leu Asp Pro Thr Leu Ala Glu Gln
290                 295                 300

Val Ile Ala Thr Phe Asp Cys Thr Leu Gln Gln Val Phe Gly Met Ala
305                 310                 315                 320

Glu Gly Leu Leu Cys Phe Thr Arg Leu Asp Asp Pro His Ala Thr Ile
                325                 330                 335

Leu His Ser Gln Gly Arg Pro Leu Ser Pro Leu Asp Glu Ile Arg Ile
                340                 345                 350

Val Asp Gln Asp Glu Asn Asp Val Ala Pro Gly Glu Thr Gly Gln Leu
            355                 360                 365

Leu Thr Arg Gly Pro Tyr Thr Ile Ser Gly Tyr Tyr Arg Ala Pro Ala
370                 375                 380

His Asn Ala Gln Ala Phe Thr Ala Gln Gly Phe Tyr Arg Thr Gly Asp
385                 390                 395                 400

Asn Val Arg Leu Asp Glu Val Gly Asn Leu His Val Glu Gly Arg Ile
                405                 410                 415

Lys Glu Gln Ile Asn Arg Ala Gly Glu Lys Ile Ala Ala Glu Val
            420                 425                 430

Glu Ser Ala Leu Leu Arg Leu Ala Glu Val Gln Asp Cys Ala Val Val
            435                 440                 445

Ala Ala Pro Asp Thr Leu Leu Gly Glu Arg Ile Cys Ala Phe Ile Ile
450                 455                 460

Ala Gln Gln Val Pro Thr Asp Tyr Gln Gln Leu Arg Gln Gln Leu Thr
465                 470                 475                 480

Arg Met Gly Leu Ser Ala Trp Lys Ile Pro Asp Gln Ile Glu Phe Leu
                485                 490                 495

Asp His Trp Pro Leu Thr Ala Val Gly Lys Ile Asp Lys Lys Arg Leu
                500                 505                 510

Thr Ala Leu Ala Val Asp Arg Tyr Arg His Ser Ala Gln
            515                 520                 525

<210> SEQ ID NO 15
<211> LENGTH: 267
<212> TYPE: PRT
<213> ORGANISM: Yersinia pestis

<400> SEQUENCE: 15

Met Thr Gln Ser Ala Met Cys Ile Pro Leu Trp Pro Ala Arg Asn Gly
1               5                   10                  15

Asn Thr Ala His Leu Val Met Cys Pro Phe Ala Gly Gly Ser Ser Ser
            20                  25                  30

Ala Phe Arg His Trp Gln Ala Glu Gln Leu Thr Asp Cys Ala Leu Ser
        35                  40                  45

Leu Val Thr Trp Pro Gly Arg Asp Arg Leu His Leu Glu Pro Leu
    50                  55                  60

Arg Ser Ile Thr Gln Leu Ala Ala Leu Leu Ala Asn Glu Leu Glu Ala
65                  70                  75                  80

```
Ser Val Ser Pro Asp Thr Pro Leu Leu Leu Ala Gly His Ser Met Gly
                85                  90                  95

Ala Gln Val Ala Phe Glu Thr Cys Arg Leu Leu Glu Gln Arg Gly Leu
            100                 105                 110

Ala Pro Gln Gly Leu Ile Ile Ser Gly Cys His Ala Pro His Leu His
        115                 120                 125

Ser Glu Arg Gln Leu Ser His Arg Asp Asp Ala Asp Phe Ile Ala Glu
    130                 135                 140

Leu Ile Asp Ile Gly Gly Cys Ser Pro Glu Leu Arg Glu Asn Gln Glu
145                 150                 155                 160

Leu Met Ser Leu Phe Leu Pro Leu Leu Arg Ala Asp Phe Tyr Ala Thr
                165                 170                 175

Glu Ser Tyr His Tyr Asp Ser Pro Asp Val Cys Pro Pro Leu Arg Thr
            180                 185                 190

Pro Ala Leu Leu Leu Cys Gly Ser His Asp Arg Glu Ala Ser Trp Gln
        195                 200                 205

Gln Val Asp Ala Trp Arg Gln Trp Leu Ser His Val Thr Gly Pro Val
    210                 215                 220

Val Ile Asp Gly Asp His Phe Tyr Pro Ile Gln Gln Ala Arg Ser Phe
225                 230                 235                 240

Phe Thr Gln Ile Val Arg His Phe Pro His Ala Phe Ser Ala Met Thr
                245                 250                 255

Ala Leu Gln Lys Gln Pro Ser Thr Ser Glu Arg
            260                 265

<210> SEQ ID NO 16
<211> LENGTH: 366
<212> TYPE: PRT
<213> ORGANISM: Yersinia pestis

<400> SEQUENCE: 16

Met Met Pro Ser Ala Ser Pro Lys Gln Arg Val Leu Ile Val Gly Ala
1               5                   10                  15

Lys Phe Gly Glu Met Tyr Leu Asn Ala Phe Met Gln Pro Pro Glu Gly
            20                  25                  30

Leu Glu Leu Val Gly Leu Leu Ala Gln Gly Ser Ala Arg Ser Arg Glu
        35                  40                  45

Leu Ala His Ala Phe Gly Ile Pro Leu Tyr Thr Ser Pro Glu Gln Ile
    50                  55                  60

Thr Arg Met Pro Asp Ile Ala Cys Ile Val Val Arg Ser Thr Val Ala
65                  70                  75                  80

Gly Gly Thr Gly Thr Gln Leu Ala Arg His Phe Leu Thr Arg Gly Val
                85                  90                  95

His Val Ile Gln Glu His Pro Leu His Pro Asp Asp Ile Ser Ser Leu
            100                 105                 110

Gln Thr Leu Ala Gln Glu Gln Gly Cys Cys Tyr Trp Val Asn Thr Phe
        115                 120                 125

Tyr Pro His Thr Arg Ala Gly Arg Thr Trp Leu Arg Asp Ala Gln Gln
    130                 135                 140

Leu Arg Arg Cys Leu Ala Lys Thr Pro Pro Val Val His Ala Thr Thr
145                 150                 155                 160

Ser Arg Gln Leu Leu Tyr Ser Thr Leu Asp Leu Leu Leu Ala Leu
                165                 170                 175

Gly Val Asp Ala Ala Ala Val Glu Cys Asp Val Val Gly Ser Phe Ser
```

180                 185                 190
Asp Phe His Cys Leu Arg Leu Phe Trp Pro Glu Gly Glu Ala Cys Leu
                195                 200                 205

Leu Leu Gln Arg Tyr Leu Asp Pro Asp Pro Asp Met His Ser Leu
        210                 215                 220

Ile Met His Arg Leu Leu Leu Gly Trp Pro Glu Gly His Leu Ser Leu
225                 230                 235                 240

Glu Ala Ser Tyr Gly Pro Val Ile Trp Ser Ser Leu Phe Val Ala
                245                 250                 255

Asp His Gln Glu Asn Ala His Ser Leu Tyr Arg Arg Pro Glu Ile Leu
            260                 265                 270

Arg Asp Leu Pro Gly Leu Thr Arg Ser Ala Ala Pro Leu Ser Trp Arg
        275                 280                 285

Asp Cys Cys Glu Thr Val Gly Pro Glu Gly Val Ser Trp Leu Leu His
        290                 295                 300

Gln Leu Arg Ser His Leu Ala Gly Glu His Pro Pro Ala Ala Cys Gln
305                 310                 315                 320

Ser Val His Gln Ile Ala Leu Ser Arg Leu Trp Gln Gln Ile Leu Arg
                325                 330                 335

Lys Thr Gly Asn Ala Glu Ile Arg Arg Leu Thr Pro Pro His His Asp
            340                 345                 350

Arg Leu Ala Gly Phe Tyr Asn Asp Asp Lys Glu Ala Leu
        355                 360                 365

<210> SEQ ID NO 17
<211> LENGTH: 3163
<212> TYPE: PRT
<213> ORGANISM: Yersinia pestis

<400> SEQUENCE: 17

Met Asp Asn Leu Arg Phe Ser Ser Ala Pro Thr Ala Asp Ser Ile Asp
1               5                   10                  15

Ala Ser Ile Ala Gln His Tyr Pro Asp Cys Glu Pro Val Ala Val Ile
                20                  25                  30

Gly Tyr Ala Cys His Phe Pro Glu Ser Pro Asp Gly Glu Thr Phe Trp
            35                  40                  45

Gln Asn Leu Leu Glu Gly Arg Glu Cys Ser Arg Arg Phe Thr Arg Glu
        50                  55                  60

Glu Leu Leu Ala Val Gly Leu Asp Ala Ala Ile Ile Asp Asp Pro His
65                  70                  75                  80

Tyr Val Asn Ile Gly Thr Val Leu Asp Asn Ala Asp Cys Phe Asp Ala
                85                  90                  95

Thr Leu Phe Gly Tyr Ser Arg Gln Glu Ala Glu Ser Met Asp Pro Gln
            100                 105                 110

Gln Arg Leu Phe Leu Gln Ala Val Trp His Ala Leu Glu His Ala Gly
        115                 120                 125

Tyr Ala Pro Gly Ala Val Pro His Lys Thr Gly Val Phe Ala Ser Ser
    130                 135                 140

Arg Met Ser Thr Tyr Pro Gly Arg Glu Ala Leu Asn Val Thr Glu Val
145                 150                 155                 160

Ala Gln Val Lys Gly Leu Gln Ser Leu Met Gly Asn Asp Lys Asp Tyr
                165                 170                 175

Ile Ala Thr Arg Ala Ala Tyr Lys Leu Asn Leu His Gly Pro Ala Leu
            180                 185                 190

```
Ser Val Gln Thr Ala Cys Ser Ser Leu Val Ala Val His Leu Ala
    195                 200                 205

Cys Glu Ser Leu Arg Ala Gly Glu Ser Asp Met Ala Val Ala Gly Gly
210                 215                 220

Val Ala Leu Ser Phe Pro Gln Gln Ala Gly Tyr Arg Tyr Gln Pro Gly
225                 230                 235                 240

Met Ile Phe Ser Pro Asp Gly His Cys Arg Pro Phe Asp Ala Ser Ala
                245                 250                 255

Glu Gly Thr Trp Ala Gly Asn Gly Leu Gly Cys Val Val Leu Arg Arg
                260                 265                 270

Leu Arg Asp Ala Leu Leu Ser Gly Asp Pro Ile Ile Ser Val Ile Leu
        275                 280                 285

Ser Ser Ala Val Asn Asn Asp Gly Asn Arg Lys Val Gly Tyr Thr Ala
    290                 295                 300

Pro Ser Val Ala Gly Gln Gln Ala Val Ile Glu Glu Ala Leu Met Leu
305                 310                 315                 320

Ala Ala Ile Asp Asp Arg Gln Val Gly Tyr Ile Glu Thr His Gly Thr
                325                 330                 335

Gly Thr Pro Leu Gly Asp Ala Ile Glu Ile Glu Ala Leu Arg Asn Val
                340                 345                 350

Tyr Ala Pro Arg Pro Gln Asp Gln Arg Cys Ala Leu Gly Ser Val Lys
        355                 360                 365

Ser Asn Met Gly His Leu Asp Thr Ala Ala Gly Ile Ala Gly Leu Leu
    370                 375                 380

Lys Thr Val Leu Ala Val Ser Arg Gly Gln Ile Pro Pro Leu Leu Asn
385                 390                 395                 400

Phe His Thr Pro Asn Pro Ala Leu Lys Leu Glu Glu Ser Pro Phe Thr
                405                 410                 415

Ile Pro Val Ser Ala Gln Ala Trp Gln Asp Glu Met Arg Tyr Ala Gly
                420                 425                 430

Val Ser Ser Phe Gly Ile Gly Gly Thr Asn Cys His Met Ile Val Ala
        435                 440                 445

Ser Leu Pro Asp Ala Leu Asn Ala Arg Leu Pro Asn Thr Asp Ser Gly
    450                 455                 460

Arg Lys Ser Thr Ala Leu Leu Leu Ser Ala Ala Ser Asp Ser Ala Leu
465                 470                 475                 480

Arg Arg Leu Ala Thr Asp Tyr Ala Gly Ala Leu Arg Glu Asn Ala Asp
                485                 490                 495

Ala Ser Ser Leu Ala Phe Thr Ala Leu His Ala Arg Arg Leu Asp Leu
                500                 505                 510

Pro Phe Arg Leu Ala Ala Pro Leu Asn Arg Glu Thr Ala Glu Ala Leu
        515                 520                 525

Ser Ala Trp Ala Gly Glu Lys Ser Gly Ala Leu Val Tyr Ser Gly His
    530                 535                 540

Gly Ala Ser Gly Lys Gln Val Trp Leu Phe Thr Gly Gln Gly Ser His
545                 550                 555                 560

Trp Arg Thr Met Gly Gln Thr Met Tyr Gln His Ser Thr Ala Phe Ala
                565                 570                 575

Asp Thr Leu Asp Arg Cys Phe Ser Ala Cys Ser Glu Met Leu Thr Pro
                580                 585                 590

Ser Leu Arg Glu Ala Met Phe Asn Pro Asp Ser Ala Gln Leu Asp Asn
        595                 600                 605

Met Ala Trp Ala Gln Pro Ala Ile Val Ala Phe Glu Ile Ala Met Ala
```

```
            610                615                620
Ala His Trp Arg Ala Glu Gly Leu Lys Pro Asp Phe Ala Ile Gly His
625                630                635                640

Ser Val Gly Glu Phe Ala Ala Val Val Cys Gly His Tyr Thr Ile
            645                650                655

Glu Gln Val Met Pro Leu Val Cys Arg Arg Gly Ala Leu Met Gln Gln
                660                665                670

Cys Ala Ser Gly Ala Met Val Ala Val Phe Ala Asp Glu Asp Thr Leu
            675                680                685

Met Pro Leu Ala Arg Gln Phe Glu Leu Asp Leu Ala Ala Asn Asn Gly
690                695                700

Thr Gln His Thr Val Phe Ser Gly Pro Glu Ala Arg Leu Ala Val Phe
705                710                715                720

Cys Ala Thr Leu Ser Gln His Asp Ile Asn Tyr Arg Arg Leu Ser Val
                725                730                735

Thr Gly Ala Ala His Ser Ala Leu Leu Glu Pro Ile Leu Asp Arg Phe
            740                745                750

Gln Asp Ala Cys Ala Gly Leu His Ala Glu Pro Gly Gln Ile Pro Ile
            755                760                765

Ile Ser Thr Leu Thr Ala Asp Val Ile Asp Glu Ser Thr Leu Asn Gln
770                775                780

Ala Asp Tyr Trp Arg Arg His Met Arg Gln Pro Val Arg Phe Ile Gln
785                790                795                800

Ser Ile Gln Val Ala His Gln Leu Gly Ala Arg Val Phe Leu Glu Met
                805                810                815

Gly Pro Asp Ala Gln Leu Val Ala Cys Gly Gln Arg Glu Tyr Arg Asp
            820                825                830

Asn Ala Tyr Trp Ile Ala Ser Ala Arg Arg Asn Lys Glu Ala Ser Asp
            835                840                845

Val Leu Asn Gln Ala Leu Leu Gln Leu Tyr Ala Ala Gly Val Ala Leu
850                855                860

Pro Trp Ala Asp Leu Leu Ala Gly Asp Gly Gln Arg Ile Ala Ala Pro
865                870                875                880

Cys Tyr Pro Phe Asp Thr Glu Arg Tyr Trp Lys Glu Arg Val Ser Pro
            885                890                895

Ala Cys Glu Pro Ala Asp Ala Ala Leu Ser Ala Gly Leu Glu Val Ala
                900                905                910

Ser Arg Ala Ala Thr Ala Leu Asp Leu Pro Arg Leu Glu Ala Leu Lys
            915                920                925

Gln Cys Ala Thr Arg Leu His Ala Ile Tyr Val Asp Gln Leu Val Gln
930                935                940

Arg Cys Thr Gly Asp Ala Ile Glu Asn Gly Val Asp Ala Met Thr Ile
945                950                955                960

Met Arg Arg Gly Arg Leu Leu Pro Arg Tyr Gln Gln Leu Leu Gln Arg
                965                970                975

Leu Leu Asn Asn Cys Val Val Asp Gly Asp Tyr Arg Cys Thr Asp Gly
            980                985                990

Arg Tyr Val Arg Ala Arg Pro Ile Glu His Gln Gln Arg Glu Ser Leu
            995                1000               1005

Leu Thr Glu Leu Ala Gly Tyr Cys Glu Gly Phe Gln Ala Ile Pro
            1010               1015               1020

Asp Thr Ile Ala Arg Ala Gly Asp Arg Leu Tyr Glu Met Met Ser
            1025               1030               1035
```

```
Gly Ala Glu Glu Pro Val Ala Ile Ile Phe Pro Gln Ser Ala Ser
    1040            1045                1050

Asp Gly Val Glu Val Leu Tyr Gln Glu Phe Ser Phe Gly Arg Tyr
    1055            1060                1065

Phe Asn Gln Ile Ala Ala Gly Val Leu Arg Gly Ile Val Gln Thr
    1070            1075                1080

Arg Gln Pro Arg Gln Pro Leu Arg Ile Leu Glu Val Gly Gly Gly
    1085            1090                1095

Thr Gly Gly Thr Thr Ala Trp Leu Leu Pro Glu Leu Asn Gly Val
    1100            1105                1110

Pro Ala Leu Glu Tyr His Phe Thr Asp Ile Ser Ala Leu Phe Thr
    1115            1120                1125

Arg Arg Ala Gln Gln Lys Phe Ala Asp Tyr Asp Phe Val Lys Tyr
    1130            1135                1140

Ser Glu Leu Asp Leu Glu Lys Glu Ala Gln Ser Gln Gly Phe Gln
    1145            1150                1155

Ala Gln Ser Tyr Asp Leu Ile Val Ala Ala Asn Val Ile His Ala
    1160            1165                1170

Thr Arg His Ile Gly Arg Thr Leu Asp Asn Leu Arg Pro Leu Leu
    1175            1180                1185

Lys Pro Gly Gly Arg Leu Leu Met Arg Glu Ile Thr Gln Pro Met
    1190            1195                1200

Arg Leu Phe Asp Phe Val Phe Gly Pro Leu Val Leu Pro Leu Gln
    1205            1210                1215

Asp Leu Asp Ala Arg Glu Gly Glu Leu Phe Leu Thr Thr Ala Gln
    1220            1225                1230

Trp Gln Gln Gln Cys Arg His Ala Gly Phe Ser Lys Val Ala Trp
    1235            1240                1245

Leu Pro Gln Asp Gly Ser Pro Thr Ala Gly Met Ser Glu His Ile
    1250            1255                1260

Ile Leu Ala Thr Leu Pro Gly Gln Ala Val Ser Ala Val Thr Phe
    1265            1270                1275

Thr Ala Pro Ser Glu Pro Val Leu Gly Gln Ala Leu Thr Asp Asn
    1280            1285                1290

Gly Asp Tyr Leu Ala Asp Trp Ser Asp Cys Ala Gly Gln Pro Glu
    1295            1300                1305

Arg Phe Asn Ala Arg Trp Gln Glu Ala Trp Arg Leu Leu Ser Gln
    1310            1315                1320

Arg His Gly Asp Ala Leu Pro Val Glu Pro Pro Val Ala Ala
    1325            1330                1335

Pro Glu Trp Leu Gly Lys Val Arg Leu Ser Trp Gln Asn Glu Ala
    1340            1345                1350

Phe Ser Arg Gly Gln Met Arg Val Glu Ala Arg His Pro Thr Gly
    1355            1360                1365

Glu Trp Leu Pro Leu Ser Pro Ala Ala Pro Leu Pro Ala Pro Gln
    1370            1375                1380

Thr His Tyr Gln Trp Arg Trp Thr Pro Leu Asn Val Ala Ser Ile
    1385            1390                1395

Asp His Pro Leu Thr Phe Ser Phe Ser Ala Gly Thr Leu Ala Arg
    1400            1405                1410

Ser Asp Glu Leu Ala Gln Tyr Gly Ile Ile His Asp Pro His Ala
    1415            1420                1425
```

```
Ser Ser Arg Leu Met Ile Val Glu Glu Ser Glu Asp Thr Leu Ala
1430                1435                1440

Leu Ala Glu Lys Val Ile Ala Ala Leu Thr Ala Ser Ala Ala Gly
1445                1450                1455

Leu Ile Val Val Thr Arg Arg Ala Trp Arg Val Glu Glu Asn Glu
1460                1465                1470

Ala Leu Ser Ala Ser His His Ala Leu Trp Ala Leu Leu Arg Val
1475                1480                1485

Ala Ala Asn Glu Gln Pro Glu Arg Leu Leu Ala Ala Ile Asp Leu
1490                1495                1500

Ala Glu Asn Thr Pro Trp Glu Thr Leu His Gln Gly Leu Ser Ala
1505                1510                1515

Val Ser Leu Ser Gln Arg Trp Leu Ala Ala Arg Gly Asp Thr Leu
1520                1525                1530

Trp Leu Pro Ser Leu Ala Pro Asn Thr Gly Cys Ala Ala Glu Leu
1535                1540                1545

Pro Ala Asn Val Phe Thr Gly Asp Ser Arg Trp His Leu Val Thr
1550                1555                1560

Gly Ala Phe Gly Gly Leu Gly Arg Leu Ala Val Asn Trp Leu Arg
1565                1570                1575

Glu Lys Gly Ala Arg Arg Ile Ala Leu Leu Ala Pro Arg Val Asp
1580                1585                1590

Glu Ser Trp Leu Arg Asp Val Glu Gly Gly Gln Thr Arg Val Cys
1595                1600                1605

Arg Cys Asp Val Gly Asp Ala Gly Gln Leu Ala Thr Val Leu Asp
1610                1615                1620

Asp Leu Ala Ala Asn Gly Gly Ile Ala Gly Ala Ile His Ala Ala
1625                1630                1635

Gly Val Leu Ala Asp Ala Pro Leu Gln Glu Leu Asp Asp His Gln
1640                1645                1650

Leu Ala Ala Val Phe Ala Val Lys Ala Gln Ala Ala Ser Gln Leu
1655                1660                1665

Leu Gln Thr Leu Arg Asn His Asp Gly Arg Tyr Leu Ile Leu Tyr
1670                1675                1680

Ser Ser Ala Ala Ala Thr Leu Gly Ala Pro Gly Gln Ser Ala His
1685                1690                1695

Ala Leu Ala Cys Gly Tyr Leu Asp Gly Leu Ala Gln Gln Phe Ser
1700                1705                1710

Thr Leu Asp Ala Pro Lys Thr Leu Ser Val Ala Trp Gly Ala Trp
1715                1720                1725

Gly Glu Ser Gly Arg Ala Ala Thr Pro Glu Met Leu Ala Thr Leu
1730                1735                1740

Ala Ser Arg Gly Met Gly Ala Leu Ser Asp Ala Glu Gly Cys Trp
1745                1750                1755

His Leu Glu Gln Ala Val Met Arg Gly Ala Pro Trp Arg Leu Ala
1760                1765                1770

Met Arg Val Phe Thr Asp Lys Met Pro Pro Leu Gln Gln Ala Leu
1775                1780                1785

Phe Asn Ile Ser Ala Thr Glu Lys Ala Ala Thr Pro Val Ile Pro
1790                1795                1800

Pro Ala Asp Asp Asn Ala Phe Asn Gly Ser Leu Ser Asp Glu Thr
1805                1810                1815

Ala Val Met Ala Trp Leu Lys Lys Arg Ile Ala Val Gln Leu Arg
```

```
                    1820                1825                1830
Leu Ser Asp Pro Ala Ser Leu His Pro Asn Gln Asp Leu Leu Gln
    1835                1840                1845
Leu Gly Met Asp Ser Leu Leu Phe Leu Glu Leu Ser Ser Asp Ile
    1850                1855                1860
Gln His Tyr Leu Gly Val Arg Ile Asn Ala Glu Arg Ala Trp Gln
    1865                1870                1875
Asp Leu Ser Pro His Gly Leu Thr Gln Leu Ile Cys Ser Lys Pro
    1880                1885                1890
Glu Ala Thr Pro Ala Ala Ser Gln Pro Glu Val Leu Arg His Asp
    1895                1900                1905
Ala Asp Glu Arg Tyr Ala Pro Phe Pro Leu Thr Pro Ile Gln His
    1910                1915                1920
Ala Tyr Trp Leu Gly Arg Thr His Leu Ile Gly Tyr Gly Gly Val
    1925                1930                1935
Ala Cys His Val Leu Phe Glu Trp Asp Lys Arg His Asp Glu Phe
    1940                1945                1950
Asp Leu Ala Ile Leu Glu Lys Ala Trp Asn Gln Leu Ile Ala Arg
    1955                1960                1965
His Asp Met Leu Arg Met Val Asp Ala Asp Gly Gln Gln Arg
    1970                1975                1980
Ile Leu Ala Thr Thr Pro Glu Tyr His Ile Pro Arg Asp Asp Leu
    1985                1990                1995
Arg Ala Leu Ser Pro Glu Glu Gln Arg Ile Ala Leu Glu Lys Arg
    2000                2005                2010
Arg His Glu Leu Ser Tyr Arg Val Leu Pro Ala Asp Gln Trp Pro
    2015                2020                2025
Leu Phe Glu Leu Val Val Ser Glu Ile Asp Asp Cys His Tyr Arg
    2030                2035                2040
Leu His Met Asn Leu Asp Leu Leu Gln Phe Asp Val Gln Ser Phe
    2045                2050                2055
Lys Val Met Met Asp Asp Leu Ala Gln Val Trp Arg Gly Glu Thr
    2060                2065                2070
Leu Ala Pro Leu Ala Ile Thr Phe Arg Asp Tyr Val Met Ala Glu
    2075                2080                2085
Gln Ala Arg Arg Gln Thr Ser Ala Trp His Asp Ala Trp Asp Tyr
    2090                2095                2100
Trp Gln Glu Lys Leu Pro Gln Leu Pro Leu Ala Pro Glu Leu Pro
    2105                2110                2115
Val Val Glu Thr Pro Pro Glu Thr Pro His Phe Thr Thr Phe Lys
    2120                2125                2130
Ser Thr Ile Gly Lys Thr Glu Trp Gln Ala Val Lys Gln Arg Trp
    2135                2140                2145
Gln Gln Gln Gly Val Thr Pro Ser Ala Ala Leu Leu Thr Leu Phe
    2150                2155                2160
Ala Ala Thr Leu Glu Arg Trp Ser Arg Thr Thr Thr Phe Thr Leu
    2165                2170                2175
Asn Leu Thr Phe Phe Asn Arg Gln Pro Ile His Pro Gln Ile Asn
    2180                2185                2190
Gln Leu Ile Gly Asp Phe Thr Ser Val Thr Leu Val Asp Phe Asn
    2195                2200                2205
Phe Ser Ala Pro Val Thr Leu Gln Glu Gln Met Gln Gln Thr Gln
    2210                2215                2220
```

-continued

```
Gln Arg Leu Trp Gln Asn Met Ala His Ser Glu Met Asn Gly Val
2225                2230                2235

Glu Val Ile Arg Glu Leu Gly Arg Leu Arg Gly Ser Gln Arg Gln
2240                2245                2250

Pro Leu Met Pro Val Val Phe Thr Ser Met Leu Gly Met Thr Leu
2255                2260                2265

Glu Gly Met Thr Ile Asp Gln Ala Met Ser His Leu Phe Gly Glu
2270                2275                2280

Pro Cys Tyr Val Phe Thr Gln Thr Pro Gln Val Trp Leu Asp His
2285                2290                2295

Gln Val Met Glu Ser Asp Gly Glu Leu Met Phe Ser Trp Tyr Cys
2300                2305                2310

Met Asp Asn Val Leu Glu Pro Gly Ala Ala Glu Ala Met Phe Asn
2315                2320                2325

Asp Tyr Cys Ala Ile Leu Gln Ala Val Ile Ala Ala Pro Glu Ser
2330                2335                2340

Leu Lys Thr Leu Ala Ser Gly Ile Ala Gly His Ile Pro Arg Arg
2345                2350                2355

Arg Trp Pro Leu Asn Ala Gln Ala Asp Tyr Asp Leu Arg Asp Ile
2360                2365                2370

Glu Gln Ala Thr Leu Glu Tyr Pro Gly Ile Arg Gln Ala Arg Ala
2375                2380                2385

Glu Ile Thr Glu Gln Gly Ala Leu Thr Leu Asp Ile Val Met Ala
2390                2395                2400

Asp Asp Pro Ser Pro Ser Ala Ala Met Pro Asp Glu His Glu Leu
2405                2410                2415

Thr Gln Leu Ala Leu Pro Leu Pro Glu Gln Ala Gln Leu Asp Glu
2420                2425                2430

Leu Glu Ala Thr Trp Arg Trp Leu Glu Ala Arg Ala Leu Gln Gly
2435                2440                2445

Ile Ala Ala Thr Leu Asn Arg His Gly Leu Phe Thr Thr Pro Glu
2450                2455                2460

Ile Ala His Arg Phe Ser Ala Ile Val Gln Ala Leu Ser Ala Gln
2465                2470                2475

Ala Ser His Gln Arg Leu Leu Arg Gln Trp Leu Gln Cys Leu Thr
2480                2485                2490

Glu Arg Glu Trp Leu Ile Arg Glu Gly Glu Ser Trp Arg Cys Arg
2495                2500                2505

Ile Pro Leu Ser Glu Ile Pro Glu Pro Gln Glu Ala Cys Pro Gln
2510                2515                2520

Ser Gln Trp Ser Gln Ala Leu Ala Gln Tyr Leu Glu Thr Cys Ile
2525                2530                2535

Ala Arg His Asp Ala Leu Phe Ser Gly Gln Cys Ser Pro Leu Glu
2540                2545                2550

Leu Leu Phe Asn Glu Gln His Arg Val Thr Asp Ala Leu Tyr Arg
2555                2560                2565

Asp Asn Pro Ala Ser Ala Cys Leu Asn Arg Tyr Thr Ala Gln Ile
2570                2575                2580

Ala Ala Leu Cys Ser Ala Glu Arg Ile Leu Glu Val Gly Ala Gly
2585                2590                2595

Thr Ala Ala Thr Thr Ala Pro Val Leu Lys Ala Thr Arg Asn Thr
2600                2605                2610
```

-continued

```
Arg Gln Ser Tyr His Phe Thr Asp Val Ser Ala Gln Phe Leu Asn
2615                2620                2625

Asp Ala Arg Ala Arg Phe His Asp Glu Ser Gln Val Ser Tyr Ala
2630                2635                2640

Leu Phe Asp Ile Asn Gln Pro Leu Asp Phe Thr Ala His Pro Glu
2645                2650                2655

Ala Gly Tyr Asp Leu Ile Val Ala Val Asn Val Leu His Asp Ala
2660                2665                2670

Ser His Val Val Gln Thr Leu Arg Arg Leu Lys Leu Leu Leu Lys
2675                2680                2685

Ala Gly Gly Arg Leu Leu Ile Val Glu Ala Thr Glu Arg Asn Ser
2690                2695                2700

Val Phe Gln Leu Ala Ser Val Gly Phe Ile Glu Gly Leu Ser Gly
2705                2710                2715

Tyr Arg Asp Phe Arg Arg Arg Asp Glu Lys Pro Met Leu Thr Arg
2720                2725                2730

Ser Ala Trp Gln Glu Val Leu Val Gln Ala Gly Phe Ala Asn Glu
2735                2740                2745

Leu Ala Trp Pro Ala Gln Glu Ser Ser Pro Leu Arg Gln His Leu
2750                2755                2760

Leu Val Ala Arg Ser Pro Gly Val Asn Arg Pro Asp Lys Lys Ala
2765                2770                2775

Val Ser Arg Tyr Leu Gln Gln Arg Phe Gly Thr Gly Leu Pro Ile
2780                2785                2790

Leu Gln Ile Arg Gln Arg Glu Ala Leu Phe Thr Pro Leu His Ala
2795                2800                2805

Pro Ser Asp Ala Pro Thr Glu Pro Ala Lys Pro Thr Pro Val Ala
2810                2815                2820

Gly Gly Asn Pro Ala Leu Glu Lys Gln Val Ala Glu Leu Trp Gln
2825                2830                2835

Ser Leu Leu Ser Arg Pro Val Ala Arg His His Asp Phe Phe Glu
2840                2845                2850

Leu Gly Gly Asp Ser Leu Met Ala Thr Arg Met Val Ala Gln Leu
2855                2860                2865

Asn Arg Arg Gly Ile Ala Arg Ala Asn Leu Gln Asp Leu Phe Ser
2870                2875                2880

His Ser Thr Leu Ser Asp Phe Cys Ala His Leu Gln Ala Ala Thr
2885                2890                2895

Ser Gly Glu Asp Asn Pro Ile Pro Leu Cys Gln Gly Asp Gly Glu
2900                2905                2910

Glu Thr Leu Phe Val Phe His Ala Ser Asp Gly Asp Ile Ser Ala
2915                2920                2925

Trp Leu Pro Leu Ala Ser Ala Leu Asn Arg Arg Val Phe Gly Leu
2930                2935                2940

Gln Ala Lys Ser Pro Gln Arg Phe Ala Thr Leu Asp Gln Met Ile
2945                2950                2955

Asp Glu Tyr Val Gly Cys Ile Arg Arg Gln Gln Pro His Gly Pro
2960                2965                2970

Tyr Val Leu Ala Gly Trp Ser Tyr Gly Ala Phe Leu Ala Ala Gly
2975                2980                2985

Ala Ala Gln Arg Leu Tyr Ala Lys Gly Glu Gln Val Arg Met Val
2990                2995                3000

Leu Ile Asp Pro Val Cys Arg Gln Asp Phe Cys Cys Glu Asn Arg
```

```
                       3005                3010                3015

Ala  Ala  Leu  Leu  Arg  Leu  Leu  Ala  Glu  Gly  Gln  Thr  Pro  Leu  Ala
         3020                3025                3030

Leu  Pro  Glu  His  Phe  Asp  Gln  Gln  Thr  Pro  Asp  Ser  Gln  Leu  Ala
         3035                3040                3045

Asp  Phe  Ile  Ser  Leu  Ala  Lys  Thr  Ala  Gly  Met  Val  Ser  Gln  Asn
         3050                3055                3060

Leu  Thr  Leu  Gln  Ala  Ala  Glu  Thr  Trp  Leu  Asp  Asn  Ile  Ala  His
         3065                3070                3075

Leu  Leu  Arg  Leu  Leu  Thr  Glu  His  Thr  Pro  Gly  Glu  Ser  Val  Pro
         3080                3085                3090

Val  Pro  Cys  Leu  Met  Val  Tyr  Ala  Ala  Gly  Arg  Pro  Ala  Arg  Trp
         3095                3100                3105

Thr  Pro  Ala  Glu  Thr  Glu  Trp  Gln  Gly  Trp  Ile  Asn  Asn  Ala  Asp
         3110                3115                3120

Asp  Ala  Val  Ile  Glu  Ala  Ser  His  Trp  Gln  Ile  Met  Met  Glu  Ala
         3125                3130                3135

Pro  His  Val  Gln  Ala  Cys  Ala  Gln  His  Ile  Thr  Arg  Trp  Leu  Cys
         3140                3145                3150

Ala  Thr  Ser  Thr  Gln  Pro  Glu  Asn  Thr  Leu
         3155                3160

<210> SEQ ID NO 18
<211> LENGTH: 2035
<212> TYPE: PRT
<213> ORGANISM: Yersinia pestis

<400> SEQUENCE: 18

Met  Ile  Ser  Gly  Ala  Pro  Ser  Gln  Asp  Ser  Leu  Leu  Pro  Asp  Asn  Arg
1                   5                   10                  15

His  Ala  Ala  Asp  Tyr  Gln  Gln  Leu  Arg  Glu  Arg  Leu  Ile  Gln  Glu  Leu
            20                  25                  30

Asn  Leu  Thr  Pro  Gln  Gln  Leu  His  Glu  Glu  Ser  Asn  Leu  Ile  Gln  Ala
        35                  40                  45

Gly  Leu  Asp  Ser  Ile  Arg  Leu  Met  Arg  Trp  Leu  His  Trp  Phe  Arg  Lys
50                  55                  60

Asn  Gly  Tyr  Arg  Leu  Thr  Leu  Arg  Glu  Leu  Tyr  Ala  Ala  Pro  Thr  Leu
65                  70                  75                  80

Ala  Ala  Trp  Asn  Gln  Leu  Met  Leu  Ser  Arg  Ser  Pro  Glu  Asn  Ala  Glu
                85                  90                  95

Glu  Glu  Thr  Pro  Pro  Asp  Glu  Ser  Ser  Trp  Pro  Asn  Met  Thr  Glu  Ser
            100                 105                 110

Thr  Pro  Phe  Pro  Leu  Thr  Pro  Val  Gln  His  Ala  Tyr  Leu  Thr  Gly  Arg
        115                 120                 125

Met  Pro  Gly  Gln  Thr  Leu  Gly  Gly  Val  Gly  Cys  His  Leu  Tyr  Gln  Glu
130                 135                 140

Phe  Glu  Gly  His  Cys  Leu  Thr  Ala  Ser  Gln  Leu  Glu  Gln  Ala  Ile  Thr
145                 150                 155                 160

Thr  Leu  Leu  Gln  Arg  His  Pro  Met  Leu  His  Ile  Ala  Phe  Arg  Pro  Asp
                165                 170                 175

Gly  Gln  Gln  Val  Trp  Leu  Pro  Gln  Pro  Tyr  Trp  Asn  Gly  Val  Thr  Val
            180                 185                 190

His  Asp  Leu  Arg  His  Asn  Asp  Ala  Glu  Ser  Arg  Gln  Ala  Tyr  Leu  Asp
        195                 200                 205
```

```
Ala Leu Arg Gln Arg Leu Ser His Arg Leu Leu Arg Val Glu Ile Gly
    210                 215                 220

Glu Thr Phe Asp Phe Gln Leu Thr Leu Leu Pro Asp Asn Arg His Arg
225                 230                 235                 240

Leu His Val Asn Ile Asp Leu Leu Ile Met Asp Ala Ser Ser Phe Thr
                245                 250                 255

Leu Phe Phe Asp Glu Leu Asn Ala Leu Leu Ala Gly Glu Ser Leu Pro
            260                 265                 270

Ala Ile Asp Thr Arg Tyr Asp Phe Arg Ser Tyr Leu Leu His Gln Gln
        275                 280                 285

Lys Ile Asn Gln Pro Leu Arg Asp Asp Ala Arg Ala Tyr Trp Leu Ala
290                 295                 300

Lys Ala Ser Thr Leu Pro Pro Ala Pro Val Leu Pro Leu Ala Cys Glu
305                 310                 315                 320

Pro Ala Thr Leu Arg Glu Val Arg Asn Thr Arg Arg Met Ile Val
                325                 330                 335

Pro Ala Thr Arg Trp His Ala Phe Ser Asn Arg Ala Gly Glu Tyr Gly
            340                 345                 350

Val Thr Pro Thr Met Ala Leu Ala Thr Cys Phe Ser Ala Val Leu Ala
        355                 360                 365

Arg Trp Gly Gly Leu Thr Arg Leu Leu Asn Ile Thr Leu Phe Asp
370                 375                 380

Arg Gln Pro Leu His Pro Ala Val Gly Ala Met Leu Ala Asp Phe Thr
385                 390                 395                 400

Asn Ile Leu Leu Leu Asp Thr Ala Cys Asp Gly Asp Thr Val Ser Asn
                405                 410                 415

Leu Ala Arg Lys Asn Gln Leu Thr Phe Thr Glu Asp Trp Glu His Arg
            420                 425                 430

His Trp Ser Gly Val Glu Leu Arg Glu Leu Lys Arg Gln Gln Arg
        435                 440                 445

Tyr Pro His Gly Ala Pro Val Val Phe Thr Ser Asn Leu Gly Arg Ser
    450                 455                 460

Leu Tyr Ser Ser Arg Ala Glu Ser Pro Leu Gly Glu Pro Glu Trp Gly
465                 470                 475                 480

Ile Ser Gln Thr Pro Gln Val Trp Ile Asp His Leu Ala Phe Glu His
                485                 490                 495

His Gly Glu Val Trp Leu Gln Trp Asp Ser Asn Asp Ala Leu Phe Pro
            500                 505                 510

Pro Ala Leu Val Glu Thr Leu Phe Asp Ala Tyr Cys Gln Leu Ile Asn
        515                 520                 525

Gln Leu Cys Asp Asp Glu Ser Ala Trp Gln Lys Pro Phe Ala Asp Met
530                 535                 540

Met Pro Ala Ser Gln Arg Ala Ile Arg Glu Arg Val Asn Ala Thr Gly
545                 550                 555                 560

Ala Pro Ile Pro Glu Gly Leu Leu His Glu Gly Ile Phe Arg Ile Ala
                565                 570                 575

Leu Gln Gln Pro Gln Ala Leu Ala Val Thr Asp Met Arg Tyr Gln Trp
            580                 585                 590

Asn Tyr His Glu Leu Thr Asp Tyr Ala Arg Arg Cys Ala Gly Arg Leu
        595                 600                 605

Ile Glu Cys Gly Val Gln Pro Gly Asp Asn Val Ala Ile Thr Met Ser
610                 615                 620

Lys Gly Ala Gly Gln Leu Val Ala Val Leu Ala Val Leu Leu Ala Gly
```

```
                625                 630                 635                 640
Ala Val Tyr Val Pro Val Ser Leu Asp Gln Pro Ala Ala Arg Arg Glu
                    645                 650                 655

Lys Ile Tyr Ala Asp Ala Ser Val Arg Leu Val Leu Ile Cys Gln His
                    660                 665                 670

Asp Ala Ser Ala Gly Ser Asp Ile Pro Val Leu Ala Trp Gln Gln
                    675                 680                 685

Ala Ile Glu Ala Glu Pro Ile Ala Asn Pro Val Arg Ala Pro Thr
    690                 695                 700

Gln Pro Ala Tyr Ile Ile Tyr Thr Ser Gly Ser Thr Gly Thr Pro Lys
705                 710                 715                 720

Gly Val Val Ile Ser His Arg Gly Ala Leu Asn Thr Cys Cys Asp Ile
                    725                 730                 735

Asn Thr Arg Tyr Gln Val Gly Pro His Asp Arg Val Leu Ala Leu Ser
                740                 745                 750

Ala Leu His Phe Asp Leu Ser Val Tyr Asp Ile Phe Gly Val Leu Arg
                755                 760                 765

Ala Gly Gly Ala Leu Val Met Val Met Glu Asn Gln Arg Arg Asp Pro
    770                 775                 780

His Ala Trp Cys Glu Leu Ile Gln Arg His Gln Val Thr Leu Trp Asn
785                 790                 795                 800

Ser Val Pro Ala Leu Phe Asp Met Leu Leu Thr Trp Cys Glu Gly Phe
                    805                 810                 815

Ala Asp Ala Thr Pro Glu Asn Leu Arg Ala Val Met Leu Ser Gly Asp
                820                 825                 830

Trp Ile Gly Leu Asp Leu Pro Ala Arg Tyr Arg Ala Phe Arg Pro Gln
    835                 840                 845

Gly Gln Phe Ile Ala Met Gly Gly Ala Thr Glu Ala Ser Ile Trp Ser
    850                 855                 860

Asn Ala Cys Glu Ile His Asp Val Pro Ala His Trp Arg Ser Ile Pro
865                 870                 875                 880

Tyr Gly Phe Pro Leu Thr Asn Gln Arg Tyr Arg Val Val Asp Glu Gln
                885                 890                 895

Gly Arg Asp Cys Pro Asp Trp Val Pro Gly Glu Leu Trp Ile Gly Gly
                900                 905                 910

Ile Gly Val Ala Glu Gly Tyr Phe Asn Asp Pro Leu Arg Ser Glu Gln
                915                 920                 925

Gln Phe Leu Thr Leu Pro Asp Glu Arg Trp Tyr Arg Thr Gly Asp Leu
    930                 935                 940

Gly Cys Tyr Trp Pro Asp Gly Thr Ile Glu Phe Leu Gly Arg Arg Asp
945                 950                 955                 960

Lys Gln Val Lys Val Gly Gly Tyr Arg Ile Glu Leu Gly Glu Ile Glu
                965                 970                 975

Ser Ala Leu Ser Gln Leu Ala Gly Val Lys Gln Ala Thr Val Leu Ala
                980                 985                 990

Ile Gly Glu Lys Glu Lys Thr Leu Ala Ala Tyr Val Val Pro Gln Gly
    995                 1000                1005

Glu Ala Phe Cys Val Thr Asp His Arg Asn Pro Ala Leu Pro Gln
    1010                1015                1020

Ala Trp His Thr Leu Ala Gly Thr Leu Pro Cys Cys Ala Ile Ser
    1025                1030                1035

Pro Glu Ile Ser Ala Glu Gln Val Ala Asp Phe Leu Gln His Arg
    1040                1045                1050
```

-continued

```
Leu Leu Lys Leu Lys Pro Gly His Thr Ala Gly Ala Asp Pro Leu
    1055            1060                1065

Pro Leu Met Asn Ser Leu Ala Ile Gln Pro Arg Trp Gln Ala Val
    1070            1075                1080

Val Glu Arg Trp Leu Ala Phe Leu Val Thr Gln Arg Arg Leu Lys
    1085            1090                1095

Pro Ala Ala Glu Gly Tyr Gln Val Cys Ala Gly Glu Glu Arg Glu
    1100            1105                1110

Asp Glu His Pro His Phe Ser Gly His Asp Leu Thr Leu Ser Gln
    1115            1120                1125

Ile Leu Arg Gly Ala Arg Asn Glu Leu Ser Leu Leu Asn Asp Ala
    1130            1135                1140

Gln Trp Ser Pro Glu Ser Leu Ala Phe Asn His Pro Ala Ser Ala
    1145            1150                1155

Pro Tyr Ile Gln Glu Leu Ala Thr Ile Cys Gln Gln Leu Ala Gln
    1160            1165                1170

Arg Leu Gln Arg Pro Val Arg Leu Leu Glu Val Gly Thr Arg Thr
    1175            1180                1185

Gly Arg Ala Ala Glu Ser Leu Leu Ala Gln Leu Asn Ala Gly Gln
    1190            1195                1200

Ile Glu Tyr Val Gly Leu Glu Gln Ser Gln Glu Met Leu Leu Ser
    1205            1210                1215

Ala Arg Gln Arg Leu Ala Pro Trp Pro Gly Ala Arg Leu Ser Leu
    1220            1225                1230

Trp Asn Ala Asp Thr Leu Ala Ala His Ala His Ser Ala Asp Ile
    1235            1240                1245

Ile Trp Leu Asn Asn Ala Leu His Arg Leu Leu Pro Glu Asp Pro
    1250            1255                1260

Gly Leu Leu Ala Thr Leu Gln Gln Leu Ala Val Pro Gly Ala Leu
    1265            1270                1275

Leu Tyr Val Met Glu Phe Arg Gln Leu Thr Pro Ser Ala Leu Leu
    1280            1285                1290

Ser Thr Leu Leu Leu Thr Asn Gly Gln Pro Glu Ala Leu Leu His
    1295            1300                1305

Asn Ser Ala Asp Trp Ala Ala Leu Phe Ser Ala Ala Ala Phe Asn
    1310            1315                1320

Cys Gln His Gly Asp Glu Val Ala Gly Leu Gln Arg Phe Leu Val
    1325            1330                1335

Gln Cys Pro Asp Arg Gln Val Arg Arg Asp Pro Arg Gln Leu Gln
    1340            1345                1350

Ala Ala Leu Ala Gly Arg Leu Pro Gly Trp Met Val Pro Gln Arg
    1355            1360                1365

Ile Val Phe Leu Asp Ala Leu Pro Leu Thr Ala Asn Gly Lys Ile
    1370            1375                1380

Asp Tyr Gln Ala Leu Lys Arg Arg His Thr Pro Glu Ala Glu Asn
    1385            1390                1395

Pro Ala Glu Ala Asp Leu Pro Gln Gly Asp Ile Glu Lys Gln Val
    1400            1405                1410

Ala Ala Leu Trp Gln Gln Leu Leu Ser Thr Gly Asn Val Thr Arg
    1415            1420                1425

Glu Thr Asp Phe Phe Gln Gln Gly Gly Asp Ser Leu Leu Ala Thr
    1430            1435                1440
```

```
Arg Leu Thr Gly Gln Leu His Gln Ala Gly Tyr Glu Ala Gln Leu
    1445                1450                1455

Ser Asp Leu Phe Asn His Pro Arg Leu Ala Asp Phe Ala Ala Thr
    1460                1465                1470

Leu Arg Lys Thr Asp Val Pro Val Glu Gln Pro Phe Val His Ser
    1475                1480                1485

Pro Glu Asp Arg Tyr Gln Pro Phe Ala Leu Thr Asp Val Gln Gln
    1490                1495                1500

Ala Tyr Leu Val Gly Arg Gln Pro Gly Phe Ala Leu Gly Gly Val
    1505                1510                1515

Gly Ser His Phe Phe Val Glu Phe Glu Ile Ala Asp Leu Asp Leu
    1520                1525                1530

Thr Arg Leu Glu Thr Val Trp Asn Arg Leu Ile Ala Arg His Asp
    1535                1540                1545

Met Leu Arg Ala Ile Val Arg Asp Gly Gln Gln Gln Val Leu Glu
    1550                1555                1560

Gln Thr Pro Pro Trp Val Ile Pro Ala His Thr Leu His Thr Pro
    1565                1570                1575

Glu Glu Ala Leu Arg Val Arg Glu Lys Leu Ala His Gln Val Leu
    1580                1585                1590

Asn Pro Glu Val Trp Pro Val Phe Asp Leu Gln Val Gly Tyr Val
    1595                1600                1605

Asp Gly Met Pro Ala Arg Leu Trp Leu Cys Leu Asp Asn Leu Leu
    1610                1615                1620

Leu Asp Gly Leu Ser Met Gln Ile Leu Leu Ala Glu Leu Glu His
    1625                1630                1635

Gly Tyr Arg Tyr Pro Gln Gln Leu Leu Pro Pro Leu Pro Val Thr
    1640                1645                1650

Phe Arg Asp Tyr Leu Gln Gln Pro Ser Leu Gln Ser Pro Asn Pro
    1655                1660                1665

Asp Ser Leu Ala Trp Trp Gln Ala Gln Leu Asp Asp Ile Pro Pro
    1670                1675                1680

Ala Pro Ala Leu Pro Leu Arg Cys Leu Pro Gln Glu Val Glu Thr
    1685                1690                1695

Pro Arg Phe Ala Arg Leu Asn Gly Ala Leu Asp Ser Thr Arg Trp
    1700                1705                1710

His Arg Leu Lys Lys Arg Ala Ala Asp Ala His Leu Thr Pro Ser
    1715                1720                1725

Ala Val Leu Leu Ser Val Trp Ser Thr Val Leu Ser Ala Trp Ser
    1730                1735                1740

Ala Gln Pro Glu Phe Thr Leu Asn Leu Thr Leu Phe Asp Arg Arg
    1745                1750                1755

Pro Leu His Pro Gln Ile Asn Gln Ile Leu Gly Asp Phe Thr Ser
    1760                1765                1770

Leu Met Leu Leu Ser Trp His Pro Gly Glu Ser Trp Leu His Ser
    1775                1780                1785

Ala Gln Ser Leu Gln Gln Arg Leu Ser Gln Asn Leu Asn His Arg
    1790                1795                1800

Asp Val Ser Ala Ile Arg Val Met Arg Gln Leu Ala Gln Arg Gln
    1805                1810                1815

Asn Val Pro Ala Val Pro Met Pro Val Val Phe Thr Ser Ala Leu
    1820                1825                1830

Gly Phe Glu Gln Asp Asn Phe Leu Ala Arg Arg Asn Leu Leu Lys
```

```
                    1835                1840                1845

Pro Val Trp Gly Ile Ser Gln Thr Pro Gln Val Trp Leu Asp His
        1850                1855                1860

Gln Ile Tyr Glu Ser Glu Gly Glu Leu Arg Phe Asn Trp Asp Phe
        1865                1870                1875

Val Ala Ala Leu Phe Pro Ala Gly Gln Val Glu Arg Gln Phe Glu
        1880                1885                1890

Gln Tyr Cys Ala Leu Leu Asn Arg Met Ala Glu Asp Glu Ser Gly
        1895                1900                1905

Trp Gln Leu Pro Leu Ala Ala Leu Val Pro Pro Val Lys His Ala
        1910                1915                1920

Gly Gln Cys Ala Glu Arg Ser Pro Arg Val Cys Pro Glu His Ser
        1925                1930                1935

Gln Pro His Ile Ala Ala Asp Glu Ser Thr Val Ser Leu Ile Cys
        1940                1945                1950

Asp Ala Phe Arg Glu Val Val Gly Glu Ser Val Thr Pro Ala Glu
        1955                1960                1965

Asn Phe Phe Glu Ala Gly Ala Thr Ser Leu Asn Leu Val Gln Leu
        1970                1975                1980

His Val Leu Leu Gln Arg His Glu Phe Ser Thr Leu Thr Leu Leu
        1985                1990                1995

Asp Leu Phe Thr His Pro Ser Pro Ala Ala Leu Ala Asp Tyr Leu
        2000                2005                2010

Ala Gly Val Ala Thr Val Glu Lys Thr Lys Arg Pro Arg Pro Val
        2015                2020                2025

Arg Arg Arg Gln Arg Arg Ile
        2030                2035

<210> SEQ ID NO 19
<211> LENGTH: 434
<212> TYPE: PRT
<213> ORGANISM: Yersinia pestis

<400> SEQUENCE: 19

Met Lys Ile Ser Glu Phe Leu His Leu Ala Leu Pro Glu Glu Gln Trp
1               5                   10                  15

Leu Pro Thr Ile Ser Gly Val Leu Arg Gln Phe Ala Glu Glu Cys
            20                  25                  30

Tyr Val Tyr Glu Arg Gln Pro Cys Trp Tyr Leu Gly Lys Gly Cys Gln
            35                  40                  45

Ala Arg Leu His Ile Asn Ala Asp Gly Thr Gln Ala Thr Phe Ile Asp
50                  55                  60

Asp Ala Gly Glu Gln Lys Trp Ala Val Asp Ser Ile Ala Asp Cys Ala
65                  70                  75                  80

Arg Arg Phe Met Ala His Pro Gln Val Lys Gly Arg Arg Val Tyr Gly
                85                  90                  95

Gln Val Gly Phe Asn Phe Ala Ala His Ala Arg Gly Ile Ala Phe Asn
                100                 105                 110

Ala Gly Glu Trp Pro Leu Leu Thr Leu Thr Val Pro Arg Glu Glu Leu
            115                 120                 125

Ile Phe Glu Lys Gly Asn Val Thr Val Tyr Ala Asp Ser Ala Asp Gly
            130                 135                 140

Cys Arg Arg Leu Cys Glu Trp Val Lys Glu Ala Gly Thr Thr Thr Gln
145                 150                 155                 160
```

```
Asn Ala Pro Leu Ala Val Asp Thr Ala Leu Asn Gly Glu Ala Tyr Lys
                165                 170                 175
Gln Gln Val Ala Arg Ala Val Ala Glu Ile Arg Arg Gly Glu Tyr Val
            180                 185                 190
Lys Val Ile Val Ser Arg Ala Ile Pro Leu Pro Ser Arg Ile Asp Met
        195                 200                 205
Pro Ala Thr Leu Leu Tyr Gly Arg Gln Ala Asn Thr Pro Val Arg Ser
    210                 215                 220
Phe Met Phe Arg Gln Glu Gly Arg Glu Ala Leu Gly Phe Ser Pro Glu
225                 230                 235                 240
Leu Val Met Ser Val Thr Gly Asn Lys Val Val Thr Glu Pro Leu Ala
                245                 250                 255
Gly Thr Arg Asp Arg Met Gly Asn Pro Glu His Asn Lys Ala Lys Glu
            260                 265                 270
Ala Glu Leu Leu His Asp Ser Lys Glu Val Leu Glu His Ile Leu Ser
        275                 280                 285
Val Lys Glu Ala Ile Ala Glu Leu Glu Ala Val Cys Gln Pro Gly Ser
    290                 295                 300
Val Val Val Glu Asp Leu Met Ser Val Arg Gln Arg Gly Ser Val Gln
305                 310                 315                 320
His Leu Gly Ser Gly Val Ser Gly Gln Leu Ala Glu Asn Lys Asp Ala
                325                 330                 335
Trp Asp Ala Phe Thr Val Leu Phe Pro Ser Ile Thr Ala Ser Gly Ile
            340                 345                 350
Pro Lys Asn Ala Ala Leu Asn Ala Ile Met Gln Ile Glu Lys Thr Pro
        355                 360                 365
Arg Glu Leu Tyr Ser Gly Ala Ile Leu Leu Asp Asp Thr Arg Phe
    370                 375                 380
Asp Ala Ala Leu Val Leu Arg Ser Val Phe Gln Asp Ser Gln Arg Cys
385                 390                 395                 400
Trp Ile Gln Ala Gly Ala Gly Ile Ile Ala Gln Ser Thr Pro Glu Arg
                405                 410                 415
Glu Leu Thr Glu Thr Arg Glu Lys Leu Ala Ser Ile Ala Pro Tyr Leu
            420                 425                 430
Met Val
```

<210> SEQ ID NO 20
<211> LENGTH: 215
<212> TYPE: PRT
<213> ORGANISM: Artificial Sequence
<220> FEATURE:
<223> OTHER INFORMATION: yebF gene pAES40

<400> SEQUENCE: 20

```
Met Ala Lys Lys Arg Gly Ala Phe Leu Gly Leu Leu Leu Val Ser Ala
1               5                   10                  15
Cys Ala Ser Val Phe Ala Ala Asn Asn Glu Thr Ser Lys Ser Val Thr
                20                  25                  30
Phe Pro Lys Cys Glu Asp Leu Asp Ala Ala Gly Ile Ala Ala Ser Val
            35                  40                  45
Lys Arg Asp Tyr Gln Gln Asn Arg Val Ala Arg Trp Ala Asp Asp Gln
        50                  55                  60
Lys Ile Val Gly Gln Ala Asp Pro Val Ala Trp Val Ser Leu Gln Asp
65                  70                  75                  80
Ile Gln Gly Lys Asp Asp Lys Trp Ser Val Pro Leu Ala Val Arg Gly
```

```
                        85                  90                  95
Lys Ser Ala Asp Ile His Tyr Gln Val Ser Val Asp Cys Lys Ala Gly
                100                 105                 110
Met Ala Glu Tyr Gln Arg Arg Leu Glu Asp Asp Asp Lys Gly Thr
                115                 120                 125
Leu Lys Ser Thr Ser Leu Pro Thr Ser Asn Glu Tyr Gln Asn Glu Lys
    130                 135                 140
Leu Ala Asn Glu Leu Lys Ser Leu Leu Asp Glu Leu Asn Val Asn Glu
145                 150                 155                 160
Leu Ala Thr Gly Ser Leu Asn Thr Tyr Tyr Lys Arg Thr Ile Lys Ile
                165                 170                 175
Ser Gly Gln Lys Ala Met Tyr Ala Leu Lys Ser Lys Asp Phe Lys Lys
                180                 185                 190
Met Ser Glu Ala Lys Tyr Gln Leu Gln Lys Ile Tyr Asn Glu Ile Asp
                195                 200                 205
Glu Ala Leu Lys Ser Lys Tyr
    210                 215

<210> SEQ ID NO 21
<211> LENGTH: 213
<212> TYPE: PRT
<213> ORGANISM: Artificial Sequence
<220> FEATURE:
<223> OTHER INFORMATION: YebF Fusion lacking trypsin site

<400> SEQUENCE: 21

Met Ala Lys Lys Arg Gly Ala Phe Leu Gly Leu Leu Leu Val Ser Ala
1               5                   10                  15
Cys Ala Ser Val Phe Ala Ala Asn Asn Glu Thr Ser Lys Ser Val Thr
                20                  25                  30
Phe Pro Lys Cys Glu Asp Leu Asp Ala Ala Gly Ile Ala Ala Ser Val
                35                  40                  45
Lys Arg Asp Tyr Gln Gln Asn Arg Val Ala Arg Trp Ala Asp Asp Gln
    50                  55                  60
Lys Ile Val Gly Gln Ala Asp Pro Val Ala Trp Val Ser Leu Gln Asp
65                  70                  75                  80
Ile Gln Gly Lys Asp Asp Lys Trp Ser Val Pro Leu Ala Val Arg Gly
                85                  90                  95
Lys Ser Ala Asp Ile His Tyr Gln Val Ser Val Asp Cys Lys Ala Gly
                100                 105                 110
Met Ala Glu Tyr Gln Arg Arg Leu Glu Asp Asp Asp Lys Gly Thr
                115                 120                 125
Ser Thr Ser Leu Pro Thr Ser Asn Glu Tyr Gln Asn Glu Lys Leu Ala
    130                 135                 140
Asn Glu Leu Lys Ser Leu Leu Asp Glu Leu Asn Val Asn Glu Leu Ala
145                 150                 155                 160
Thr Gly Ser Leu Asn Thr Tyr Tyr Lys Arg Thr Ile Lys Ile Ser Gly
                165                 170                 175
Gln Lys Ala Met Tyr Ala Leu Lys Ser Lys Asp Phe Lys Lys Met Ser
                180                 185                 190
Glu Ala Lys Tyr Gln Leu Gln Lys Ile Tyr Asn Glu Ile Asp Glu Ala
                195                 200                 205
Leu Lys Ser Lys Tyr
    210
```

```
<210> SEQ ID NO 22
<211> LENGTH: 256
<212> TYPE: DNA
<213> ORGANISM: Artificial Sequence
<220> FEATURE:
<223> OTHER INFORMATION: YebF mature sequence, codon optimized
      nucleotide sequence which eliminates low GC content

<400> SEQUENCE: 22
tctaccagcc tgccgacctc taacgaatat caaaacgaga aactggcaaa cgagctgaag      60
agtctgctgg atgagctgaa cgtcaacgag ctggcgaccg ctccctgaa  cacctattac     120 aaacgtacta ttaaaatcag cggccagaaa gcaatgtatg cgctaaaatc taaagacttc    180
aaaaaaatgt ctgaagctaa ataccagctg cagaaaatct acaacgaaat cgatgaggcg    240
ctgaaaagca aatatd                                                    256

<210> SEQ ID NO 23
<211> LENGTH: 393
<212> TYPE: PRT
<213> ORGANISM: Artificial Sequence
<220> FEATURE:
<223> OTHER INFORMATION: fusion of Pseudomonas ice nucleation protein
      (INP) sequence with the mature sequence of the lectin pathway
      inhibitor (LPI)

<400> SEQUENCE: 23
```

Met Thr Leu Asp Lys Ala Leu Val Leu Arg Thr Cys Ala Asn Asn Met
1 5 10 15

Ala Asp His Cys Gly Leu Ile Trp Pro Ala Ser Gly Thr Val Glu Ser
20 25 30

Arg Tyr Trp Gln Ser Thr Arg Arg His Glu Asn Gly Leu Val Gly Leu
35 40 45

Leu Trp Gly Ala Gly Thr Ser Ala Phe Leu Ser Val His Ala Asp Ala
50 55 60

Arg Trp Ile Val Cys Glu Val Ala Val Ala Asp Ile Ile Ser Leu Glu
65 70 75 80

Glu Pro Gly Met Val Lys Phe Pro Arg Ala Glu Val Val His Val Gly
85 90 95

Asp Arg Ile Ser Ala Ser His Phe Ile Ser Ala Arg Gln Ala Asp Pro
100 105 110

Ala Ser Thr Ser Thr Ser Thr Ser Thr Ser Thr Leu Thr Pro Met Pro
115 120 125

Thr Ala Ile Pro Thr Pro Met Pro Ala Val Ala Ser Val Thr Leu Pro
130 135 140

Val Ala Glu Gln Ala Arg His Glu Val Phe Asp Val Ala Ser Val Ser
145 150 155 160

Ala Ala Ala Ala Pro Val Asn Thr Leu Pro Val Thr Thr Pro Gln Asn
165 170 175

Leu Gln Thr Ala Thr Tyr Gly Ser Thr Leu Ser Gly Asp Asn His Ser
180 185 190

Arg Leu Ile Ala Gly Tyr Gly Ser Asn Glu Thr Ala Gly Asn His Ser
195 200 205

Asp Leu Ile Gly Gly His Asp Cys Thr Leu Met Ala Gly Asp Gln Ser
210 215 220

Arg Leu Thr Ala Gly Lys Asn Ser Val Leu Thr Ala Gly Ala Arg Ser
225 230 235 240

Lys Leu Ile Gly Ser Glu Gly Ser Thr Leu Ser Ala Gly Glu Asp Ser
245 250 255

-continued

```
Thr Leu Ile Phe Arg Leu Trp Asp Gly Lys Arg Tyr Arg Gln Leu Val
            260                 265                 270

Ala Arg Thr Gly Glu Asn Gly Val Glu Ala Asp Ile Pro Tyr Tyr Val
        275                 280                 285

Asn Glu Asp Asp Ile Val Asp Lys Pro Asp Glu Asp Asp Asp Trp
290                 295                 300

Ile Glu Val Lys Ser Thr Ser Leu Pro Thr Ser Asn Glu Tyr Gln Asn
305                 310                 315                 320

Glu Lys Leu Ala Asn Glu Leu Lys Ser Leu Leu Asp Glu Leu Asn Val
                325                 330                 335

Asn Glu Leu Ala Thr Gly Ser Leu Asn Thr Tyr Tyr Lys Arg Thr Ile
            340                 345                 350

Lys Ile Ser Gly Gln Lys Ala Met Tyr Ala Leu Lys Ser Lys Asp Phe
        355                 360                 365

Lys Lys Met Ser Glu Ala Lys Tyr Gln Leu Gln Lys Ile Tyr Asn Glu
    370                 375                 380

Ile Asp Glu Ala Leu Lys Ser Lys Tyr
385                 390
```

```
<210> SEQ ID NO 24
<211> LENGTH: 215
<212> TYPE: PRT
<213> ORGANISM: Artificial Sequence
<220> FEATURE:
<223> OTHER INFORMATION: Fusion of YebF pAES40 having a trypsin cleavage
      site LK with complement pathway inhibitor LPI

<400> SEQUENCE: 24

Met Ala Lys Lys Arg Gly Ala Phe Leu Gly Leu Leu Leu Val Ser Ala
1               5                   10                  15

Cys Ala Ser Val Phe Ala Ala Asn Asn Glu Thr Ser Lys Ser Val Thr
            20                  25                  30

Phe Pro Lys Cys Glu Asp Leu Asp Ala Ala Gly Ile Ala Ala Ser Val
        35                  40                  45

Lys Arg Asp Tyr Gln Gln Asn Arg Val Ala Arg Trp Ala Asp Asp Gln
50                  55                  60

Lys Ile Val Gly Gln Ala Asp Pro Val Ala Trp Val Ser Leu Gln Asp
65                  70                  75                  80

Ile Gln Gly Lys Asp Asp Lys Trp Ser Val Pro Leu Ala Val Arg Gly
                85                  90                  95

Lys Ser Ala Asp Ile His Tyr Gln Val Ser Val Asp Cys Lys Ala Gly
            100                 105                 110

Met Ala Glu Tyr Gln Arg Arg Leu Glu Asp Asp Asp Lys Gly Thr
        115                 120                 125

Leu Lys Ser Ser Leu Asp Lys Tyr Leu Thr Glu Ser Gln Phe His Asp
130                 135                 140

Lys Arg Ile Ala Glu Glu Leu Arg Thr Leu Leu Asn Lys Ser Asn Val
145                 150                 155                 160

Tyr Ala Leu Ala Ala Gly Ser Leu Asn Pro Tyr Tyr Lys Arg Thr Ile
                165                 170                 175

Met Met Asn Glu Tyr Arg Ala Lys Ala Leu Lys Lys Asn Asp Phe
            180                 185                 190

Val Ser Met Ala Asp Ala Lys Val Ala Leu Glu Lys Ile Tyr Lys Glu
        195                 200                 205

Ile Asp Glu Ile Ile Asn Arg
```

<210> SEQ ID NO 25
<211> LENGTH: 213
<212> TYPE: PRT
<213> ORGANISM: Artificial Sequence
<220> FEATURE:
<223> OTHER INFORMATION: Fusion of yebF pAES50 with complement pathway
      inhibitor LPI

<400> SEQUENCE: 25

```
Met Ala Lys Lys Arg Gly Ala Phe Leu Gly Leu Leu Leu Val Ser Ala
1               5                   10                  15

Cys Ala Ser Val Phe Ala Ala Asn Asn Glu Thr Ser Lys Ser Val Thr
            20                  25                  30

Phe Pro Lys Cys Glu Asp Leu Asp Ala Ala Gly Ile Ala Ala Ser Val
        35                  40                  45

Lys Arg Asp Tyr Gln Gln Asn Arg Val Ala Arg Trp Ala Asp Asp Gln
50                  55                  60

Lys Ile Val Gly Gln Ala Asp Pro Val Ala Trp Val Ser Leu Gln Asp
65                  70                  75                  80

Ile Gln Gly Lys Asp Asp Lys Trp Ser Val Pro Leu Ala Val Arg Gly
                85                  90                  95

Lys Ser Ala Asp Ile His Tyr Gln Val Ser Val Asp Cys Lys Ala Gly
            100                 105                 110

Met Ala Glu Tyr Gln Arg Arg Leu Glu Asp Asp Asp Lys Gly Thr
        115                 120                 125

Ser Ser Leu Asp Lys Tyr Leu Thr Glu Ser Gln Phe His Asp Lys Arg
130                 135                 140

Ile Ala Glu Glu Leu Arg Thr Leu Leu Asn Lys Ser Asn Val Tyr Ala
145                 150                 155                 160

Leu Ala Ala Gly Ser Leu Asn Pro Tyr Tyr Lys Arg Thr Ile Met Met
                165                 170                 175

Asn Glu Tyr Arg Ala Lys Ala Ala Leu Lys Lys Asn Asp Phe Val Ser
            180                 185                 190

Met Ala Asp Ala Lys Val Ala Leu Glu Lys Ile Tyr Lys Glu Ile Asp
        195                 200                 205

Glu Ile Ile Asn Arg
    210
```

<210> SEQ ID NO 26
<211> LENGTH: 213
<212> TYPE: PRT
<213> ORGANISM: Artificial Sequence
<220> FEATURE:
<223> OTHER INFORMATION: fusion ofPseudomonas ice nucleation protein
      (INP) with internal deletion followed by the mature sequence of
      the lectin pathway inhibitor LPI

<400> SEQUENCE: 26

```
Met Ala Lys Lys Arg Gly Ala Phe Leu Gly Leu Leu Leu Val Ser Ala
1               5                   10                  15

Cys Ala Ser Val Phe Ala Ala Asn Asn Glu Thr Ser Lys Ser

```
Lys Ile Val Gly Gln Ala Asp Pro Val Ala Trp Val Ser Leu Gln Asp
 65                  70                  75                  80

Ile Gln Gly Lys Asp Asp Lys Trp Ser Val Pro Leu Ala Val Arg Gly
                 85                  90                  95

Lys Ser Ala Asp Ile His Tyr Gln Val Ser Val Asp Cys Lys Ala Gly
            100                 105                 110

Met Ala Glu Tyr Gln Arg Arg Leu Glu Asp Asp Asp Lys Gly Thr
        115                 120                 125

Ser Ser Leu Asp Lys Tyr Leu Thr Glu Ser Gln Phe His Asp Lys Arg
130                 135                 140

Ile Ala Glu Glu Leu Arg Thr Leu Leu Asn Lys Ser Asn Val Tyr Ala
145                 150                 155                 160

Leu Ala Ala Gly Ser Leu Asn Pro Tyr Tyr Lys Arg Thr Ile Met Met
                165                 170                 175

Asn Glu Tyr Arg Ala Lys Ala Ala Leu Lys Lys Asn Asp Phe Val Ser
                180                 185                 190

Met Ala Asp Ala Lys Val Ala Leu Glu Lys Ile Tyr Lys Glu Ile Asp
            195                 200                 205

Glu Ile Ile Asn Arg
            210

<210> SEQ ID NO 27
<211> LENGTH: 139
<212> TYPE: PRT
<213> ORGANISM: Artificial Sequence
<220> FEATURE:
<223> OTHER INFORMATION: Fusion of YebF pAES40 with trypsin cleavage LK
      followed by tumor penetrating peptide

<400> SEQUENCE: 27

Met Ala Lys Lys Arg Gly Ala Phe Leu Gly Leu Leu Leu Val Ser Ala
  1               5                  10                  15

Cys Ala Ser Val Phe Ala Ala Asn Asn Glu Thr Ser Lys Ser Val Thr
                 20                  25                  30

Phe Pro Lys Cys Glu Asp Leu Asp Ala Ala Gly Ile Ala Ala Ser Val
            35                  40                  45

Lys Arg Asp Tyr Gln Gln Asn Arg Val Ala Arg Trp Ala Asp Asp Gln
 50                  55                  60

Lys Ile Val Gly Gln Ala Asp Pro Val Ala Trp Val Ser Leu Gln Asp
 65                  70                  75                  80

Ile Gln Gly Lys Asp Asp Lys Trp Ser Val Pro Leu Ala Val Arg Gly
                 85                  90                  95

Lys Ser Ala Asp Ile His Tyr Gln Val Ser Val Asp Cys Lys Ala Gly
            100                 105                 110

Met Ala Glu Tyr Gln Arg Arg Leu Glu Asp Asp Asp Lys Gly Thr
        115                 120                 125

Leu Lys Cys Arg Gly Asp Lys Gly Pro Asp Cys
130                 135

<210> SEQ ID NO 28
<211> LENGTH: 137
<212> TYPE: PRT
<213> ORGANISM: Artificial Sequence
<220> FEATURE:
<223> OTHER INFORMATION: Fusion of YebF pAES40 with tumor penetrating
      peptide

<400> SEQUENCE: 28
```

```
Met Ala Lys Lys Arg Gly Ala Phe Leu Gly Leu Leu Leu Val Ser Ala
1               5                   10                  15

Cys Ala Ser Val Phe Ala Asn Asn Glu Thr Ser Lys Ser Val Thr
            20                  25                  30

Phe Pro Lys Cys Glu Asp Leu Asp Ala Ala Gly Ile Ala Ala Ser Val
            35                  40                  45

Lys Arg Asp Tyr Gln Gln Asn Arg Val Ala Arg Trp Ala Asp Asp Gln
50                  55                  60

Lys Ile Val Gly Gln Ala Asp Pro Val Ala Trp Val Ser Leu Gln Asp
65                  70                  75                  80

Ile Gln Gly Lys Asp Lys Trp Ser Val Pro Leu Ala Val Arg Gly
                85                  90                  95

Lys Ser Ala Asp Ile His Tyr Gln Val Ser Val Asp Cys Lys Ala Gly
            100                 105                 110

Met Ala Glu Tyr Gln Arg Arg Leu Glu Asp Asp Asp Lys Gly Thr
            115                 120                 125

Cys Arg Gly Asp Lys Gly Pro Asp Cys
130                 135
```

<210> SEQ ID NO 29
<211> LENGTH: 317
<212> TYPE: PRT
<213> ORGANISM: Artificial Sequence
<220> FEATURE:
<223> OTHER INFORMATION: Fusion of Pseudomonas ice nucleation protein
      having internal deletion, with mature sequence of tumor
      penetrating peptide

<400> SEQUENCE: 29

```
Met Thr Leu Asp Lys Ala Leu Val Leu Arg Thr Cys Ala Asn Asn Met
1               5                   10                  15

Ala Asp His Cys Gly Leu Ile Trp Pro Ala Ser Gly Thr Val Glu Ser
            20                  25                  30

Arg Tyr Trp Gln Ser Thr Arg Arg His Glu Asn Gly Leu Val Gly Leu
            35                  40                  45

Leu Trp Gly Ala Gly Thr Ser Ala Phe Leu Ser Val His Ala Asp Ala
50                  55                  60

Arg Trp Ile Val Cys Glu Val Ala Val Ala Asp Ile Ile Ser Leu Glu
65                  70                  75                  80

Glu Pro Gly Met Val Lys Phe Pro Arg Ala Glu Val Val His Val Gly
                85                  90                  95

Asp Arg Ile Ser Ala Ser His Phe Ile Ser Ala Arg Gln Ala Asp Pro
            100                 105                 110

Ala Ser Thr Ser Thr Ser Thr Ser Thr Ser Thr Leu Thr Pro Met Pro
            115                 120                 125

Thr Ala Ile Pro Thr Pro Met Pro Ala Val Ala Ser Val Thr Leu Pro
130                 135                 140

Val Ala Glu Gln Ala Arg His Glu Val Phe Asp Val Ala Ser Val Ser
145                 150                 155                 160

Ala Ala Ala Ala Pro Val Asn Thr Leu Pro Val Thr Thr Pro Gln Asn
                165                 170                 175

Leu Gln Thr Ala Thr Tyr Gly Ser Thr Leu Ser Gly Asp Asn His Ser
            180                 185                 190

Arg Leu Ile Ala Gly Tyr Gly Ser Asn Glu Thr Ala Gly Asn His Ser
            195                 200                 205

Asp Leu Ile Gly Gly His Asp Cys Thr Leu Met Ala Gly Asp Gln Ser
```

```
                210               215                220
Arg Leu Thr Ala Gly Lys Asn Ser Val Leu Thr Ala Gly Ala Arg Ser
225                 230                 235                 240

Lys Leu Ile Gly Ser Glu Gly Ser Thr Leu Ser Ala Gly Glu Asp Ser
                245                 250                 255

Thr Leu Ile Phe Arg Leu Trp Asp Gly Lys Arg Tyr Arg Gln Leu Val
            260                 265                 270

Ala Arg Thr Gly Glu Asn Gly Val Glu Ala Asp Ile Pro Tyr Tyr Val
        275                 280                 285

Asn Glu Asp Asp Asp Ile Val Asp Lys Pro Glu Asp Asp Trp
    290                 295                 300

Ile Glu Val Lys Cys Arg Gly Asp Lys Gly Pro Asp Cys
305                 310                 315

<210> SEQ ID NO 30
<211> LENGTH: 9
<212> TYPE: PRT
<213> ORGANISM: Artificial Sequence
<220> FEATURE:
<223> OTHER INFORMATION: vascular homing motif peptide

<400> SEQUENCE: 30

Cys Arg Gly Asp Arg Gly Pro Asp Cys
1               5

<210> SEQ ID NO 31
<211> LENGTH: 9
<212> TYPE: PRT
<213> ORGANISM: Artificial Sequence
<220> FEATURE:
<223> OTHER INFORMATION: Vascular homing peptide motif

<400> SEQUENCE: 31

Cys Arg Gly Asp Lys Gly Pro Glu Cys
1               5

<210> SEQ ID NO 32
<211> LENGTH: 9
<212> TYPE: PRT
<213> ORGANISM: Artificial Sequence
<220> FEATURE:
<223> OTHER INFORMATION: Vascular homing motif peptide

<400> SEQUENCE: 32

Cys Arg Gly Asp Arg Gly Pro Glu Cys
1               5

<210> SEQ ID NO 33
<211> LENGTH: 4
<212> TYPE: PRT
<213> ORGANISM: Artificial Sequence
<220> FEATURE:
<223> OTHER INFORMATION: Vascular homing peptide motif
<220> FEATURE:
<221> NAME/KEY: X
<222> LOCATION: (4)..(4)
<223> OTHER INFORMATION: R or K or H

<400> SEQUENCE: 33

Arg Gly Asp Xaa
1

<210> SEQ ID NO 34
<211> LENGTH: 9
```

```
-continued

<212> TYPE: PRT
<213> ORGANISM: Artificial Sequence
<220> FEATURE:
<223> OTHER INFORMATION: Vascular homing peptide motif
<220> FEATURE:
<221> NAME/KEY: X
<222> LOCATION: (5)..(5)
<223> OTHER INFORMATION: R or K or H
<220> FEATURE:
<221> NAME/KEY: X
<222> LOCATION: (8)..(8)
<223> OTHER INFORMATION: D or H

<400> SEQUENCE: 34

Cys Arg Gly Asp Xaa Gly Pro Xaa Cys
1               5

<210> SEQ ID NO 35
<211> LENGTH: 9
<212> TYPE: PRT
<213> ORGANISM: Artificial Sequence
<220> FEATURE:
<223> OTHER INFORMATION: Varcular homing motif peptide
<220> FEATURE:
<221> NAME/KEY: X
<222> LOCATION: (5)..(5)
<223> OTHER INFORMATION: R or K or H
<220> FEATURE:
<221> NAME/KEY: X
<222> LOCATION: (8)..(8)
<223> OTHER INFORMATION: D or E or H

<400> SEQUENCE: 35

Cys Arg Gly Asp Xaa Gly Pro Xaa Cys
1               5

<210> SEQ ID NO 36
<211> LENGTH: 9
<212> TYPE: PRT
<213> ORGANISM: Artificial Sequence
<220> FEATURE:
<223> OTHER INFORMATION: Vascular homing motif peptide
<220> FEATURE:
<221> NAME/KEY: X
<222> LOCATION: (5)..(5)
<223> OTHER INFORMATION: R or K or H
<220> FEATURE:
<221> NAME/KEY: X
<222> LOCATION: (7)..(7)
<223> OTHER INFORMATION: P or V
<220> FEATURE:
<221> NAME/KEY: X
<222> LOCATION: (8)..(8)
<223> OTHER INFORMATION: D or E or H

<400> SEQUENCE: 36

Cys Arg Gly Asp Xaa Gly Xaa Xaa Cys
1               5

<210> SEQ ID NO 37
<211> LENGTH: 9
<212> TYPE: PRT
<213> ORGANISM: Artificial Sequence
<220> FEATURE:
<223> OTHER INFORMATION: Vascular homing motif peptide

<400> SEQUENCE: 37

Cys Arg Gly Asp His Gly Pro Asp Cys
1               5

<210> SEQ ID NO 38
```

```
<211> LENGTH: 9
<212> TYPE: PRT
<213> ORGANISM: Artificial Sequence
<220> FEATURE:
<223> OTHER INFORMATION: Vascular homing motif peptide

<400> SEQUENCE: 38

Cys Arg Gly Asp His Gly Pro Glu Cys
1               5

<210> SEQ ID NO 39
<211> LENGTH: 9
<212> TYPE: PRT
<213> ORGANISM: Artificial Sequence
<220> FEATURE:
<223> OTHER INFORMATION: Vascular homing motif peptide

<400> SEQUENCE: 39

Cys Arg Gly Asp His Gly Pro His Cys
1               5

<210> SEQ ID NO 40
<211> LENGTH: 9
<212> TYPE: PRT
<213> ORGANISM: Artificial Sequence
<220> FEATURE:
<223> OTHER INFORMATION: Vascular homing motif peptide

<400> SEQUENCE: 40

Cys Arg Gly Asp His Gly Val Asp Cys
1               5

<210> SEQ ID NO 41
<211> LENGTH: 9
<212> TYPE: PRT
<213> ORGANISM: Artificial Sequence
<220> FEATURE:
<223> OTHER INFORMATION: Vascular homing motif peptide

<400> SEQUENCE: 41

Cys Arg Gly Asp His Gly Val Glu Cys
1               5

<210> SEQ ID NO 42
<211> LENGTH: 9
<212> TYPE: PRT
<213> ORGANISM: Artificial Sequence
<220> FEATURE:
<223> OTHER INFORMATION: Vascular homing motif peptide

<400> SEQUENCE: 42

Cys Arg Gly Asp His Gly Val His Cys
1               5

<210> SEQ ID NO 43
<211> LENGTH: 9
<212> TYPE: PRT
<213> ORGANISM: Artificial Sequence
<220> FEATURE:
<223> OTHER INFORMATION: Vascular homing motif peptide

<400> SEQUENCE: 43

Cys Arg Gly Asp Lys Gly Pro His Cys
1               5

<210> SEQ ID NO 44
<211> LENGTH: 9
```

```
<212> TYPE: PRT
<213> ORGANISM: Artificial Sequence
<220> FEATURE:
<223> OTHER INFORMATION: Vascular homing motif peptide

<400> SEQUENCE: 44

Cys Arg Gly Asp Lys Gly Val Asp Cys
1               5

<210> SEQ ID NO 45
<211> LENGTH: 9
<212> TYPE: PRT
<213> ORGANISM: Artificial Sequence
<220> FEATURE:
<223> OTHER INFORMATION: Vascular homing motif peptide

<400> SEQUENCE: 45

Cys Arg Gly Asp Lys Gly Val Glu Cys
1               5

<210> SEQ ID NO 46
<211> LENGTH: 9
<212> TYPE: PRT
<213> ORGANISM: Artificial Sequence
<220> FEATURE:
<223> OTHER INFORMATION: Vascular homing motif peptide

<400> SEQUENCE: 46

Cys Arg Gly Asp Lys Gly Val His Cys
1               5

<210> SEQ ID NO 47
<211> LENGTH: 9
<212> TYPE: PRT
<213> ORGANISM: Artificial Sequence
<220> FEATURE:
<223> OTHER INFORMATION: Vascular homing motif peptide

<400> SEQUENCE: 47

Cys Arg Gly Asp Arg Gly Pro Glu Cys
1               5

<210> SEQ ID NO 48
<211> LENGTH: 9
<212> TYPE: PRT
<213> ORGANISM: Artificial Sequence
<220> FEATURE:
<223> OTHER INFORMATION: Vascular homing motif peptide

<400> SEQUENCE: 48

Cys Arg Gly Asp Arg Gly Pro His Cys
1               5

<210> SEQ ID NO 49
<211> LENGTH: 9
<212> TYPE: PRT
<213> ORGANISM: Artificial Sequence
<220> FEATURE:
<223> OTHER INFORMATION: Vascular homing motif peptide

<400> SEQUENCE: 49

Cys Arg Gly Asp Arg Gly Val Asp Cys
1               5

<210> SEQ ID NO 50
<211> LENGTH: 9
<212> TYPE: PRT
```

```
<213> ORGANISM: Artificial Sequence
<220> FEATURE:
<223> OTHER INFORMATION: Vascular homing motif peptide

<400> SEQUENCE: 50

Cys Arg Gly Asp Arg Gly Val Glu Cys
1               5

<210> SEQ ID NO 51
<211> LENGTH: 9
<212> TYPE: PRT
<213> ORGANISM: Artificial Sequence
<220> FEATURE:
<223> OTHER INFORMATION: Vascular homing motif peptide

<400> SEQUENCE: 51

Cys Arg Gly Asp Arg Gly Val His Cys
1               5

<210> SEQ ID NO 52
<211> LENGTH: 9
<212> TYPE: PRT
<213> ORGANISM: Artificial Sequence
<220> FEATURE:
<223> OTHER INFORMATION: Aminopeptidase N binding peptide

<400> SEQUENCE: 52

Cys Arg Asn Gly Arg Gly Pro Asp Cys
1               5

<210> SEQ ID NO 53
<211> LENGTH: 10
<212> TYPE: PRT
<213> ORGANISM: Artificial Sequence
<220> FEATURE:
<223> OTHER INFORMATION: Matrix metalloprotease inhibitor peptide

<400> SEQUENCE: 53

Cys Thr Thr His Trp Gly Phe Thr Leu Cys
1               5                   10

<210> SEQ ID NO 54
<211> LENGTH: 9
<212> TYPE: PRT
<213> ORGANISM: Artificial Sequence
<220> FEATURE:
<223> OTHER INFORMATION: Tumor targeting peptide LyP-1

<400> SEQUENCE: 54

Cys Gly Asn Lys Arg Thr Arg Gly Cys
1               5

<210> SEQ ID NO 55
<211> LENGTH: 4
<212> TYPE: PRT
<213> ORGANISM: Artificial Sequence
<220> FEATURE:
<223> OTHER INFORMATION: Albumin Binding Domain Fusing sequence, CendR
      peptide
<220> FEATURE:
<221> NAME/KEY: X
<222> LOCATION: (1)..(1)
<223> OTHER INFORMATION: R or K
<220> FEATURE:
<221> NAME/KEY: X
<222> LOCATION: (2)..(3)
<223> OTHER INFORMATION: any amino acid
<220> FEATURE:
<221> NAME/KEY: X
```

```
<222> LOCATION: (4)..(4)
<223> OTHER INFORMATION: R or K

<400> SEQUENCE: 55

Xaa Xaa Xaa Xaa
1

<210> SEQ ID NO 56
<211> LENGTH: 9
<212> TYPE: PRT
<213> ORGANISM: Artificial Sequence
<220> FEATURE:
<223> OTHER INFORMATION: Protease recognition site, e.g., K

<400> SEQUENCE: 56

Cys Arg Gly Asp Lys Gly Pro Asp Cys
1               5
```